US007615554B2

(12) United States Patent
Selliah et al.

(10) Patent No.: US 7,615,554 B2
(45) Date of Patent: Nov. 10, 2009

(54) ERASTIN AND ERASTIN BINDING PROTEINS, AND USES THEREOF

(75) Inventors: Robert Selliah, Midvale, UT (US); Longwu Qi, Salt Lake City, UT (US); Paul B. Robbins, Park City, UT (US); Sudhir R. Sahasrabudhe, Sandy, UT (US); Brent R. Stockwell, New York, NY (US); Raj Gopal Venkat, Salt Lake City, UT (US)

(73) Assignees: Prolexys Pharmaceuticals, Inc., Salt Lake City, UT (US); Whitehead Institute for Biomedical Research, Cambridge, MA (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/340,430

(22) Filed: Jan. 25, 2006

(65) Prior Publication Data

US 2006/0211683 A1 Sep. 21, 2006

Related U.S. Application Data

(60) Provisional application No. 60/762,221, filed on Jan. 24, 2006, provisional application No. 60/647,303, filed on Jan. 25, 2005.

(51) Int. Cl.
*A61K 31/497* (2006.01)
*A01N 43/62* (2006.01)
*C07D 243/08* (2006.01)
*C07D 239/72* (2006.01)

(52) U.S. Cl. .................. 514/252.17; 514/218; 540/575; 544/287

(58) Field of Classification Search ............ 514/252.17, 514/218; 544/287; 540/575
See application file for complete search history.

(56) References Cited

U.S. PATENT DOCUMENTS

| 6,831,085 | B1 * | 12/2004 | Bergnes et al. ............ 514/266.2 |
| 2003/0171316 | A1 | 9/2003 | Jupe ............................ 514/44 |
| 2004/0096444 | A1 | 5/2004 | Pizzo et al. .............. 524/143.1 |
| 2004/0248221 | A1 | 12/2004 | Stockwell | |

FOREIGN PATENT DOCUMENTS

| JP | 07-258224 | | 10/1995 |
| JP | 07-258224 | A * | 10/1995 |
| WO | WO-99/21988 | A | 5/1999 |
| WO | WO-01/68641 | | 9/2001 |
| WO | WO-02/40717 | | 5/2002 |
| WO | WO-02/083143 | A1 | 10/2002 |
| WO | WO-02/099122 | A | 12/2002 |
| WO | WO-2004/018058 | A2 | 3/2004 |
| WO | WO-2004/030615 | A | 4/2004 |
| WO | WO-2004/055519 | A2 | 7/2004 |

OTHER PUBLICATIONS

Machine Translation of JP 07-258224, 1995.*
Ahmed, S. Ansar et al., "A new rapid and simple non-radioacive assay to monitor and determine the proliferation of lymphocytes: an alternative to [3H] thymidine incorporation assay", Journal of Immunological Methods, 170(2): 211-224 (1994) (Abstract).
Aiken C.T., et al., "A Cell-Based Screen For Drugs to Treat Huntington's Disease", Neurobiology of Disease, 16:546-555 (2004).
Andoh, T., et al., "Characterization of a mammalian mutant with a camptothecin-resistant DNA topoisomerase I," Proc Natl Acad Sci U S A, 84:5565-5569 (1987).
Bjornsti, M-A., et al., "Expression of Human DNA Topoisomerase I in Yeast Cells Lacking Yeast DAN Topoisomerase I: Restoration of Sensitivity of the Cells to the Antitumor Drug Camptotchecin," Cancer Res, 49:6318-23 (1989).
Bosch, F.X., et al., "The causal relation between human papillomavirus and cervical cancer," J Clin Pathol, 55:244-265 (2002).
Brown, E.J., et al., "A mammalian protein targeted by G1-arresting rapamycin-receptor complex," Nature, 369:756-758 (1994).
Calin, G.A., et al., "Low frequency of alterations of the α (PPP2R1A) and β (PPP2R1B) isoforms of the subunit A of the serine-threonine phosphatase 2A in human neoplasms," Oncogene, 19:1191-1195 (2000).
Capdeville, R., et al., "Glivec (STI571, IMATINIB), A Rationally Developed, Targeted Anticancer Drug," Nat Rev Drug Discov, 1:493-502 (2002).
Champoux, J.J., "Structure-Based Analysis of the Effects of Camptothecin on the Activities of Human Topoisomerase I," Annals New York Acad Sci, 922:56-64 (2000).
Chan, Y-M, et al., "Caspase inhibitors promote the survival of avulsed spinal motoneurons in neonatal rats," NeuroReport, 12(3):541-5 (2001).
D'Arpa, P., et al., "Involvement of Nucleic Acid Synthesis in Cell Killing Mechanisms of Topoisomerase Poisons," Cancer Res, 50:6919-24 (1990).
DeVita, V.T., Jr., et al., "Principles of Cancer Management: Chemotherapy," Cancer: Principles & Practice of Oncology, Fifth Edition, 333-347 (1997).
Druker, B.J. et al., "Effects of a selective inhibitor of the Abl tyrosine kinase on the growth of Bcr-Abl positive cells", Nature Medicine, 2:561-566 (1996) (Abstract).
Elenbaas, B. et al., "Human breast cancer cells generated by oncogenic transformation of primary mammary epithelial cells", Genes & Development, 15:50-65 (2001).
Eng, W-K., et al., "Evidence that DNA Topoisomerase I Is Necessary for the Cytotoxic Effects of Camptothecin," Mol Pharmacol, 34:755-60 (1988).

(Continued)

Primary Examiner—James O. Wilson
Assistant Examiner—Tamthom N Truong
(74) Attorney, Agent, or Firm—Ropes & Gray LLP

(57) ABSTRACT

The invention relates to methods of screening for binding partners, especially binding partners essential for the biological activity of erastin (e.g. VDACs such as VDAC3). The invention also provides reagents and methods for effective killing of cancer cells with erastin and related compounds or derivatives.

23 Claims, 30 Drawing Sheets

OTHER PUBLICATIONS

Hahn, W. C. and Weinberg, R. A., "Modelling the Molecular Circuitry of Cancer", Nature Reviews Cancer, 2:331-341 (2002).
Hahn, W.C., et al., "Creation of human tumour cells with defined genetic elements," Nature, 400:464-468 (1999).
Hahn, W.C., et al., "Enumeration of the Simian Virus 40 Early Region Elements Necessary for Human Cell Transformation," *Mol Cell Biol*, 22(7):2111-23 (2002).
Hahn, W.C., et al., "Inhibition of telomerase limits the growth of human cancer cells," Nat Med, 5(10):1164-1170 (1999).
Hamad, N. M. et al., "Distinct requirements for Ras oncogenesis in human versus mouse cells", Genes & Development, 16:2045-2057 (2002).
Harley, C.B., "Telomerases," *Pathol Biol (Paris)*, 42:342-5 (1994).
Hsiang, Y-H. and Liu, L.F., "Identification of Mammalian DNA Topoisomerase I as an Intracellular Target of the Anticancer Drug Camptothecin," *Cancer Res*, 48:1722-6 (1988).
Hsiang, Y-H., et al., "Arrest of Replication Forks by Drug-stabilized Topoisomerase I-DNA Cleavable Complexes as a Mechanism of Cell Killing by Camptothecin," *Cancer Res*, 49:5077-82 (1989).
Jorcyk, C.L., et al., "Development and Characterization of a Mouse Prostate Adenocarcinoma Cell Line: Ductal Formation Determined by Extracellular Matrix," The Prostate, 34:10-22 (1998).
Kohno, T., et al., "Alterations of the *PPP1R3* Gene in Human Cancer," *Cancer Res*, 59:4170-4 (1999).
Laurent, G. and Jaffrezou, J-P., "Signaling pathways activated by daunorubicin," Blood, 98(4):913-924 (2001).
Lessnick, S.L., et al., "The Ewing's sarcoma oncoprotein EWS/FLI induces a p53- dependent growth arrest in primary human fibroblasts," Cancer Cell, 1:393-401 (2002).
Liu, L.F., et al., "Mechanism of Action of Camptothecin," Annals N Y Acad Sci, 922:1-10 (2000).
Loomis, C.R. and Bell, R.M., "Sangivamycin, a Nucleoside Analogue, Is a Potent Inhibitor of Protein Kinase C*," J Biol Chem, 263(4):1682-1692 (1998).
Madden, K.R., and Champoux, J.J., "Overexpression of Human Topoisomerase I in Baby Hamster Kidney Cells: Hypersensitivity of Clonal Isolates to Camptothecin," *Cancer Res*, 52:525-32 (1992).
Majno, G. and Joris, I., "Apoptosis, Oncosis, and Necrosis," *Am J Pathol*, 146(1):3-15 (1995).
Makin, G., "Targeting apoptosis in cancer chemotherapy," *Expert Opin Ther Targets*, 6(1):73-84 (2002).
Miller, M.L. and Ojima, I., "Chemistry and Chemical Biology of Taxane Anticancer Agents," Chem. Record, 1:195-211 (2001).
Millward, T.A., et al., "Regulation of protein kinase cascades by protein phosphatase 2A," Trends Biochem Sci, 24:186-91 (1999).
Mokbel, K. and Hassanally, D., "From HER2 to Herceptin," *Curr Med Res Opin*, 17(1):51-9 (2001).
Muller, I., et al., Anthracycline-derived chemotherapeutics in apoptosis and free radical cytotoxicity (Review), *Int J Mol Med*, 1:491-4 (1998).
Nociari, M.M., et al., "A novel one-step, highly sensitive fluorometric assay to evaluate cell-mediated cytotoxicity," *J. Immunol. Methods*, 213:157-167 (1998).
Pallas, D.C., et al, "Polyoma small and middle T antigens and SV40 small t antigen form stable complexes with protein phosphatase 2A," Cell, 60:167-176 (1990).
Perez-Stable, C., et al., "Prostate Cancer Progression, Metastasis, and Gene Expression in Transgenic Mice," *Cancer Res*, 57:900-6 (1997).
Rao, K.V., "Structure of Sangivamycin," *J Med Chem*, 11:939-41 (1968).
Richard, D., et al., "Free radical production and labile iron pool decrease triggered by subtoxic concentration of aclarubicin in human leukemia cell lines," Leukemia Res, 26:927-931 (2002).
Ruediger, R., et al., "Alterations in protein phosphatase 2A subunit interaction in human carcinomas of the lung and colon with mutations in the Aβ subunit gene," Oncogene, 20:1892-1899 (2001).
Ruediger, R., et al., "Disruption of protein phoshatase 2A subunit interaction in human cancers with mutations in the Aα subunit gene," Oncogene, 20:10-15 (2001).

Sabatini, D.M., et al., "RAFT1: A mammalian protein that binds to KFBP12 in a rapamycin-dependent fashion and is homologous to yeast TORs," Cell, 78:35-43 (1994).
Sandmoller, A., et al., "A Transgenic Mouse Model for Lung Adenocarcinoma," *Cell Growth & Differ*, 6:97-103 (1995).
Schreiber, S.L., Chemical Genetics Resulting from a Passion for Synthetic Organic Chemistry, Bioorg. Med. Chem., 6:1127-1152 (1998).
Sellers, W.R. and Kaelin, W.G., "Role of the retinoblastoma protein in the pathogenesis of human cancer," J Clin Oncol, 15:3301-3312 (1997).
Shawver, L.K., et al., "Smart drugs: Tyrosine kinase inhibitors in cancer therapy," Cancer Cell, 1:117-123 (2002).
Sherr, C.J., "The *INK4a/ARF* Network in Tumour Suppression," Nat Rev Mol Cell Biol, 2:731-737 (2001).
Shi, Y., et al., "Enhanced Sensitivity of Multiple Myeloma Cells Containing *PTEN* Mutations to CCI-779," *Cancer Res*, 62:5027-34 (2002).
Simons, A., et al., "Establishment of a Chemical Synthetic Lethality Screen in Cultured Human Cells," Genome Res, 11:266-273 (2001).
Stedman's Medical Dictionary 27th Edition (2000), (Definition of analog).
Stockwell, B. R., "Chemical Genetic Screening Approaches to Neurobiology," Neuron, 36:559-562 (2002).
Stockwell, B. R., "Frontiers in chemical genetics", Trends Biotechnol 18, 449-55, (2000).
Stockwell, B.R., Chemical Genetics: Ligand-Based Discovery of Gene Function, Nat Rev Genet, 1:116-125 (2000).
Stockwell, B.R., "The biological magic behind the bullets," Nature Biotechnology, 22(1):37-38 (2004).
Stockwell, B.R., et al., "High-throughput screening of small molecules in miniaturized mammalian cell-based assays involving post-translational modifications," Chem. Biol, 6:71-83 (1999).
Testa, J.R. and Giordano, A., "SV40 and cell cycle perturbations in malignant mesothelioma," Seminars In Cancer Biol, 11:31-8 (2001).
Torrance, C.J., et al., "Use of isogenic human cancer cells for high-throughput screening and drug discovery," Nat Biotechnol, 19:940-945 (2001).
Traganos, F., et al., "Induction of Apoptosis by Camptothecin and Topotecan," *Ann N Y Acad Sci*, 803:101-10 (1996).
Tsao, Y-P., et al., "Interaction between Replication Forks and Topoisomerase I-DNA Cleavable Complexes: Studies in a Cell-free SV40 DNA Replication System," *Cancer Res*, 53:5908-14 (1993).
Van Dyke, M, M. and Dervan, Peter B., "Echinomycin Binding Sites on DNA", Science 225:1122-1127 (1984).
Vonsattel J.P.G., "Neuropathology of Huntington's Disease," *Neuroscience News*, 3(2-3):45-53 (2000).
Wang, S.S., et al., "Alterations of the *PPP2R1B* Gene in Human Lung and Colon Cancer," Science, 282:284-287 (1998).
Wang, X. M. et al., "A new microcellular cytotoxicity test based on calcein AM release", Human Immunology, 37(4):264-270 (1993) (Abstract).
Waring, M.J. and Wakelin, L.P.G., "Echinomycin: a bifunctional intercalating antibiotic," *Nature*, 252:653-7 (1974).
Weinstein, J.N., et al, "An Information-Intensive Approach to the Molecular Pharmacology of Cancer," Science, 275:343-347 (1997).
Zalacin, M., et al., "The mode of action of the antitumor drug bouvardin, an inhibitor of protein synthesis in eukaryotic cells," FEBS Lett, 148(1):95-97 (1982).
Adam, et al., "Comprehensive Proteomic Analysis of Breast Cancer Cell Membranes Reveals Unique Proteins with Potential Roles in Clinical Cancer," JBC Papers in Press, 1-60 (2002).
Figys, et al., "VDAC Can Control Apoptosis By Controlling Metabolism," Biophysical J., 86(1):463A-464A (2004).
Ikonen, et al., "Prohibitin, an antiproliferative protein, is localized to mitochondria," FEBS Letters, 358(3):273-277 (1995).
Abdel-Alim, et al., "Synthesis and biological activities of 6-bromo-2,3-disubstituted-4-(3H)-quinazolinones," Indian Journal of Chemistry, 33(B):260-265 (1994).
Ager, et al., "Synthesis and Central Nervous System Activity of Quinazolones Related to 2-Methyl-3-(o-tolyl)-4(3H)-quinazolone (Methaqualone)," J. Med.Chem., 20(3):379-386 (1977).

Dolma, et al., "Identification of genotype-selective antitumor agents using synthetic lethal chemical screening in engineered human tumor cells," Cancer Cell, 3:285-296 (2003).

Gupta, et al., "A Novel Class of Hypoglycaemic Agents: Syntheses & SAR in 2-Substituted 4(3H)-Quinazolones, 2-Substituted 4-Hydroxypolymethylene[5,6]pyrimidines & 3-Substituted 4-Oxo-pyrido[1,2-α]pyrimidines," Indian Journal of Chemistry, 9:201-206 (1971).

Kozhevnikov, et al., "Synthesis in the 2-aminoethyl-3-(2'-tolyl)-4-quinazolone," Khimiko-Farmatsevticheskii Zhurnal, 4(11):22-25 (1970).

Tani, et al., "Studies on Biologically Active Halogenated Compounds II. Chemical Modifications of 6-amino-2-fluoromethyl-3-(o-tolyl)-4(3H)-quinazoline and the CNS Depressant Activities of Related Compounds," Chem. Pharm. Bull., 27(11):2675-2687 (1979).

Verma, et al., "A New Potent Anti-Inflammatory Quinazolone," Pharm. Res. Comm., Italian Pharmacological Society, IT, 13(10):967-979 (1981).

Database Registry Chemical Abstracts Service, Columbus, Ohio, US; (May 21, 2001), XP002405284, RN 336853-04-4.

Database Registry Chemical Abstracts Service, Columbus, Ohio, US; (May 21, 2001), XP002405285, RN 336813-90-2.

Rich, J.N., et al., "A Genetically Tractable Model of Human Glioma Formation," Cancer Res, 61:3556-60 (2001).

Database Registry Chemical Abstracts Service, Columbus, Ohio, US; (May 21, 2005), XP002466905, RN 723739-48-8.

* cited by examiner

Erastin A

ERASTIN AND ERASTIN BINDING PROTEINS, AND USES THEREOF

CROSS-REFERENCE TO RELATED APPLICATIONS

This application claims the benefit of U.S. Provisional Application No. 60/647,303, filed Jan. 25, 2005, and U.S. Provisional Application No. 60/762,221, filed Jan. 24, 2006, the specifications of which are hereby incorporated by reference in their entireties.

GOVERNMENT FUNDING

Work described herein was funded, in whole or in part, by National Cancer Institute Grant 1R01CA97061-01. The United States government has certain rights in the invention.

BACKGROUND OF THE INVENTION

Many drugs administered to treat a disease are targeted against general differences between a diseased cell and a normal cell. For example, paclitaxel, which is used to treat ovarian and breast cancer and inhibits microtubule function, is thought to exhibit tumor cell specificity based on the greater rate of proliferation of tumor cells relative to normal cells (Miller and Ojima, *Chem. Rec.* 1:195-211, 2002). However, despite this consensus view, paclitaxel's in vitro activity varies widely across tumor cell lines (Weinstein et al., *Science* 275:343-349, 1997), indicating that genetic factors can modify sensitivity of tumor cells to paclitaxel and that the responsiveness of tumor cells is not simply determined by their rate of proliferation.

Molecularly targeted therapeutics represent a promising new approach to anti-cancer drug discovery (Shawver et al., *Cancer Cell* 1: 117-23, 2002). Using this approach, small molecules are designed to inhibit directly the very oncogenic proteins that are mutated or overexpressed in specific tumor cell types. By targeting specific molecular defects found within tumor cells, this approach may ultimately yield therapies tailored to each tumor's genetic makeup. Two recent examples of successful molecularly targeted anti-cancer therapeutics are Gleevec (imatinib mesylate), an inhibitor of the breakpoint cluster region-abelsen kinase (BCR-ABL) oncoprotein found in Philadelphia chromosome-positive chronic myelogenous leukemia (Capdeville et al., *Nat Rev Drug Discov* 1: 493-502, 2002) and Herceptin (trastuzumab), a monoclonal antibody targeted against the HER2/NEU oncoprotein found in metastatic breast cancers (Mokbel and Hassanally, *Curr Med Res Opin* 17: 51-9, 2001).

A complementary strategy involves searching for genotype-selective anti-tumor agents that become lethal to tumor cells only in the presence of specific oncoproteins or in the absence of specific tumor suppressors. Such genotype-selective compounds might target oncoproteins directly or they might target other critical proteins involved in oncoprotein-linked signaling networks. Compounds that have been reported to display synthetic lethality include (i) the rapamycin analog CCI-779 in myeloma cells lacking PNEN (Shi et al., *Cancer Res* 62: 5027-34, 2002), (ii) Gleevec in BCR-ABL-transformed cells (Druker et al., *Nat Med* 2: 561-6, 1996) and (iii) a variety of less well-characterized compounds (Stockwell et al., *Chem Biol* 6: 71-83, 1999; Torrance et al., *Nat Biotechnol* 19: 940-5, 2001).

Despite the research discussed above, there remains a significant need to develop and/or identify compounds that selectively target tumor cells.

SUMMARY OF THE INVENTION

Using a synthetic lethal screening method, particularly a synthetic lethal high-throughout screening method, which is useful to identify agents or drugs for treating or preventing conditions or diseases such as the presence or development of tumors or other conditions characterized by hyperproliferation of cells (e.g., leukemia), Applicants have identified a number of compounds/agents/drugs useful for treating or preventing cancer (e.g., tumors or leukemia) in an individual, such as a human in need of treatment or prevention. The invention also provides cellular proteins that directly or indirectly bind certain identified compounds/agents of therapeutic value. Such cellular proteins provide additional methods for treating diseases or conditions characterized by hyperproliferation of cells (e.g., leukemia).

As used herein, the terms "agent" and "drug" are used interchangeably; they can be compounds or molecules.

In one embodiment, the present invention is directed to a compound disclosed herein, including salts thereof.

In another embodiment, the present invention is directed to a pharmaceutical composition comprising a pharmaceutically acceptable carrier and a compound disclosed herein.

In yet another embodiment, the invention is a method of promoting cell death, that includes administering to the cell an effective amount of a compound disclosed herein.

In one aspect, the present invention is a method for identifying a candidate anti-tumor agent, which includes the steps of:
a) contacting a cell with a sufficient amount of a test agent under suitable conditions; and
b) determining whether the test agent enhances or inhibits the level of an erastin binding protein or a nucleic acid encoding an erastin binding protein.

The method can further include the steps of:
a) contacting the test agent with a tumor cell (in vitro or in vivo); and
b) determining whether the test agent inhibits growth of the tumor cell.

In another aspect, the present invention is a method for identifying a candidate anti-tumor agent, which includes:
a) contacting an erastin binding protein or a cell expressing an erastin binding protein with a test agent, where the erastin binding protein or the test agent is optionally labeled with a detectable marker; and
b) determining whether the test agent binds to the erastin binding protein.

The method can further include:
a) contacting the test agent with a tumor cell (in vivo or in vitro); and
b) determining if the test agent inhibits growth of the tumor cell.

The two methods described immediately above can be repeated using a library of different test agents.

In a further aspect, the present invention relates to screening methods for identifying compounds that kill or inhibit the growth of tumorigenic cells, such as engineered tumorigenic cells, but not their isogenic normal cell counterparts. The method has been used to identify known and novel compounds with genotype-selective activity, including the known compounds doxorubicin, daunorubicin, mitoxantrone, camptothecin, sangivamycin, echinomycin, bouvardin, NSC146109 and a novel compound referred to herein as erastin. These compounds generally have increased activity in the presence of one or more of the following: hTERT oncoprotein, the SV40 large T oncoprotein (LT), small T oncoprotein (ST), human papillomavirus type 16 (HPV) E6 oncoprotein, HPV E7 oncoprotein, and oncogenic HRAS, NRAS and KRAS. Applicants determined that over-expression of hTERT and either E7 or LT increased expression of topoisomerase 2a and that overexpressing RAS$^V$12 and ST in cells expressing hTERT both increased expression of topoisomerase 1 and sensitized cells to a non-apoptotic cell death process initiated by erastin.

The invention relates to a method of identifying agents (e.g. drugs) that are selectively toxic to (e.g., kill or inhibit the growth of) tumorigenic cells, such as engineered tumorigenic cells, including human tumorigenic cells (e.g., engineered human tumorigenic cells and/or tumor cells). In one embodiment, the invention relates to a method of identifying an agent (e.g., drug) that selectively kills or inhibits the growth of (is toxic to) engineered human tumorigenic cells, comprising contacting test cells, which are engineered human tumorigenic cells, with a candidate agent; determining viability of test cells contacted with the candidate agent; and comparing the viability of the test cells with the viability of an appropriate control. In all embodiments, viability is assessed by determining the ability of an agent (e.g., drug) to kill cells or inhibit growth proliferation of cells, or both. If the viability of the test cells is less than that of the control cells, then an agent (e.g., drug) that is selectively toxic to (kills or inhibits the growth of) engineered human tumorigenic cells is identified. An appropriate control is a cell that is the same type of cell as the test cell, except that the control cell is not engineered to be tumorigenic. For example, control cells may be the parental primary cells from which the test cells are derived. Control cells are contacted with the candidate agent under the same conditions as the test cells. An appropriate control may be run simultaneously, or it may be pre-established (e.g., a pre-established standard or reference).

In one embodiment, the method of identifying an agent selectively toxic to tumorigenic cells comprises further assessing the toxicity of an agent identified as a result of screening in engineered human tumorigenic cells in an appropriate animal model or in an additional cell-based or non-cell-based system or assay. For example, an agent or drug so identified can be assessed for its toxicity to cancer cells such as tumor cells or leukemia cells obtained from individuals or its toxicity to a (one or more) cancer (tumor) cell line. For example, the method can comprise further assessing the selective toxicity of an agent (e.g., drug) to tumorigenic cells in an appropriate mouse model or nonhuman primate. The invention further relates to a method of producing an agent (e.g., drug) that is identified by the method of the present invention such as an agent (e.g., drug) that is selectively toxic to engineered human tumorigenic cells. An agent (e.g., drug) that is shown to be selectively toxic to tumorigenic cells is synthesized using known methods.

The invention additionally relates to a method of identifying agents (e.g., drugs) that are toxic to engineered tumorigenic cells, such as engineered human tumorigenic cells. In one embodiment, the invention relates to a method of identifying an agent (e.g., drug) that kills or inhibits the growth of (is toxic to) engineered human tumorigenic cells, comprising contacting test cells, which are engineered human tumorigenic cells, with a candidate agent; determining viability of the test cells contacted with the candidate agent; and comparing the viability of the test cells with the viability of an appropriate control. If the viability of the test cells is less than that of the control cells, then an agent (e.g., drug) that is toxic to (kills or inhibits the growth of) engineered human tumorigenic cells is identified. Here, an appropriate control is a cell that is the same type of cell (e.g., engineered human tumorigenic cell) as the test cells, except that the control cell is not contacted with the candidate agent. An appropriate control may be run simultaneously, or it may be pre-established (e.g., a pre-established standard or reference). For example, an agent or drug so identified can be assessed for its toxicity to cancer cells such as tumor cells or leukemia cells obtained from individuals or its toxicity to a (one or more) cancer (tumor) cell line.

In one embodiment, the method of identifying an agent toxic to engineered tumorigenic cells comprises further assessing the toxicity of an agent identified as a result of screening in engineered human tumorigenic cells in an appropriate animal model or in an additional cell-based or non-cell-based system or assay. For example, the method can comprise further assessing the toxicity of an agent (e.g., drug) to tumorigenic cells in an appropriate mouse model or nonhuman primate. The invention further relates to a method of producing an agent (e.g., drug) that is identified by the method of the present invention, such as an agent (e.g., drug) that is toxic to engineered human tumorigenic cells. An agent (e.g., drug) that is shown to be toxic to tumorigenic cells is synthesized using known methods.

In another embodiment, the present invention is a method of reducing the growth rate of a tumor, comprising administering an amount of a therapeutic agent sufficient to reduce the growth rate of the tumor, wherein the therapeutic agent is:
   (a) an agent which enhances or inhibits the level of a VDAC protein;
   (b) an agent which enhances or inhibits activity of a VDAC protein;
   (c) an agent which binds to a VDAC protein;
   (d) an agent which binds and/or modulates a protein complex comprising at least one VDAC and optionally one or more other proteins;
   (e) an agent comprising a VDAC polypeptide or functional variants thereof; or
   (f) an agent comprising a nucleic acid encoding a VDAC polypeptide or functional variants thereof.

Suitable agents can have the recited activity in the existing form or after complete or partial metabolism.

In one aspect, the invention is a method for treating a patient suffering from a cancer, comprising administering to the patient a therapeutic agent selected from:
   (a) an agent which enhances or inhibits the level of a VDAC protein;
   (b) an agent which enhances or inhibits activity of a VDAC protein;
   (c) an agent which binds to a VDAC protein;
   (d) an agent which binds and/or modulates a protein complex comprising at least one VDAC and optionally one or more other proteins;
   (e) an agent comprising a VDAC polypeptide or functional variants thereof; and
   (f) an agent comprising a nucleic acid encoding a VDAC polypeptide or functional variants thereof.

Suitable agents can have the recited activity in the existing form or after complete or partial metabolism.

Agents suitable for use in reducing the growth rate of a tumor and in treating a patient suffering from cancer include, but are not limited to, small organic molecules, peptides, proteins, peptidomimetics, nucleic acids, antibodies and combinations thereof. Such agents are typically formulated with a pharmaceutically acceptable carrier, and can be administered intravenously, orally, bucally, parenterally, by an inhalation spray, by topical application or transdermally. An agent can also be administered by local administration. An agent can additionally be administered in conjunction with at least one additional anti-cancer chemotherapeutic agent that inhibits cancer cells in an additive or synergistic manner.

In another aspect, the invention is a method of increasing sensitivity of a tumor cell to a chemotherapeutic agent, where a tumor cell is contacted with a compound that increases or decreases the abundance of an erastin binding protein. In a related aspect, the invention is a method of reducing the sensitivity of a normal cell to a chemotherapeutic agent, where a normal cell is contacted with a compound that decreases or increases the abundance of an erastin binding protein.

In certain embodiments of the invention, a candidate agent is identified by screening an annotated compound library, a combinatorial library, or other library which comprises unknown or known compounds (e.g., agents, drugs) or both.

In certain embodiments, the invention is a method of identifying a candidate therapeutic agent for inhibiting unwanted cell proliferation, which includes:

a) admixing a test agent and a VDAC protein or a protein complex comprising at least one VDAC protein and optionally one or more other proteins;

b) determining whether the test agent binds to the VDAC protein; and c) if the test agent binds to the VDAC protein, contacting the test agent with a cell (in vivo or in vitro) and determining if the test agent alters proliferation of the cell.

Binding of the VDAC protein to the test agent can be detected, for example, by a physical binding assay, such as an immunobinding assay, yeast two-hybrid assay, fluorescence polarization assay, surface plasma resonance or fluorescence resonance energy transfer (FRET) assay.

In certain embodiments, the invention relates to the compound erastin and a class of erastin-related compounds (e.g., the compounds of the present invention).

In additional embodiments, the invention relates to the compound, erastin B and its related compounds.

In additional embodiments, the invention relates to the compound, erastin A and its related compounds.

In further embodiments of the invention, the invention relates to analogs of erastin that selectively kill or inhibit the growth of (are toxic to) engineered human tumorigenic cells. Optionally, these compounds of the invention are formulated with a pharmaceutically acceptable carrier as pharmaceutical compositions.

The invention further relates to methods of identifying cellular components involved in tumorigenesis. Cellular components include, for example, proteins (e.g., enzymes, receptors), nucleic acids (e.g., DNA, RNA), and lipids (e.g., phospholipids). In one embodiment, the invention relates to a method of identifying a (one or more) cellular component involved in tumorigenesis wherein (a) a cell, such as an engineered human tumorigenic cell, is contacted with erastin; and (b) a cellular component that interacts with erastin, either directly or indirectly, is identified. The cellular component that is identified is a cellular component involved in tumorigenesis. In an additional embodiment, the invention relates to a method of identifying a (one or more) cellular component that interacts with erastin wherein (a) a cell, such as an engineered human tumorigenic cell, a tissue, an organ, an organism or a lysate or an extract of one of the above is contacted with erastin; and (b) a cellular component that interacts with erastin, either directly or indirectly, is identified. The cellular component that is identified is a cellular component that interacts with erastin, either directly or indirectly.

The invention additionally relates to methods of treating or preventing cancer. In one embodiment, the invention relates to a method of treating or preventing cancer in which a therapeutically effective amount of a compound, such as, for example, erastin or its analog, or a compound of formulas I-V below, is administered to an individual in need of treatment of cancer. In certain embodiments, the cancer is characterized by cells in which the RAS pathway is activated. In certain further embodiments, the cancer is characterized by cells expressing SV40 small T oncoprotein, or are phenotypically similar to cells expressing ST, and/or oncogenic HRAS. In certain preferred embodiments, the cells express substantially wild-type level of Rb (e.g., at least about 50%, 60%, 70%, 80%, 90%, 100%, 110%, 120%, 130%, or 150%, etc.).

The invention also relates to methods of identifying agents (e.g. drugs) that interact with one or more cellular components that interacts, directly or indirectly, with erastin. In one embodiment, the invention relates to a method of identifying an agent that interacts with a cellular component that interacts with erastin, comprising (a) contacting a cell, a tissue, an organ, an organism or a lysate or an extract of one of the above with erastin; (b) identifying a cellular component that interacts (directly or indirectly) with erastin; (c) contacting a cell, a tissue, an organ, an organism or a lysate or an extract of one of the above with a candidate agent, which is an agent or drug to be assessed for its ability to interact with a cellular component(s) that interacts with erastin; and (d) determining whether the agent interacts (directly or indirectly) with the cellular component in (b). If the agent interacts with the cellular component in (b), it is an agent that interacts with a cellular component that interacts with erastin.

In a related aspect, the invention also relates to methods of identifying agents (e.g., drugs) that interact with one or more cellular components that are known to interact, directly or indirectly, with erastin, the method comprising: (a) contacting a cell, a tissue, an organ, an organism or a lysate or an extract of one of the above with a candidate agent, which is an agent or drug to be assessed for its ability to interact with the cellular component(s) that is known to interact with erastin; and (b) determining whether the agent interacts (directly or indirectly) with the cellular component in (a). If the agent interacts with the cellular component in (a), it is an agent that interacts with the cellular component that interacts with erastin.

In certain embodiments, the cell is an engineered human tumorigenic cell. In further embodiments, the invention relates to compounds that interact, directly or indirectly, with a (one or more) cellular component that interacts with erastin. In certain embodiments, the cellular component that interacts with erastin is involved in tumorigenesis. An agent (e.g., drug) that is shown to interact with a cellular component that interacts with erastin is synthesized using known methods.

The invention further relates to a method of identifying an agent (e.g., drug) that induces death in tumor cells, such as by an apoptotic or a non-apoptotic mechanism. In one embodiment, a method of identifying an agent that induces death in tumor cells by a non-apoptotic mechanism comprises (a) contacting test cells, which are tumor cells, (or an organ or tissue containing tumor cells) with a candidate agent that induces death in tumor cells; (b) assessing whether the agent in (a) induces apoptosis in test cells; and (c) comparing induction of apoptosis in cells in (b) with an appropriate control. If apoptosis is induced in the control cells but not in test cells, then an agent (e.g., drug) that induces death in tumor cells by a non-apoptotic mechanism is identified. An appropriate control is a cell that is the same type of cell as that of test cells except that the control cell is contacted with an agent known to induce apoptosis in the cell. An appropriate control may be run simultaneously, or it may be pre-established (e.g., a pre-established standard or reference). In certain embodiments, the test cells are engineered human tumorigenic cells.

As used herein, "a" and "an" refer to one or more of the things referred to.

In certain aspects, the present invention provides methods of conducting a drug discovery business. In one embodiment, the invention relates to a method of conducting a drug discovery business, comprising: (a) identifying an agent (e.g., drug) that is selectively toxic to engineered human tumorigenic cells; (b) assessing the efficacy and toxicity of an agent identified in (a), or analogs thereof, in animals; and (c) formulating a pharmaceutical preparation including one or more agents assessed in (b). The efficacy assessed may be the ability of an agent to selectively induce cell death in tumorigenic cells in an animal. In a further embodiment, the method of conducting a drug discovery business comprises establishing a distribution system for distributing the pharmaceutical preparation for sale. Optionally, a sales group is established for marketing the pharmaceutical preparation. In an additional embodiment, the invention relates to a method of conducting a proteomics business, comprising identifying an agent (e.g., drug) that is selectively toxic to engineered human tumorigenic cells and licensing, to a third party, the rights for further drug development of agents that is selectively toxic to engineered human tumorigenic cells.

In another embodiment, the invention relates to a method of conducting a drug discovery business, comprising: (a) identifying an (one or more) agent (e.g., drug) that is toxic to engineered human tumorigenic cells; (b) assessing the efficacy and toxicity of an agent identified in (a), or analogs thereof, in animals; and (c) formulating a pharmaceutical preparation including one or more agents assessed in (b)) For example, the agent identified is erastin. The efficacy assessed may be the ability of an agent to selectively induce alterations in cell growth, toxicity or cell death in tumorigenic cells in an animal. In a further embodiment, the method of conducting a drug discovery business comprises establishing a distribution system for distributing the pharmaceutical preparation for sale. Optionally, a sales group is established for marketing the pharmaceutical preparation. In an additional embodiment, the invention relates to a method of conducting a proteomics business, comprising identifying an agent (e.g., drug) that is toxic to engineered human tumorigenic cells and licensing, to a third party, the rights for further drug development of agents that are toxic to engineered human tumorigenic cells.

In a further embodiment, the invention relates to a method of conducting a drug discovery business, comprising: (a) identifying an (one or more) agent (e.g., drug) that interacts with a cellular component that interacts with erastin; (b) assessing the efficacy and toxicity of an agent identified in (a), or analogs thereof, in animals; and (c) formulating a pharmaceutical preparation including one or more agents assessed in (b). The efficacy assessed of an agent may be its ability to selectively induce cell death in tumorigenic cells in an animal. In a further embodiment, the method of conducting a drug discovery business comprises establishing a distribution system for distributing the pharmaceutical preparation for sale. Optionally, a sales group is established for marketing the pharmaceutical preparation. In an additional embodiment, the invention relates to a method of conducting a proteomics business, comprising identifying an agent (e.g., drug) that interacts with a cellular component that interacts with erastin and licensing, to a third party, the rights for further drug development of agents that interact with a cellular component that interacts with erastin.

In yet another embodiment, the invention is a method of conducting a pharmaceutical business, which includes:
(a) identifying a candidate therapeutic agent for inhibiting cell proliferation, where the candidate therapeutic agent is
(i) an agent which enhances or inhibits a level of a VDAC protein;
(ii) an agent which enhances or inhibits activity of a VDAC protein;
(iii) an agent which binds to a VDAC protein;
(iv) an agent which binds and/or modulates a protein complex comprising at least one VDAC and optionally one or more other proteins;
(v) an agent comprising a VDAC polypeptide or functional variants thereof;
(vi) an agent comprising a nucleic acid encoding a VDAC polypeptide or functional variants thereof; or
(vii) a compound of disclosed herein,
(b) conducting therapeutic profiling of the candidate therapeutic agent identified in step (a) for efficacy and toxicity in animals; and
(c) formulating a pharmaceutical preparation including one or more the candidate therapeutic agent identified in step (b) as having an acceptable therapeutic profile.

Instead of or in addition to one or both of steps (b) and (c), the method can include licensing to a third party the rights for further development of the candidate therapeutic agent. In a further embodiment, the method of conducting a drug discovery business comprises establishing a distribution system for distributing the pharmaceutical preparation for sale. Optionally, a sales group is established for marketing the pharmaceutical preparation.

In a further embodiment, the invention is a method of conducting a pharmaceutical business that includes:
(a) identifying a candidate therapeutic agent for inhibiting cell proliferation, where the candidate therapeutic agent is
(i) an agent which enhances or inhibits a VDAC protein; or
(ii) an agent which enhances or inhibits interactions between a VDAC protein and a second protein, and
(b) licensing to a third party the rights for further development of the candidate therapeutic agent.

In a further embodiment, the method of conducting a drug discovery business comprises establishing a distribution system for distributing the pharmaceutical preparation for sale. Optionally, a sales group is established for marketing the pharmaceutical preparation.

Another aspect of the invention is a method of conducting a pharmaceutical business that includes one or more of marketing, producing, licensing to a third party the rights to market and licensing to a third party the rights to produce a kit, wherein the kit comprises:
(a) one or more reagents for determining levels of an erastin binding protein, the activity of an erastin binding protein, or both in a biological sample; and
(b) instructions for interpreting the results of the assay.

Generally, the instructions indicate whether levels and/or activity of the erastin binding protein are normal, increased or decreased relative to their desired level and/or activity, such that one can determine whether the level and/or activity should be altered or predict whether a therapy (partially) dependent upon the level and/or activity (e.g., cancer chemotherapy) will be successful.

In certain embodiments, the instructions include guidance regarding one or more of normal, decreased and elevated levels or activity of an erastin binding protein.

In certain embodiments, instructions include guidance regarding subsequent treatment with one or more of:
  (i) an agent which enhances or inhibits the level of a VDAC protein;
  (ii) an agent which enhances or inhibits activity of a VDAC protein;
  (iii) an agent which binds to a VDAC protein;
  (iv) an agent which binds, modulates, or binds and modulates a protein complex comprising at least one VDAC and optionally one or more other proteins;
  (v) an agent comprising a VDAC polypeptide or functional variant thereof;
  (vi) an agent comprising a nucleic acid encoding a VDAC polypeptide or functional variants thereof; and
  (vii) a compound disclosed herein, based upon the level of an erastin binding protein, the activity of an erastin binding protein, or both.

In certain embodiments, the instructions include guidance regarding whether treatment with one or more of the following was successful:
  (i) an agent which enhances or inhibits the level of a VDAC protein;
  (ii) an agent which enhances or inhibits activity of a VDAC protein;
  (iii) an agent which binds to a VDAC protein;
  (iv) an agent which binds, modulates, or binds and modulates a protein complex comprising at least one VDAC and optionally one or more other proteins;
  (v) an agent comprising a VDAC polypeptide or functional variant thereof;
  (vi) an agent comprising a nucleic acid encoding a VDAC polypeptide or functional variants thereof; and
  (vii) a compound disclosed herein, based upon the level of an erastin binding protein, the activity of an erastin binding protein, or both.

In certain embodiments, the instructions include guidance regarding the probability of success of a cancer therapy based upon the level of an erastin binding protein, the activity of an erastin binding protein, or both.

Identifying genetic alterations that increase the sensitivity of human cells to specific compounds may ultimately allow for mechanistic dissection of oncogenic signaling networks and tailoring chemotherapy to specific tumor types. Applicants have developed a systematic process for discovering small molecules with increased activity in cells harboring specific genetic changes. Using this system, they determined that several clinically used anti-tumor agents are more potent and more active in the presence of specific genetic elements. Moreover, they identified a novel compound that selectively kills cells expressing the Small T oncoprotein and oncogenic RAS. These genetically-targeted small molecules may also serve as leads for development of anti-cancer drugs with a favorable therapeutic index.

The present invention further provides packaged pharmaceuticals. In one embodiment, the packaged pharmaceutical comprises: (i) a therapeutically effective amount of an agent that is selectively toxic to engineered human tumorigenic cells; and (ii) instructions and/or a label for administration of the agent for the treatment of patients having cancer. In a particular embodiment, the agent is erastin. In another embodiment, the packaged pharmaceutical comprises: (i) a therapeutically effective amount of an agent that is toxic to engineered human tumorigenic cells; and (ii) instructions and/or a label for administration of the agent for the treatment of patients having cancer. In another related embodiment, the packaged pharmaceutical comprises: (i) a therapeutically effective amount of an agent that interacts with a cellular component that interacts with erastin; and (ii) instructions and/or a label for administration of the agent for the treatment of patients having cancer.

The instruction or label may be stored on an electronic medium such as CD, DVD, floppy disk, memory card, etc, which may be readable by a computer.

The present invention further provides use of any agent identified by the present invention in the manufacture of a medicament for the treatment of cancer, for example, the use of erastin or its analogs in the manufacture of medicament for the treatment of cancer.

In certain embodiments, the methods of the invention further comprise conjointly administering one or more agents, such as chemotherapeutic agents that typically kill the cells through an apoptotic methanism. Agents suitable for use in reducing the growth rate of a tumor and in treating a patient suffering from cancer include but are not limited to small organic molecules, peptides, proteins, peptidomimetics, nucleic acids, antibodies, and combinations thereof. It is contemplated that all embodiments of the invention can be combined with one or more other embodiments.

In another aspect, the present invention relates to screening methods for identifying compounds that suppress cellular toxicity of a protein in engineered cells, but not their isogenic normal cell counterparts. These methods have been used to identify known and novel compounds with genotype-selective activity. Optionally, these compounds have increased activity in the presence of a mutant protein.

The invention relates to a method of identifying agents (e.g., drugs) that selectively suppress cellular toxicity in engineered cells. In one embodiment, the invention relates to a method of identifying an agent (e.g., drug) that suppresses the cellular toxicity of a mutant protein in engineered cells, comprising contacting test cells (e.g., engineered cells expressing a mutant protein) with a candidate agent; determining viability of the test cells contacted with the candidate agent; and comparing the viability of the test cells with the viability of an appropriate control. If the viability of the test cells is more than that of the control cells, then an agent (e.g., drug) that selectively suppresses the cellular toxicity is identified. An appropriate control is a cell that is the same type of cell as that of test cells except that the control cell is not engineered to express a protein which causes toxicity. For example, control cells may be the parental primary cells from which the test cells are derived. Control cells are contacted with the candidate agent under the same conditions as the test cells. An appropriate control may be run simultaneously, or it may be pre-established (e.g., a pre-established standard or reference).

In certain aspects, the present invention provides methods of treating a condition in a mammal, comprising administering to the mammal a therapeutically effective amount of an analog of erastin, e.g., a compound represented by the general formula I:

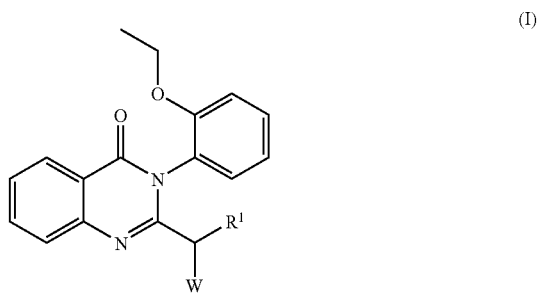

where the condition is characterized by cells with enhanced Ras signaling activity and altered (e.g., reduced or increased) activity of a cellular target protein of the SV40 small t antigen; and optionally substantially wild-type level of Rb activity; and where:

$R^1$ is selected from H, -Z-Q-Z, —$C_{1-8}$alkyl-N($R^2$)($R^4$), —$C_{1-8}$alkyl-O$R^3$, 3- to 8-membered carbocyclic or heterocyclic, aryl, heteroaryl, and $C_{1-4}$aralkyl;

$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N atom and not both H, they are different, and that when both $R^2$ and $R^4$ are on the same N and either $R^2$ or $R^4$ is acyl, alkylsulfonyl, or arylsulfonyl, then the other is selected from H, $C_{1-8}$alkyl, aryl, $C_{1-4}$aralkyl, and heteroaryl;

$R^3$ is selected from H, $C_{1-4}$alkyl, $C_{1-4}$aralkyl, aryl, and heteroaryl;

W is selected from

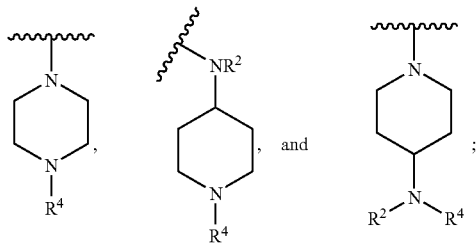

Q is selected from O and N$R^2$; and

Z is independently for each occurrence selected from $C_{1-6}$alkyl, $C_{2-6}$alkenyl, and $C_{2-6}$alkynyl. When Z is an alkenyl or alkynyl group, the double or triple bond or bonds are preferably not at the terminus of the group (thereby excluding, for example, enol ethers, alkynol ethers, enamines and/or ynamines).

In certain embodiments, W is selected from

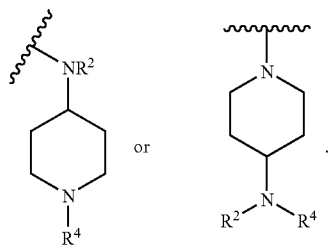

In certain such embodiments, $R^1$ is selected from -Z-Q-Z, —$C_{1-8}$alkyl-N($R^2$)($R^4$), —$C_{1-8}$alkyl-O$R^3$, aryl, heteroaryl, and $C_{1-4}$aralkyl.

In certain embodiments, W is

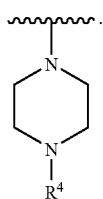

In certain such embodiments, $R^1$ is selected from -Z-Q-Z, —$C_{1-8}$alkyl-N($R^2$)($R^4$), —$C_{1-8}$alkyl-O$R^3$, aryl, heteroaryl, and $C_{1-4}$aralkyl.

In certain embodiments, $R^1$ is selected from -Z-Q-Z, —$C_{1-8}$alkyl-N($R^2$)($R^4$), —$C_{1-8}$alkyl-O$R^3$, aryl, heteroaryl, and $C_{1-4}$aralkyl.

In certain embodiments, $R^4$ is selected from $C_{1-4}$aralkyl and acyl. In certain such embodiments, $R^4$ is acyl.

In certain embodiments, where $R^4$ is acyl, $R^4$ is —C(O)—$C_{1-3}$alkyl-Y, and Y is selected from H, alkyl, alkoxy, aryloxy, aryl, heteroaryl, heteroaryloxy, and cycloalkyl. In certain such embodiments, Y is selected from aryloxy, aryl, heteroaryl, heteroaryloxy and cycloalkyl. In preferred such embodiments, Y is selected from aryloxy and heteroaryloxy. In more preferred such embodiments, $C_{1-3}$alkyl-Y is —CH$_2$O-phenyl, wherein phenyl is optionally substituted with halogen, preferably chloro. In certain preferred embodiments where Y is —CH$_2$O-phenyl, the remainder of the values are selected such that erastin is excluded from the embodiment.

In certain embodiments, aryl is optionally substituted with a group selected from $C_{1-6}$alkyl, CF$_3$, hydroxyl, $C_{1-4}$alkoxy, aryl, aryloxy, halogen, —N$R^2R^4$, nitro, carboxylic acid, carboxylic ester, and sulfonyl.

Suitable agents can have the recited activity in the existing form or after complete or partial metabolism.

In certain embodiments the condition is characterized by cells with substantially wild-type level of Rb activity. In certain such embodiments, the cells are further characterized by enhanced Ras signaling activity and/or altered (e.g., reduced or increased) activity of a cellular target protein of the SV40 small t antigen.

In certain embodiments, the compound kills the cells by a non-apoptotic mechanism.

In certain embodiments, the compound kills the cells by a mechanism other than a non-apoptotic mechanism.

In certain embodiments, the cells have enhanced Ras pathway activity (e.g., RasV12), overexpress SV40 small t antigen, have substantially reduced activity of phosphatase PP2A, and/or modulate (e.g., enhance or inhibit) VDAC levels or activity, such as VDAC2 or VDAC3.

In certain embodiments, the condition is cancer.

In certain embodiments, the cells are induced to express SV40 small t antigen, e.g., by infecting said cells with a viral vector overexpressing SV40 small t antigen, such as a retroviral vector or an adenoviral vector.

In certain embodiments, the viral vector is a retroviral vector or an adenoviral vector.

In certain embodiments, the method further comprises conjointly administering to said mammal an agent, such as a chemotherapeutic agent, that kills the cells through an apoptotic mechanism. In certain embodiments, the conjointly administered agent is selected from: an EGF-receptor antagonist, arsenic sulfide, adriamycin, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenolic acid, daunorubicin, deferoxamine, floxuridine, doxifluridine, raltitrexed, idarubicin, epirubican, pirarubican, zorubicin, mitoxantrone, bleomycin sulfate, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, enediynes, levamisole, aflacon, interferon, interleukins, aldesleukin, filgrastim, sargramostim, rituximab, BCG, tretinoin, betamethosone, gemcitabine hydrochloride, verapamil, VP-16, altretamine, thapsigargin, oxaliplatin, iproplatin, tetraplatin, lobaplatin, DCP, PLD-147, JM118, JM216, JM335, satraplatin, docetaxel, deoxygenated paclitaxel, TL-139, 5'-nor-anhydrovinblastine (hereinafter: 5'-nor-vinblastine), camptothecin, irinotecan (Camptosar, CPT-11), topotecan (Hycamptin), BAY 38-3441, 9-nitrocamptothecin (Orethecin, rubitecan), exatecan (DX-8951), lurtotecan (GI-147211C), gimatecan, homocamptothecins diflomotecan (BN-80915) and 9-aminocamptothecin (IDEC-13'), SN-38, ST1481, karanitecin (BNP1350), indolocarbazoles (e.g., NB-506), protoberberines, intoplicines, idenoisoquinolones, benzo-phenazines or NB-506.

Another aspect of the invention provides a method of killing a cell, promoting cell death or inhibiting cellular proliferation, comprising administering to the cell: (1) an effective amount of a compound represented by the general formula I:

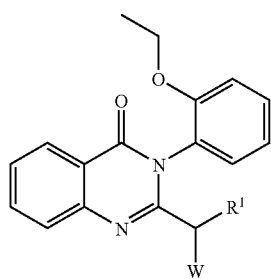

where:

$R^1$ is selected from H, -Z-Q-Z, $—C_{1-8}alkyl-N(R^2)(R^4)$, $—C_{1-8}alkyl-OR^3$, 3- to 8-membered carbocyclic or heterocyclic, aryl, heteroaryl, and $C_{1-4}$aralkyl;

$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N atom and not both H, they are different, and that when both $R^2$ and $R^4$ are on the same N and either $R^2$ or $R^4$ is acyl, alkylsulfonyl, or arylsulfonyl, then the other is selected from H, $C_{1-8}$alkyl, aryl, $C_{1-4}$aralkyl, and heteroaryl;

$R^3$ is selected from H, $C_{1-4}$alkyl, $C_{1-4}$aralkyl, aryl, and heteroaryl;

W is selected from

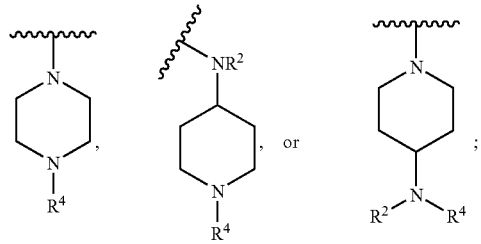

Q is selected from O and NR2; and

Z is independently for each occurrence selected from $C_{1-6}$alkyl, $C_{2-6}$alkenyl, and $C_{2-6}$alkynyl (when Z is an alkenyl or alkynyl group, the double or triple bond or bonds are preferably not at the terminus of the group); and (2) an agent that increases the abundance of VDAC (e.g., VDAC2, VDAC3) in the cell.

Another aspect of the invention provides a method of killing a cell, comprising administering to the cell: (1) an effective amount of a compound represented by the general formula I:

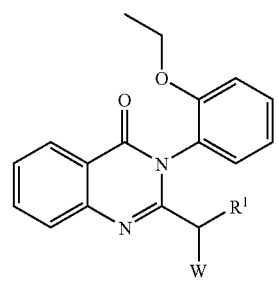

where:

$R^1$ is selected from H, -Z-Q-Z, $—C_{1-8}alkyl-N(R^2)(R^4)$, $—C_{1-8}alkyl-OR^3$, 3- to 8-membered carbocyclic or heterocyclic, aryl, heteroaryl, and $C_{1-4}$aralkyl;

$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N atom and not both H, they are different, and that when both $R^2$ and $R^4$ are on the same N and either $R^2$ or $R^4$ is acyl, alkylsulfonyl, or arylsulfonyl, then the other is selected from H, $C_{1-8}$alkyl, aryl, $C_{1-4}$aralkyl, and heteroaryl;

$R^3$ is selected from H, $C_{1-4}$alkyl, $C_{1-4}$aralkyl, aryl, and heteroaryl;

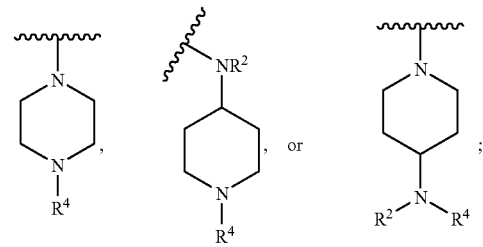

W is selected from

Q is selected from O and NR2; and

Z is independently for each occurrence selected from $C_{1-6}$alkyl, $C_{2-6}$alkenyl, and $C_{2-6}$alkynyl (when Z is an alkenyl or alkynyl group, the double or triple bond or bonds are preferably not at the terminus of the group); and (2) an agent that decreases the abundance of VDAC (e.g., VDAC2, VDAC3) in the cell.

In another embodiment, the invention is a method of promoting cell death that includes administering to the cell an effective amount of a compound of formula (I).

In certain embodiments, the compound is as described above.

In certain embodiments, the cell is a cancer cell.

In certain embodiments, the agent comprises a polynucleotide encoding a VDAC, such as VDAC3.

In certain embodiments, the agent is a VDAC protein (e.g., VDAC3) adapted to be transported into the cell, e.g., fused with a heterologous internalization domain.

In certain embodiments, the agent is a liposorrie preparation comprising a VDAC protein (e.g., VDAC3).

In certain embodiments, the agent enhances or inhibits endogenous VDAC (e.g., VDAC3) expression, stimulates or suppresses VDAC (e.g., VDAC3) expression or enhances or inhibits the function of a VDAC (e.g., VDAC3) inhibitor.

In certain aspects, the method also involves administering an agent that increases the abundance of VDAC (e.g., VDAC1, VDAC2, VDAC3) in the cell. In certain aspects, the method also involves administering an agent that decreases the abundance of VDAC (e.g., VDAC1, VDAC2, VDAC3) in the cell.

In another aspect, the invention is a method of increasing sensitivity of a tumor cell to a chemotherapeutic agent (e.g., additively or synergistically), where a tumor cell is contacted with a compound disclosed herein. In a related aspect, the invention is a method of reducing the sensitivity of a normal cell to a chemotherapeutic agent, where a normal cell is contacted with a compound disclosed herein.

In one embodiment, the invention is a method of identifying patients which are likely to respond to a treatment with compounds of the invention. Using standard characterization methods known in the art, patients identified as possessing neoplasias displaying one or more of the following attributes would be expected to be responsive: aberrant Ras signaling pathway activity as characterized by activation of one or more pathway members (e.g., phosphorylated Erk1/2, phosphorylated MEK etc.), and/or expression of VDAC proteins (1, 2 or 3) and/or sensitivity of a cell line of similar or identical genotype to exposure of compounds of the invention either in vitro or in vivo.

Another aspect of the invention provides a compound represented by the general formula I:

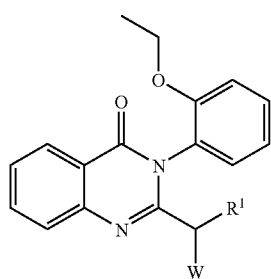

(I)

where:

$R^1$ is selected from H, Z-Q-Z, —$C_{1-8}$alkyl-N($R^2$)($R^4$), —$C_{1-8}$alkyl-O$R^3$, 3- to 8-membered carbocyclic or heterocyclic, aryl, heteroaryl, and $C_{1-4}$aralkyl;

$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N atom, they are different (except in certain embodiments where $R^2$ and $R^4$ are both H), and that when both $R^2$ and $R^4$ are on the same N and either R2 or $R^4$ is acyl, alkylsulfonyl, or arylsulfonyl, then the other is selected from H, $C_{1-8}$alkyl, aryl, $C_{1-4}$aralkyl, and heteroaryl;

$R^3$ is selected from H, $C_{1-4}$alkyl, $C_{1-4}$aralkyl, aryl, and heteroaryl;

W is selected from

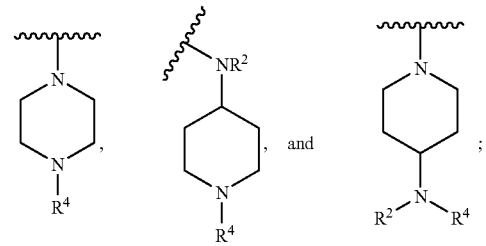

$Q$ is selected from O and $NR^2$; and

Z is independently for each occurrence selected from $C_{1-6}$alkyl, $C_{2-6}$alkenyl, and $C_{2-6}$alkynyl, and when Z is an alkenyl or alkynyl group, the double or triple bond or bonds are preferably not at the terminus of the group, or a pharmaceutically acceptable salt thereof.

Another aspect of the invention provides a compound represented by the general formula II:

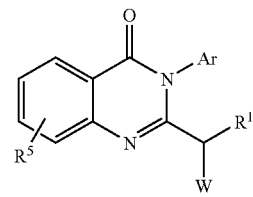

(II)

wherein

Ar is a substituted phenyl;

$R^1$ is selected from H, $C_{1-8}$alkyl, -Z-Q-Z, —$C_{1-8}$alkyl-N($R^2$)($R^4$), —$C_{1-8}$alkyl-O$R^3$, 3- to 8-membered carbocyclic or heterocyclic, aryl, heteroaryl, and $C_{1-4}$aralkyl;

$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N and either $R^2$ or $R^4$ is acyl, alkylsulfonyl, or arylsulfonyl, then the other is selected from H, $C_{1-8}$alkyl, aryl, $C_{1-4}$aralkyl, aryl, and heteroaryl;

$R^3$ is selected from H, $C_{1-4}$alkyl, $C_{1-4}$aralkyl, aryl, and heteroaryl;

$R^5$ represents 0-4 substituents on the ring to which it is attached;

W is

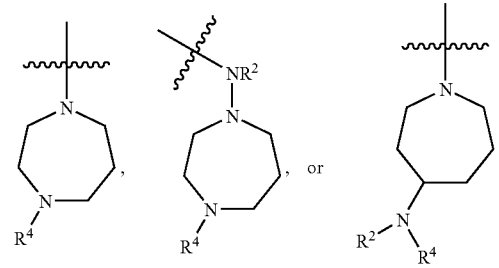

$Q$ is selected from O and $NR^2$; and

Z is independently for each occurrence selected from $C_{1-6}$alkyl, $C_{2-6}$alkenyl, and $C_{2-6}$alkynyl. When Z is an alkenyl or alkynyl group, the double or triple bond or bonds are preferably not at the terminus of the group.

Another aspect of the invention provides a compound represented by the general formula III:

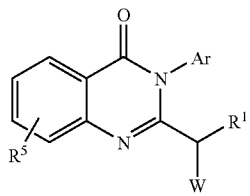
(III)

wherein

Ar is a substituted or unsubstituted phenyl;

$R^1$ is selected from H, $C_{1-8}$alkyl, -Z-Q-Z, —$C_{1-8}$alkyl-N$(R^2)(R^4)$, —$C_{1-8}$alkyl-OR$^3$, 3- to 8-membered carbocyclic or heterocyclic, aryl, heteroaryl, and $C_{1-4}$aralkyl;

$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N atom and either $R^2$ or $R^4$ is acyl, alkylsulfonyl, or arylsulfonyl, then the other is selected from H, $C_{1-8}$alkyl, aryl, $C_{1-4}$aralkyl, and heteroaryl;

$R^3$ is selected from H, $C_{1-4}$alkyl, $C_{1-4}$aralkyl, aryl, and heteroaryl;

$R^5$ represents 0-4 substituents on the ring to which it is attached;

W is selected from

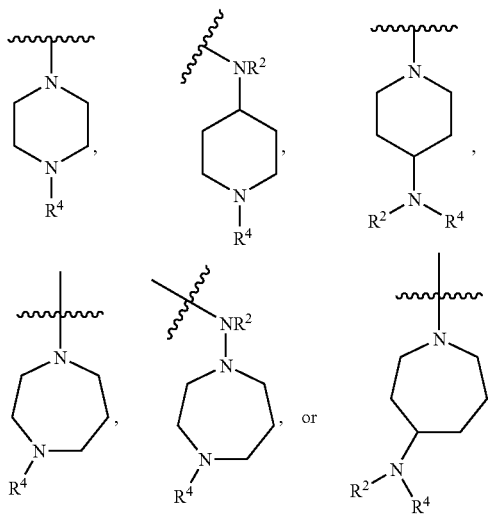

Q is selected from O and NR$^2$; and

Z is independently for each occurrence selected from $C_{1-6}$alkyl, $C_{2-6}$alkenyl, and $C_{2-6}$alkynyl. When Z is an alkenyl or alkynyl group, the double or triple bond or bonds are preferably not at the terminus of the group.

Another aspect of the invention provides a compound represented by the general formula IV:

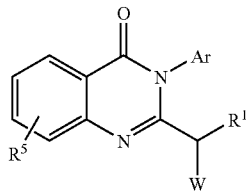
(IV)

wherein

Ar is a substituted or unsubstituted phenyl;

$R^1$ is $C_{1-8}$alkyl;

$R^2$ and $R^4$ are each independently for each occurrence selected from H and $C_{1-8}$alkyl;

$R^5$ represents 0-4 substituents on the ring to which it is attached;

W is selected from

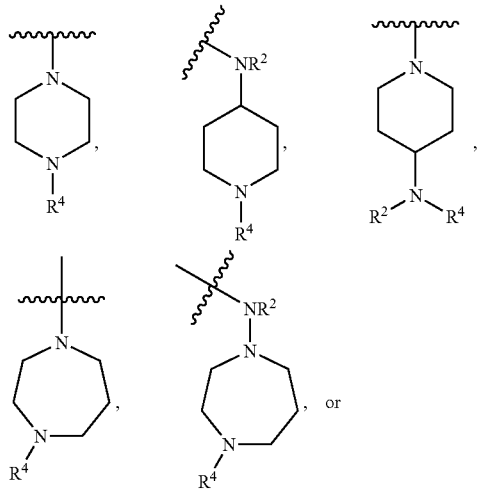

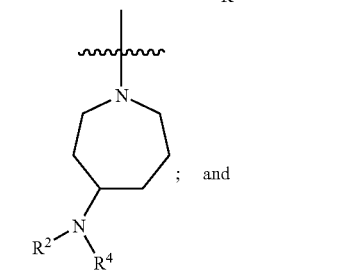

; and

Q is selected from O and NR$^2$.

Another aspect of the invention provides a compound represented by the general formula V:

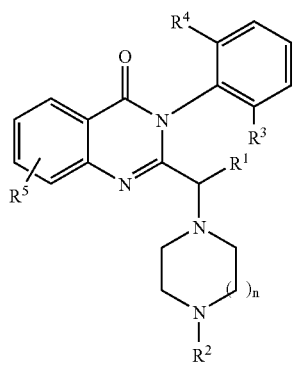
(V)

wherein $R^1$ is selected from H and $C_{1-8}$alkyl;

R2 is selected from H and $C_{1-8}$alkyl;

$R^3$ is selected from halogen, $C_{1-8}$alkoxy and $C_{1-8}$alkyl;

$R^4$ is selected from H, halogen, $C_{1-8}$alkoxy and $C_{1-8}$alkyl;

$R^5$ is selected from H, halogen and nitro; and n is 1 or 2.

It is contemplated that any of the compounds represented by formulas I-V above can be used for a method of 1) treating a condition in a mammal comprising administering to the mammal a therapeutically effective amount of said compound, 2) killing a cell comprising administering to the cell a) an effective amount of said compound, and b) an agent that increases the abundance of VDAC (e.g., VDAC2, VDAC3) in the cell, or 3) killing a cell comprising administering to the cell a) an effective amount of said compound, and b) an agent that decreases the abundance of VDAC (e.g., VDAC2, VDAC3) in the cell.

It is contemplated that all embodiments of the invention can be combined with one or more other embodiments, even those described under different aspects of the invention. In certain embodiments of the invention, a compound or agent is not a compound disclosed in Table 2.

DETAILED DESCRIPTION OF THE INVENTION

Figure 1:
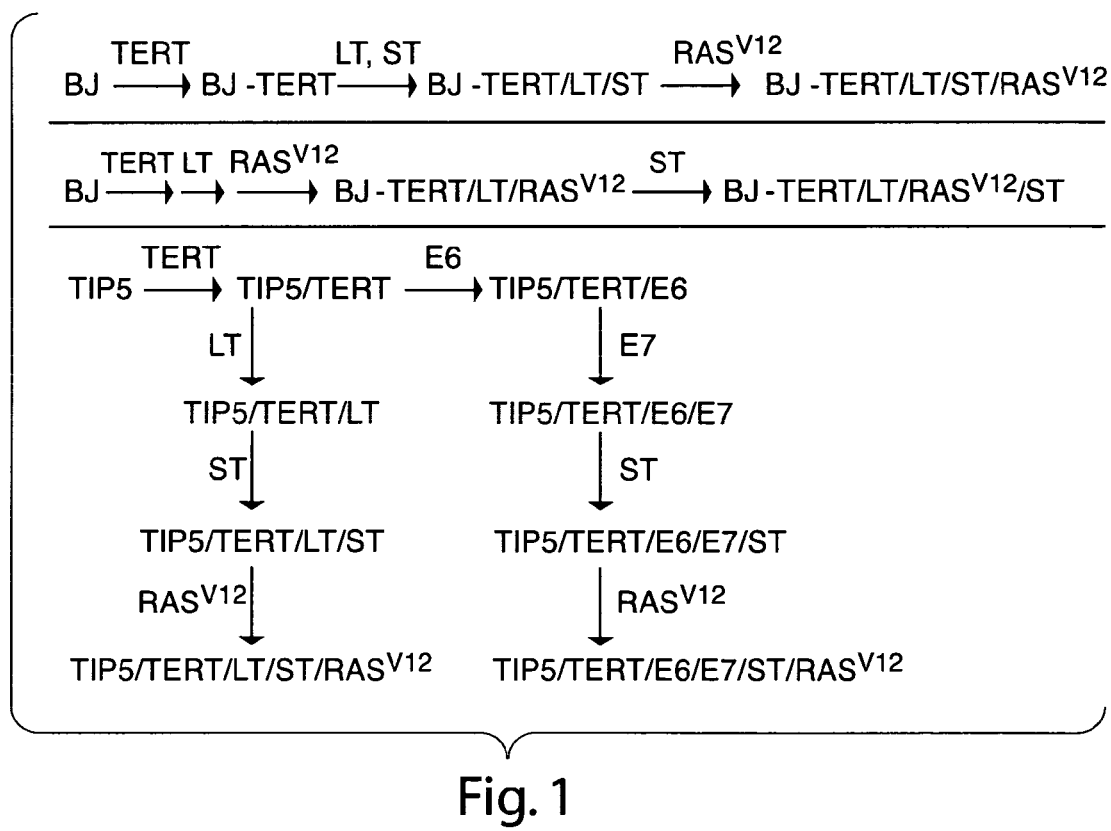
FIG. 1 is a schematic showing the relationships among experimentally transformed human cells. BJ cells are primary human foreskin fibroblasts. BJ-TERT cells are derived from BJ cells and express hTERT, the catalytic subunit of the enzyme telomerase. BJ-TERT/LT/ST cells are derived from BJ-TERT cells by introduction of a genomic construct encoding both simian virus 40 large (LT) and small T (ST) oncoproteins. BJ-TERT/LT/ST/RAS$^{V12}$ tumor cells are derived from BJ-TERT/LT/ST cells by introduction of an oncogenic allele of HRAS (RAS$^{V12}$) (Hahn et al., 1999, Nat Med 5, 1164-70). BJ-TERT/LT/RAS$^{V12}$ cells are derived from BJ cells by introduction of cDNA constructs encoding TERT, LT, RAS$^{V12}$ and a control vector (Hahn et al., 2002, Nat Rev Cancer 2, 331-41). BJ-TERT/LT/RAS$^{V12}$/ST cells are derived from BJ-TERT/LT/RAS$^{V12}$ cells by introduction of a cDNA encoding ST (Hahn et al., 2002, Nat Rev Cancer 2, 331-41). TIP5 cells are primary human foreskin fibroblasts. The TIP5-derived cell lines were prepared by introducing vectors encoding hTERT, LT, ST, RAS, or the papillomavirus E6 or E7 proteins, as shown. E6 and E7 can jointly substitute for LT (Lessnick et al., 2002, Cancer Cell 1, 393-401).

The ability of genotype-selective compounds to serve as molecular probes is based on the premise of chemical genetics, that small molecules can be used to identify proteins and pathways underlying biological effects (Schreiber, 1998, Bioorg. Med. Chem. 6, 1127-1152; Stockwell, 2000, Nat Rev Genet 1, 116-25; Stockwell, 2000, Trends Biotechnol 18, 449-55). For example, the observation that the natural product rapamycin retards cell growth made possible the discovery of the mammalian Target of Rapamycin (mTOR) as a protein that regulates cell growth (Brown et al., 1994, Nature 369, 756-758; Sabatini et al., 1994, Cell 78, 35-43). Applicants have combined these two approaches, chemical and molecular genetic, to discover pathways affected by mutations associated with human diseases such as cancer.

Applicants have engineered a series of human tumor cells with defined genetic elements for use in identifying those critical pathways whose disruption leads to a tumorigenic phenotype (Hahn et al., 1999, Nat Med 5, 1164-70; Hahn et al., 2002, Nat Rev Cancer 2, 331-41; lessnick et al., 2002, Cancer Cell 1, 393401). Applicants postulated that these experimentally transformed cells would make it possible to identify genotype-selective agents from both known and novel compound sources that exhibit synthetic lethality in the presence of specific cancer-related alleles. Compounds with genotype-selective lethality may serve as molecular probes of signaling networks present in tumor cells and as leads for subsequent development of clinically effective drugs with a favorable therapeutic index and/or as an effective drug.

Using this approach, Applicants have conducted several high-throughput screening studies of natural and synthetic compound libraries, and have identified compounds that exhibit strong cancer killing activities. Among these compounds are erastin and erastin analogs such as erastin B and erastin A. Nevertheless, a wide variety of test agents or compounds can be used in the screening studies (e.g., methods of identifying anti-tumor candidates) described herein. Such test agents include, but are not limited to, small organic molecules, peptides, peptidomimetics, proteins (including antibodies), nucleic acids, carbohydrates.

Thus, the invention provides compounds of formula I that kill cancer cells, especially genotype-specific cancer cells, such as those with elevated Ras signaling activity, altered SV40 small t antigen target activity, and/or substantially intact Rb activity.

Applicants have also identified several cellular proteins that directly or indirectly bind erastin and/or its analogs. These proteins include: Voltage-Dependent Anion Channels (VDAC1, VDAC2, and VDAC3), Prohibitin, Ribophorin, Sec61a and Sec22b. Quantitative RT-PCR also suggests that cells sensitive to erastin killing have elevated levels (e.g., 2-6 fold higher, typically 2-2.5 fold higher) of VDAC3 expression. While not wishing to be bound by any particular theory, these experiments suggest that high levels of VDAC, particularly VDAC3 and VDAC2, expression enhance erastin (and its analog)-mediated cell killing, and may even be required for effectiveness. Thus, one aspect of the invention provides a method to selectively kill cancer cells, especially those with elevated Ras activity, altered SV40 small t antigen target activity, and preferably substantially intact Rb and/or p53 activity, the method comprising administering to a mammalian patient in need of treatment a therapeutically effective amount of a compound represented by the general formula I:

(I)

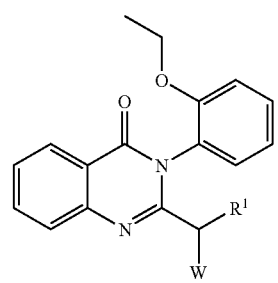

wherein:

$R^1$ is selected from H, -Z-Q-Z, —$C_{1-8}$alkyl-N($R^2$)($R^4$), —$C_{1-8}$alkyl-O$R^3$, 3- to 8-membered carbocyclic or heterocyclic, aryl, heteroaryl, and $C_{1-4}$aralkyl; $R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N atom and not both H they are different and that when both $R^2$ and $R^4$ are on the same N and either $R^2$ or $R^4$ is acyl, alkylsulfonyl, or arylsulfonyl, then the other is selected from H, $C_{1-8}$alkyl, aryl, $C_{1-4}$aralkyl, and heteroaryl;

$R^3$ is selected from H, $C_{1-4}$alkyl, $C_{1-4}$aralkyl, aryl, and heteroaryl;

W is selected from

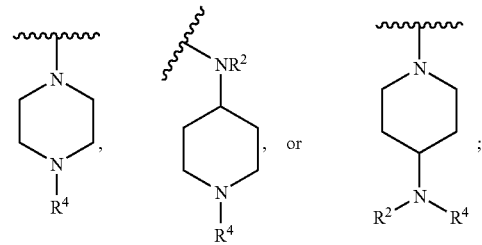

Q is selected from O and $NR^2$; and

Z is independently for each occurrence selected from $C_{1-6}$alkyl, $C_{2-6}$alkenyl, and $C_{2-6}$alkynyl. When Z is an alkenyl or alkynyl group, the double or triple bond or bonds are preferably not at the terminus of the group.

In certain embodiments, the compounds of formula I do not include erastin or erastin A.

As is well-known in the art, the constitutive activation of Ras appears to be an important factor for the malignant growth of human cancer cells. Mutations of the RAS proto-oncogenes (H-RAS, N-RAS, K-RAS) are frequent genetic aberrations found in 20% to 30% of all human tumors, although the incidences in tumor type vary greatly (Bos, Cancer Res.49: 4682-4689, 1989). The highest rates of RAS mutations were detected in adenocarcinomas of the pancreas (90%), the colon (50%), and the lung (30%). In follicular and undifferentiated carcinomas of the thyroid, the incidence of RAS mutations is also considerable (50%). The most commonly observed RAS mutations arise at sites critical for Ras regulation—namely, codons 12, 13, and 61. Each of these mutations results in the abrogation of the normal GTPase activity of Ras. Ras activation is also frequently observed in hematologic malignancies such as myeloid leukemias and multiple myelomas. In about one-third of the myelodysplastic syndromes (MDS) and acute myeloid leukemias (AML), RAS genes are mutationally activated. RAS mutations occur in about 40% of newly diagnosed multiple myeloma patients, and the frequency increases with disease progression.

On the other hand, polyomaviruses infect a wide variety of vertebrates (12 members now known). Murine polyomavirus was isolated by Ludwig Gross in-1953 while he was studying leukemia in mice and named because it caused solid tumors at multiple sites. The second member of the family, Simian Vacuolating Virus 40 (SV40) was isolated by Sweet and Hilleman in 1960 in primary monkey kidney cells cultures being used to grow Sabin OPV (Hilleman, Dev Biol Stand 94: 183-190, 1998). Two human polyomaviruses were isolated in 1971, cBK Virus (BKV) and JC Virus (JCV).

The polyomaviruses encode three proteins involved in cellular transformation termed large tumor antigen (LT), middle T antigen (mT), and small tumor antigen (sT). These three proteins result from the differential splicing of the early region transcript and contain homologous sequences. The large T antigen of polyoma interacts' with the tumor suppressor protein, pRb and is able to immortalize primary fibroblasts in culture. The Dna J domain located at its N-terminus, particularly the HPDKYG sequence found between residues 42 and 47, is critical for functional inactivation of Rb family proteins, as is also the case with SV40 large T antigen. The expression of LT is not sufficient to produce a fully transformed cell phenotype—this requires mT, which is the major transforming protein of the polyomavirus. Mouse polyoma middle T consists of 421 amino acids and can be divided into at least three domains, some of which are shared with LT and sT. The amino terminal domain comprises the first 79 amino acids and is also present in LT and sT. Adjacent to it, between residues 80-192, is a domain that is also present in the polyoma sT and contains two cysteine rich regions, Cys-X-Cys-X-X-Cys, which have also been identified in small t of SV40. Mutation of these cysteines abolishes the ability of mT to transform cells. The remaining 229 amino acids are unique to mT and contain the major tyrosine phosphorylation site of mouse mT and a hydrophobic region (approximately 20 amino acids at the carboxy-terminus) involved in membrane localization of this protein which is necessary for its transforming activity.

Small t antigen of SV40 comprises 174 amino acids. The region between residues 97-103 interacts with the protein phosphatase 2A (PP2A). This interaction reduces the ability of PP2A to inactivate ERK1 and MEK1 protein kinases, resulting in stimulation of proliferation of quiescent monkey kidney cells. Small t antigen-dependent assays also identified other regions which had the ability to enhance cellular transformation. These regions are located in the N-terminal part which is shared by the small and large T antigens of SV40 and can potentially function as a Dna J domain. Small t antigen can also associate with tubulin and it has been suggested that this plays a role in its biological function.

Applicants discovered that cells with both activated Ras activity and small t antigen expression (and thus diminished small t antigen target protein activity, e.g., diminished PP2A, etc., or enhanced ERK1 and MEK1) can be selectively killed by erastin and its analogs, likely via a non-apoptotic mechanism. In a preferred embodiment, the cell expresses a substantially wild-type level of Rb and/or p53 (or other E6/E7 protein targets).

Thus, in certain embodiments, cancer cells of certain specific genotypes can be selectively killed by the compounds of the invention. These may include cancers harboring constitutively active Ras mutations or Ras signaling pathway mutations, and enhanced ERK1, MEK1 activity or reduced PP2A activity.

In certain other embodiments, the genotype of the target cells may be selectively altered (e.g., to express small t antigen of SV40, express ERK1 or MEK1, or inhibit PP2A, etc.), so that target cells previously not susceptible to erastin and erastin analog killing are now susceptible to such killing.

Specifically, the invention provides a method of selectively killing cancer cells that have elevated Ras activity and small t antigen expression (or altered small t antigen target protein activity, such as PP2A activity, enhanced ERK1 or MEK1 activity or a mechanism that mimics the effects of sT, including but not limited to mutations in the PP2A regulatory subunit), while protecting relatively normal cells that does not have elevated Ras activity, even when these cells also express small t antigen. This can be useful since many cancers harbor the somatic RasV12 or other similar mutations leading to elevated Ras signaling activity in cancer cells, while normal cells in the same patient/individual usually do not have the same RasV12 or other Ras pathway mutations. Erastin and its analogs may be used to selectively kill these cancer cells, if the cancer cells also express small t antigen (or have altered small t antigen target protein activity). Even though other normal cells in the individual/patient also express the small t antigen, the subject method would still be effective in killing cancer cells since normal cells likely do not have elevated Ras signaling activity. Even if the individual does not express small t antigen, small t antigen may be delivered to the patient (either as protein or as vector-encoded DNA) to confer susceptibility to erastin/erastin analog killing in cancer (but not normal) cells.

Since small t antigen by itself is not understood to be sufficient to induce adverse effects on the patient, the side effects of the treatment (providing small t antigen to the patient) would be minimal or non-existent. In fact, as many as 30 million Americans are thought to have been exposed to SV40 through polio vaccinations between 1955 and 1963. SV40 found its way into the vaccine through macaque kidney cells used to grow polio virus. That method is no longer used and polio vaccines have been free of the virus since 1963. DNA studies in the 1990's found SV40 in some human tumors. However, association of virus DNA with dividing cells in tumor tissue does not prove that the virus caused the formation of the tumor. In October 2002, a scientific panel from the U.S. Institute of Medicine concluded that there is no way to determine whether widespread use of polio vaccine contaminated with simian virus SV40 decades ago led to increased cancer rates in humans.

In some embodiments, the elevated Ras activity is manifested by a constitutively active Ras (N-, H-, or K-Ras) mutation at amino acid positions 12, 13, and/or 61.

In some other embodiments, the elevated Ras activity is manifested by enhanced activity of one or more downstream components of the Ras pathway proteins, including but are not limited to Ras, MEK, MAPK, etc.

In yet other embodiments, the small t antigen expression can be accomplished by infection of target cells with vectors, such as adenoviral or retroviral vectors expressing SV40 small t antigen (see below).

Alternatively, the small t antigen may be directly provided to the target cells. For example, small t antigen may be introduced into the target cells using various methods known in the art (see details below). In one embodiment, the small t antigen may be provided to the target cell by entrapping it in liposomes bearing positive charges on their surface (e.g., lipofectins) and which are optionally tagged with antibodies against cell surface antigens of the target tissue, e.g., antibodies against a cancer cell surface antigen. In another embodiment, the small t antigen may be provided to the target cells by transcytosis, using any of the "internalizing peptides" capable of mediating this effect, including but not limited to the N-terminal domain of the HIV protein Tat (e.g., residues 1-72 of Tat or a smaller fragment thereof which can promote transcytosis), all or a portion of the *Drosophila antenopedia* III protein, a sufficient portion of mastoparan, etc. (see below).

In other embodiments, the diminished PP2A (and/or other small t antigen target proteins) may be achieved by delivering an antibody, RNAi (siRNA, short hairpin RNA, etc.), antisense sequence, or small molecule inhibitor specific for such target protein.

Delivering of such antagonists of a protein to a target cell is well known in the art. See, for example, WO04078940A2, EP1439227A1, WO04048545A2, US20040029275A1, WO03076592A2, WO04076674A1, WO9746671A1, all incorporated herein by reference.

Another aspect of the invention provides a conjoint therapeutic method using erastin/erastin analogs and one or more agents or therapies (e.g., radiotherapy) that kill cells via an apoptotic mechanism. Such agents include many of the chemotherapeutic drugs described below.

It is believed that certain proteins have elevated expression levels in erastin-sensitive cells. One such protein, VDAC3, is elevated 2-2.5 fold in abundance when exposed to erastin, for example, and while Applicants do not wish to be bound by theory, its presence or even increased abundance is believed to be essential for erastin-mediated killing.

Thus in another aspect of the invention, a method is provided to kill or slow the rate of proliferation of cells that have an elevated level of a VDAC such as VDAC2 or VDAC3, comprising contacting the target cells with erastin and/or an erastin analog of formulas I-IV.

In certain embodiments, target cells are manipulated to express a higher level of a VDAC such as VDAC2 or VDAC3 so as to enhance the susceptibility of killing or slowing the rate of proliferation by erastin and its functional analogs.

For example, a VDAC protein may be introduced into the target cells using various methods known in the art (see details below). In one embodiment, the VDAC protein may be provided to the target cell by entrapping it in liposomes bearing positive charges on their surface (e.g., lipofectins) and which are optionally tagged with antibodies against cell surface antigens of the target tissue, e.g., antibodies against a cancer cell surface antigen. In another embodiment, the VDAC protein may be provided to the target cells by transcytosis, using any of the "internalizing peptides" capable of mediating this effect, including but not limited to the N-terminal domain of the HIV protein Tat (e.g., residues 1-72 of Tat or a smaller fragment thereof which can promote transcytosis), all or a portion of the *Drosophila antennapedia* III protein, a sufficient portion of mastoparan, etc. (see below).

Alternatively, nucleic acids encoding a functional VDAC may be introduced into such target cells, using, for example, adenoviral or retroviral vectors expressing VDAC.

In addition, endogenous VDAC (e.g., VDAC3) activity may be stimulated by an agent that either stimulates VDAC expression, or suppresses the activity of a VDAC inhibitor (transcription or translation inhibitor, or inhibitor that promotes VDAC turnover in the cell).

In certain aspects, the method of the invention also involves administering an agent that increases the abundance of VDAC (e.g. VDAC1, VDAC2, VDAC3) in the cell. The agent for increasing the abundance of VDAC can, for example, include a polynucleotide encoding VDAC, such as VDAC3; be a VDAC protein (e.g., VDAC3) adapted to be transported into the cell, e.g., fused with a heterologous internalization domain or formulated in liposome preparation.

In certain aspects, the method of the invention also involves administering an agent that decreases the abundance of VDAC (e.g. VDAC1, VDAC2, VDAC3) in the cell. The agent for decreasing the abundance of VDAC can, for example, inhibit endogenous VDAC (e.g. VDAC3) expression, suppress VDAC (e.g. VDAC3) expression or enhance the function of a VDAC (e.g., VDAC3) inhibitor.

The following sections describe certain exemplary embodiments of the invention, which are contemplated to be capable to combining with one another. In addition, the embodiments are for illustrative purposes only, and should not be construed to be limiting in any respect.

Engineered Cell Lines

In one aspect, the present invention relates to engineered tumorigenic cell lines.

Previous reports have indicated that it is possible to convert primary human cells into tumorigenic cells by introduction of vectors expressing the hTERT and oncogenic RAS proteins as well as others that disrupt the function of p53, RB and PP2A (Hahn et al., 2002, Mol Cell Biol 22, 2111-23; Hahn et al., 1999, Nature 400, 464-8; Hahn and Weinberg, 2002, Nat Rev Cancer 2, 331-41; Lessnick et al., 2002, Cancer Cell 1, 393-401). Applicants made use of a series of engineered human tumorigenic cells and their precursors, which were created by introducing specific genetic elements into primary human foreskin fibroblasts (FIG. 1). A variety of characteristics of these engineered tumorigenic cells have been reported previously, including their doubling time, their resistance to replicative senescence and crisis in culture, their response to gamma irradiation, their ability to grow in an anchorage-independent fashion and their ability to form tumors in immunodeficient mice (Hahn et al., 1999, supra; Hahn et al., 2002, supra; Lessnick et al., 2002, supra).

In one series of engineered cells, the following genetic elements were introduced sequentially into primary BJ fibroblasts: the human catalytic subunit of the enzyme telomerase (hTERT), a genomic construct encoding the Simian Virus 40 large (LT) and small T (ST) oncoproteins, and an oncogenic allele of HRAS (RAS$^{V12}$). The resulting transformed cell lines were named, respectively: BJ-TERT, BJ-TERT/LT/ST, and BJ-TERT/LT/ST/RAS$^{V12}$. In a second series, cell lines were created in which complementary DNA (cDNA) constructs encoding LT and ST were used in place of the SV40 genomic construct that encodes both of these viral proteins. In this latter series, ST was introduced in the last stage, enabling Applicants to test compounds in the presence or absence of ST. This latter engineered human tumorigenic cell line was named BJ-TERT/LT/RAS$^{V12}$/ST.

In a third series, cell lines derived from independently prepared human TIP5 foreskin fibroblasts created by introducing cDNA constructs encoding hTERT, LT, ST and RAS$^{V12}$ (Lessnick et al., 2002, Cancer Cell 1, 393-401) were used. These cell lines were called, respectively: TIP5/MRT, TIP5/TERT/LT, TIP5/TERT/LT/ST, and TIP5/TERT/LT/ST/RAS$^{V12}$. In a fourth series, cell lines derived from TIP5 fibroblasts created by introducing cDNA constructs encoding hTERT, E6, E7, ST and RAS$^{V12}$ were used. These cell lines were named, respectively: TIP5/TERT/E6, TIP5/TERT/E6/E7, TIP5/TERT/E6/E7/ST, and TIP5/TERT/E6/E7/ST/RAS$^{V12}$. In this series, HPV E6 and E7, which inactivate p53 and RB, respectively, serve a similar function as LT in the previous series. However, by using HPV E6 and E7, Applicants were able to observe the effects of inactivating, separately and independently, p53 and RB. Results of a large-scale screen for compounds that display selective killing of these engineered tumorigenic cell lines are described in the examples that follow.

Methods of Screening for Genotype-Selective Compounds

In certain embodiments, the invention relates to large-scale screens for compounds that display selective killing of or inhibiting the growth of (are selectively toxic to) engineered tumorigenic cell lines. As used herein, the terms agent and drug are used interchangeably. As used herein, the term "is toxic to" refers to the ability of an agent or compound to kill or inhibit the growth/proliferation of tumorigenic cells. Large-scale screens include screens wherein hundreds or thousands of compounds are screened in a high-throughput format for selective toxicity to engineered tumorigenic cells. In one embodiment of the invention, selective toxicity is determined by comparing cell viability of test cells, which are engineered tumorigenic cells, and control cells after contact with a candidate agent. An appropriate control is a cell that is the same type of cell as that of test cells except that the control cell is not engineered to be tumorigenic. For example, control cells may be the parental primary cells from which the test cells are derived. Control cells are contacted with the candidate agent under the same conditions as the test cells. An appropriate control may be run simultaneously, or it may be pre-established (e.g., a pre-established standard or reference). In certain embodiments, the candidate agent is selected from a compound library, such as a combinatorial library. Cell viability may be determined by any of a variety of means known in the art, including the use of dyes such as calcein acetoxymethyl ester (calcein AM) and Alamar Blue. In certain embodiments of the invention, a dye such as calcein AM is applied to test and control cells after treatment with a candidate agent. In live cells, calcein AM is cleaved by intracellular esterases, forming the anionic fluorescent derivative calcein, which cannot diffuse out of live cells. Hence, live cells exhibit a green fluorescence when incubated with calcein AM, whereas dead cells do not. The green fluorescence that is exhibited by live cells can be detected and can thereby provide a measurement of cell viability.

In certain embodiments of the invention, an agent that has been identified as one that selectively induces cell death in an engineered tumorigenic cell is further characterized in an animal model. Animal models include mice, rats, rabbits, and monkeys, which can be nontransgenic (e.g., wild-type) or transgenic animals. The effect of the agent that selectively induces cell death in engineered tumorigenic cells may be assessed in an animal model for any number of effects, such as its ability to selectively induce cell death in tumorigenic cells in the animal and its general toxicity to the animal. For example, the method can comprise further assessing the selective toxicity of an agent (drug) to tumorigenic cells in an appropriate mouse model.

The effect of the agent that induces death in engineered tumorigenic cells may be assessed in an animal model for any number of effects, such as its ability to induce death in tumorigenic cells in the animal and its general toxicity to the animal. For example, the method can comprise further assessing the toxicity of an agent (drug) to tumorigenic cells in an appropriate mouse model. To illustrate, an agent can be further evaluated by using a tumor growth assay which assesses the ability of tested agent to inhibit the growth of established solid tumors in mice. The assay can be performed by implanting tumor cells into the fat pads of nude mice. Tumor cells are then allowed to grow to a certain size before the agents are administered. The volumes of tumors are monitored for a set number of weeks, e.g., three weeks. General health of the tested animals is also monitored during the course of the assay.

In additional embodiments of the invention, an agent that has been identified as one that selectively kills or inhibits the growth/proliferation of engineered tumorigenic cells is further characterized in cell-based assays to assess its mechanism of action. For example, the agent may be tested in apoptosis assays to assess its ability to induce cell death by means of a pro-apoptotic pathway. In further embodiments of the invention, an agent that induces death in tumor cells is assessed for its ability to induce death in tumorigenic cells by a non-apoptotic pathway. For example, the agent may be tested in apoptosis assays to assess its inability to induce cell death by means of a pro-apoptotic pathway.

In other embodiments, the invention relates to a method of identifying agents (drugs) that selectively suppress the cellular toxicity in engineered cells. In one embodiment, the invention relates to a method of identifying an agent (drug) that suppresses the cellular toxicity, comprising contacting test cells with a candidate agent; determining viability of the test cells contacted with the candidate agent; and comparing the viability of the test cells with the viability of an appropriate control. If the viability of the test cells is more than that of the control cells, then an agent (drug) that selectively suppresses the cellular toxicity is identified. An appropriate control is a cell that is the same type of cell as that of test cells except that the control cell is not engineered to express a protein which causes toxicity. For example, control cells may be the parental primary cells from which the test cells are derived. Control cells are contacted with the candidate agent under the same conditions as the test cells. An appropriate control may be run simultaneously, or it may be pre-established (e.g., a preestablished standard or reference).

In certain embodiments, the genotype-selective compounds of the invention (anti-tumor agents) can be any chemical (element, molecule, compound, drug), whether made synthetically, made by recombinant techniques, or isolated from a natural source. For example, these compounds can be peptides, polypeptides, peptoids, sugars, hormones, or nucleic acid molecules (such as antisense or RNAi nucleic acid molecules). In addition, these compounds can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. These compounds can also be natural or genetically engineered products isolated from lysates or growth media of cells—bacterial, animal or plant—or can be the cell lysates or growth media themselves. Presentation of these compounds to a test system can be in either an isolated form or as mixtures of compounds, especially in initial screening steps.

Genotype-Selective Compounds of The Invention

Applicants' results demonstrate that it is possible to identify compounds with increased potency and activity in the presence of specific genetic elements. Although previous reports indicated that it may be possible to identify such genotype-selective compounds in the case of one genetic element of interest (Simons et al., 2001, Genome Res 11, 266-73; Stockwell et al., 1999, Chem Biol 6, 71-83; Torrance et al., 2001, Nat Biotechnol 19, 940-5), work described herein provides a systematic testing of synthetic lethality using more than 23,000 compounds and one or more cancer-related genetic elements.

The nine selective compounds identified help to define consequences of introducing TERT and one or more of LT, ST, E6, E7 and oncogenic RAS into normal human cells. One effect of these genetic changes is to increase the rate of cell proliferation and to allow sensitivity to small molecules that inhibit DNA synthesis. Although it is well established that such agents preferentially target rapidly replicating tumor cells, it is reassuring to see this principle emerge from this unbiased screening approach. Moreover, the methodology made it possible to readily distinguish between compounds that have a clear basis for genetic selectivity and those that do not.

Results showed that expression of hTERT and either E7 or LT sensitizes cells to topoisomerase II poisons. Since loss or inactivation of RB (Sellers and Kaelin, 1997, J Clin Oncol 15, 3301-12; Sherr, 2001, Nat Rev Mol Cell Biol 2, 731-7) and activation of telomerase (Hahn and Weinberg, 2002, Nat Rev Cancer 2, 331-41; Harley, 1994, Pathol Biol (Paris) 42, 342-5) are found in most human cancers, these observations may explain, in part, the activity of these agents in a diverse range of human tumor types.

Applicants discovered that camptothecin is selectively lethal to cells harboring both ST and oncogenic RAS because of the combined effect of these two genes on expression of topoisomerase I. Rapidly dividing tumor cells use topoisomerase I to unwind supercoiled DNA to effect continuous and rapid cell division. When these two pathways are simultaneously altered, topoisomerase I is upregulated, perhaps indirectly, and such tumor cells are rendered sensitive to topoisomerase I poisons.

These observations suggest that one aspect of the ability of ST to transform human cells along with $RAS^{V12}$, LT and hTERT may be the effect of ST and $RAS^{V12}$ on expression of topoisomerase I. Mutations in HRAS and KRAS have been described in many types of human cancers. Moreover, the inactivation of PPP2R1B, a component of PP2A, has recently been reported in colon and lung tumors (Wang et al., 1998, Science 282, 284-7), while mutations in a different PP2A subunit have been described in melanoma, lung, breast and colon cancers (Calin et al., 2000, Oncogene 19, 1191-5; Kohno et al., 1999, Cancer Res 59, 4170-4; Ruediger et al., 2001, Oncogene 20, 1892-9; Ruediger et al., 2001, Oncogene 20, 10-5). At present, it remains unclear whether simultaneous alteration of these two pathways occurs at high frequency in human tumors or whether cancers in which both of these pathways are perturbed show increased susceptibility to these compounds.

Figure 8:
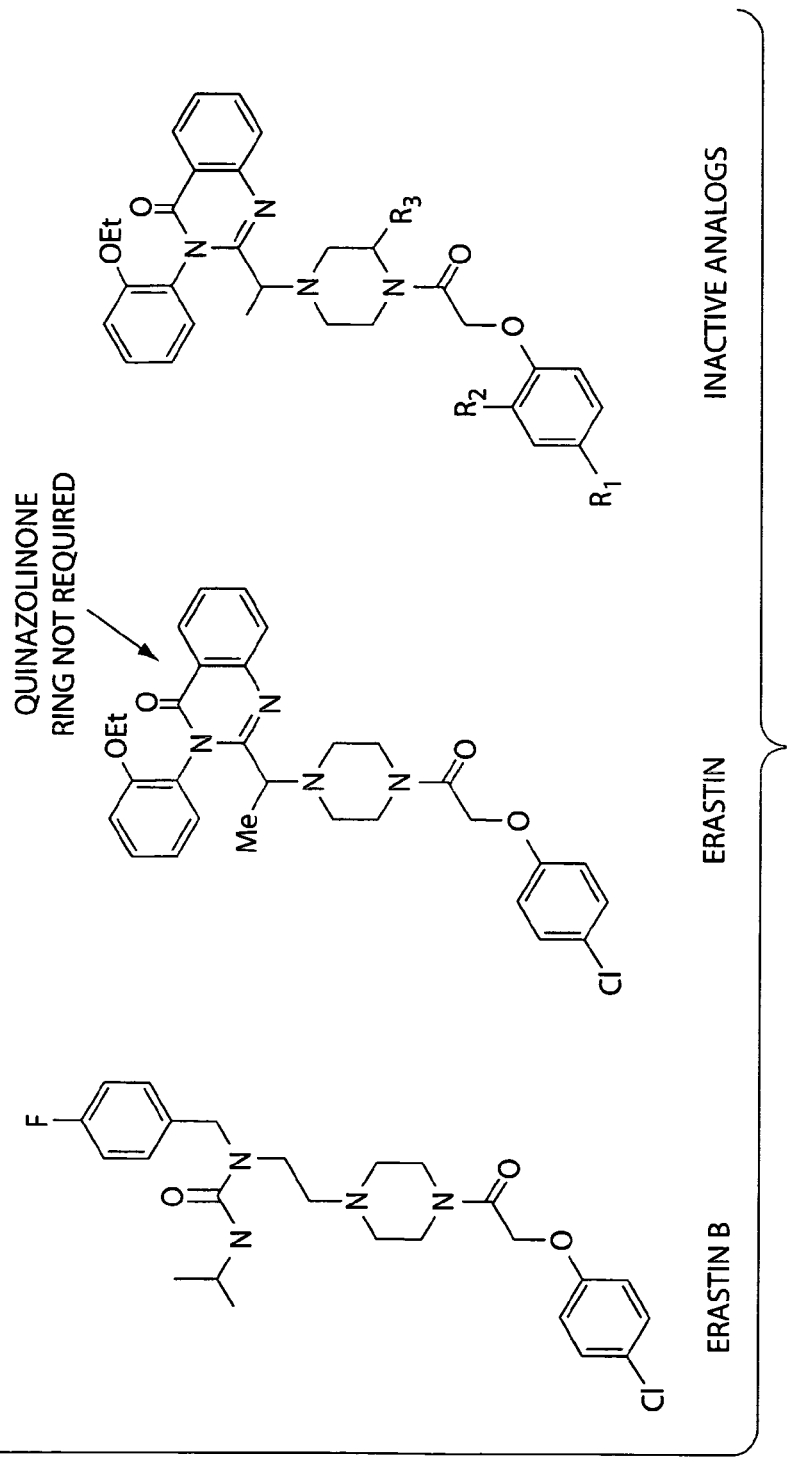
FIG. 8 shows the chemical structures of erastin and erastin B.

Further, Applicants identified a novel compound, dubbed erastin (see FIG. 8), that is lethal to cells expressing both ST and $RAS^{V12}$. Treatment of cells with this compound failed to kill cells lacking $RAS^{V12}$ and ST, even when used at concentrations eight-fold higher than was required to observe an effect on cells expressing both $RAS^{V12}$ and ST, indicating a degree of specificity. The lethal effect of erastin is rapid and irreversible once obtained.

Erastin may be used to induce cell death in any tumor cell wherein contact of the tumor cell with erastin results in cell death. Tumorigenic cells in which lethality may be produced by erastin activity include not only engineered tumorigenic cells, such as engineered cells expressing both ST and $RAS^{V12}$, but also tumorigenic cells comprising an activated RAS pathway independent of ST and $RAS^{V12}$ expression.

Applicants additionally tested 135 analogs of erastin for activity and selectivity in tumor cells versus normal cells. 134 of these analogs were inactive. One was active and selective, but less potent than erastin. This compound was named erastin B (see FIG. 8). In certain embodiments of the invention, the invention relates to the compound, erastin. In further embodiments, the invention relates to analogs of the compound, erastin, which analogs exhibit selective toxicity to engineered tumorigenic cells, such as engineered human tumorigenic cells. In one embodiment, the analog of erastin, which exhibits selective toxicity to engineered human tumorigenic cells, is erastin B. In certain embodiments, the invention relates to a racemic mixture of a compound of the invention, which mixture exhibits selective toxicity to engineered tumorigenic cells.

For both camptothecin (CPT) and erastin, Applicants identified synergy between pathways altered by expression of $RAS^{V12}$ and ST. Expression of $RAS^{V12}$ leads to the activation of several well-characterized signaling pathways, including the RAF-MEK-MAPK signaling cascade, the phosphatidylinositol 3-kinase (PI3K) signaling pathway and the Ral-guanine dissociation factor pathway (Ral-GDS). Each of these pathways has been implicated in human cancers, and recent work demonstrates that these pathways work in concert in this system of cell transformation (Hamad et al., 2002, Genes Dev 16, 2045-57). In addition, ST binds to and inactivates PP2A, a widely expressed serine-threonine phosphatase. Although the specific enzymatic targets of PP2A that are perturbed upon expression of ST are not yet known, there is substantial overlap among pathways altered by PP2A and RAS (Millward et al., 1999, Trends Biochem Sci 24, 186-91). Understanding further the mechanism by which erastin induces death in cells harboring alterations of these two signaling pathways may provide clues to the nature and extent of functional overlap between these two pathways.

Erastin analogs of the invention, other than erastin B and erastin A, are represented by the general formula I:

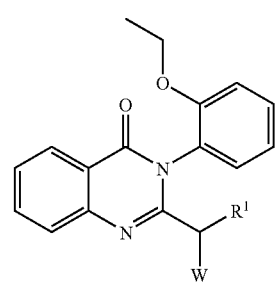

(I)

wherein $R^1$ is selected from H, -Z-Q-Z, —$C_{1-8}$alkyl-N($R^2$)($R^4$), —$C_{1-8}$alkyl-O$R^3$, 3- to 8-membered carbocyclic or heterocyclic, aryl, heteroaryl, and $C_{1-4}$aralkyl;

$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N and either $R^2$ or $R^4$ is acyl, alkylsulfonyl, or arylsulfonyl, then the other is selected from H, $C_{1-8}$alkyl, aryl, $C_{1-4}$aralkyl, and heteroaryl;

$R^3$ is selected from H, $C_{1-4}$alkyl, $C_{1-4}$aralkyl, aryl, and heteroaryl;

W is selected from

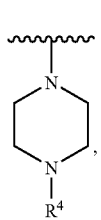, 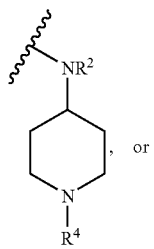, or 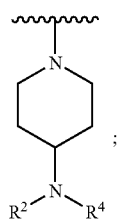;

Q is selected from O and $NR^2$; and

Z is independently for each occurrence selected from $C_{1-6}$alkyl, $C_{2-6}$alkenyl, and $C_{2-6}$alkynyl. When Z is an alkenyl or alkynyl group, the double or triple bond or bonds are preferably not at the terminus of the group.

In certain preferred embodiments when both $R^2$ and $R^4$ are on the same N atom they are either both H or are different.

In certain embodiments, $R^1$ is H.

In certain embodiments, W is

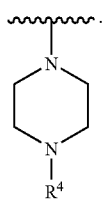.

In certain embodiments, $R^4$ is selected from H or substituted or unsubstituted lower alkyl.

In certain embodiments, $R^1$ is H, W is

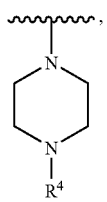, and $R^4$ is selected from H or substituted or unsubstituted lower alkyl.

Exemplary compounds of formula I include:

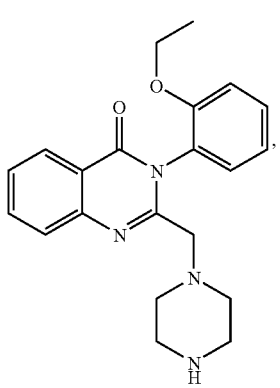

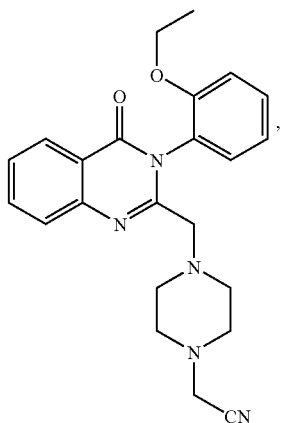

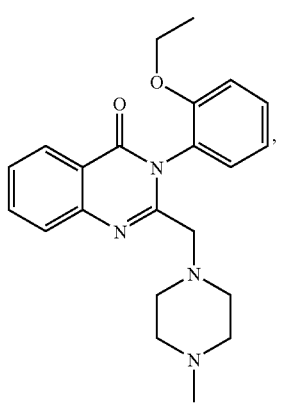

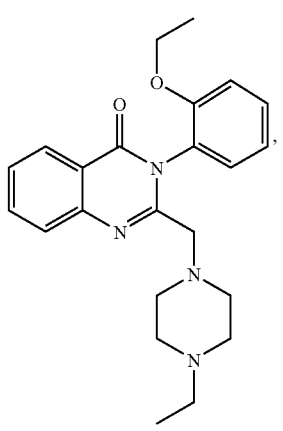

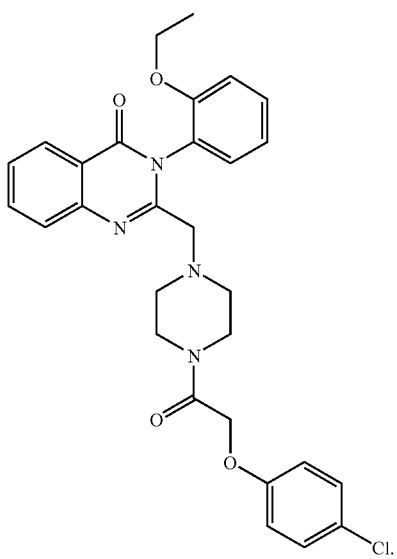

Additional erastin analogs of the invention, are represented by the general formula II:

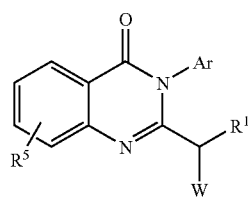
(II)

wherein

Ar is a substituted phenyl;

$R^1$ is selected from H, $C_{1-8}$alkyl, -Z-Q-Z, —$C_{1-8}$alkyl-N($R^2$)($R^4$), —$C_{1-8}$alkyl-OR$^3$, 3- to 8-membered carbocyclic or heterocyclic, aryl, heteroaryl, and $C_{1-4}$aralkyl;

$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N and either $R^2$ or $R^4$ is acyl, alkylsulfonyl, or arylsulfonyl, then the other is selected from H, $C_{1-8}$alkyl, aryl, $C_{1-4}$aralkyl, aryl, and heteroaryl;

$R^3$ is selected from H, $C_{1-4}$alkyl, $C_{1-4}$aralkyl, aryl, and heteroaryl;

$R^5$ represents 0-4 substituents on the ring to which it is attached;

W is 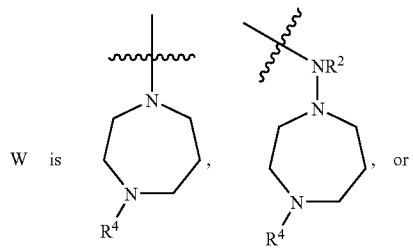,

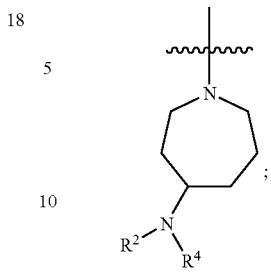

Q is selected from O and NR$^2$; and

Z is independently for each occurrence selected from $C_{1-6}$alkyl, $C_{2-6}$alkenyl, and $C_{2-6}$alkynyl. When Z is an alkenyl or alkynyl group, the double or triple bond or bonds are preferably not at the terminus of the group.

In certain embodiments, $R^5$ represents 1-4 substituents, such as halogen or nitro. In certain embodiments $R^5$ represents one substituent, such as halogen or nitro, especially chloro, situated para to the carbonyl of the quinazolinone ring. In other embodiments, $R_5$ represents no substituents on the ring (i.e., all substituents are hydrogen atoms).

In certain embodiments, Ar is mono-substituted wherein the substituent is halogen, lower alkoxy, or lower alkyl. In certain embodiments, Ar has a substituent at the ortho position wherein the substituent is halogen, lower alkoxy, or lower alkyl. In certain embodiments, Ar is 2,6-disubstituted such that one substituent is halogen, lower alkoxy, or lower alkyl and the second substituent is halogen, lower alkoxy, or lower alkyl.

In certain embodiments, the compounds of formula II do not include those wherein the substituent on Ar is ethoxy at a position ortho to the bond to the nitrogen of the quinazolinone ring. In further embodiments, the compounds of formula II do not include those wherein Ar does not have a lower alkoxy or lower alkyl substituent ortho to the bond to the nitrogen of the quinazolinone ring.

In certain embodiments of the compounds of formula II, Ar has at least one halogen substituent. In certain embodiments, Ar has a halogen substituent in the ortho position. In preferred embodiments, the compounds of formula II include those wherein Ar is a 2,6-disubstituted phenyl ring wherein the substituents are halogen atoms.

Exemplary compounds of formula II include:

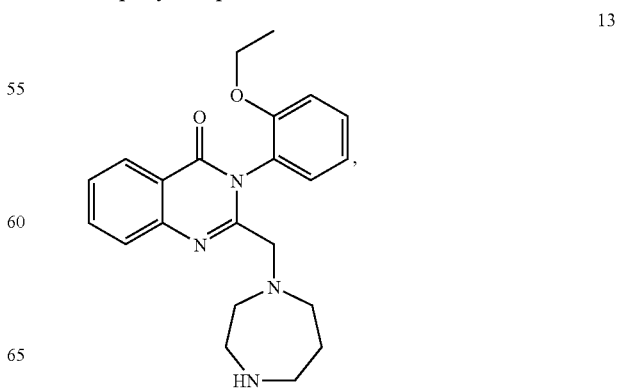

-continued

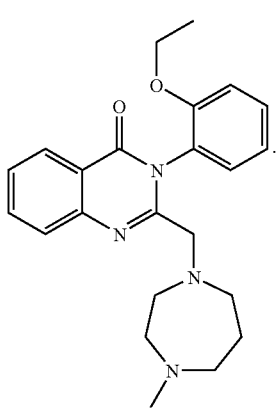
12

Additional erastin analogs of the invention, are represented by the general formula III:

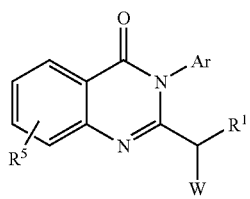
(III)

wherein
Ar is a substituted or unsubstituted phenyl;
$R^1$ is selected from H, $C_{1-8}$alkyl, -Z-Q-Z, —$C_{1-8}$alkyl-N$(R^2)(R^4)$, —$C_{1-8}$alkyl-OR$^3$, 3- to 8-membered carbocyclic or heterocyclic, aryl, heteroaryl, and $C_{1-4}$aralkyl;
$R^2$ and $R^4$ are each independently for each occurrence selected from H, $C_{1-4}$alkyl, $C_{1-4}$aralkyl, aryl, heteroaryl, acyl, alkylsulfonyl, and arylsulfonyl, provided that when both $R^2$ and $R^4$ are on the same N atom and either $R^2$ or $R^4$ is acyl, alkylsulfonyl, or arylsulfonyl, then the other is selected from H, $C_{1-8}$alkyl, aryl, $C_{1-4}$aralkyl, and heteroaryl;
$R^3$ is selected from H, $C_{1-4}$alkyl, $C_{1-4}$aralkyl, aryl, and heteroaryl;
$R^5$ represents 0-4 substituents on the ring to which it is attached;
W is selected from

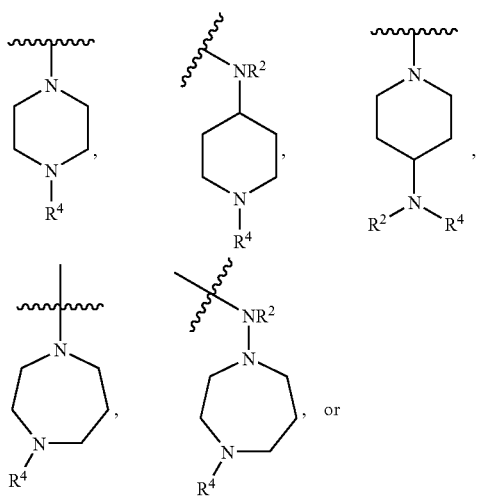

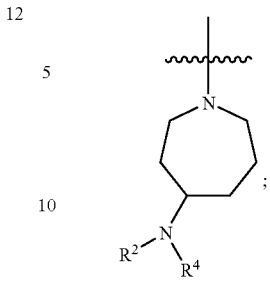

Q is selected from O and $NR^2$; and
Z is independently for each occurrence selected from $C_{1-6}$alkyl, $C_{2-6}$alkenyl, and $C_{2-6}$alkynyl. When Z is an alkenyl or alkynyl group, the double or triple bond or bonds are preferably not at the terminus of the group.

In certain embodiments, $R^2$ and $R^4$ are either both H or are different.

In certain embodiments, $R^5$ represents from 1-4 substituents on the ring to which it is attached, such as halogen or nitro. In certain embodiments, $R_5$ represents one substituent, such as halogen or nitro, especially chloro, situated para to the carbonyl of the quinazolinone ring. In other embodiments, $R_5$ represents no substituents on the ring (i.e., all substituents are hydrogen atoms).

In certain embodiments, the compounds of formula III do not include those wherein the substituent on Ar is ethoxy at a position ortho to the bond to the nitrogen of the quinazolinone ring. In further embodiments, the compounds of formula III do not include those wherein Ar does not have a lower alkoxy or lower alkyl substituent ortho to the bond to the nitrogen of the quinazolinone ring.

In preferred embodiments of the present invention, Ar is a substituted phenyl. In certain embodiments of the compounds of formula III, Ar has at least one halogen substituent. In certain embodiments, Ar has a halogen substituent in the ortho position. In preferred embodiments, the compounds of formula III include those wherein Ar is a 2,6-disubstituted phenyl ring wherein the substituents are halogen atoms.

Exemplary compounds of formula III include:

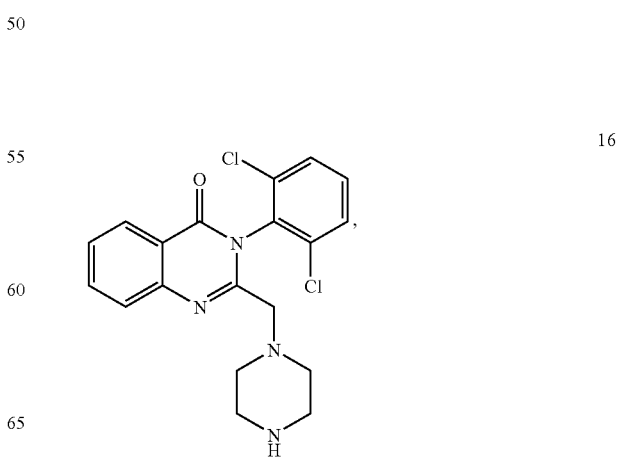
16

-continued

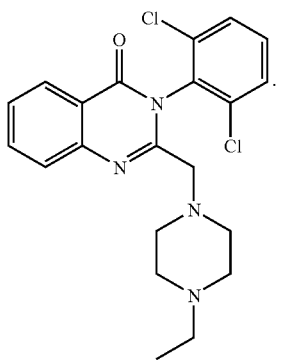
17

Additional erastin analogs of the invention, are represented by the general formula IV:

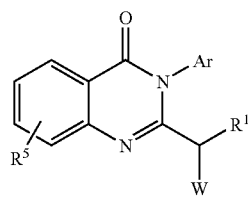
(IV)

wherein

Ar is substituted or unsubstituted phenyl;

$R^1$ is $C_{1-8}$alkyl;

$R^2$ and $R^4$ are each independently for each occurrence selected from H and $C_{1-8}$alkyl;

$R^5$ represents 0-4 substituents on the ring to which it is attached;

W is selected from

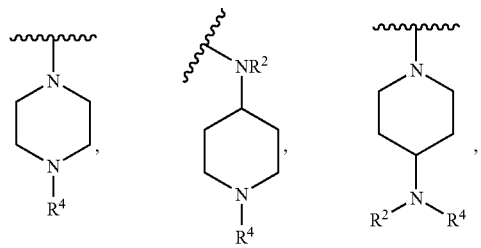

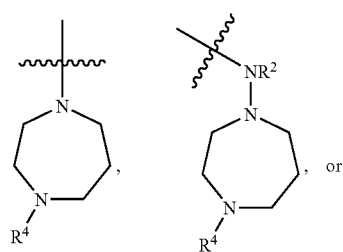

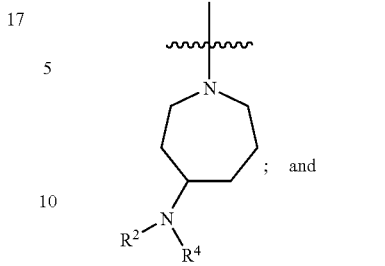

Q is selected from O and $NR^2$.

In certain embodiments, $R^5$ represents from 1-4 substituents on the ring to which it is attached, such as halogen or nitro. In certain embodiments, $R_5$ represents one substituent, such as halogen or nitro, especially chloro, situated para to the carbonyl of the quinazolinone ring. In other embodiments, $R_5$ represents no substituents on the ring (i.e., all substituents are hydrogen atoms).

In preferred embodiments of the present invention, Ar is a substituted phenyl. In certain embodiments, Ar is mono-substituted wherein the substituent is halogen, lower alkoxy, or lower, alkyl. In certain embodiments, Ar has a substituent at the ortho position wherein the substituent is halogen, lower alkoxy, or lower alkyl. In certain embodiments, Ar is 2,6-disubstituted such that one substituent is halogen, lower alkoxy, or lower alkyl and the second substituent is halogen, lower alkoxy, or lower alkyl.

In certain embodiments, the compounds of formula IV do not include those wherein the substituent on Ar is ethoxy at a position ortho to the bond to the nitrogen of the quinazolinone ring. In further embodiments, the compounds of formula IV do not include those wherein Ar does not have a lower alkoxy or lower alkyl substituent ortho to the bond to the nitrogen of the quinazolinone ring.

In certain embodiments of the compounds of formula IV, Ar has at least one halogen substituent. In certain embodiments, Ar has a halogen substituent in the ortho position. In preferred embodiments, the compounds of formula IV include those wherein Ar is a 2,6-disubstituted phenyl ring wherein the substituents are halogen atoms.

Exemplary compounds of formula IV include:

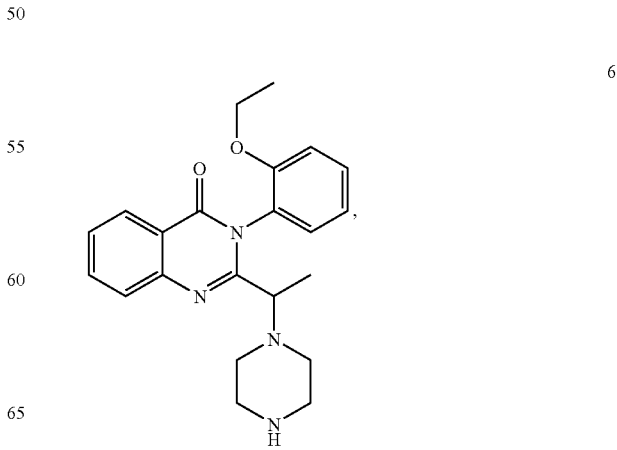
6

-continued

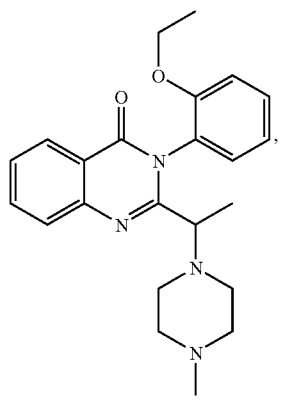
8

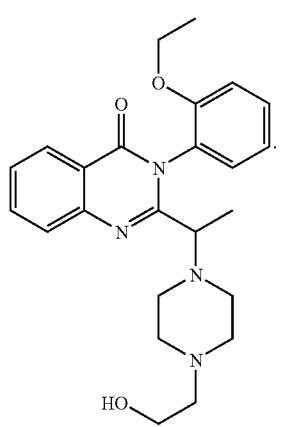
9

Additional erastin analogs of the invention are represented by the general formula V:

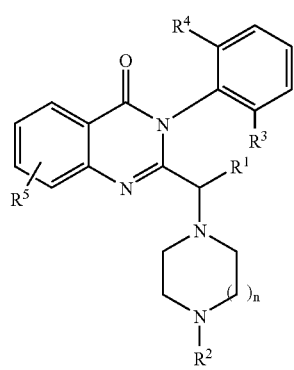
(V)

wherein
R$^1$ is selected from H and C$_{1-8}$alkyl;
R$^2$ is selected from H and C$_{1-8}$alkyl;
R$^3$ is selected from halogen, C$_{1-8}$alkoxy and C$_{1-8}$alkyl;
R$^4$ is selected from H, halogen, C$_{1-8}$alkoxy and C$_{1-8}$alkyl;
R$^5$ is selected from H, halogen and nitro; and
n is 1 or 2.

Exemplary compounds of formula V include:

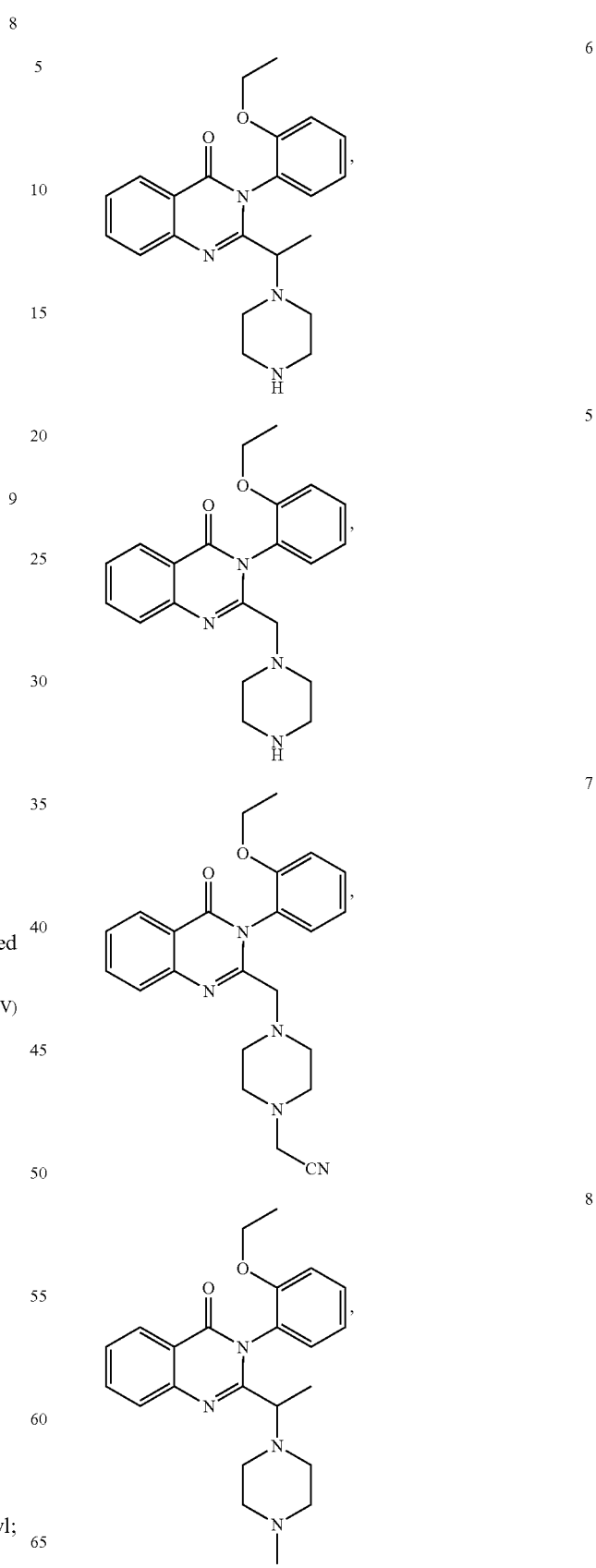

-continued
9
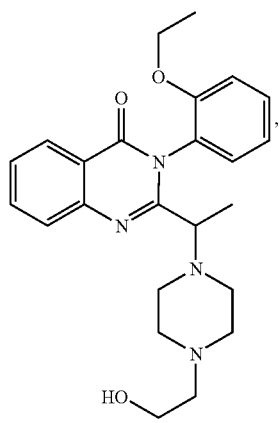
10
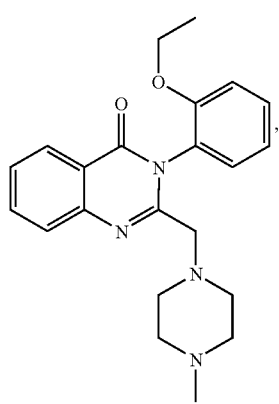
11
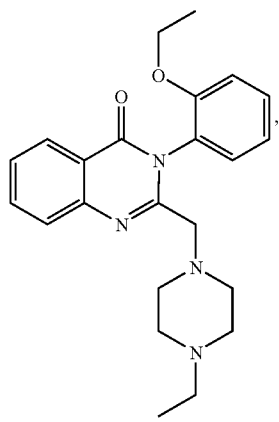
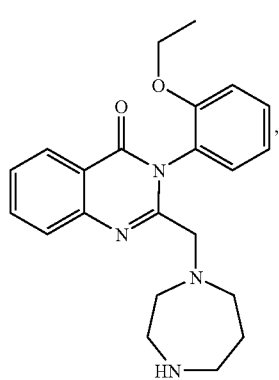
-continued
12
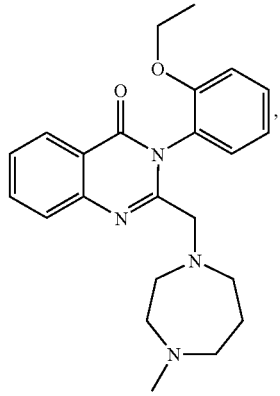
14
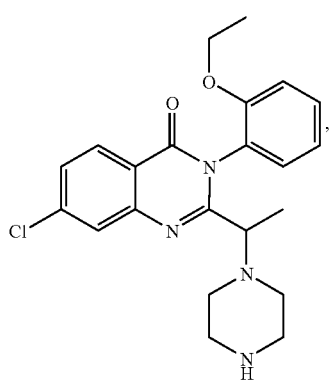
15
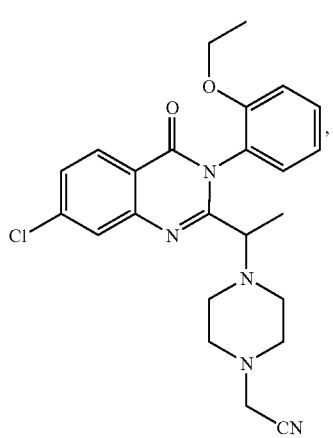
16
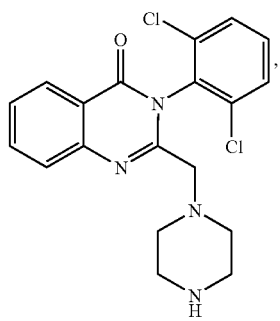

17

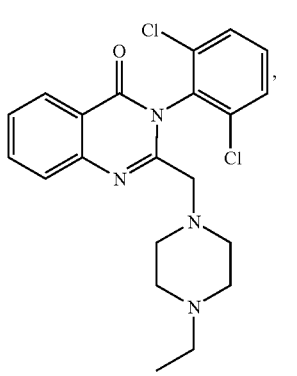

Any of the compounds of formulas I-V can be used for any of the methods described herein for erastin and erastin analogs.

Compounds included in the invention include enantiomers and diastereomers of the compounds disclosed herein. The invention also includes salts, particularly pharmaceutically acceptable salts of the compounds disclosed herein. In addition, the invention includes solvates, hydrates and polymorph crystalline forms of the compounds disclosed herein.

Suitable agents can have the recited activity in the existing form or after complete or partial metabolism.

The invention also provides for the synthesis or manufacture of a compound of the invention.

In certain embodiments the present invention provides for the preparation of a compound A

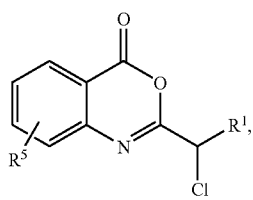

A wherein $R^5$ and $R^1$ are as described for structures II-V.

In certain embodiments a step of the synthesis of compound A is the reaction of a compound B,

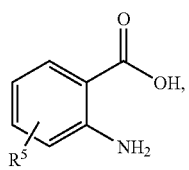

B with a compound C,

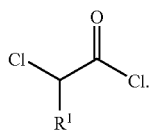

C

In certain embodiments the reaction of compound B with compound C is performed in a polar aprotic solvent such as acetonitrile, DMSO, diethyl ether, butanone, cyclohexanone, acetophenone, tetrahydrofuran, acetone, dichlormethane, sulfolane, or dimethylformamide. In preferred embodiments the solvent is dichloromethane or dimethylformamide. In certain embodiments the reaction is performed under an atmosphere of nitrogen. In certain embodiments, an organic base, such as pyridine, diisopropylamine, 2,6-lutidine, trialkylamines (e.g., triethylamine), pyrrolidine, imidazole or piperidine, is added to a solution of compound B followed by the addition of compound C to the resulting solution. In preferred embodiments the organic base is an amine base such as a trialkyl amine such as triethyl amine. In preferred embodiments the reaction is performed at a range of 0-10° C.

The invention further provides for the preparation of a compound of structure D,

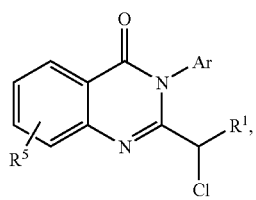

D wherein $R^5$, $R^1$ and Ar are as described for structures II-V. In certain embodiments, a step in the synthesis of D is the reaction of compound A with compound E, Ar—$NH_2$.

In certain embodiments the reaction of compound A with compound E is performed in a polar aprotic solvent such as acetonitrile, DMSO, diethyl ether, butanone, cyclohexanone, acetophenone, tetrahydrofuran, acetone, dichlormethane, sulfolane, or dimethylformamide. In preferred embodiments the solvent is acetonitrile. In certain embodiments the reaction is performed under an atmosphere of nitrogen. In certain embodiments the reaction is performed in a presence of trichlorophosphine. In certain embodiments the reaction is maintained in a range of 40-60° C. for a period of time such as 5-15 hours. In other embodiments phosphoryl trichloride is added to the stirred solution of A and E and the resulting mixture is heated to reflux for a period of time, such as 1-5 hours.

The invention also provides for the preparation of a compound of structure F,

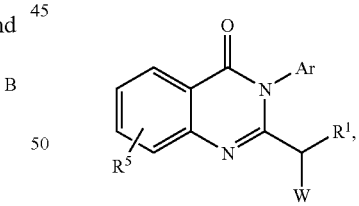

F wherein $R^5$, $R^1$, Ar and W are as described for structures II-V. In certain embodiments, a step in the synthesis of compound F is the reaction of compound D with $HNR_2$ where $HNR_2$ is equivalent to HW. In certain embodiments the reaction is performed in the presence of potassium carbonate and an iodide source, such as copper iodide, potassium iodide, cesium iodide, sodium iodide, or tetrabutylammonium iodide, in a polar aprotic solvent. In certain embodiments compound D and potassium carbonate are combined, and $HNR_2$ is added, followed by the iodide source. In preferred embodiments the solvent is acetonitrile. In certain embodiments the iodide reagent is tetrabutylammonium iodide; in certain embodiments the iodide reagent is sodium iodide. In certain embodiments the mixture is maintained in the range of 50-70° C. for a period of time such as 5-15 hours. In certain embodiments $HNR_2$ (HW) includes a second nitrogen atom on which there is an amine protecting group. In some embodiments the protecting group may be tert-butoxycarbonyl, benzyloxycarbonyl, allyloxycarbonyl, 9-fluorenylmethoxycarbonyl, 2-(trimethylsilyl)ethoxycarbonyl, or 2,2,2-trichloroethoxycarbonyl. In certain embodiments the reaction is performed in the presence of a base, such as potassium carbonate, sodium carbonate, pyridine, diisopropylamine, 2,6-lutidine, triethylamine, pyrrolidine, imidazole, or piperidine, and an iodide source in a polar aprotic solvent. In certain embodiments the base is potassium carbonate or triethyl amine. In certain embodiments compound D and the base are combined and $HNR_2$ is added followed by the iodide source. In preferred embodiments the solvent is acetonitrile or acetone. In certain embodiments the iodide reagent is tetrabutylammonium iodide; in certain embodiments the iodide reagent is sodium iodide. In certain embodiments the mixture is maintained in a range of 70-90° C. for a period of time such as 1-10 hours. Following the completion of the addition reaction the protecting group can be removed from the resulting product by a suitable deprotection reaction. For example, when the protecting group is tert-butoxycarbonyl the protecting group may be removed by adding an acid to a solution of the compound (e.g. adding a solution of 4N HCl in dioxane to a solution of the product in dioxane). In certain embodiments the reaction is then diluted with water and an organic solvent before neutralizing the mixture. In certain embodiments the mixture is made basic by the addition of a saturated aqueous solution of sodium carbonate.

It is contemplated that all embodiments of the invention can be combined with one or more other embodiments, even those described under different aspects of the invention.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

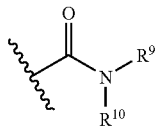

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

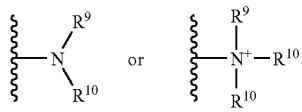

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

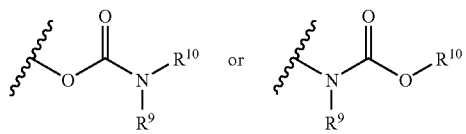

wherein $R^9$ and $R^{10}$ independently represent hydrogen or a hydrocarbyl group.

The terms "carbocycle", "carbocyclyl", and "carbocyclic", as used herein, refers to a non-aromatic saturated or unsaturated ring in which each atom of the ring is carbon; Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—$R^9$, wherein $R^9$ represents a hydrocarbyl group.

The term "carboxy", as used herein, refers to a group represented by the formula —$CO_2H$.

The term "ester", as used herein, refers to a group —C(O)O$R^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole; pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

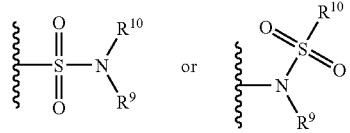

wherein R$^9$ and R$^{10}$ independently represents hydrogen or hydrocarbyl.

The term "sulfoxide" is art-recognized and refers to the group —S(O)—R$^9$, wherein R$^9$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^9$, wherein R$^9$ represents a hydrocarbyl.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

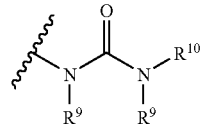

wherein R$^9$ and R$^{10}$ independently represent hydrogen or a hydrocarbyl.

The term "small organic molecule" refers to a non-polymeric compound having a molecular weight of less than 2000 amu. Typically, such molecules have a molecular weight of less than 1000 amu, such as less than 500 amu.

Methods of Identifying Targets for Genotype-Selective Compounds

In certain embodiments, the invention relates to the use of the subject genotype-selective compound, also referred to herein as "ligand" (e.g., erastin), to identify targets (also referred to herein as "cellular components" (e.g., proteins, nucleic acids, or lipids) involved in conferring the phenotype of diseased cells.

In one embodiment, the invention provides a method to identify cellular components involved in tumorigenesis, whereby a tumorigenic cell, such as an engineered human tumorigenic cell, tissue, organ, organism or a lysate or an extract thereof is contacted with a subject anti-tumor compound; and after contact, cellular components that interact (directly or indirectly) with erastin are identified, resulting in identification of cellular components involved in tumorigenesis. In another embodiment, the invention provides a method to identify cellular components involved in tumorigenesis. In this method, (a) a tumorigenic cell, such as an engineered human tumorigenic cell, tissue, organ, organism or a lysate or an extract thereof is contacted with an inhibitor of erastin and contacted with erastin; and (b) cellular components that interact (directly or indirectly) with the inhibitor of erastin are identified, which cellular components are involved in tumorigenesis. The cell can be contacted with erastin and the inhibitor of erastin sequentially or simultaneously. Cellular components that interact with erastin or any agent of the present invention may be identified by known methods.

As described herein, the subject compound (or ligand) of these methods may be created by any chemical method. Alternatively, the subject compound may be a naturally occurring biomolecule synthesized in vivo or in vitro. The ligand may be optionally derivatized with another compound. One advantage of this modification is that the derivatizing compound may be used to facilitate ligand target complex collection or ligand collection, e.g., after separation of ligand and target. Non-limiting examples of derivatizing groups include biotin, fluorescein, digoxygenin, green fluorescent protein, isotopes, polyhistidine, magnetic beads, glutathione S transferase, photoactivatible crosslinkers or any combinations thereof. Derivatizing groups can also be used in conjunction with targets (e.g., an erastin binding protein) in order to facilitate their detection.

According to the present invention, a target (cellular component) may be a naturally occurring biomolecule synthesized in vivo or in vitro. A target may be comprised of amino acids, nucleic acids, sugars, lipids, natural products or any combinations thereof. An advantage of the instant invention is that no prior knowledge of the identity or function of the target is necessary.

The interaction between the ligand and target may be covalent or non-covalent. Optionally, the ligand of a ligand-target pair may or may not display affinity for other targets. The target of a ligand-target pair may or may not display affinity for other ligands.

For example, binding between a ligand and a target can be identified at the protein level using in vitro biochemical methods, including photo-crosslinking, radiolabeled ligand binding, and affinity chromatography (Jakoby W B et al., 1974, Methods in Enzymology 46: 1). Alternatively, small molecules can be immobilized on a suitable solid support or affinity matrix such as an agarose matrix and used to screen extracts of a variety of cell types and organisms. Similarly, the small molecules can be contacted with the cell, tissue, organ, organism or lysate or extract thereof and the solid support can be added later to retrieve the small molecules and associate target proteins.

Expression cloning can be used to test for the target within a small pool of proteins (King R W et. al., 1997, Science 277:973). Peptides (Kieffer et. al., 1992, PNAS 89:12048), nucleoside derivatives (Haushalter K A et. al., 1999, Curr. Biol. 9:174), and drug-bovine serum albumin (drug-BSA) conjugate (Tanaka et. al., 1999, Mol. Pharmacol. 55:356) have been used in expression cloning.

Another useful technique to closely associate ligand binding with DNA encoding the target is phage display. In phage display, which has been predominantly used in the monoclonal antibody field, peptide or protein libraries are created on the viral surface and screened for activity (Smith GP, 1985, Science 228:1315). Phages are panned for the target which is connected to a solid phase (Parmley S F et al., 1988, Gene 73:305). One of the advantages of phage display is that the cDNA is in the phage and thus no separate cloning step is required.

A non-limiting example includes binding reaction conditions where the ligand comprises a marker such as biotin, fluorescein, digoxygenin, green fluorescent protein, radioisotope, histidine tag, a magnetic bead, an enzyme or combinations thereof. In one embodiment of the invention, the targets may be screened in a mechanism based assay, such as an assay to detect ligands which bind to the target. This may include a solid phase or fluid phase binding event with either the ligand or the protein or an indicator of either being detected. Alternatively, the gene encoding the protein with previously undefined function can be transfected with a reporter system (e.g., β-galactosidase, luciferase, or green fluorescent protein) into a cell and screened against the library preferably by a high throughput screening or with individual members of the library. Other mechanism based binding assays may be used, for example, biochemical assays measuring an effect on enzymatic activity, cell based assays in which the target and a reporter system (e.g., luciferase or β-galactosidase) have been introduced into a cell, and binding assays which detect changes in free energy. Binding assays can be performed with the target fixed to a well, bead or chip or captured by an immobilized antibody or resolved by capillary electrophoresis. The bound ligands may be detected usually using colorimetric or fluorescence or surface plasmon resonance.

In certain embodiments, the present invention further contemplates methods of treating or preventing a disease (e.g., cancer) by modulating the function (e.g., activity or expression) of a target (cellular component) that is identified according to the invention. To illustrate, if a target is identified to promote tumor growth, a therapeutic agent can be used to modify or reduce the function (activity or expression) of the target. Alternatively, if a target is identified to inhibit tumor growth, a therapeutic agent can be used to enhance the function (activity or expression) of the target. The therapeutic agent includes, but is not limited to, an antibody, a nucleic acid (e.g., an antisense oligonucleotide or a small inhibitory RNA for RNA interference), a protein, a small molecule (e.g., a compound of the invention) or a peptidomimetic.

Erastin Targets

In certain embodiments, the present invention provides targets of erastin and erastin analogs, which are generally referred to herein as erastin targets. The erastin targets may directly or indirectly bind to erastin or an erastin analog as described above. Optionally, the erastin target may mediate the anti-tumor activity of a compound such as erastin or an erastin analog in a cell. Exemplary erastin targets include, but are not limited to, VDAC1, VDAC2, VDAC3, Prohibitin, Ribophorin, Sec61a, and Sec22b.

Voltage-dependent anion channels (VDACS) are a family of pore-forming proteins encoded by different genes, with at least three protein products (VDAC1, VDAC2, and VDAC3) expressed in mammalian tissues. The major recognized functional role of VDACs is to permit the almost free permeability of the outer mitochondrial membrane (ODF). See, e.g., Shoshan-Barmatz et al., 2003, Cell Biochem Biophys 39:279-92. VDAC2 and VDAC3 might have an alternative structural organization and different functions in ODF than in mitochondria (Hinsch et al., 2004, J Biol Chem. 279:15281-8). Representative VDAC sequences of various species have been deposited in GenBank. For example, human VDAC1 amino acid and nucleic acid sequences can be found in GenBank Accession numbers NP_003365 and NM_003374; human VDAC2 amino acid and nucleic acid sequences can be found in GenBank Accession numbers NP_003366 and NM_003375; and human VDAC3 amino acid and nucleic acid sequences can be found in GenBank Accession numbers NP_005653 and NM_005662.

Prohibitin is an evolutionarily conserved gene that is ubiquitously expressed. It is thought to be a negative regulator of cell proliferation and may be a tumor suppressor (e.g., Fusaro et al., 2003, J. Biol. Chem. 278: 47853-47861; Fusaro et al., 2002, Oncogene 21: 4539-4548). Representative prohibitin sequences of various species have been deposited in GenBank. For example, human prohibitin amino acid and nucleic acid sequences can be found in GenBank Accession numbers NP_002625 and NM_002634.

Ribophorins (e.g., I and II) are proteins that appear to be involved in ribosome binding. They are abundant, highly conserved glycoproteins located exclusively in the membranes of the rough endoplasmic reticulum (e.g., Fu et al., 2000, J. Biol. Chem. 275: 3984-3990; Crimaudo et al., 1987, EMBO J. 6: 75-82). Representative ribophorin sequences of various species have been deposited in GenBank. For example, human ribophorin I amino acid and nucleic acid sequences can be found in GenBank Accession numbers NP_002941 and NM_002950; and human ribophorin II amino acid and nucleic acid sequences can be found in GenBank Accession numbers NP_002942 and NM_002951.

Sec61-alpha proteins are suggested to play a role in the insertion of secretory and membrane polypeptides into the endoplasmic reticulum (see, e.g., Higy et al., 2004, Biochemistry 43:12716-22). Representative Sec61alpha sequences of various species have been deposited in GenBank. For example, human Sec61-alpha-I amino acid and nucleic acid sequences can be found in GenBank Accession numbers NP_037468 and NM_013336; and human Sec61-alpha-II amino acid and nucleic acid sequences can be found in GenBank Accession numbers NP_060614 and NM_018144.

Sec22-beta proteins are suggested to play a role in the ER-Golgi protein trafficking and complex with SNARE (e.g., Parlati et al., 2000, Nature 407:194-198; Mao et al., 1998, Proc. Natl. Acad. Sci. U.S.A. 95:8175-8180). Representative Sec61-beta sequences of various species have been deposited in GenBank. For example, human Sec61-beta amino acid and nucleic acid sequences can be found in GenBank Accession numbers NP_004883 and NM_004892.

In certain embodiments, the present invention relates to methods of identifying candidate anti-tumor therapeutic agents by use of an erastin target. In such methods, a test agent which binds to an erastin target or increases or decreases function (e.g., activity or expression or interactions) of an erastin target can be identified as a candidate anti-tumor therapeutic agent. The candidate anti-tumor therapeutic agent can be. further tested in vivo or in vitro for its anti-tumor activity. Methods of identifying candidate anti-tumor therapeutic agents can be similarly carried out by the screening methods as described above.

Delivery Methods

Certain embodiments of the invention use methods of delivering proteins (e.g., small t antigen, VDAC, PP2A inhibitors, etc.) or DNA encoding such proteins to a target cell, which can be accomplished by any standard molecular biology and molecular medicine techniques. The embodiments illustrated below are but a few such techniques that can be used for such purposes.

In one aspect of the invention, expression constructs of the subject proteins, or for generating antisense molecules, may be administered in any biologically effective carrier, e.g., any formulation or composition capable of effectively transfecting cells in vivo with a recombinant gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (e.g., lipofectin) or derivatized (e.g., antibody conjugated), polylysine conjugates, gramacidin S, artificial viral envelopes or other such intracellular carriers, as well as direct injection of the gene construct or CaPO$_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g., locally or systemically.

A preferred approach for in vivo introduction of nucleic acid encoding one of the subject proteins into a cell is by use of a viral vector containing a nucleic acid, e.g., a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retroviral vectors and adeno-associated viral vectors are generally understood to be the recombinant gene delivery systems of choice for the transfer of exogenous genes in vivo, particularly into humans. These vectors provide efficient delivery of genes into cells, and the transferred nucleic acids are stably integrated into the chromosomal DNA of the host. A subset of the retrovirus family termed "lentiviruses" for the long duration of their latent phases following integration, are represented by the human immunodeficiency virus (HIV) and the feline immunodeficiency virus (FIV). Vector systems derived from both of these viruses have been used effectively in pre-clinical models and show great promise for therapeutic application (Humeau et al., Mol Ther. 2004, 9(6):902-13; Curran et al., Mol Ther. 2000, 1(1):31-8; Engel and Kohn, Front Biosci. 199, 4:e26-33). Unlike most retroviruses, HIV and FIV (and vectors derived from them) have the ability to transduce non-dividing cells (Humeau et al., Mol Ther. 2004, 9(6):902-13; Curran et al., Mol Ther. 2000, 1(1):31-8). This property may be advantageous depending upon the target cell type. In addition, FIV may distinguish itself from other retroviruses by its increased transgene carrying capacity (Curran et al., Mol Ther. 2000, 1(1):31-8). A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A.D., Blood 76:271, 1990). Thus, recombinant retrovirus can be constructed in which part of the retroviral coding sequence (gag, pol, env) has been replaced by nucleic acid encoding a subject polypeptide, rendering the retrovirus replication-defective. The replication-defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F.M. et al., (eds.), John Wiley & Sons, Inc., Greene Publishing Associates, (2001), Sections 9.9-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., Science 230:1395-1398, 1985; Danos and Mulligan, PNAS USA 85:6460-6464, 1988; Wilson et al., PNAS USA 85:3014-3018, 1988; Armentano et al., PNAS USA 87:6141-6145, 1990; Huber et al., PNAS USA 88:8039-8043, 1991; Ferry et al., PNAS USA 88:8377-8381, 1991; Chowdhury et al., Science 254:1802-1805, 1991; van Beusechem et al., PNAS USA 89:7640-7644, 1992; Kay et al., Human Gene Therapy 3:641-647, 1992; Dai et al., PNAS USA 89:10892-10895, 1992; Hwu et al., J. Immunol. 150:41044115, 1993; U.S. Pat. No. 4,868,116; U.S. Pat. No.: 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., PNAS USA 86:9079-9083, 1989; Julan et al., J. Gen Virol 73:3251-3255, 1992; and Goud et al., Virology 163:251-254, 1983); or coupling cell surface ligands to the viral env proteins (Neda et al., J. Biol. Chem. 266:14143-14146, 1991). Coupling can be in the form of the chemical cross-linking with a protein or other variety (e.g., lactose to convert the env protein to an asialoglycoprotein), as well as by generating fusion proteins (e.g., single-chain antibody/env fusion proteins). This technique, while useful to limit or otherwise direct the infection to certain tissue types, and can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactive in terms of its ability to replicate in a normal lytic viral life cycle (see, for example, Berkner et al., BioTechniques 6:616, 1988; Rosenfeld et al., Science 252:431-434, 1991; and Rosenfeld et al., Cell 68:143-155, 1992). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., PNAS USA 89:6482-6486, 1992), hepatocytes (Herz and Gerard, PNAS USA 90:2812-2816, 1993) and muscle cells (Quantin et al., PNAS USA 89:2581-2584, 1992). Furthermore, the virus particle is relatively stable, amenable to purification and concentration, and as described above, can be modified to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham J., Virol. 57:267, 1986). Most replication-defective adenoviral vectors currently in use and therefore favored by the present invention are deleted for all or parts of the viral E1 and E3 genes but retain as much as 80% of the adenoviral genetic material (see, e.g., Jones et al., Cell 16:683, 1979; Berkner et al., supra; and Graham et al., in Methods in *Molecular Biology*, E. J. Murray, Ed. (Humana, Clifton, NJ, 1991) vol. 7. pp. 109-127). Expression of the inserted subject gene can be under control of, for example, the E1A promoter, the major late promoter (MLP) and associated leader sequences, the viral E3 promoter, or exogenously added promoter sequences.

Yet another viral vector system useful for delivery of the subject genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., *Curr. Topics in Micro. Immunol* (1992) 158:97-129, 1992.) It is also one of the few viruses that may integrate its DNA into non-dividing cells, and exhibits a high frequency of stable integration (see for example Flotte et al., Am. J. Respir. Cell. Mol. Biol. 7:349-356, 1992; Samulski et al., J. Virol. 63:3822-3828, 1989; and McLaughlin et al., J. Virol. 62:1963-1973, 1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260, 1985 can be used to introduce DNA into cells. A variety of nucleic acids have been introduced into different cell types using AAV vectors (see for example Hermonat et al., PNAS USA 81:6466-6470, 1984; Tratschin et al., Mol. Cell. Biol. 4:2072-2081, 1985; Wondisford et al., Mol. Endocrinol. 2:32-39, 1988; Tratschin et al., J. Virol. 51:611-619, 1984; and Flotte et al., J. Biol. Chem. 268:3781-3790, 1993).

Other viral vector systems that may have application in gene therapy have been derived from herpes virus, vaccinia virus, and several RNA viruses. In particular, herpes virus vectors may provide a unique strategy for persistence of the subject recombinant gene in cells of the central nervous system and ocular tissue (Pepose et al., Invest Ophthalmol Vis Sci 35:2662-2666, 1994).

In addition to viral transfer methods, such as those illustrated above, non-viral methods can also be employed to cause expression of a subject protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes.

In a representative embodiment, a gene encoding a subject polypeptide can be entrapped in liposomes bearing positive charges on their surface (e.g., lipofectins) and (optionally) which are tagged with antibodies against cell surface antigens of the target tissue (Mizuno et al., No Shinkei Geka 20:547-551, 1992; PCT publication WO91/06309; Japanese patent application 1047381; and European patent publication EP-A43075). For example, lipofection of neuroglioma cells can be carried out using liposomes tagged with monoclonal antibodies against glioma-associated antigen (Mizuno et al., Neurol. Med. Chir. 32:873-876, 1992).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, the subject gene construct can be used to transfect specific cells in vivo using a soluble polynucleotide carrier comprising an antibody conjugated to a poly-cation, e.g., poly-lysine (see U.S. Pat. No. 5,166,320). It will also be appreciated that effective delivery of the subject nucleic acid constructs via peptide-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., Science 260-926, 1993; Wagner et al., PNAS USA 89:7934, 1992; and Christiano et al., PNAS USA 90:2122, 1993).

In clinical settings, the gene delivery systems can be introduced into a patient by any of a number of methods, each of which is familiar in the art. For instance, a pharmaceutical preparation of the gene delivery system can be introduced systemically, e.g., by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al., PNAS USA 91: 3054-3057, 1994).

In addition, the subject proteins can be provided as a fusion peptide along with a second peptide which promotes "transcytosis", e.g., uptake of the peptide by target cells. To illustrate, the subject protein can be provided as part of a fusion polypeptide with all or a fragment of the N-terminal domain of the HIV protein Tat, e.g., residues 1-72 of Tat or a smaller fragment thereof which can promote transcytosis. In other embodiments, the subject polypeptide can be provided as a fusion polypeptide with all or a portion of the antennapedia III protein. Synthetic peptides have also been effectively used to transport proteins, peptides and small molecules across biological membranes including the blood brain barrier and therefore, may be applicable to this application.(Rothbard et al., Nat Med. 2000, 6(11): 1253-7; Rothbard et al., J Med Chem. 2002, 45(17):3612-8). While the synthetic protein transduction sequence examples provided are characterized by a high density of arginine residues, other functionally similar but structurally dissimilar molecules or sequences could be substituted.

To further illustrate, the subject polypeptide (or peptidomimetic) can be provided as a chimeric peptide which includes a heterologous peptide sequence ("internalizing peptide" or "internalization domain") which drives the translocation of an extracellular form of a subject polypeptide sequence across a cell membrane in order to facilitate intracellular localization of the subject polypeptide. In this regard, the therapeutic subject polypeptide is one which is active intracellularly. The internalizing peptide, by itself, is capable of crossing a cellular membrane by, e.g., transcytosis, at a relatively high rate. The internalizing peptide is conjugated, e.g., as a fusion protein, to the subject polypeptide, optionally in a cleavable manner. The resulting chimeric peptide is transported into cells at a higher rate relative to the activator polypeptide alone, thereby providing a means for enhancing its introduction into cells to which it is applied, e.g., to enhance topical applications of the subject polypeptide. In addition to proteins and peptidomimetics, an agent of the drug can be coupled to a compound that enhances delivery to a substance (e.g., receptor-mediated compounds such as Vitamin $B_{12}$).

In one embodiment, the internalizing peptide is derived from the *Drosophila antennapedia* protein, or homologs thereof. The 60 amino acid long homeodomain of the homeoprotein antennapedia has been demonstrated to translocate through biological membranes and can facilitate the translocation of heterologous polypeptides to which it is coupled. See, for example, Derossi et al. (1994) J Biol Chem 269: 10444-10450; and Perez et al. (1992) J Cell Sci 102:717-722. It has been demonstrated that fragments as small as 16 amino acids long of this protein are sufficient to drive internalization. See Derossi et al. (1996) J Biol Chem 271:18188-18193.

The present invention also provides a polypeptide (small t antigen or VDAC) or peptidomimetic sequence as described herein, and at least a portion of the Antennapedia protein (or homolog thereof) sufficient to increase the transmembrane transport of the chimeric protein, relative to the subject polypeptide or peptidomimetic, by a statistically significant amount. Such polypeptide or peptidomimetic thereof may be used in the subject methods to assist in efficient and specific killing of cancer cells.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol. 63:1-8).

Another exemplary transcellular polypeptide can be generated to include a sufficient portion of mastoparan (T. Higashijima et al., (1990) J. Biol. Chem. 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefore serve as an internalizing peptide for the subject transcellular peptides and peptidomimetics. Preferred growth factor-derived internalizing peptides include EGF (epidermal growth factor)-derived peptides, such as CMHIESLDSYTC and CMYMALD-KYAC; TGF-beta (transforming growth factor beta )-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of subject polypeptide and peptidomimetics, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5-7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA (EALA)4-EALEALAA-amide, which represents a modification of the peptide sequence of Subbarao et al. (Biochemistry 26:2964, 1987). Within this peptide sequence, the first amino acid residue (aa1) is preferably a unique residue, such as cysteine or lysine, that facilitates chemical conjugation of the internalizing peptide to a targeting protein conjugate. Amino acid residues 2-3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2-3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention includes hydrophobic domains that are "hidden" at physiological pH, but are exposed in the low pH environmnent of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or *Diphtheria* toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the subject polypeptide or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocatinglinternalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (Eubanks et al., in: Peptides. Chemistry and Biology, Garland Marshall (ed.), ESCOM, Leiden, 1988, pp. 566-69). In this construct, an internalizing peptide would be attached to the C-terminus of the accessory peptide, since the N-terminal glycine is critical for the accessory moiety's activity. This hybrid peptide, upon attachment to an E2 peptide or peptidomimetic at its C-terminus, is N-myristylated and further anchored to the target cell membrane, e.g., it serves to increase the local concentration of the peptide at the cell membrane.

To further illustrate use of an accessory peptide, a phosphorylatable accessory peptide is first covalendy attached to the C-terminus of an internalizing peptide and then incorporated into a fusion protein with a subject polypeptide or peptidomimetic. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) Ann. Rev. Biochem. 56:63-87). Accessory peptides that contain the sequence x-NLT-x thus will enhance target cell retention of corresponding polypeptide.

In another embodiment of this aspect of the invention, an accessory peptide can be used to enhance interaction of a polypeptide or peptidomimetic with the target cell. Exemplary accessory peptides in this regard include peptides derived from cell adhesion proteins containing the sequence "RGD", or peptides derived from laminin containing the sequence CDPGYIGSRC. Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type I, lambda receptor of *E. Coli*, fibrinogen and Sindbis coat protein (E. Ruoslahti, Ann. Rev. Biochem. 57:375-413, 1988). Cell surface receptors that recognize RGD sequences have been grouped into a superfamily of related proteins designated "integrins". Binding of "RGD peptides" to cell surface integrins will promote cell-surface retention, and ultimately translocation, of the polypeptide.

As described above, the internalizing and accessory peptides can each, independently, be added to the polypeptide or peptidomimetic by either chemical cross-linking or in the form of a fusion protein. In the instance of fusion proteins, unstructured polypeptide linkers can be included between each of the peptide moieties.

In general, the internalization peptide will be sufficient for the direct export of the polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In an exemplary embodiment, a polypeptide or peptidomimetic is engineered to include an integrin-binding RGD peptide/SV40 nuclear localization signal (see, for example Hart S L et al., 1994; J. Biol. Chem.,269:12468-12474), such as encoded by the nucleotide sequence provided in the NdeI-EcoRI fragment: catatggtutgactgccgtggcgatatgt-tcggttgcggtgctcctccaaaaaagaagagaaaggtagctggattc, which encodes the RGD/SV40 nucleotide sequence: MGGCRGD-MFGCGAPPKKKRKVAGF. In another embodiment, the protein can be engineered with the HIV-1 tat(1-72) polypeptide, e.g., as provided by the NdeI-EcoRI fragment: catatg-gagccagtagatcctagactagagccctggaagcatccaggaagtcagcctaaa actgcttgtaccaattgctattgtaaaaagtgttgctttcattgccaagtgtttc ataa-caaaagcccttggcatctcctatggcaggaagaagcgagacagcgacgaaga-cctcctcaaggcagtcagact catcaagtttctctaagtaagcaaggattc, which encodes the HIV-1 tat(1-72) peptide sequence: MEPVD-PRLEPWKHPGSQPKTACTNCYCKKCCFHCQVCFITK-ALGISYGRKK RRQRRRPPQGSQTHQVSLSKQ. In still another embodiment, the fusion protein includes the HSV-1 VP22 polypeptide (Elliott G., O'Hare P (1997) Cell, 88:223-233) provided by the Nde1-EcoR1 fragment. In still another embodiment, the fusion protein includes the C-terminal domain of the VP22 protein from, e.g., the nucleotide sequence (Nde1-EcoR1 fragment).

In certain instances, it may also be desirable to include a nuclear localization signal as part of the subject polypeptide. In the generation of fusion polypeptides including a polypeptide, it may be necessary to include unstructured linkers in order to ensure proper folding of the various peptide domains. Many synthetic and natural linkers are known in the art and can be adapted for use in the present invention, including the $(Gly_3Ser)_4$ linker.

Methods of Treatment In certain embodiments, the invention provides a method to treat or prevent cancer in an individual. The terms "cancer," "tumor," and "neoplasia" are used interchangeably herein. As used herein, a cancer (tumor or neoplasia) is characterized by one or more of the following properties: cell growth is not regulated by the normal biochemical and physical influences in the environment; anaplasia (e.g., lack of normal coordinated cell differentiation); and in some instances, metastasis. Cancer diseases include, for example, anal carcinoma, bladder carcinoma, breast carcinoma, cervix carcinoma, chronic lymphocytic leukemia, chronic myelogenous leukemia, endometrial carcinoma, hairy cell leukemia, head and neck carcinoma, lung (small cell) carcinoma, multiple myeloma, non-Hodgkin's lymphoma, follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, and soft tissue sarcoma. Additional cancer disorders can be found in, for example, Isselbacher et al. (1994) Harrison's Principles of Internal Medicine 1814-1877, herein incorporated by reference.

Typically, the cancers described above and treatable by the methods described herein exhibit deregulated VDAC expression. In one embodiment, the cancers described above contain a mutation in the Ras signaling pathway, resulting in elevated Ras signaling activity. For example, the mutation could be a constitutively active mutation in the Ras gene, such as Ras V12. In other embodiments, the cancer may contain loss of function mutations in PP2A, and/or activating mutations of MEK1 and/or ERK1. In certain further embodiments, the cancer is characterized by cells expressing SV40 small t oncoprotein, or are phenotypically similar to cells expressing ST, and/or oncogenic HRAS. In certain preferred embodiments, the cells express substantially wild-type level of Rb (e.g., at least about 50%, 60%, 70%, 80%, 90%, 100%, 110%, 120%, 130%, or 150%, etc.).

In one embodiment, the invention relates to a method of treating or preventing cancer in an individual, comprising administering to the individual a therapeutically effective amount of a compound that is selectively toxic to an engineered human tumorigenic cell, or a cancer cell of specific genotype (or specifically altered genotype). In certain embodiments, the cancer is characterized by cells comprising an activated RAS pathway. In certain further embodiments, the cancer is characterized by cells expressing SV40 small T oncoprotein, or exhibiting modulations of targets of sT and/or oncogenic RAS.

In a related embodiment, the invention contemplates the practice of the method of the invention in conjunction with other anti-tumor therapies such as conventional chemotherapy directed against solid tumors and for control of establishment of metastases. The administration of the compounds of the invention can be conducted during or after chemotherapy. Such agents are typically formulated with a pharmaceutically acceptable carrier, and can be administered intravenously, orally, bucally, parenterally, by an inhalation spray, by topical application or transdermally. An agent can also be administered by local administration. Preferably, one or more additional agents administered in conjunction with an anti-cancer chemotherapeutic agent (e.g., a compound of the invention) inhibits cancer cells in an additive or synergistic manner.

A wide array of conventional compounds has been shown to have anti-tumor activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-tumor compounds induce undesirable side effects. In many cases, when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

Therefore, compounds and pharmaceutical compositions of the present invention may be conjointly administered with a conventional anti-tumor compound. Conventional anti-tumor compounds include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinbiastine, vincristine, vindesine, and vinorelbine.

In other embodiments, compounds and pharmaceutical compositions of the present invention may be conjointly administered with a conventional anti-tumor compound selected from: an EGF-receptor antagonist, arsenic sulfide, adriamycin, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, megestrol, methopterin, mitomycin C, ecteinascidin 743, busulfan, carmustine (BCNU), lomustine (CCNU, lovastatin, 1-methyl4-phenylpyridinium ion, semustine, staurosporine, streptozocin, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenolic acid, daunorubicin, deferoxamine, floxuridine, doxifluridine, raltitrexed, idarubicin, epirubican, pirarubican, zorubicin, mitoxantrone, bleomycin sulfate, actinomycin D, safracins, saframycins, quinocarcins, discodermolides, vincristine, vinblastine, vinorelbine tartrate, vertdporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, enediynes, levamisole, aflacon, interferon, interleukins, aldesleukin, filgrastim, sargramostim, rituximab, BCG, tretinoin, betamethosone, gemcitabine hydrochloride, verapamil, VP-16, altretamine, thapsigargin, oxaliplatin, iproplatin, tetraplatin, lobaplatin, DCP, PLD-147, JM118, JM216, JM335, satraplatin, docetaxel, deoxygenated paclitaxel, TL-139, 5'-nor-anhydrovinblastine (hereinafter: 5'-nor-vinblastine), camptothecin, irinotecan (Camptosar, CPT-11), topotecan (Hycamptin), BAY 38-3441, 9-nitrocamptothecin (Orethecin, rubitecan), exatecan (DX-8951), lurtotecan (GI-147211C), gimatecan, homocamptothecins diflomotecan (BN-80915) and 9-aminocamptothecin (IDEC-13'), SN-38, ST1481, karanitecin (BNP1350), indolocarbazoles (e.g., NB-506), protoberberines, intoplicines, idenoisoquinolones, benzo-phenazines or NB-506.

In another related embodiment, the invention contemplates the practice of the method in conjunction with other anti-tumor therapies such as radiation. As used herein, the term "radiation" is intended to include any treatment of a neoplastic cell or subject by photons, neutrons, electrons, or other type of ionizing radiation. Such radiations include, but, are not limited to, X-ray, gamma-radiation, or heavy ion particles, such as alpha or beta particles. Additionally, the radiation may be radioactive. The means for irradiating neoplastic cells in a subject are well known in the art and include, for example, external beam therapy, and brachytherapy.

Methods to determine if a cancer (tumor or neoplasia) has been treated are well known to those skilled in the art and include, for example, a decrease in the number of tumor cells (e.g., a decrease in cell proliferation or a decrease in tumor size). It is recognized that the treatment of the present invention may be a lasting and complete response or can encompass a partial or transient clinical response. See for example, Isselbacher et al. (1996) Harrison's Principles of Internal Medicine 13 ed., 1814-1882, incorporated herein by reference.

Assays to test for the sensitization or the enhanced death of tumor cells are well known in the art, including, for example, standard dose response assays that assess cell viability; agarose gel electrophoresis of DNA extractions or flow cytometry to determine DNA fragmentation, a characteristic of cell death; assays that measure the activity of polypeptides involved in apoptosis; and assay for morphological signs of cell death. The details regarding such assays are described elsewhere herein. Other assays include, chromatin assays (e.g., counting the frequency of condensed nuclear chromatin) or drug resistance assays as described in, for example, Lowe et al. (1993) Cell 74:95 7-697, herein incorporated by reference. See also U.S. Pat. No. 5,821,072, also herein incorporated by reference.

Pharmaceutical Compositions

Prospective therapeutic agents can be profiled in order to determine their suitability for inclusion in a pharmaceutical composition. One common measure for such agents is the therapeutic index, which is the ratio of the therapeutic dose to a toxic dose. The thresholds for therapeutic dose (efficacy) and toxic dose can be adjusted as appropriate (e.g., the necessity of a therapeutic response or the need to minimize a toxic response). For example, a therapeutic dose can be the therapeutically effective amount of an agent (relative to treating one or more conditions) and a toxic dose can be a dose that causes death (e.g., an $LD_{50}$) or causes an undesired effect in a proportion of the treated population. Preferably, the therapeutic index of an agent is at least 2, more preferably at least 5, and even more preferably at least 10. Profiling a therapeutic agent can also include measuring the pharmacokinetics of the agent, to determine its bioavailability and/or absorption when administered in various formulations and/or via various routes.

A compound of the present invention, such as erastin or a tubulin inhibitor, may be administered to an individual in need thereof. In certain embodiments, the individual is a mammal such as a human, or a non-human mammal. When administered to an individual, the compound of the invention can be administered as a pharmaceutical composition containing, for example, the compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, the aqueous solution is pyrogen free, or substantially pyrogen free. The excipients can be chosen, for example, to effect delayed release of an agent or to selectively target one or more cells, tissues or organs.

A pharmaceutically acceptable carrier can contain physiologically acceptable agents that act, for example, to stabilize or to increase the absorption of a compound such as erastin or a tubulin inhibitor. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition (preparation) also can be a liposome or other polymer matrix, which can have incorporated therein, for example, a compound of the invention. Liposomes, for example, which consist of phospholipids or other lipids, are nontoxic, physiologically acceptable and metabolizable carriers that are relatively simple to make and administer.

A pharmaceutical composition (preparation) containing a compound of the invention can be administered to a subject by any of a number of routes of administration including, for example, orally; intramuscularly; intravenously; anally; vaginally; parenterally; nasally; intraperitoneally; subcutaneously; and topically. The composition can be administered by injection or by incubation.

In certain embodiments, the compound (e.g., erastin) of the present invention may be used alone or conjointly administered with another type of anti-tumor therapeutic agent. As used herein, the phrase "conjoint administration" refers to any form of administration in combination of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. Thus, an individual who receives such treatment can benefit from a combined effect of different therapeutic compounds.

It is contemplated that the compound (e.g., erastin) of the present invention will be administered to a subject (e.g., a mammal, preferably a human) in a therapeutically effective amount (dose). By "therapeutically effective amount" is meant the concentration of a compound that is sufficient to elicit the desired therapeutic effect (e.g., treatment of a condition, the death of a neoplastic cell). It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. Typically, for a human subject, an effective amount will range from about 0.001 mg/kg of body weight to about 50 mg/kg of body weight. A larger total dose can be delivered by multiple administrations of the agent. Methods to determine efficacy and dosage are known to those skilled in the art. See, for example, Isselbacher et al. (1996) Harrison's Principles of Internal Medicine 13 ed., 1814-1882, herein incorporated by reference.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Identification of Compounds with Increased Potency or Activity in the Presence of Specific Cancer-Related Alleles Described here is work carried out to identify compounds with increased potency or activity in the presence of hTERT, LT, ST, E6, E7 or $RAS^{V12}$. Although the work described herein made use of hTERT, LT, ST, E6, E7 and $RAS^{V12}$ as transforming genes, future studies can make use of a wide variety of cancer-associated alleles using this methodology in order to define the signaling networks that involve many oncogenes and tumor suppressors. Engineered cell lines with these genetic elements were used to screen 23,550 compounds, including 20,000 compounds from a combinatorial library, 1,990 compounds from the National Cancer Institute diversity collection, and 1,540 biologically active known compounds that were selected and purchased by Applicant and formatted into a screenable collection. The primary screen tested (in quadruplicate) the effect of treating tumorigenic BJ-TERT/LT/ST/$RAS^{V12}$ engineered tumorigenic cells with each compound for 48 hours at a concentration of 4 μg/mL, corresponding to 10 μM for a compound with a molecular weight of 400, which is the approximate median molecular weight of the libraries. Cell viability was measured using the dye calcein acetoxymethyl ester (calcein AM) (Wang et al., 1993, Hum. Immunol. 37, 264-270), which is a non-fluorescent compound that freely diffuses into cells. In live cells, calcein AM is cleaved by intracellular esterases, forming the anionic fluorescent derivative calcein, which cannot diffuse out of live cells. Hence, live cells exhibit a green fluorescence when incubated with calcein AM, whereas dead cells do not. Compounds that displayed 50% or greater inhibition of staining with the viability dye calcein AM in BJ-TERT/LT/ST/$RAS^{V12}$ cells were subsequently tested in a two-fold dilution series in BJ and BJ-TERT/LT/ST/$RAS^{V12}$ cells to identify compounds that display synthetic lethality, which is lethality in tumorigenic cells but not in isogenic primary cells. The $IC_{50}$ value (concentration required to inhibit 50% of the calcein AM signal) was calculated for each compound in each cell line (Table 1). This resulted in identification of nine compounds (FIG. 2) that were at least four-fold more potent in BJ-TERT/LT/ST/$RAS^{V12}$ tumorigenic cells relative to BJ primary cells (compounds for which at least a four-fold higher concentration was required in BJ primary cells in order to obtain the same 50% inhibition of calcein AM signal). Following is a more detailed analysis of these nine compounds.

Three of these compounds (doxorubicin, daunorubicin and mitoxantrone) are in current clinical use as anti-cancer drugs, one (camptothecin) is a natural product analog of clinically used anticancer drugs (topotecan and irinotecan), and one (echinomycin) was recently tested in phase II clinical trials. All nine compounds were subsequently tested in replicate at multiple doses in each panel of engineered cells to confirm that the observed selectivities were seen in multiple independently-derived cell lines (FIG. 1 and Table 1).

Applicants developed a selectivity metric that measures the shift in the $IC_{50}$ (concentration required for 50% inhibition of viability signal) of a compound in two different cell lines. To calculate this selectivity score between two cell lines, the $IC_{50}$ for a compound in one cell line was divided by the $IC_{50}$ for the same compound in a second cell line. Thus, a compound that must be used at a four-fold higher concentration in one cell line relative to a second cell line would have a selectivity score of 4. The "tumor selectivity score" was calculated for each compound, by dividing the $IC_{50}$ value for the compound in the parental, primary BJ cells by the $IC_{50}$ value for the compound in engineered BJ-TERTALT/ST/$RAS^{V12}$ cells, containing all four genetic elements required to create tumorigenic cells (Table 1).

These engineered tumorigenic cells make use of dominantly acting viral oncoproteins such as LT, ST, E6 and E7. These viral proteins are possibly involved in cell transformation in specific forms of cancer, namely simian virus 40-induced malignant mesothelioma (Testa and Giordano, 2001, Semin Cancer Biol 11, 31-8) and human papillomavirus-induced cervical carcinoma (Bosch et al., 2002, J Clin Pathol 55, 244-65), and have been used to disrupt p53 and pRB function to transform cells in vitro and in vivo (Elenbaas et al., 2001, Genes Dev 15, 50-65; Jorcyk et al., 1998, Prostate 34, 10-22; Perez-Stable et al., 1997, Cancer Res 57, 900-6; Rich et al., 2001, Cancer Res 61, 3556-60; Sandmoller et al., 1995, Cell Growth Differ 6, 97-103). Applicants made use of these two different methods for inactivating cellular proteins, (they tested the effects of both LT and E6/E7-based inactivation of pRB and p53) in order to control for idiosyncratic effects that might be observed with a specific viral protein. The selectivity of these compounds was also confirmed in a cell line expressing dominant negative inhibitors of p53 and pRB that are not derived from viral elements. This cell line expresses (i) a truncated form of p53 (p53DD) that disrupts tetramerization of endogenous p53, (ii) a $CDK4^{R24C}$ mutant resistant to inhibition by $p16^{INK4A}$ and $p15^{INK4B}$ (the major negative regulators of CDK4) and (iii) cyclin D1. The effects of the nine genotype-selective compounds were tested at a range of concentrations in these cells, which are referred to as BJ-TERT/p53DD/$CDK4^{R24C}$/D1/ST/$RAS^{V12}$ cells (Table 1). Results showed that there was an overall modest reduction in activity for all of the compounds when tested in these cells. However, the overall results of the analysis were unchanged by the use of non-viral proteins in this cell line (Table 1).

EXAMPLE 2

Determination of the Genetic Basis of the Selectivity of Compounds

Applicants sought to determine the genetic basis of selectivity for each compound. That is, for each compound, they attempted to define the gene or combination of genes responsible for rendering cells sensitive to the compound (Table 1). Results showed that these nine compounds could be categorized into three groups, namely (i) compounds that displayed no simple genetic selectivity, (ii) compounds that displayed selectivity for cells harboring TERT and inactive RB, and (iii) compounds that required the presence of both oncogenic RAS and ST in order to exhibit lethality.

Figure 2:
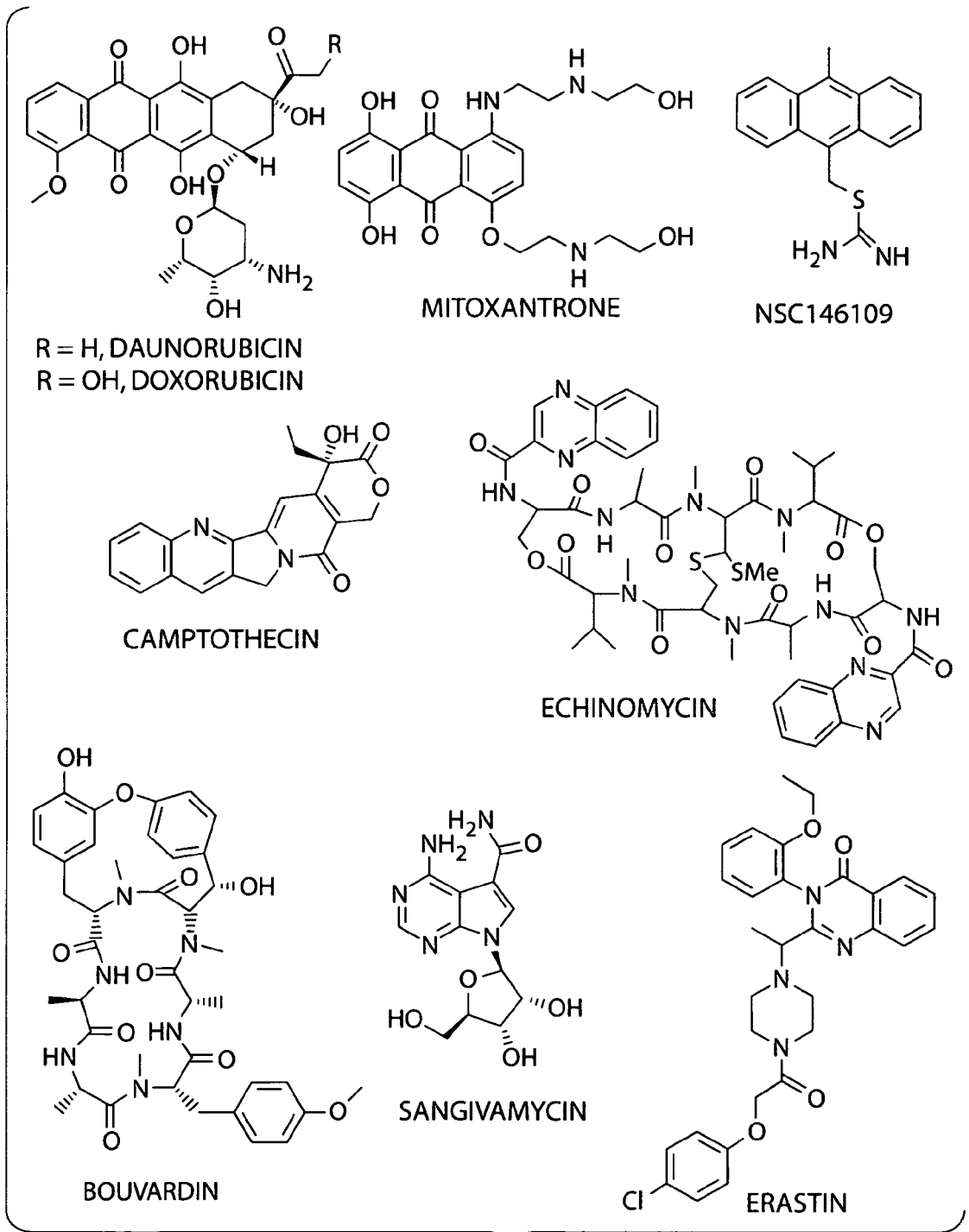
FIG. 2 shows the chemical structures of nine genotype-selective compounds.
Figure 3A:
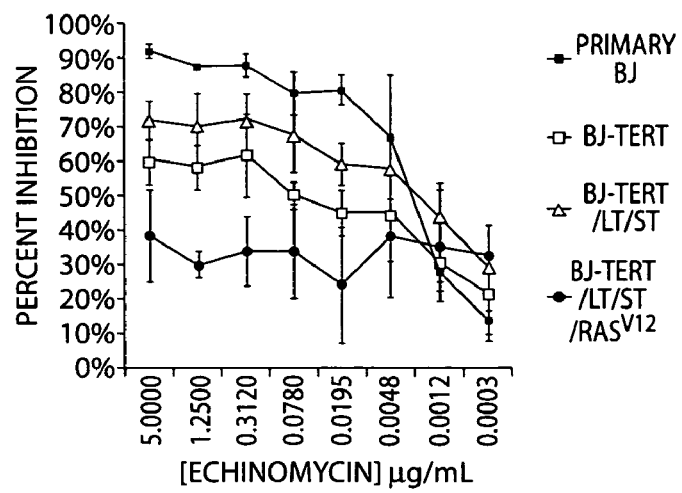
FIG. 3 shows graphic representations of the effect of echinomycin and camptothecin on engineered cells. The indicated cells were treated with echinomycin (A) or camptothecin (B, C) in 384-well plates for 48 hours. Percent inhibition of cell viability, measured using calcein AM, is shown. Error bars indicate one standard deviation. (A) Echinomycin-treated BJ, BJ-TERT, BJ-TERT/LT/ST and BJ-TERT/LT/ST/RAS$^{V12}$ cells; (B) camptothecin-treated-BJ, BJ-TERT, BJ-TERT/LT/ST and BJ-TERT/LT/ST/RAS$^{V12}$ cells; and (C) camptothecin-treated BJ-TERT/LT/RAS$^{V12}$, BJ-TERT/LT/RAS$^{V12}$/ST and BJ-TERT/LT/ST/RAS$^{V12}$ cells.

The compounds in group (i), sangivamycin, bouvardin, NSC146109 and echinomycin, have no clear genetic basis for their tumorigenic cell selectivity. For example, echinomycin becomes somewhat more active as each genetic element is introduced (FIG. 3a). Applicants have observed that the rate of cell proliferation increases when each of these genetic elements is introduced. Thus, it is likely that the compounds in group (i) are simply selective for rapidly dividing cells. Supporting this interpretation is the fact that all of these compounds are reported to act by inhibiting DNA or protein synthesis, the need for which is greater in rapidly dividing cells. For example, echinomycin is reported to function as a DNA bis-intercalator (Van Dyke and Dervan, 1984, Science 225, 1122-7; Waring and Wakelin, 1974, Nature 252, 653-7), bouvardin is reported to function as a protein synthesis inhibitor (Zalacain et al., 1982, FEBS Lett 148, 95-7), sangivamycin is a nucleotide analog (Rao, 1968, J Med Chem 11, 939-41), and NSC146109 structurally resembles a DNA intercalator (FIG. 2). It should be noted that sangivamycin has been reported to function as a PKC inhibitor (Loomis and Bell, 1988, J Biol Chem 263, 1682-92), although this activity seems unlikely to be relevant in this context because other PKC inhibitors displayed no selectivity in this system. Applicants were able to identify compounds that are simply more active in rapidly dividing cells, such as these group (i) compounds, because they show no clear genetic basis of selectivity. No further work was done with these compounds. Thus, they were able to focus the mechanistic studies on the compounds in groups (ii) and (iii), which displayed selectivity.

Figure 5A:
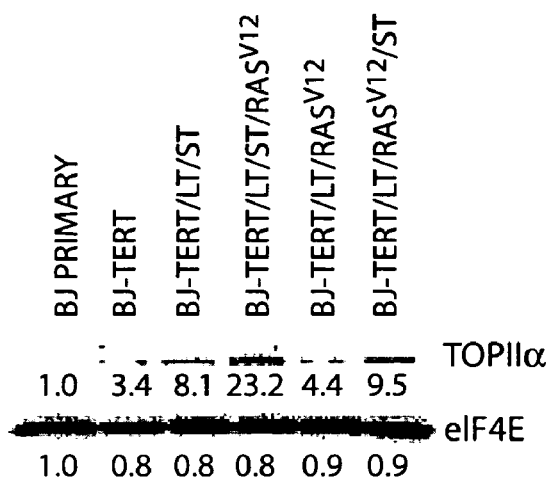
FIG. 5 shows that protein targets of tumor-selective compounds are upregulated in engineered tumorigenic cells. (A-C) Western blot of lysates from BJ, BJ-TERT, BJ-TERT/LT/ST, BJ-TERT/LT/ST/RAS$^{V12}$, BJ-TERT/LT/RAS$^{V12}$ and BJ-TERT/LT/RAS$^{V12}$/ST cells with an antibody directed against topoisomerase II (A) or TOPI (B, C). In panel (C), cells were transfected with a siRNA directed against TOPI, lamic A/C or with a control double strand DNA duplex of the same length (TOPI dsDNA). In each case, the blot was probed with an antibody against eIF-4E to identify differences in the amount of protein loaded. The relative amount is quantitated below each band. (D) A TOPI siRNA prevents cell death caused by camptothecin in engineered tumor cells. Cell number was determined after transfection with a siRNA directed against TOPI and treatment with the indicated concentrations of camptothecin. (E) Okadaic acid, an inhibitor of PP2A and other cellular phosphatases, sensitizes primary human cells to camptothecin. BJ primary cells were treated simultaneously with the indicated concentrations of both camptothecin and okadaic acid and the effect on calcein AM viability staining was determined. Although okadaic acid kills BJ cells at the highest concentrations tested, at 3.4 nM it has no effect on its own, but it renders BJ cells sensitive to camptothecin. (F) Okadaic acid stimulates expression of TOP1. BJ primary cells were treated with the indicated concentrations of okadaic acid and the expression level of TOPI was determined by western blot. The relative amount is quantitated below each band.

The compounds in group (ii), mitoxantrone, doxorubicin and daunorubicin, are topoisomerase II poisons, which bind to topoisomerase II and DNA and prevent the religation of double strand DNA breaks introduced by topoisomerase II. These compounds, and anthracyclines in general, have also been reported to induce the formation of reactive oxygen species (ROS) in some cell types (Laurent and Jaffrezou, 2001, Blood 98, 913-24; Muller et al., 1998, Int J Mol Med 1, 491-4; Richard et al., 2002, Leuk Res 26, 927-31), although Applicants did not observe the formation of ROS in these engineered cells in the presence of these three compounds. They discovered that these compounds become more potent (active at a lower concentration) when hTERT is introduced and again when RB is inactivated by introduction of LT or HPV E7. In the cells, E7 was introduced after E6, so it is possible that the increased potency of these compounds in cells harboring E7 also relies on the presence of E6, even though E6 by itself does not confer increased potency to these compounds. Introduction of hTERT and inactivation of RB caused an increase in topoisomerase IIα expression (FIG. 5A) and only a very modest increase in topoisomerase IIα expression. Introduction of oncogenic RAS causes a further increase in topoisomerase IIα expression, although Applicants did not observe a further sensitization to the topoisomerase II poisons in the presence of oncogenic RAS (FIG. 5A).

Figure 3B:
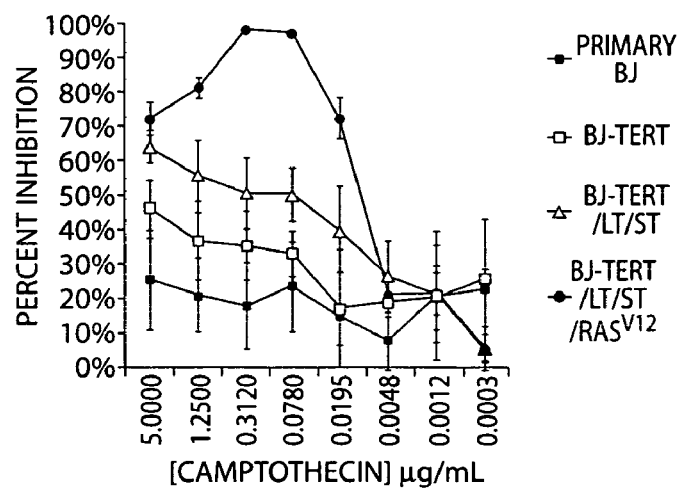
Figure 3C:
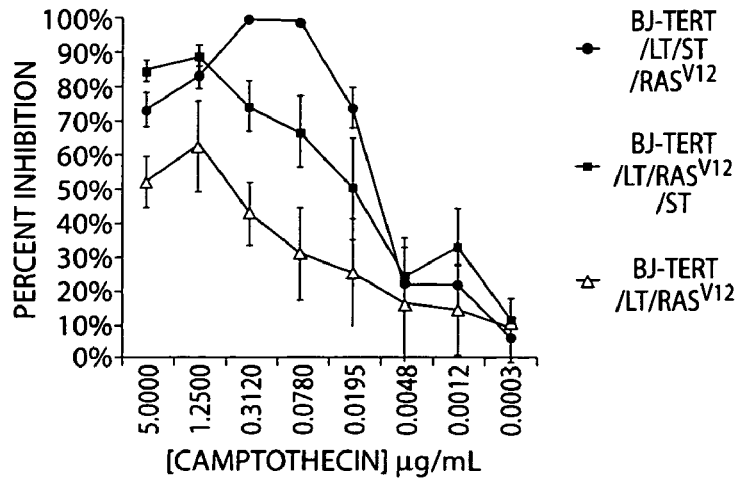
Figure 4A:
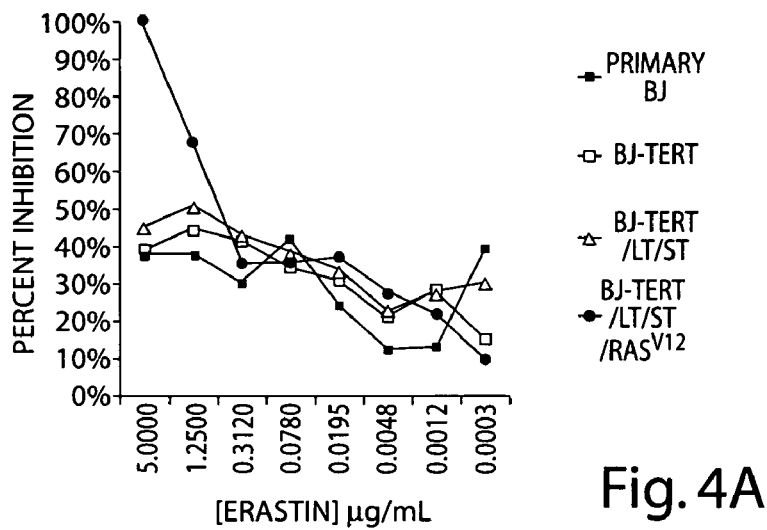
FIG. 4 shows graphic representations of the effect of erastin on engineered cells. The indicated cells were treated with erastin in 384-well plates for 48 hours. Percent inhibition of cell viability, measured using calcein AM, is shown. Error bars indicate one standard deviation. (A) Erastin-treated BJ, BJ-TERT, BJ-TERT/LT/ST and BJ-TERT/LT/ST/RAS$^{V12}$ cells; (B) erastin-treated BJ-TERT/LT/RAS$^{V12}$ cells (lacking ST), BJ-TERT/LT/RAS$^{V12}$/ST (tumorigenic cells) and BJ-TERT/LT/ST/RAS$^{V12}$ (tumorigenic cells); and (C) independently derived TIP5/TERT, TIP5/TERT/E6, TIP5/TERT/LT, TIP5/TERT/LT/ST and TIP5/TERT/LT/ST/RAS$^{V12}$ cells.
Figure 4B:
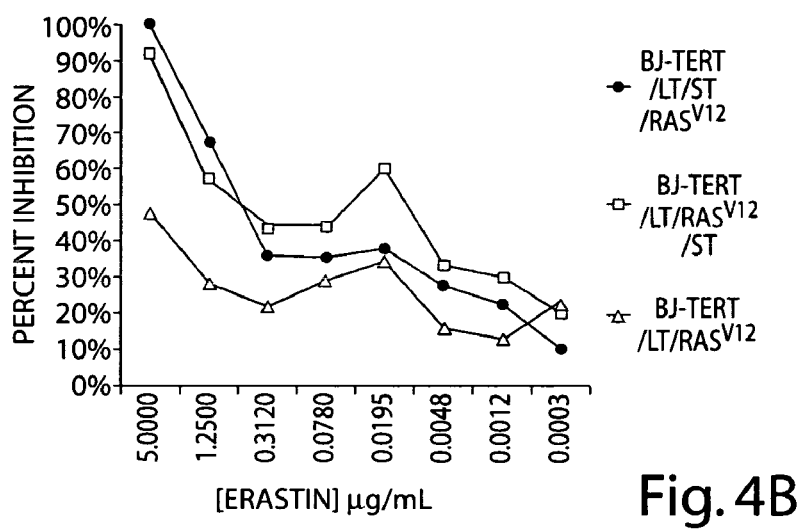
Figure 4C:
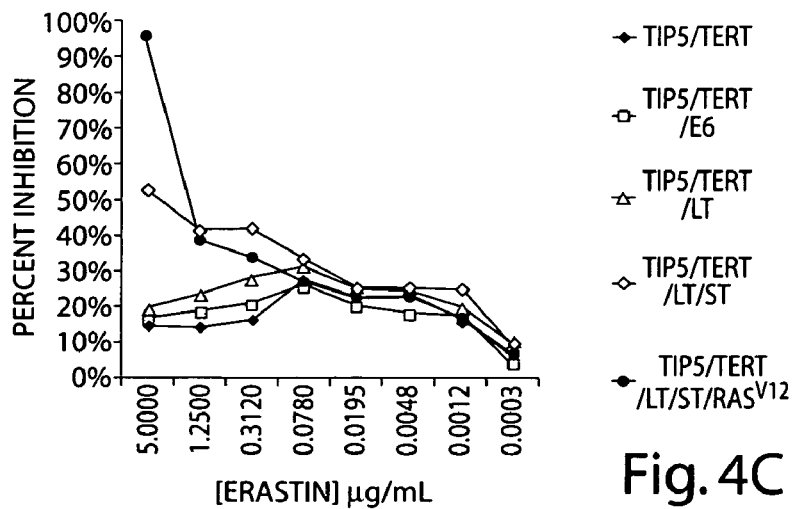
Figure 5B:
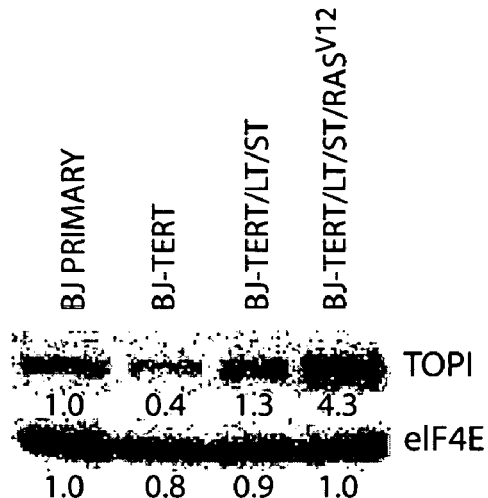
Figure 5C:
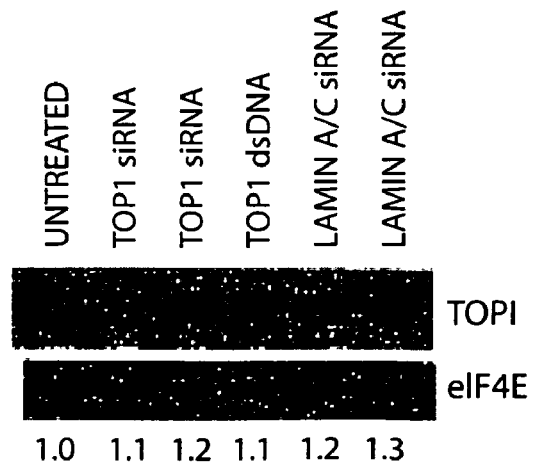
Figure 5D:
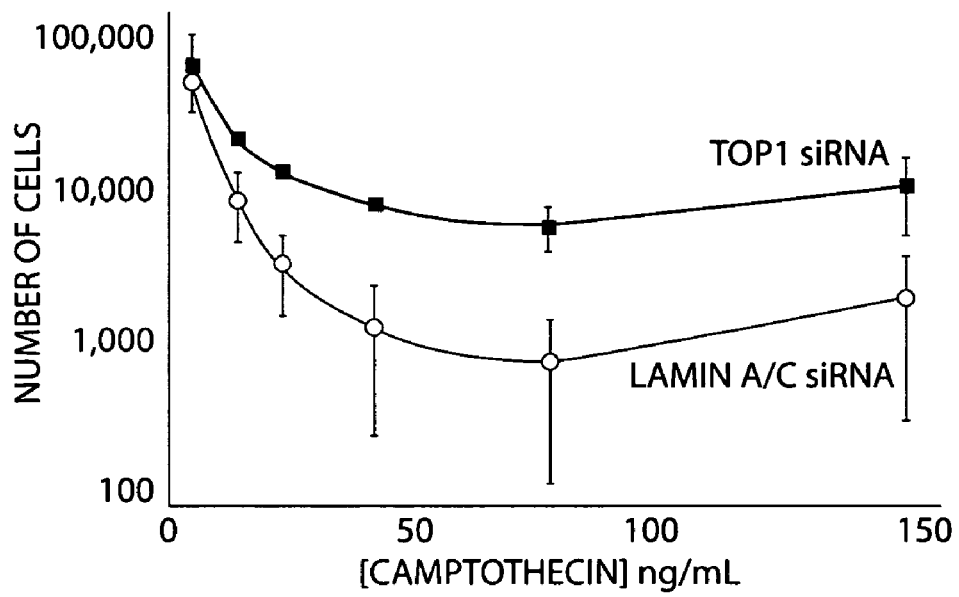
Figure 5E:
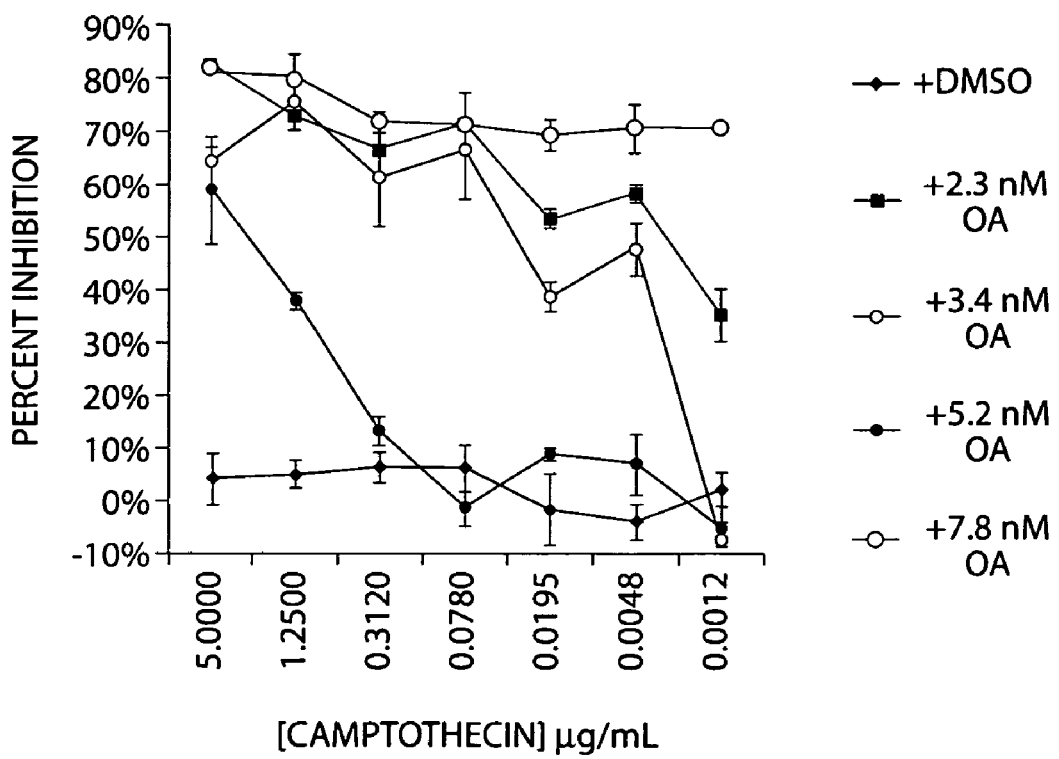
Figure 5F:
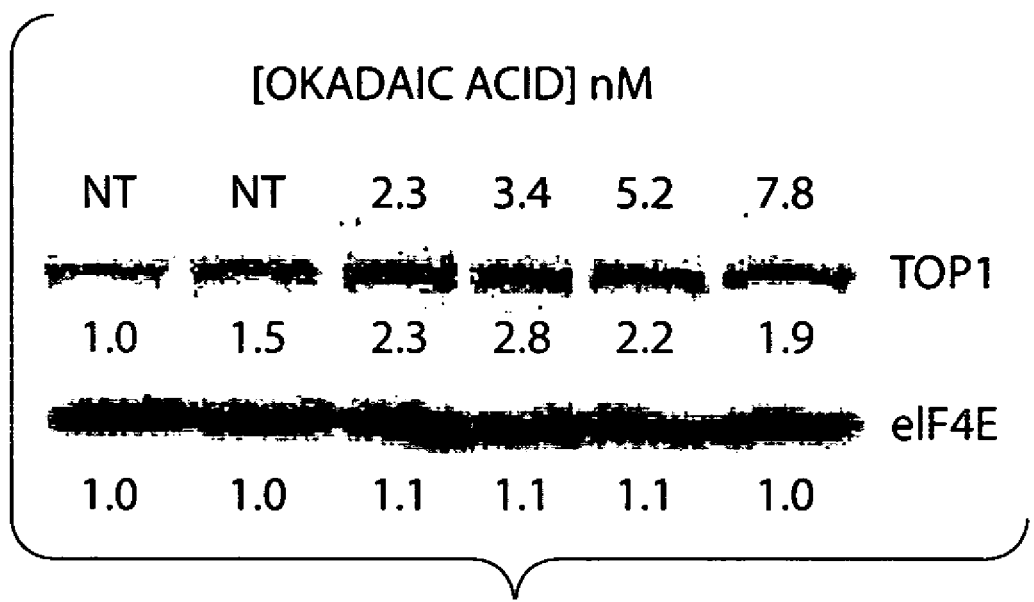

The compounds in group (iii) are camptothecin (CPT) and a novel compound from a combinatorial library, which Applicants have named erastin, for eradicator of RAS and ST-expressing cells (FIG. 2). Efficient CPT-induced and erastin-induced cell death requires the presence of both ST and $RAS^{V12}$ (FIGS. 3 and 4 and Table 1). Although CPT and erastin have a similar genetic basis of selectivity, they have distinct mechanisms of action. CPT is partially active in cells lacking RB function (via expression of E7), whereas erastin is not, and CPT requires two days to cause death in BJ-TERT/LT/ST/$RAS^{V12}$ cells, while erastin is 100% effective within 18 hours (FIGS. 3 and 4). The phosphatase inhibitor okadaic acid was capable of sensitizing otherwise resistant BJ primary cells to CPT (FIG 5E), possibly because okadaic acid upregulates TOP1 (FIG 5F). Okadaic acid does not render BJ or BJ-TERT cells sensitive to erastin, consistent with a model in which CPT and erastin act via distinct mechanisms. Moreover, Applicants found that the lethal compound podophyllotoxin, a tubulin inhibitor, does not sensitize BJ or BJ-TERT cells to CPT, confirming that the sensitization of BJ cells to CPT by okadaic acid is specific and not the result of two weak cell death stimuli having an additive, but functionally irrelevant, effect.

In attempting to understand the molecular basis for the increased sensitivity to CPT of $RAS^{V12}$ and ST-expressing cells, Applicants determined the expression level in the engineered cells of topoisomerase I (TOP1), the putative target of CPT (Andoh et al., 1987, Proc Natl Acad Sci U S A 84, 5565-9; Bjornsti et al., 1989, Cancer Res 49, 6318-23; Champoux, 2000, Ann N Y Acad Sci 922, 56-64; D'Arpa et al., 1990, Cancer Res 50, 6919-24; Eng et al., 1988, Mol Pharmacol 34, 755-60; Hsiang et al., 1989, Cancer Res 49, 5077-82; Hsiang and Liu, 1988, Cancer Res,48, 1722-6; Liu et al., 2000, Ann N Y Acad Sci 922, 1-10; Madden and Champoux, 1992, Cancer Res 52, 525-32; Tsao et al., 1993, Cancer Res 53, 5908-14). They discovered that cells expressing both $RAS^{V12}$ and ST upregulate TOP1 (FIG 5B). As CPT's putative mechanism of action in other cell types involves a gain of function, namely introduction of double strand DNA breaks in a TOP1-dependent manner (Liu et al., 2000, Ann N Y Acad Sci 922, 1-10), upregulation of TOP1 could explain the increased sensitivity of $RAS^{V12}$ and ST-expressing cells to CPT. In support of this interpretation, they found that genetic inactivation of TOP1 with a small interfering RNA (siRNA) in BJ-TERT/LT/ST/RAS$^{V12}$ cells confers partial resistance to CPT (FIG. 5C, D).

Applicants additionally tested other analogs of erastin for activity and selectivity in tumor cells versus normal cells. Another analog compound was identified as being active and selective, but less potent than erastin. This compound was named erastin B (see FIG. 8). BJELR cells are BJ-TERT/LT/ST/RAS$^{V12}$ cells, and BJEH are BJ-TERT cells.

Further compounds tested in both BJELR and BJEH cells are as follows:

EXAMPLE 3

Characterization of Cell Death

Figure 7A:
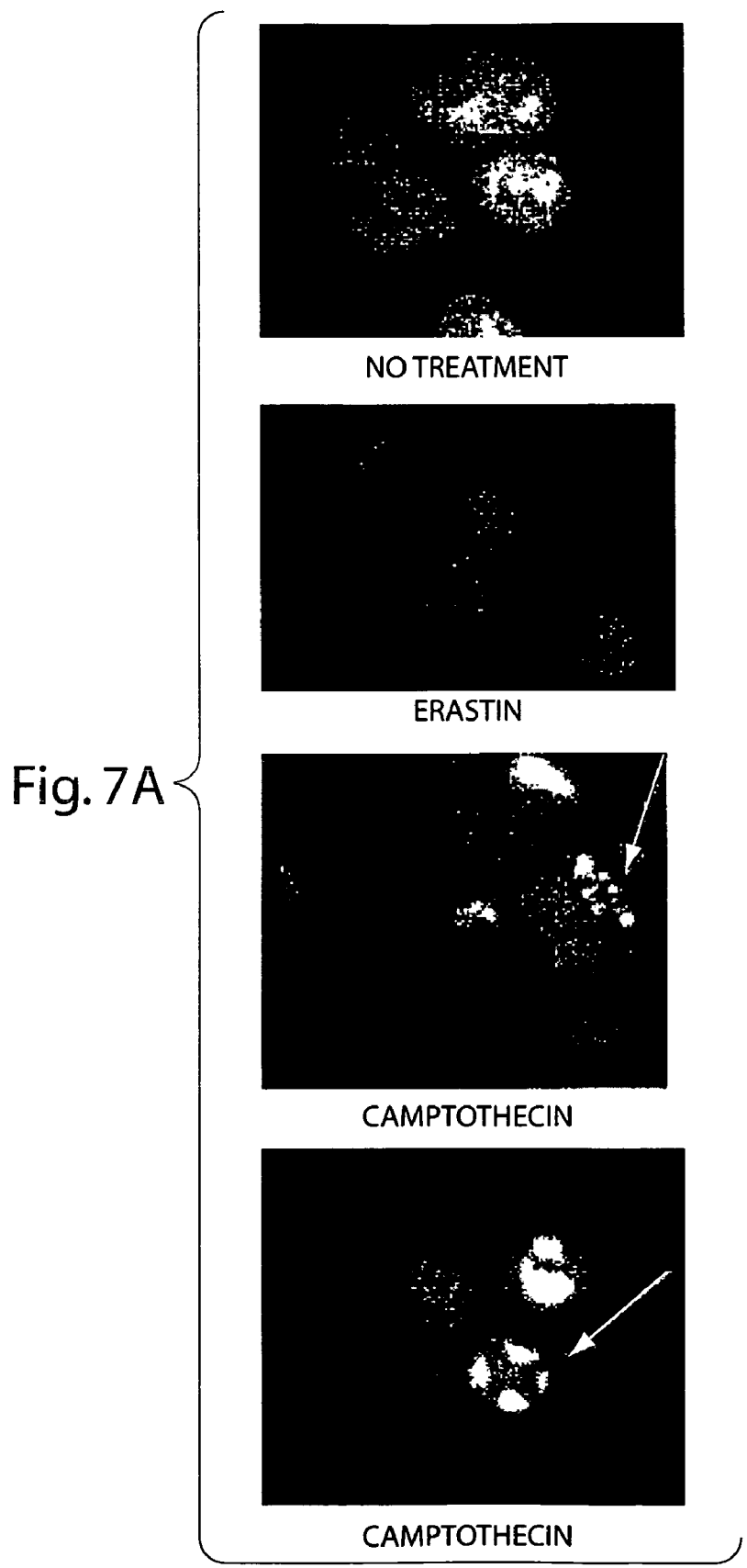
FIG. 7 shows that camptothecin, but not erastin, induces characteristics of apoptosis. (A) Camptothecin-treated, but not erastin-treated, BJ-TERT/LT/ST/RAS$^{V12}$ cells displayed fragmented nuclei (10-20% of total nuclei, red and blue arrows) as shown. (B) Camptothecin-treated, but not erastin-treated, BJ-TERT/LT/ST/RAS$^{V12}$ cells display Annexin V staining. The percentage of cells in the indicated M1 region were 6%, 6% and 38% in untreated, erastin-treated (9 μM) and camptothecin-treated (1 μM), respectively. (C) Camptothecin-treated, but not erastin-treated, BJ-TERT/LT/ST/RAS$^{V12}$ cells harbor activated caspase 3. Lysates of camptothecin and erastin treated samples were analyzed by western blot with an antibody directed against the active, cleaved form of caspase 3. The blot was reprobed with an antibody directed against eIF4E to control for loading levels.
Figure 7B:
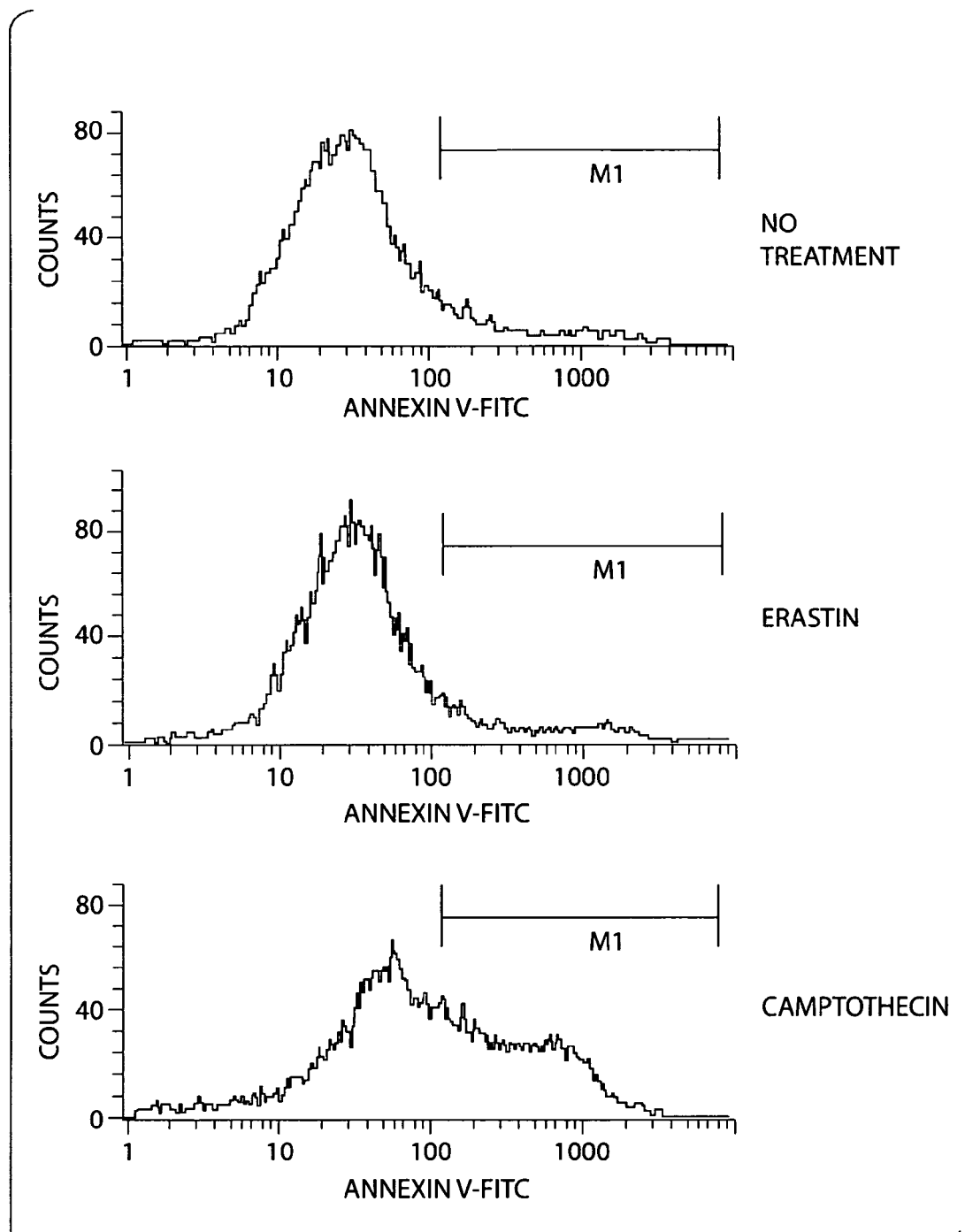
Figure 7C:
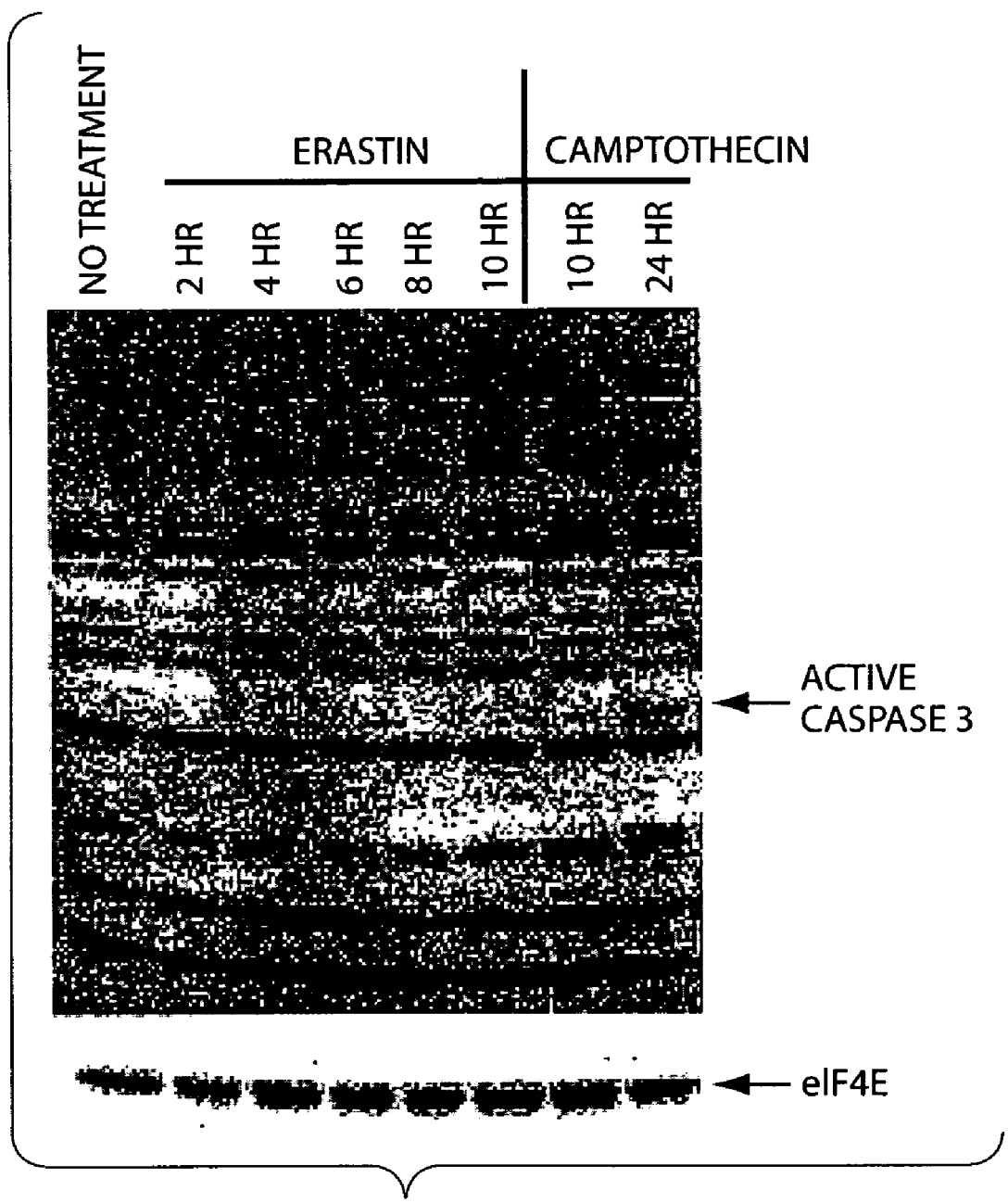
Figure 9:
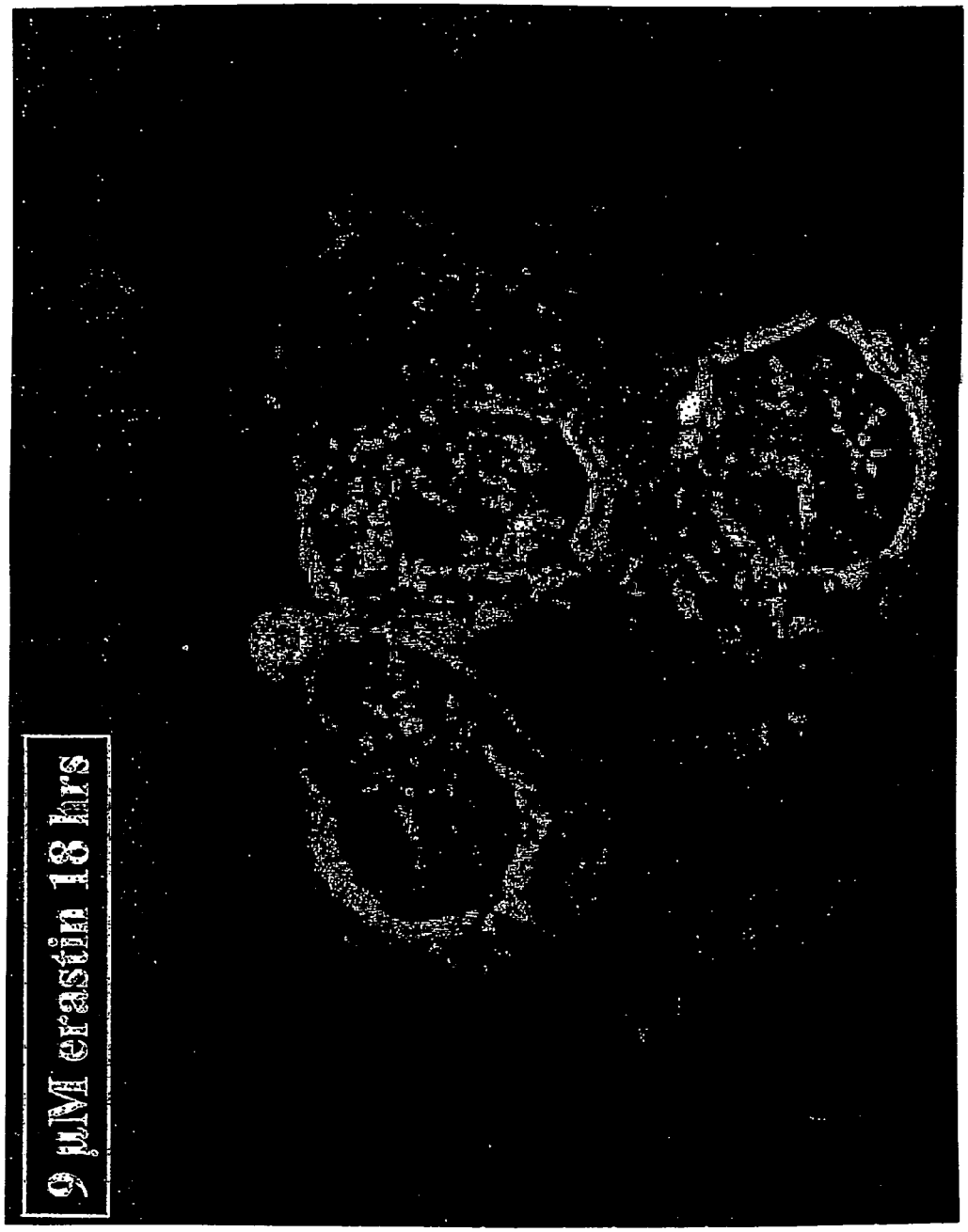
FIG. 9 shows that nuclei remain intact in erastin-treated tumor cells.

Applicants sought to characterize the type of cell death induced by CPT and erastin in tumorigenic BJ-TERT/LT/ST/RAS$^{V12}$ cells. In other contexts, CPT has been found to induce apoptotic cell death (Traganos et al., 1996, Ann N Y Acad Sci 803, 101-10), which is characterized by alterations in nuclear morphology including pyknosis, karyorhexis and/or margination of chromatin (Majno and Joris, 1995, Am J Pathol 146, 3-15). To determine whether erastin or CPT induces apoptosis in their system, Applicants monitored the nuclear morphology of CPT- and erastin-treated tumorigenic cells using fluorescence microscopy. Although karyorhexis and margination of chromatin were clearly visible in CPT-treated cells, no such morphological alternation was visible in erastin-treated cells (FIG. 7A). Since nuclear morphological change is required of apoptotic cells, Applicants conclude that cell death induced by erastin is non-apoptotic. Further supporting this conclusion were observations that CPT, but not erastin, induces DNA fragmentation (which is formation of a DNA ladder), that a pan-caspase inhibitor (50 µM Boc-Asp(Ome)-fluoromethyl ketone, Sigima #B2682 (Chan et al., 2001, Neuroreport 12, 541-545)), partially blocked cell death induced by CPT, but not by erastin, and that CPT, but not erastin, caused an increase in Annexin V staining (FIG. 7B) and the appearance of cleaved, active caspase 3 (FIG. 7C). Additionally, nuclei remained intact in erastin-treated tumor cells (FIG. 9).

Figure 6A:
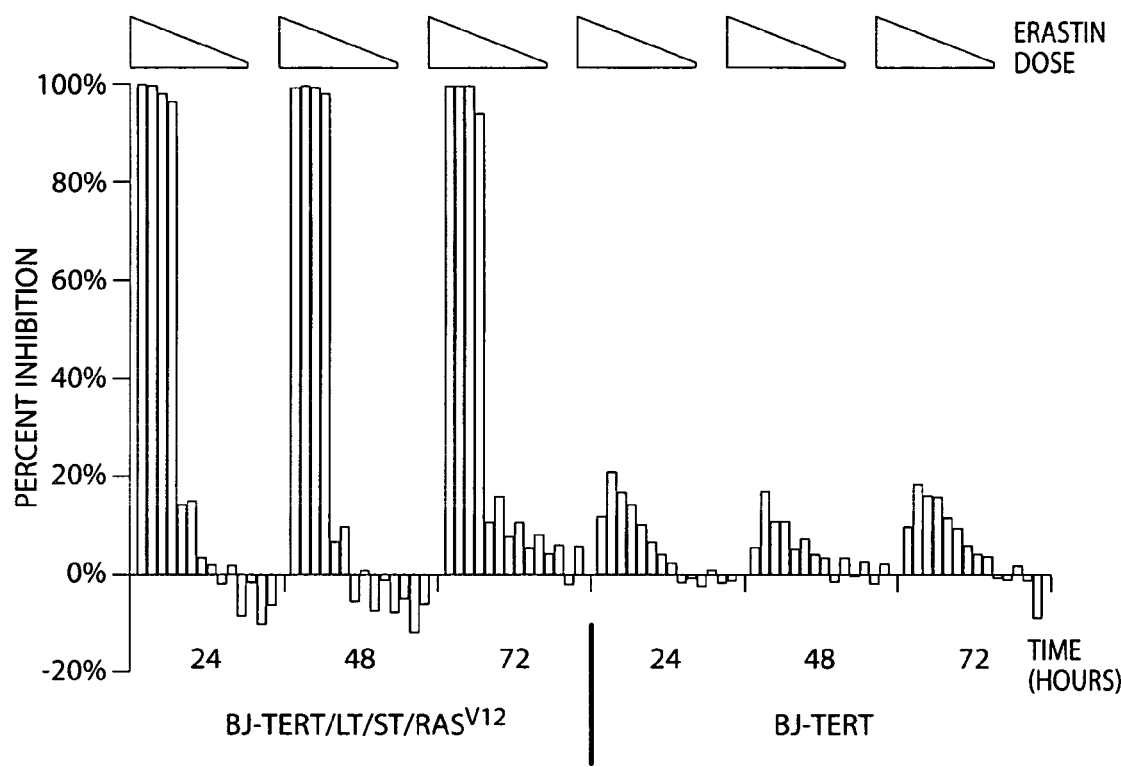
FIG. 6 shows that erastin induces rapid cell death in a ST/RAS$^{V12}$-dependent fashion. (A) Time-dependent effect of erastin on BJ-TERT and BJ-TERT/LT/ST/RAS$^{V12}$ cells. Cells were seeded in 384-well plates in the presence of the indicated concentrations of erastin. Inhibition of cell viability was determined after 24, 48 and 72 hours using calcein AM. (B) Effect of erastin on Alamar Blue viability staining in BJ-TERT (red) and BJ-TERT/LT/ST/RAS$^{V12}$ (blue) cells. (C) Photograph of BJ-TERT/LT/ST/RAS$^{V12}$ and BJ primary cells treated with erastin. Cells were allowed to attach overnight, then treated with 9 μM erastin for 24 hours and photographed.
Figure 6B:
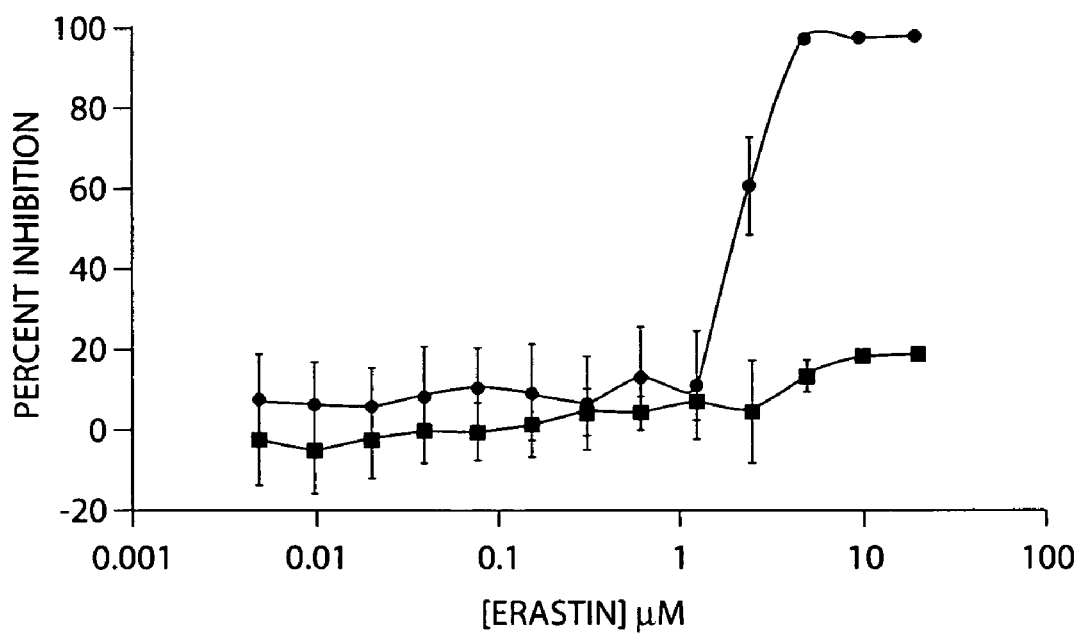
Figure 6C:
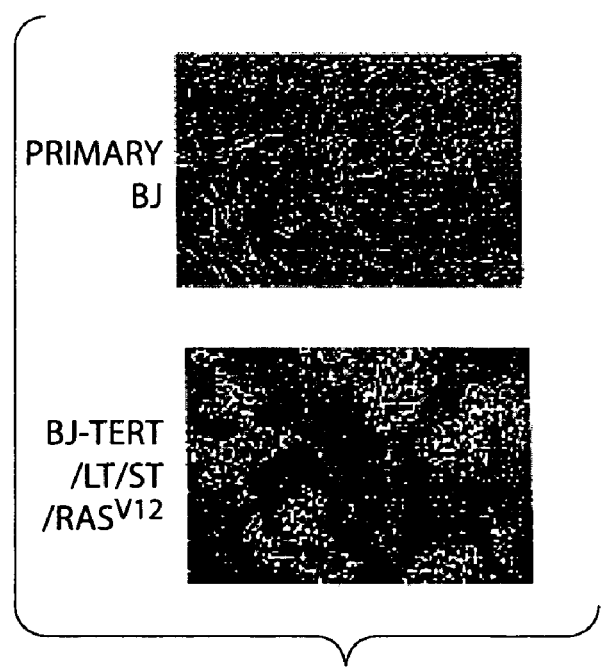

Erastin's ability to induce non-apoptotic cell death is selective for ST- and RAS$^{V12}$ expressing cells. Longer treatments and higher concentrations of erastin had little effect on the viability of cells lacking RAS$^{V12}$ or ST, confirming the qualitative nature of erastin's selectivity (FIG. 6A, C). As erastin-treated cells do not undergo apoptosis, Applicants sought to confirm that erastin genuinely induces cell death, rather than cell detachment. They quantitated cell viability in the presence of erastin using Alamar Blue (Ahmed et al., 1994, J. Immunol. Methods 170, 211-224), a viability dye that measures intracellular reductive potential. Erastin exhibited selective lethality in tumorigenic BJ-TERT/LT/ST/RAS$^{V12}$ cells relative to BJ-TERT cells in this homogeneous Alamar Blue viability assay (FIG. 6B). BJ-TERT/LT/ST/RAS$^{V12}$ cells treated with erastin for 18 hours rounded up and detached (FIG. 6C), failed to exclude the vital dye Trypan Blue, displayed a loss of mitochondrial membrane potential as assayed by the potentiometric dye JC-1, and had a small cell size characteristic of dead cells. Applicants determined that the loss of viability induced by erastin is irreversible once completed, in that BJ-TERT/LT/ST/RAS$^{V12}$ cells treated with erastin for 24 hours rounded up, detached and were unable to recover when replated in erastin-free medium. Thus, erastin induces rapid (12-24 h), irreversible, non-apoptotic cell death in a ST- and RAS$^{V12}$-dependent fashion.

Figure 10:
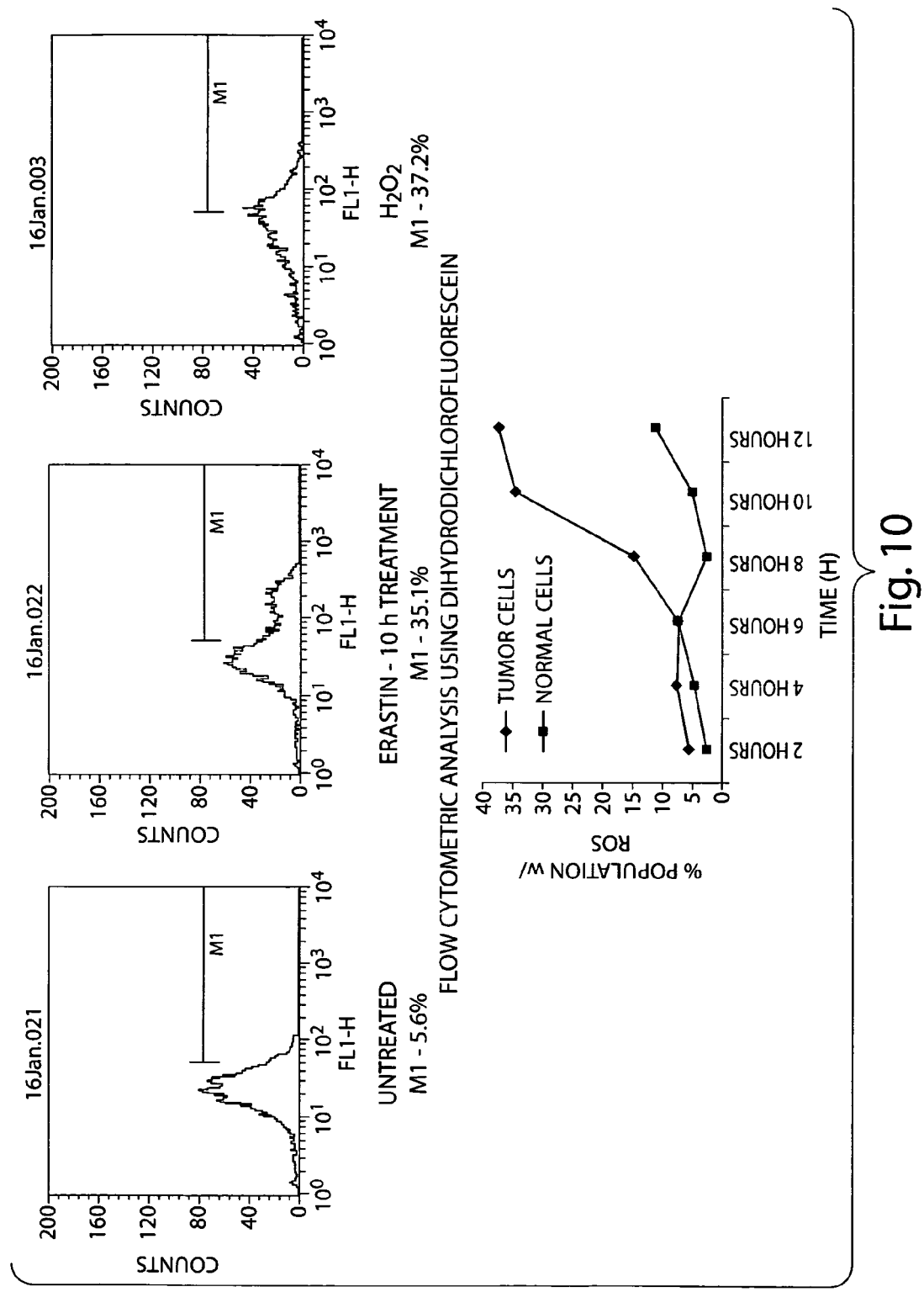
FIG. 10 shows that erastin induces the formation of reactive oxygen species.

Studies were additionally conducted that demonstrated that erastin induces the formation of reactive oxygen species (see FIG. 10).

Screens for suppressors (inhibitors) of erastin activity were carried out. Four anti-oxidants that suppress erastin activity were identified, one of which was the anti-oxidant, α-tocopherol.

The following methods and materials were used in the examples described herein.

Constructs and Retroviruses

Expression constructs for hTERT, LT, ST, SV40 Early Region, and HRAS$^{V12}$ were used as previously described (Hahn et al., 1999, supra; Hahn et al., 2002, supra)). hTERT-pWZL-Blaste, E6-pWZL-zeoe, and E6E7-pWZL-Zeoe were previously described (Lessnick et al., 2002, supra). The E6 and LT cDNAs were cloned into the pWZL-Hygroe retroviral vector (a kind gift from J. Morgenstern, Millenium Pharmaceuticals). Vesicular stomatitis virus-G glycoprotein pseudotyped retroviruses were prepared, and infections carried out as described previously (Lessnick et al., 2002, supra).

Cell Lines

TIP5 primary fibroblasts (Lessnick et al., 2002, supra) were prepared from discarded neonatal foreskins and were immortalized by infection with hTERT-pWZL-blaste or hTERT-pBabe-hygro retroviruses and selection with either blasticidin or hygromycin, respectively. BJ cells were a gift of Jim Smith. hTERT-immortalized fibroblasts were infected with the indicated retroviruses and selected for the appropriate markers. All BJ derivatives were cultured in a 1:1 mixture of DMEM and M199 supplemented with 15% inactivated fetal bovine serum, penicillin and streptomycin (pen/strep). TIP5 cells were grown in DMEM containing 10% FBS and pen/strep. All cell cultures were incubated at 37° C. in a humidified incubator containing 5% $CO_2$.

Compound Libraries

An annotated compound library (ACL) comprising 1,540 compounds, an NCI diversity set of 1,990 compounds obtained from the National Cancer Institute and a combinatorial library (Comgenex International, Inc.) containing 20,000 compounds were used in the tumor-selective synthetic lethal screens. All compound libraries were prepared as 4 mg/ml solutions in DMSO in 384-well polypropylene plates (columns 3-22) and stored at −20° C. Camptothecin (cat#C9911, MW 348.4), doxorubicin (cat#D1515 MW 580.0), daunorubicin (cat#D8809, MW 564.0), mitoxantrone (cat#M6545, MW 517.4), okadaic acid (cat#O4511, MW 805.0), echinomycin (cat#E4392, MW 1101), sangivamycin (cat#S5895, MW 309.3) were obtained from Sigma-Aldrich Co. Bouvardin (MW 772.84) and NSC146109 (MW 280.39) were obtained from the National Cancer Institute's Developmental Therapeutics Program. Erastin (MW 545.07) was obtained from Comgenex International, Inc.

Calcein AM Viability Assay

Calcein acetoxylmethyl ester (AM) is a cell membrane-permeable, non-fluorescent compound that is cleaved by intracellular esterases to form the anionic, cell-impermeable, fluorescent compound calcein. Viable cells are stained by calcein because of the presence of intracellular esterases and because the intact plasma membrane prevents fluorescent calcein from leaking out of cells (Wang et al., 1993, supra). Cells were seeded in 384-well plates using a Zymark Sciclone ALH, treated with each compound in triplicate at 4 µg/mL in the primary screen for two days, washed with phosphate-buffered saline on a Packard Minitrak with a 384-well washer and incubated for four hours with 0.7 µg/mL calcein (Molecular Probes). Total fluorescence intensity in each well was recorded on a Packard Fusion platereader, and converted to a percent inhibition of signal by subtracting the instrument background and dividing by the average signal obtained when cells were not treated with any compound.

Alamar Blue Viability Assay

Alamar Blue is reduced by mitochondrial enzyme activity in viable cells, causing both colorimetric and fluorescent changes (Nociari et al., 1998, J. Immunol. Methods 13, 157-167). Cells were seeded at a density of 6000 cells (50 µl) per well in a 384-well black, clear bottom plate using a syringe bulk dispenser (Zymark). 10 µl was removed from a two-fold serially diluted erastin plate (6×final concentration) using a 384 fixed cannula head, making the final concentration 20 µg/ml in the well with highest concentration. The plates were incubated for 24 hours. Alamar Blue (Biosource International) was added to each well by diluting 1:10 and incubated for 16 hours at 37° C. Fluorescence intensity was determined using a Packard Fusion platereader with an excitation filter centered on 535 nm and an emission filter centered on 590 nm. Average percentage inhibition at each concentration was calculated. Error bars indicate one standard deviation. The Alamar Blue assay does not involve washing the cells.

Screening

Replica daughter plates were prepared with a Zymark Sciclone ALH and integrated Twister II by diluting stock plates 50 fold in medium lacking serum and pen/strep to obtain a compound concentration in daughter plates of 80 µg/ml with 2% DMSO. Assay plates were prepared by seeding cells in black, clear bottom 384-well plates in columns 1-23 (6000 cells/well in 57 µl) using a syringe bulk dispenser. Columns 3-22 were treated with compounds from a daughter library plate by transferring 3 µl from the daughter library plate using 384-position fixed cannula array. The final compound concentrations in assay plates were thus 4 µg/ml. The assay plates were incubated for 48 hours at 37° C. in humidified incubator containing 5% $CO_2$. Plate processing for the calcein AM viability assay was performed using an integrated Minitrak/Sidetrak robotic system from Packard Bioscience (Perkin Elmer). Assay plates were washed with phosphate buffered saline, and 20 µl of calcein AM (0.7 µg/ml) per well was added. Plates were incubated at room temperature for 4 hours. Fluorescence intensity was determined using a Fusion platereader with filters centered on an excitation of 485 nm and an emission of 535 nm.

Retesting of Compounds in a Dilution Series

Compounds to be retested were purchased from manufacturers. Stocks were prepared in DMSO at a concentration of 1 mg/ml in 384-well polypropylene plates with a 16-point, two-fold dilution dose curve of each compound in a column, in duplicates. Column 1-2 and 23-24 were left empty for controls. Daughter retest plates were prepared from stock retest plate by diluting 66.6 fold in DMEM in 384-well deep-deep well plates (4.5 µl transfer into 300 µl). Cells were seeded at a density of 6000 per well in 40 µl, and 20 µl was added from a daughter retest plate. The plates were incubated for two days at 37° C. with 5% $CO_2$.

Data Analysis

Mean RFU (relative fluorescence units) for untreated cells was calculated by averaging columns 1, 2, and 23 (wells with cells but lacking compounds). The calcein background was calculated by averaging column 24 (wells with calcein, but lacking cells). Percentage inhibition of each well was calculated as [1−(RFU−calcein control)/(untreated cell−calcein control)*100]. Compounds causing at least 50% inhibition of calcein staining in the primary screen were tested for selectivity towards BJ-TERT/LT/ST/RAS$^{V12}$ engineered tumor cells by testing in BJ primary and BJ-TERT/LT/ST/RAS$^{V12}$ cells at a range of concentrations. Selective compounds were retested in all engineered cell lines.

Nuclear Morphology Assay 200,000 tumorigenic BJ-TERT/LT/ST/RAS$^{V12}$ cells were seeded in 2 mL on glass coverslips in each well of a six-well dish, treated with nothing (NT), 9 µM erastin or 1.1 µM camptothecin (CPT) in growth medium for 18 hours while incubating at 37° C. with 5% $CO_2$. Nuclei were stained with 25 µg/mL Hoechst 33342 (Molecular Probes) and viewed using an oil immersion 100× objective on a fluorescence microscope.

Cell Size Measurements 200,000 BJ-TERT/LT/ST/RAS$^{V12}$ cells were seeded in six-well dishes in 2 mL growth medium only (No treatment), with 9 µM erastin or with 1.1 µM camptothecin (CPT). After 24 hours, cells were released with trypsin/EDTA, diluted to 10 mL in growth medium, and the cell size distribution of each sample was determined on a Coulter Counter.

Cell Counting Assay for Camptothecin Activity

BJ-TERT/LT/ST/RAS$^{V12}$ cells were seeded in 6-well dishes (200 000 cells/well; 2ml per well) and transfected in serum- and antibiotic-free medium using Oligofectamine (Life Technologies), with 100 nM siRNA per well in a total volume of one milliliter. 500 µl of medium containing 30% FBS was added 4 hours after transfection. Cells were treated with the indicated concentrations of camptothecin 30 hours after transfection. 500 µl of a 5× solution of the desired camptothecin concentration was added to each well. Cells were removed with trypsin-EDTA and counted using a hemacytometer 75 hours after transfection. Control experiments indicated the transfection efficiency was approximately 10%.

Western Blot Analysis

Caspase-3

BJ-TERT/LT/ST/RAS$^{V12}$ cells were seeded prior to the experiment at 5×10$^5$ cells in 60 mm dishes. The cells were treated with 5 µg/ml erastin (9 µM) for 2, 4, 6, 8 or 10 hours. One dish was maintained for camptothecin treatment (0.4 µlg/ml for 24 h) as a positive control. Cells were lysed after each time point in lysis buffer (50 mM HEPES KOH pH 7.4, 40 nM NaCl, 2 mM EDTA, 0.5% Triton X-100, 1.5 mM Na$_3$VO$_4$, 50 mM NaF, 10 mM sodium pyrophosphate, 10 mM sodium beta-glycerophosphate and protease inhibitor tablet (Roche)). Protein content was quantified using a Biorad protein assay reagent. Equal amounts of protein were resolved on 16% SDS-polyacrylamide gel. The electrophoresed proteins were transblotted onto a PVDF membrane, blocked with 5% milk and incubated with anti-active caspase-3 polyclonal antibody (BD Pharmingen) at 1:1500 dilution overnight at 4° C. The membrane was then incubated in anti-rabbit-HRP (Santa Cruz Biotechnology) at 1:3000 dilution for 1 hour and developed with an enhanced chemiluminescence mixture (NEN life science, Renaissance). To test for equivalent loading in each lane, blots were stripped, blocked, and probed with an anti-eIF-4E antibody (BD Transduction laboratories) at 1:1000 dilution.

Topoisomerase-IIα

BJ, BJ-TERT, BJ-TERT/LT/ST, BJ-TERT/LT/ST/RAS$^{V12}$, BJ-TERT/LT/RAS$^{V12}$ and BJ-TERT/LT/RAS$^{V12}$/ST cells were seeded at 1×10$^6$ cells per dish in 60 mm dishes.

After overnight incubation of the cells at 37° C. with 5% $CO_2$, the cells were lysed as described above and proteins resolved on a 10% polyacrylamide gel. The membrane was incubated with monoclonal anti-human topoisomerase IIα p170 antibody (TopoGEN) at 1:1000 dilution overnight at 4° C. and then with anti-mouse HRP (Santa Cruz Biotechnology).

Topoisomerase 1 (TOP1)

A 21-nucleotide double stranded siRNA directed against TOP1 (nucleotides 2233-2255, numbering from the start codon, Genbank accession J03250) was synthesized (Dharmacon, purified and desalted/deproteted) and transfected (100 nM) into and BJ-TERT/LT/ST/RAS$^{V12}$ cells in six-well dishes with oligofectamine (Life Technologies). After 75 hours, cells were lysed and the expression level of TOP1 determined by Western blot (Topogen, Cat# 2012-2, 1:1000 dilution). The protein loading level was determined by stripping and reprobing the same blot with an antibody directed against eIF-4E (BD Biosciences, Cat# 610270, 1:500 dilution). Alternatively, $1\times10^6$ cells were seeded in 60 mm dishes and grown overnight at 37° C, with 5% $CO_2$, then lysed with 150 μl of lysis buffer. Cells were removed with a scraper and transferred to microcentrifuge tubes and incubated on ice for 30 minutes. The protein contents in the lysates were quantified using a Biorad protein estimation assay reagent. Equal amounts of protein were loaded on 10% gradient SDS-polyacrylamide gel. The electrophoresed proteins were transblotted onto PVDF membrane. After blocking with 5% dry milk, the membrane was incubated with mouse anti-human topoisomerase I antibody (Pharmingen) overnight at 4° C., then with anti-mouse peroxidase conjugate antibody (Santa Cruz Biotechnology).

Annexin V-FITC Apoptosis Assay

BJ-TERT/LT/ST/RAS$^{V12}$ cells were seeded at $1\times10^6$ cells per dish in 100 mm dishes and allowed to grow overnight. Cells were treated with erastin (5 or 10 μg/ml) for 6, 8 or 11 h. A camptothecin-treated (0.4 μg/ml) control was maintained, treated at the time of seeding for 20 hours. After the treatment, cells were harvested with trypsin/EDTA and washed once with fresh medium containing serum and then twice with phosphate buffered saline. Cells were resuspended in 1× binding buffer (BD Pharningen) at a concentration of $1\times10^6$ cells/ml. 100 μl (133 $10^5$ cells) was incubated with 5 μl of Annexin V-FITC (BD Pharmingen) and propidium iodide (BD Pharmingen) for 15 minutes in the dark at room temperature. Then 400 μl of the 1× binding buffer was added and the cells analyzed by flow cytometry (Becton-Dickinson). Data were acquired and analyzed using Cellquest software. Only viable cells that did not stain with propidium iodiode were analzyed for Annexin V-FITC staining using the FL1 channel.

ROS analysis: Flow Cytometry Analysis Using H2DCF-DA

2',7'-dichlorodihydrofluorescein diacetate (H2DCF-DA) is a non-fluorescent cell permeable compound. The endogenous esterase enzyme inside the cell cleaves the diacetate part, and it can no longer pass out of the cell. Thus it accumulates in the cell. Then H2DCF reacts with ROS to form fluorescent dichlorofluoroscene (DCF) which can be measured by flow cytometry in FL1 channel.

1. Seed cells at $3\times1$ cells per dish in 60mm dishes and allow to grow overnight.
2. Treat with the test compound for different period of time (1-10 hr).
3. Maintain one dish for untreated cells, compound treated cell and positive control dish (hydrogen peroxide treated) for each time point.
4. Incubate the cells with 10 μM of H2DCF-DA for 10 minutes at 37° C.
5. For positive control cells, after 5 minutes of H2DCF-DA loading, add 500 μM of hydrogen peroxide and incubate for 5 minutes further.
6. Harvest the cell by trypsinization.
7. Wash with cold PBS-twice.
8. Resuspend the pellet in 100 μl of PBS and transfer into 5 ml FACS tube.
9. Add 5 μl of propidium iodide (50 μg/ml) and incubate for 10 minutes on ice in dark.
10. Add 400 μl of PBS and analyze by flow cytometry (Becton-Dickinson).
11. Acquire the data and analyze using CellQuest software program.
12. Take only propidium iodiode negative cells (viable cells) for the analysis for DCF staining using the FL1 channel, PI in FL3 channel, plot a quadrant chart.

Screens of ACL Library for Compounds that can Suppress Erastin Activity in BJELR Cells.

Method:

ACL library comprises 1,540 compounds and all compounds were prepared in DMSO at 4 μg/ml in 384-well polypropylene plates and stored at −20° C. Replica daughter plates for each library plate were prepared using Zymark Scilone ALH. The daughter plates were diluted 50 fold in DMEM and compound concentration in the daughter plate is 80 μg/ml with 2% DMSO. In assay plate compound from the daughter plate is diluted 20 fold with cell suspension, thus final concentration of each compound is 4 μg/ml.

BJELR cells were seeded at 6000 cells/well (57 μl) (for co-treatment screen) and 5000 cells/well (57 μl) (for pretreatment screen) in 384-well black, clear bottom plates using syringe bulk dispenser. For co-treatment suppressor screen, cells were treated with 3 μl of compound from the daughter plates of ACL library (final concentration in assay plate at 4 μg/ml) and at the same time treated with 5 μg/ml of erastin. Compound transfer was done using 384 fixed cannula head. Plates were incubated for 48 hours at 37° C. in incubator with 5% $CO_2$. For the pretreatment screens, cells were pre-incubated with the compound from ACL daughter library plate for overnight and then treated with 5 μg/ml of erastin for further 48 hours. Plates were processed for Calcein assay using Mini-Trak/SideTrak robotic system from Packard BioScience. Assay plates were washed with PBS and incubated with Calcein AM (0.7 μg/ml) for 4 hours at room temperature. Fluorescence intensity was determined using Fusion platereader with filters centered in an excitation of 485 nm and emission of 535 nm. BJELR cells are BJ-TERT/LT/ST/RAS$^{V12}$ cells.

Table 1 shows the potencies of tumor-selective compounds in engineered cell lines. Nine tumor-selective compounds were retested in 16-point, two-fold dilution dose-curves in all engineered cell lines. The table lists the concentration (in μg/mL) required to achieve 50% inhibition of calcein AM staining ($IC_{50}$) for each compound in each cell line. The $IC_{50}$ in primary BJ cells was divided by the $IC_{50}$ in BJ-TERT/LT/ST/RAS$^{V12}$ tumorigenic cells to obtain a tumor selectivity ratio for each compound. The compound selectivity for each genetic element was determined by calculating the selectivity ratio for each subsequent pair of cell lines in a series. Small T oncoprotein-selective compounds were considered to be selective for PP2A (the target of small T oncoprotein), whereas E6-selective compounds were considered to be selective for loss of p53 and E7-selective compounds were considered to be selective for loss of RB.

|  | BJ | BJ-TERT | BJ-TERT/ LT/ST | BJ-TERT/ LT/ST/Ras$^{v12}$ | BJ-TERT/ LT/Ras$^{v12}$ | BJ-TERT/ LT/Ras$^{v12}$/ST | BJ-TERT/ p53DD/CDK4$^{R24C}$/ cyclinD1/ST/Ras$^{v12}$ | TIP5-TERT | TIP5-TERT/LT |
|---|---|---|---|---|---|---|---|---|---|
| Echinomycin | >5 | 0.312 | 0.0048 | 0.0012 | 0.0048 | 0.0012 | 0.078 | >5 | 5 |
| Sangivamycin | 0.312 | 0.039 | 0.195 | 0.078 | 0.078 | 0.078 | 0.078 | 1.25 | 0.312 |
| NSC146109 | >5 | 5 | 2.5 | 2.5 | 5 | 2.5 | 5 | >5 | >5 |
| Bouvardin | 0.312 | 0.078 | 0.0195 | 0.078 | 0.078 | 0.0195 | 0.156 | >5 | 0.312 |
| Mitoxantrone | 5 | 1.25 | 0.312 | 0.312 | 1.25 | 0.312 | 1.25 | >5 | 1.25 |
| Doxorubicin | >5 | 1.25 | 0.312 | 1.25 | 1.25 | 1.25 | 1.25 | >5 | 1.25 |
| Daunorubicin | 5 | 1.25 | 0.312 | 0.312 | 1.25 | 0.625 | 0.625 | >5 | 1.25 |
| Camptothecin | >5 | >5 | 1.25 | 0.0195 | 1.25 | 0.0195 | 1.25 | >5 | >5 |
| Erastin | >5 | >5 | >5 | 1.25 | >5 | 1.25 | 2.5 | >5 | >5 |

|  | TIP5-TERT/ LT/ST | TIP5-TERT/ LT/ST/ Ras$^{v12}$ | TIP-TERT/ E6 | TIP5-TERT/ E6E7 | TIP5-TERT/ E6E7/ST | TIP5-TERT/ E6E7/ST/ Ras$^{v12}$ | Tumor Selectivity | Genetic basis of Selectivity |
|---|---|---|---|---|---|---|---|---|
| Echinomycin | 0.0048 | 0.0024 | >5 | 0.048 | 0.048 | 0.0048 | >8333 | non-specific |
| Sangivamycin | 0.039 | 0.078 | 0.156 | 0.078 | 0.078 | 0.078 | 4 | non-specific |
| NSC146109 | 5 | 2.5 | 5 | 2.5 | 2.5 | 2.5 | >4 | non-specific |
| Bouvardin | 0.039 | 0.039 | 0.078 | 0.039 | 0.039 | 0.078 | 4 | non-specific |
| Mitoxantrone | 0.625 | 1.25 | 1.25 | 0.625 | 0.625 | 1.25 | 16 | TERT/RB |
| Doxorubicin | 0.625 | 0.625 | 5 | 1.25 | 1.25 | 1.25 | >8 | TERT/RB |
| Daunorubicin | 0.625 | 0.625 | 5 | 0.625 | 0.625 | 0.625 | 16 | TERT/RB |
| Camptothecin | 0.156 | 0.156 | >5 | 0.625 | 0.156 | 0.156 | >512 | RAS$^{v12}$/PP2A/RB |
| Erastin | 5 | 2.5 | >5 | >5 | >5 | 5 | >8 | RAS$^{v12}$/PP2A |

Table 2 shows the potencies of tumor-selective compounds in engineered cell lines. The table lists the inhibition (negative % values) or enhancement (positive % values) of calcein AM staining (IC$_{50}$) for each compound in each cell line.

TABLE 2

| Molecule | Average % inhibition/enhancement of BJELR cells | Average % inhibition/enhancement of BJEH cells |
|---|---|---|
| 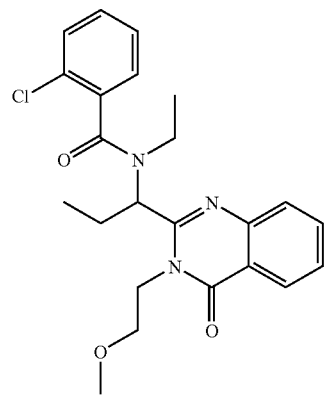 COX-0411806 | −19% | −1% |

TABLE 2-continued
| Molecule | Average % inhibition/enhancement of BJELR cells | Average % inhibition/enhancement of BJEH cells |
| --- | --- | --- |
| 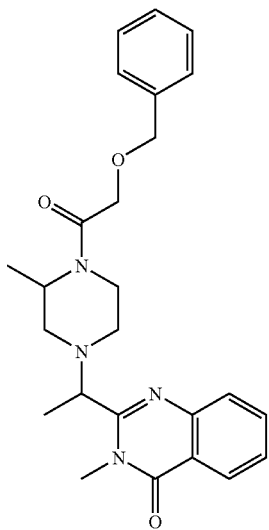<br>COX-04111086 | −41% | −10% |
| 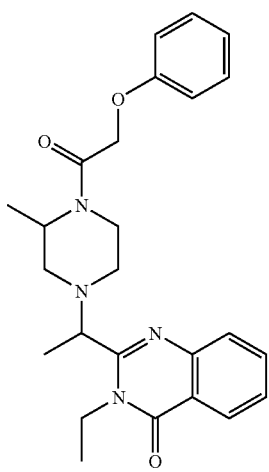<br>COX-04111530 | −6% | −9% |

TABLE 2-continued
| Molecule | Average % inhibition/enhancement of BJELR cells | Average % inhibition/enhancement of BJEH cells |
|---|---|---|
| 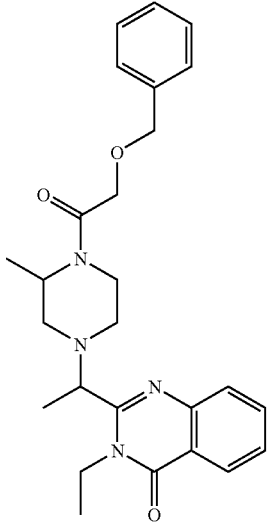 COX-04111576 | −15% | −1% |
| 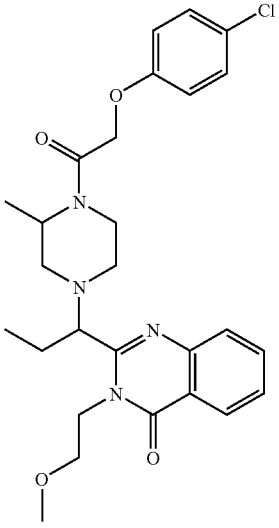 COX-0413826 | −41% | −7% |

TABLE 2-continued
| Molecule | Average % inhibition/enhancement of BJELR cells | Average % inhibition/enhancement of BJEH cells |
| --- | --- | --- |
| 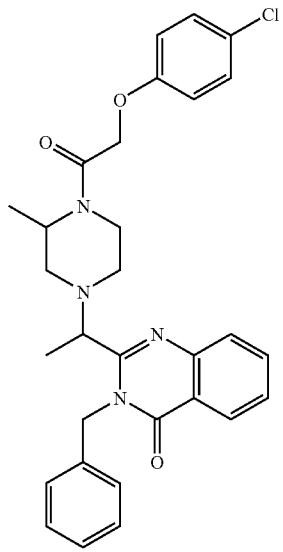 CGX-04111526 | −28% | −18% |
| 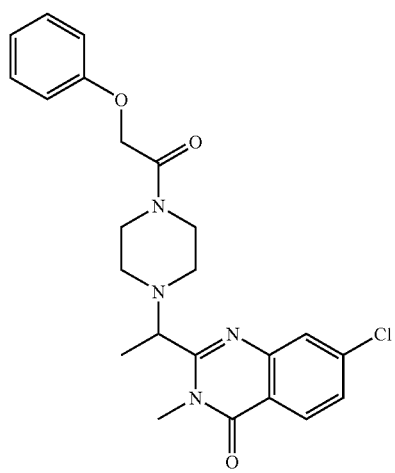 CGX-0424105 | −31% | 0% |

TABLE 2-continued
| Molecule | Average % inhibition/enhancement of BJELR cells | Average % inhibition/enhancement of BJEH cells |
|---|---|---|
| 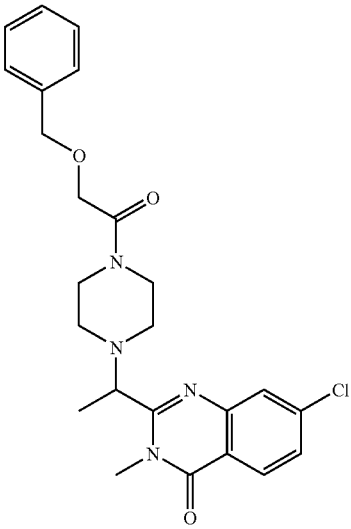 CGX-0424105 | −29% | −1% |
| 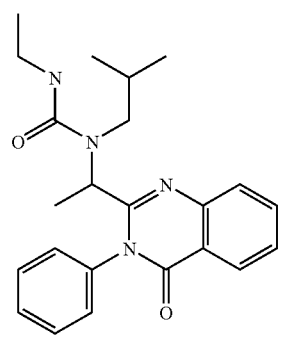 COX-0411806 | −26% | 0% |
| 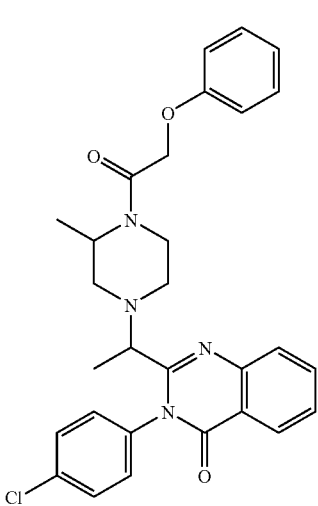 CGX-04111526 | −27% | −2% |

TABLE 2-continued
| Molecule | Average % inhibition/enhancement of BJELR cells | Average % inhibition/enhancement of BJEH cells |
| --- | --- | --- |
| 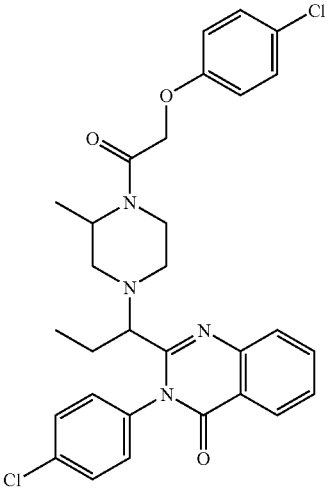<br>CGX-04111526 | −41% | 5% |
| 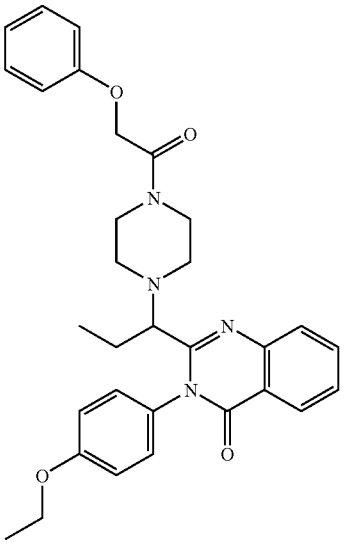<br>CGX-0424105 | −35% | −4% |

TABLE 2-continued
| Molecule | Average % inhibition/enhancement of BJELR cells | Average % inhibition/enhancement of BJEH cells |
|---|---|---|
| 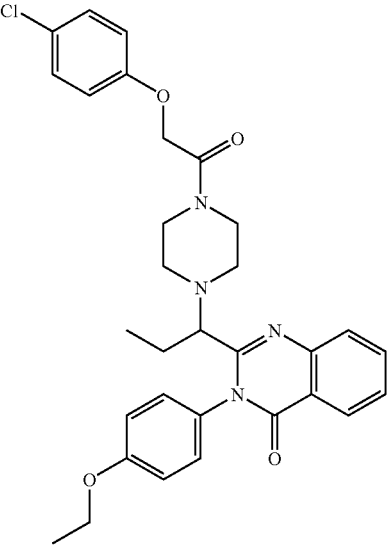<br>CGX-0424105 | −29% | 5% |
| 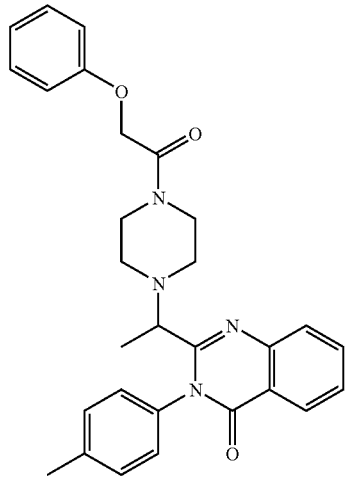<br>CGX-0424105 | −21% | −2% |

TABLE 2-continued
| Molecule | Average % inhibition/enhancement of BJELR cells | Average % inhibition/enhancement of BJEH cells |
|---|---|---|
| 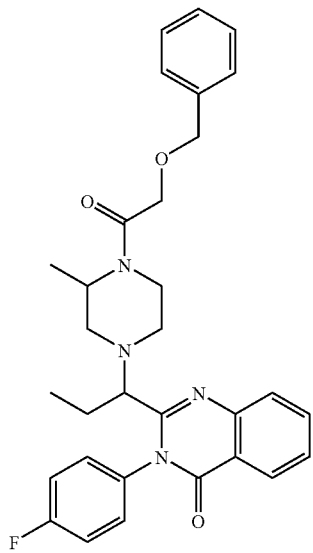 CGX-04111526 | −16% | −4% |
| 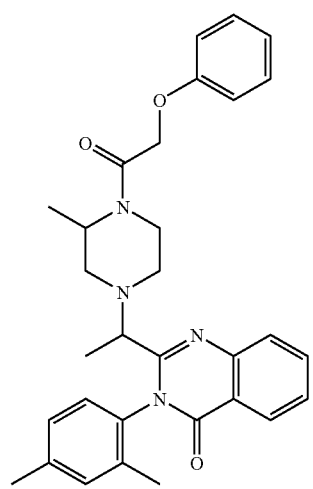 CGX-04111526 | −29% | −13% |

TABLE 2-continued
| Molecule | Average % inhibition/enhancement of BJELR cells | Average % inhibition/enhancement of BJEH cells |
| --- | --- | --- |
| 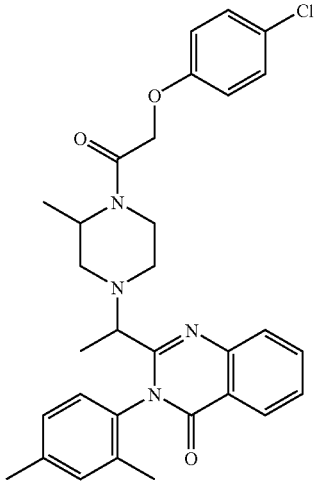CGX-04111526 | −25% | −10% |
| 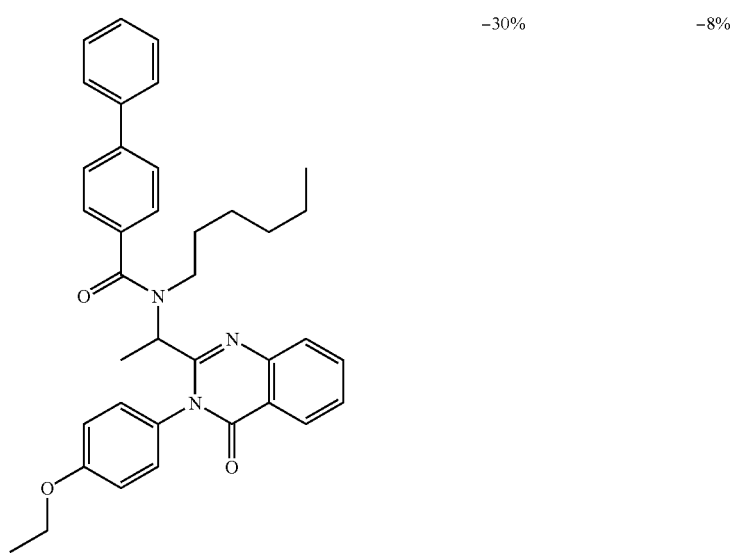CGX-0424105 | −30% | −8% |

TABLE 2-continued
| Molecule | Average % inhibition/enhancement of BJELR cells | Average % inhibition/enhancement of BJEH cells |
| --- | --- | --- |
| 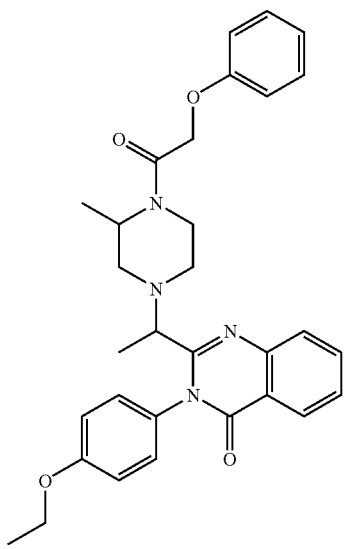<br>CGX-0424105 | −9% | −26% |
| 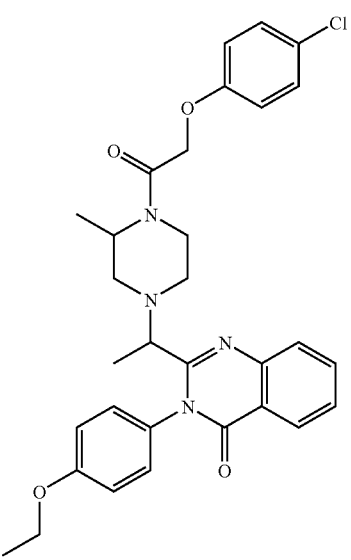<br>CGX-0424105 | −16% | −11% |

TABLE 2-continued
| Molecule | Average % inhibition/enhancement of BJELR cells | Average % inhibition/enhancement of BJEH cells |
|---|---|---|
| 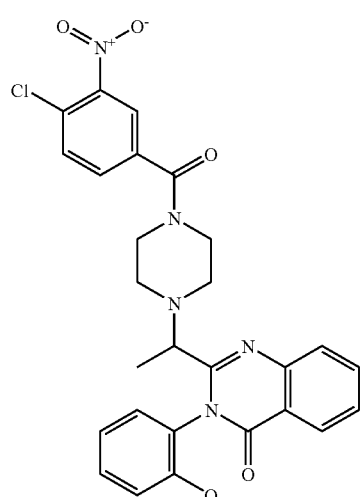 CGX-0424105 | −26% | 5% |
| 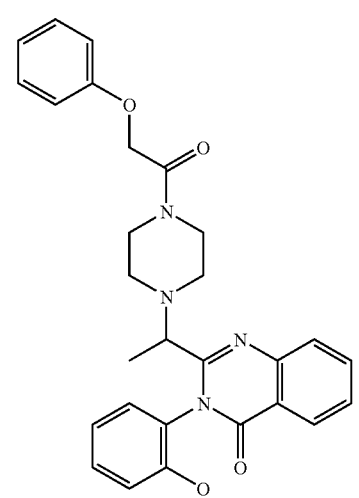 CGX-0424105 | −23% | −4% |

TABLE 2-continued
| Molecule | Average % inhibition/enhancement of BJELR cells | Average % inhibition/enhancement of BJEH cells |
| --- | --- | --- |
| 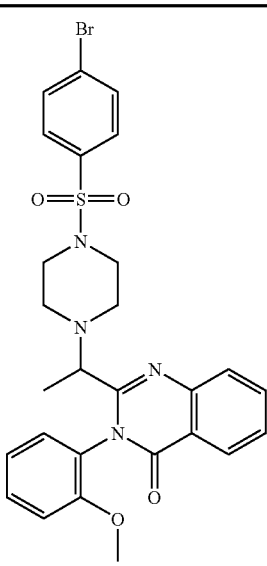<br>CGX-0424105 | −26% | 2% |
| 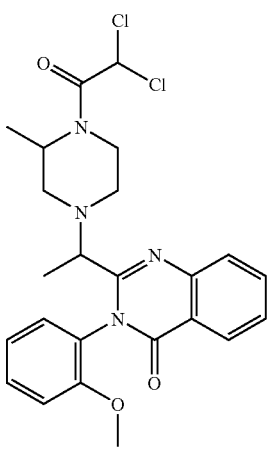<br>CGX-0424105 | −8% | −7% |
| 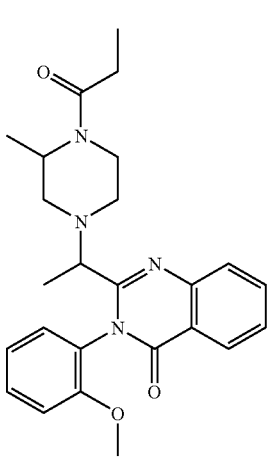<br>CGX-0424105 | 25% | 44% |

TABLE 2-continued
| Molecule | Average % inhibition/enhancement of BJELR cells | Average % inhibition/enhancement of BJEH cells |
|---|---|---|
| 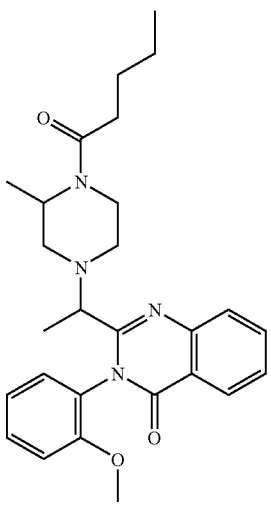<br>CGX-0424105 | −32% | 3% |
| 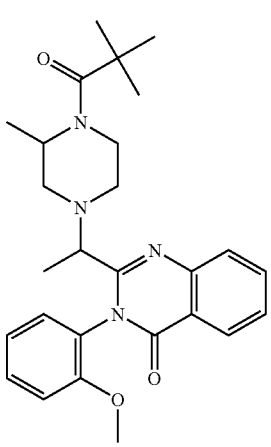<br>CGX-0424105 | −30% | −5% |
| 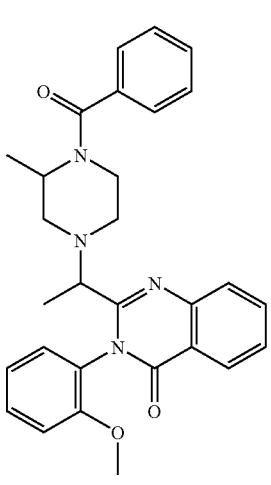<br>CGX-0424105 | −24% | 1% |

TABLE 2-continued
| Molecule | Average % inhibition/enhancement of BJELR cells | Average % inhibition/enhancement of BJEH cells |
| --- | --- | --- |
| 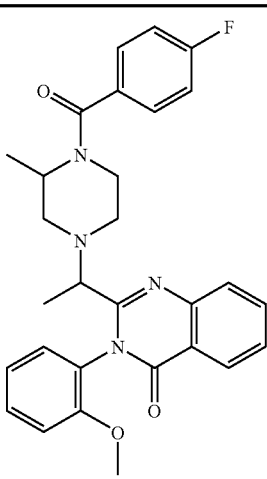<br>CGX-0424105 | −29% | −3% |
| 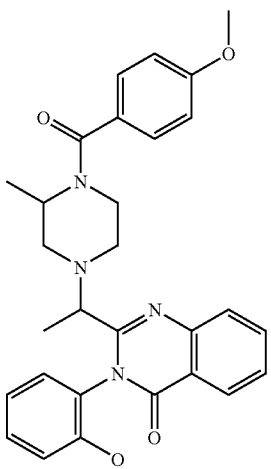<br>CGX-0424105 | −37% | 0% |
| 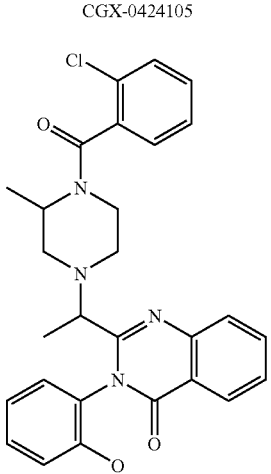<br>CGX-0424105 | −35% | −7% |

TABLE 2-continued
| Molecule | Average % inhibition/enhancement of BJELR cells | Average % inhibition/enhancement of BJEH cells |
| --- | --- | --- |
| 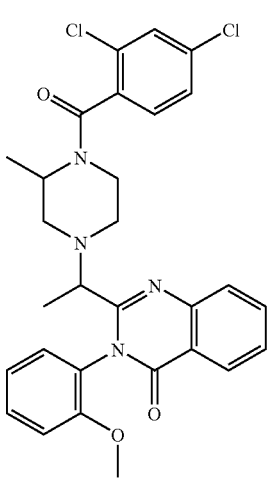<br>CGX-0424105 | −32% | 0% |
| 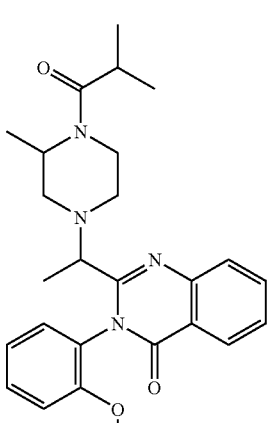<br>CGX-0424105 | −33% | 0% |

TABLE 2-continued
| Molecule | Average % inhibition/enhancement of BJELR cells | Average % inhibition/enhancement of BJEH cells |
|---|---|---|
| 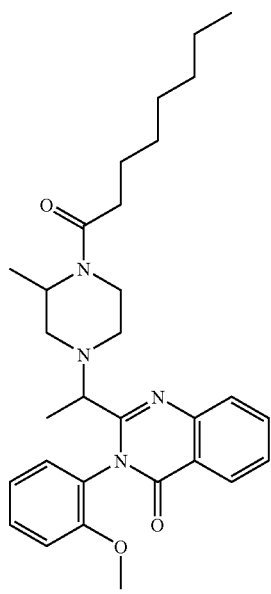<br>CGX-0424105 | −41% | −14% |
| 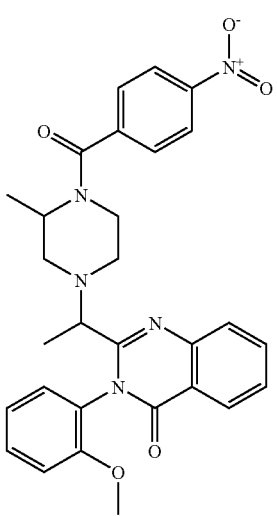<br>CGX-0424105 | −20% | 6% |

TABLE 2-continued
| Molecule | Average % inhibition/enhancement of BJELR cells | Average % inhibition/enhancement of BJEH cells |
| --- | --- | --- |
| 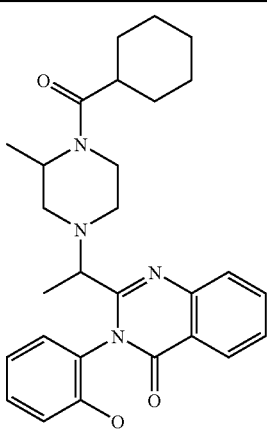<br>CGX-0424105 | −30% | −4% |
| 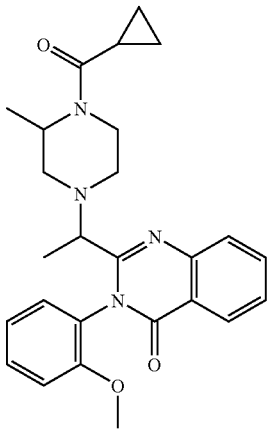<br>CGX-0424105 | 12% | 41% |
| 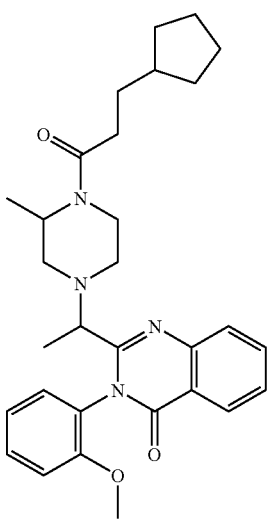<br>CGX-0424105 | 22% | 9% |

TABLE 2-continued
| Molecule | Average % inhibition/enhancement of BJELR cells | Average % inhibition/enhancement of BJEH cells |
| --- | --- | --- |
| 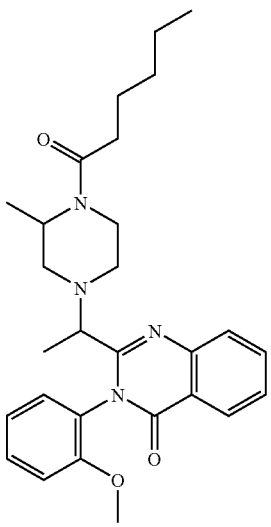<br>CGX-0424105 | −31% | 11% |
| 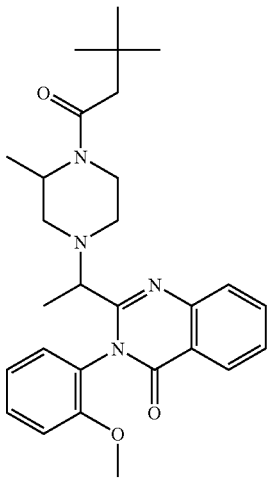<br>CGX-0424105 | −20% | 4% |

TABLE 2-continued
| Molecule | Average % inhibition/enhancement of BJELR cells | Average % inhibition/enhancement of BJEH cells |
|---|---|---|
| 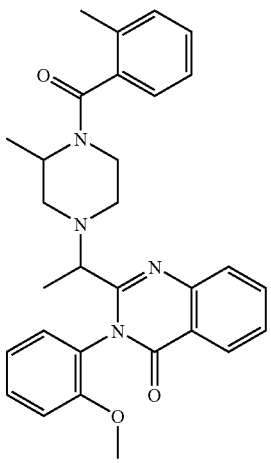<br>CGX-0424105 | −19% | 0% |
| 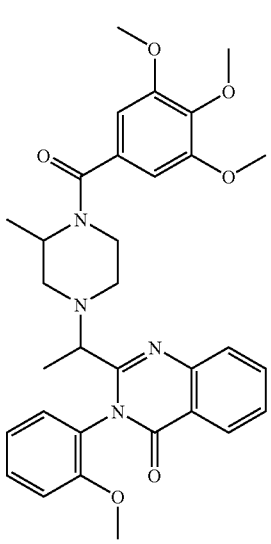<br>CGX-0424105 | −26% | 7% |

TABLE 2-continued
| Molecule | Average % inhibition/enhancement of BJELR cells | Average % inhibition/enhancement of BJEH cells |
| --- | --- | --- |
| 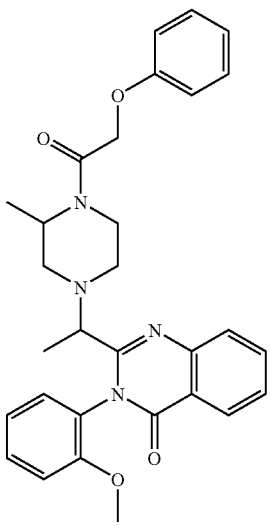 CGX-0424105 | −41% | −2% |
| 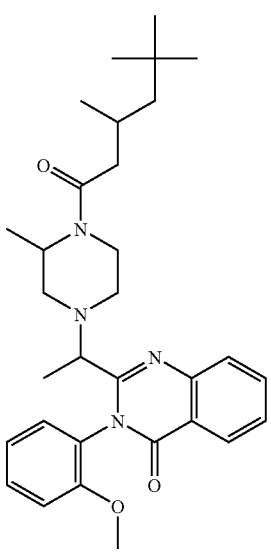 CGX-0424105 | −25% | −5% |

TABLE 2-continued
| Molecule | Average % inhibition/enhancement of BJELR cells | Average % inhibition/enhancement of BJEH cells |
| --- | --- | --- |
| 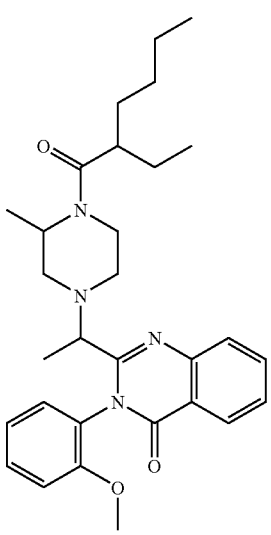
CGX-0424105 | −43% | 0% |
| 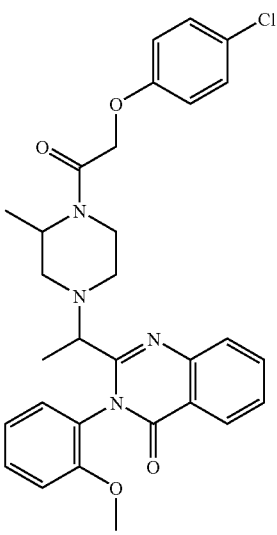
CGX-0424105 | −20% | 4% |

TABLE 2-continued
| Molecule | Average % inhibition/enhancement of BJELR cells | Average % inhibition/enhancement of BJEH cells |
| --- | --- | --- |
| 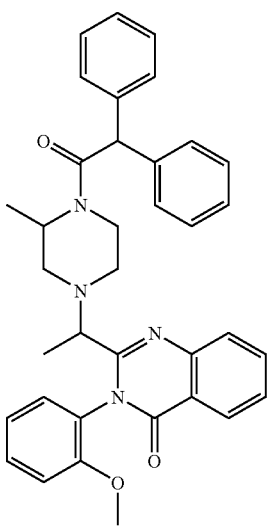<br>CGX-0424105 | −28% | 8% |
| 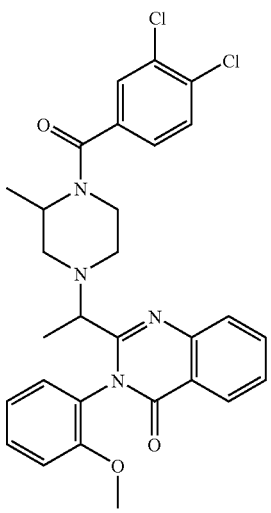<br>CGX-0424105 | −49% | −15% |

TABLE 2-continued
| Molecule | Average % inhibition/enhancement of BJELR cells | Average % inhibition/enhancement of BJEH cells |
| --- | --- | --- |
| 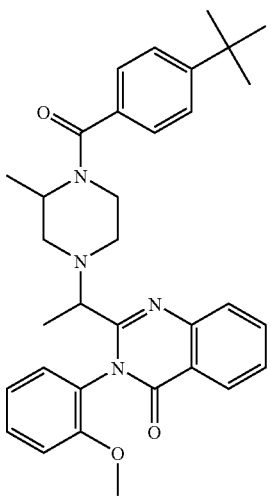<br>CGX-0424105 | −26% | 0% |
| 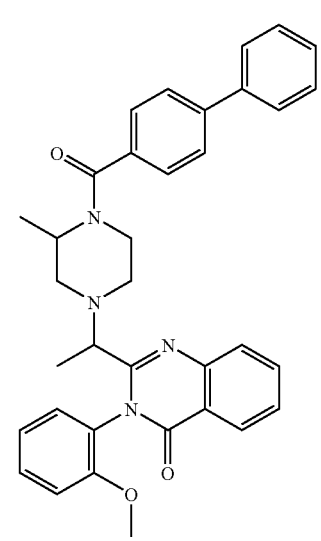<br>CGX-0424105 | −36% | −10% |

TABLE 2-continued
| Molecule | Average % inhibition/enhancement of BJELR cells | Average % inhibition/enhancement of BJEH cells |
| --- | --- | --- |
| 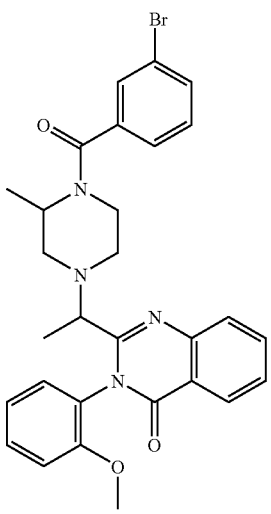
CGX-0424105 | 6% | 9% |
| 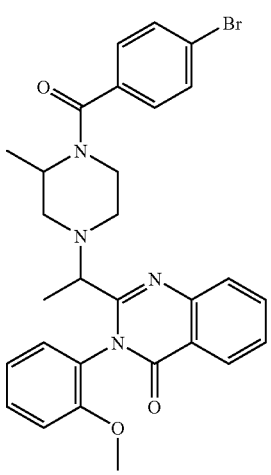
CGX-0424105 | −26% | −6% |

TABLE 2-continued
| Molecule | Average % inhibition/enhancement of BJELR cells | Average % inhibition/enhancement of BJEH cells |
| --- | --- | --- |
| 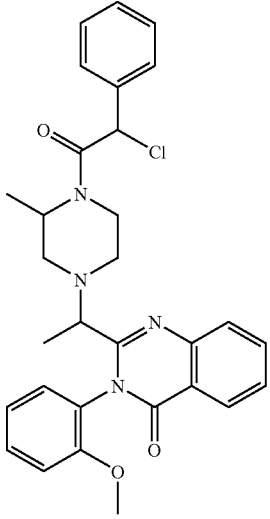<br>CGX-0424105 | −38% | −4% |
| 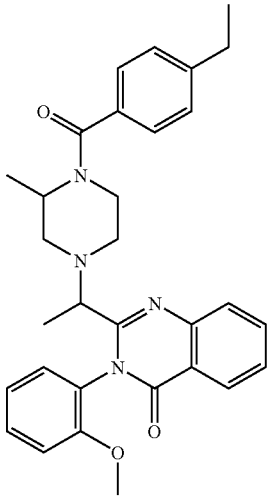<br>CGX-0424105 | −31% | −6% |

TABLE 2-continued
| Molecule | Average % inhibition/enhancement of BJELR cells | Average % inhibition/enhancement of BJEH cells |
| --- | --- | --- |
| 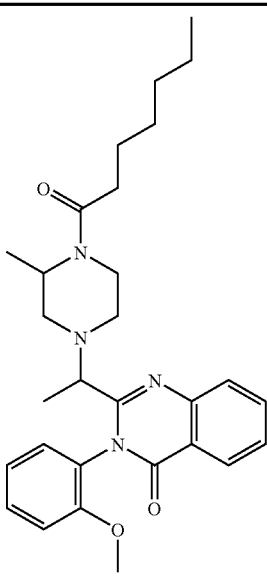<br>CGX-0424105 | −36% | −9% |
| 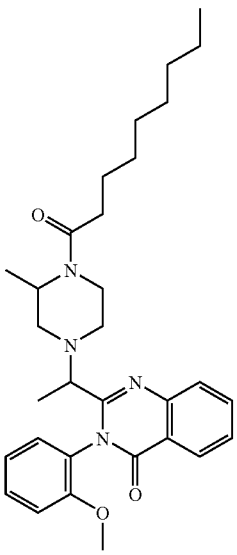<br>CGX-0424105 | −37% | −9% |

TABLE 2-continued
| Molecule | Average % inhibition/enhancement of BJELR cells | Average % inhibition/enhancement of BJEH cells |
| --- | --- | --- |
| 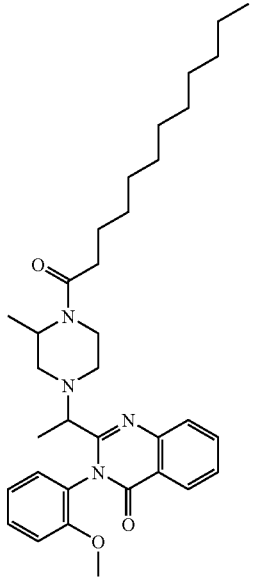 CGX-0424105 | −30% | 11% |
| 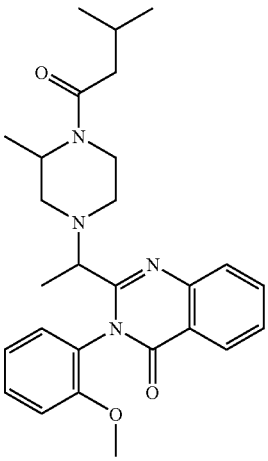 CGX-0424105 | −33% | 3% |

TABLE 2-continued
| Molecule | Average % inhibition/enhancement of BJELR cells | Average % inhibition/enhancement of BJEH cells |
|---|---|---|
| 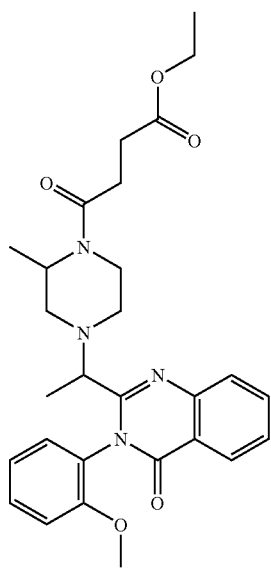<br>CGX-0424105 | −43% | −17% |
| 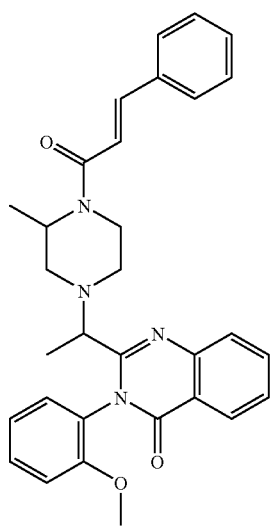<br>CGX-0424105 | −26% | 5% |

TABLE 2-continued
| Molecule | Average % inhibition/enhancement of BJELR cells | Average % inhibition/enhancement of BJEH cells |
|---|---|---|
| 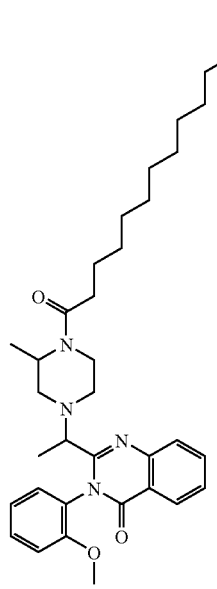 CGX-0424105 | −31% | 15% |
| 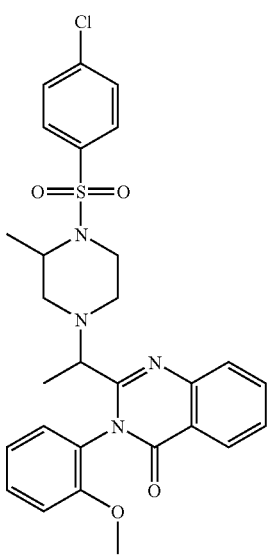 CGX-0424105 | −10% | −5% |

TABLE 2-continued
| Molecule | Average % inhibition/enhancement of BJELR cells | Average % inhibition/enhancement of BJEH cells |
| --- | --- | --- |
| 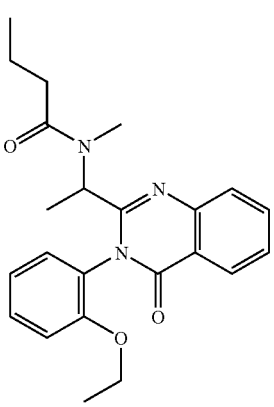
COX-0411806 | −34% | 3% |
| 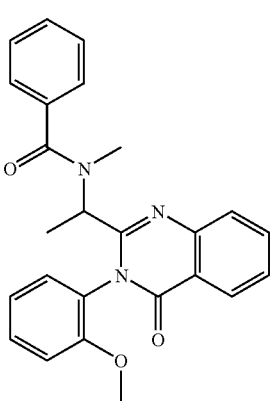
COX-0411806 | −48% | 4% |
| 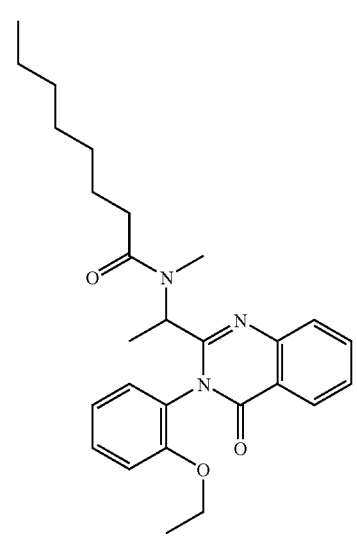
COX-0411806 | −27% | −1% |

TABLE 2-continued
| Molecule | Average % inhibition/enhancement of BJELR cells | Average % inhibition/enhancement of BJEH cells |
| --- | --- | --- |
| 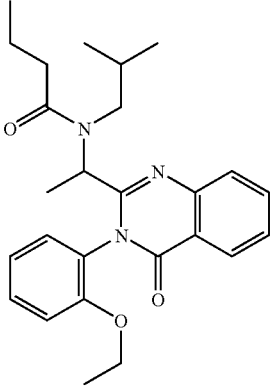<br>COX-0411806 | −33% | −10% |
| 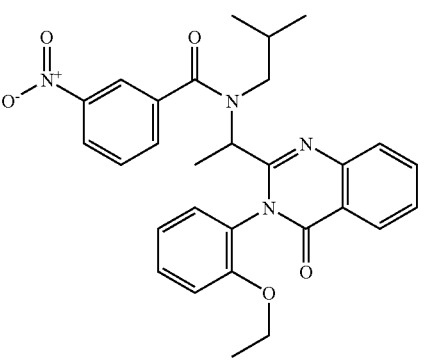<br>COX-0411806 | −23% | −5% |
| 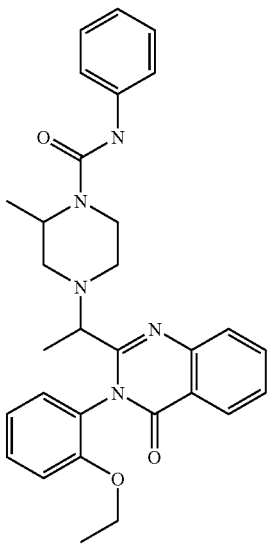<br>CGX-0424105 | −24% | −2% |

TABLE 2-continued
| Molecule | Average % inhibition/enhancement of BJELR cells | Average % inhibition/enhancement of BJEH cells |
|---|---|---|
| 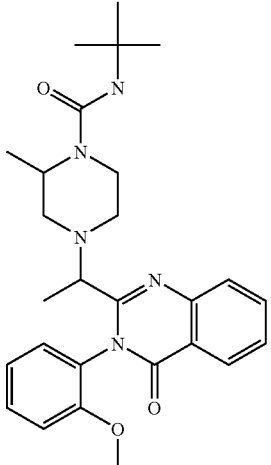<br>CGX-0424105 | −20% | −9% |
| 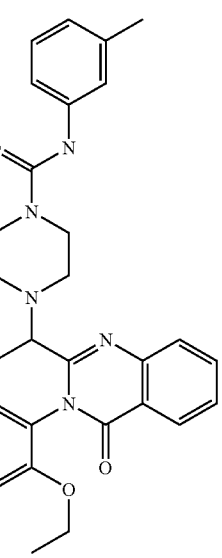<br>CGX-0424105 | −34% | −3% |

TABLE 2-continued
| Molecule | Average % inhibition/enhancement of BJELR cells | Average % inhibition/enhancement of BJEH cells |
| --- | --- | --- |
| 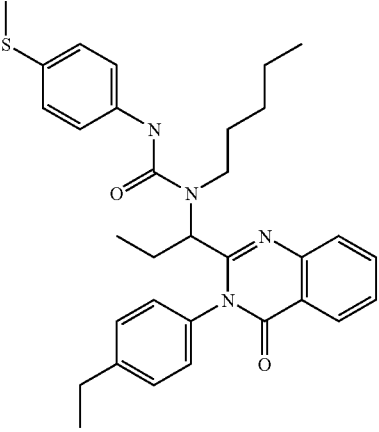  COX-0411806 | −25% | −9% |
| 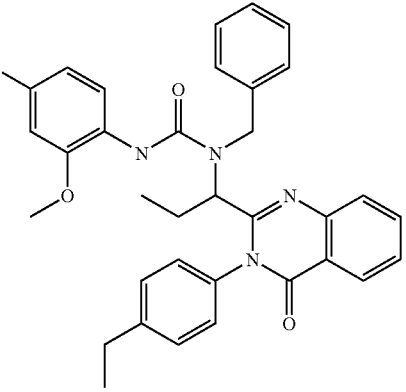  COX-0411806 | −28% | −4% |
| 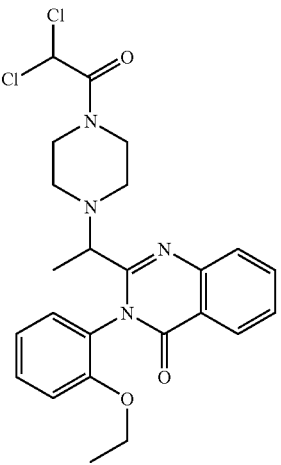  CGX-0424105 | −39% | 10% |

TABLE 2-continued
| Molecule | Average % inhibition/enhancement of BJELR cells | Average % inhibition/enhancement of BJEH cells |
|---|---|---|
| 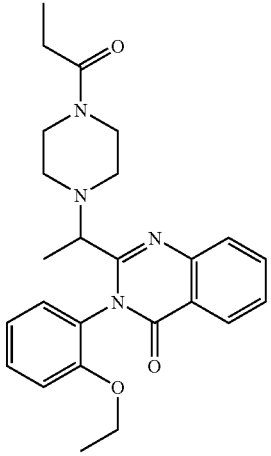<br>CGX-0424105 | −40% | −4% |
| 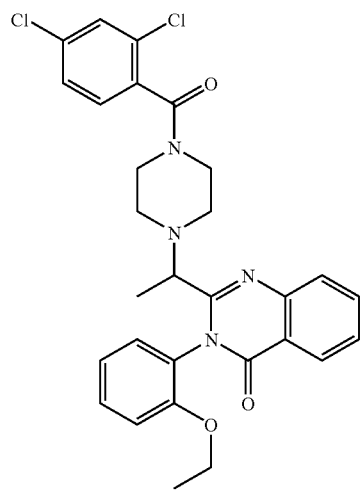<br>CGX-0424105 | −43% | 0% |
| 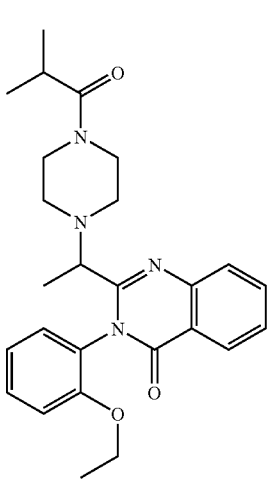<br>CGX-0424105 | 42% | 54% |

TABLE 2-continued
| Molecule | Average % inhibition/enhancement of BJELR cells | Average % inhibition/enhancement of BJEH cells |
|---|---|---|
| 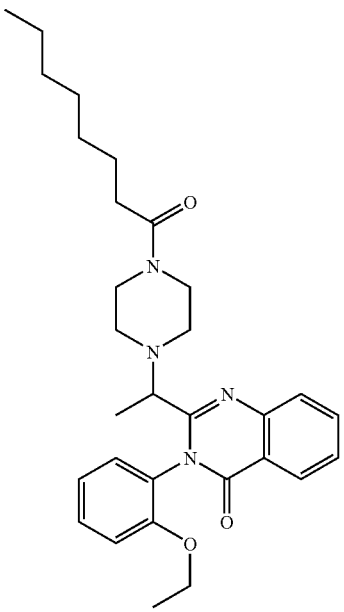 CGX-0424105 | −24% | 6% |
| 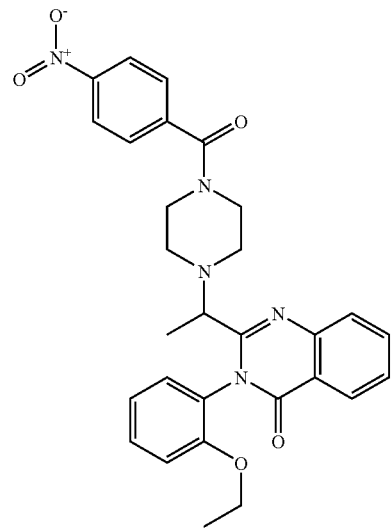 CGX-0424105 | −46% | 2% |

TABLE 2-continued
| Molecule | Average % inhibition/enhancement of BJELR cells | Average % inhibition/enhancement of BJEH cells |
|---|---|---|
| 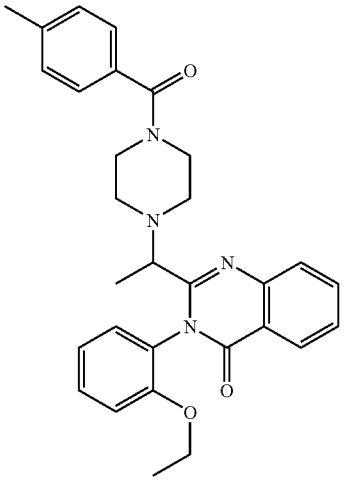 CGX-0424105 | −28% | −2% |
| 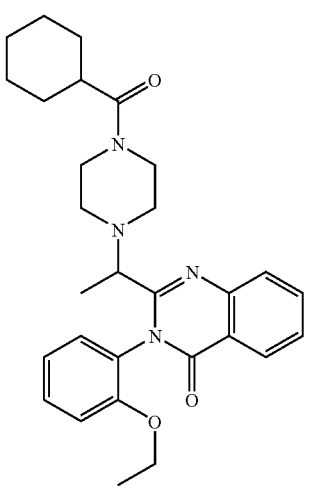 CGX-0424105 | −38% | 6% |
| 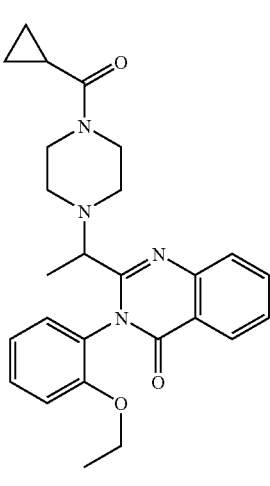 CGX-0424105 | 46% | 64% |

TABLE 2-continued
| Molecule | Average % inhibition/enhancement of BJELR cells | Average % inhibition/enhancement of BJEH cells |
|---|---|---|
| 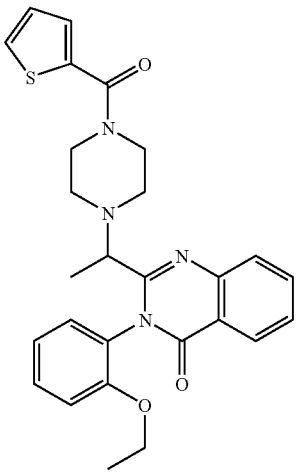 CGX-0424105 | −44% | −7% |
| 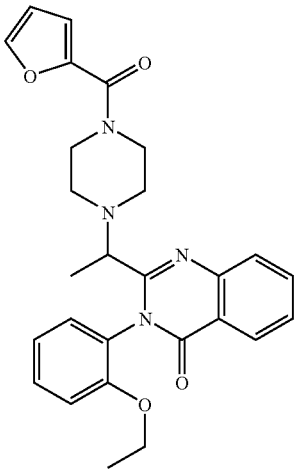 CGX-0424105 | −40% | −3% |
| 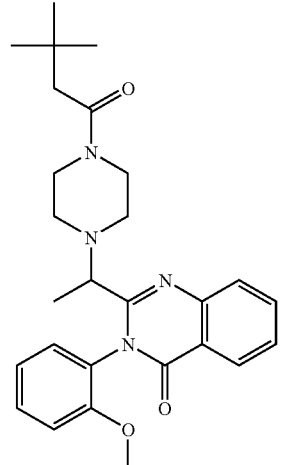 CGX-0424105 | −44% | −3% |

TABLE 2-continued
| Molecule | Average % inhibition/enhancement of BJELR cells | Average % inhibition/enhancement of BJEH cells |
|---|---|---|
| 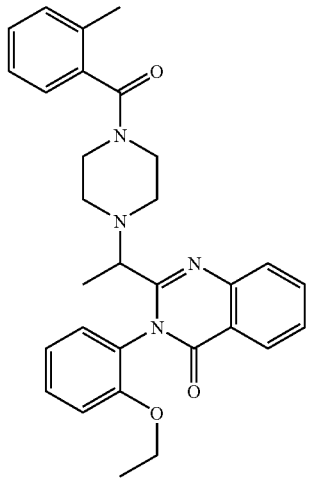 CGX-0424105 | −40% | 0% |
| 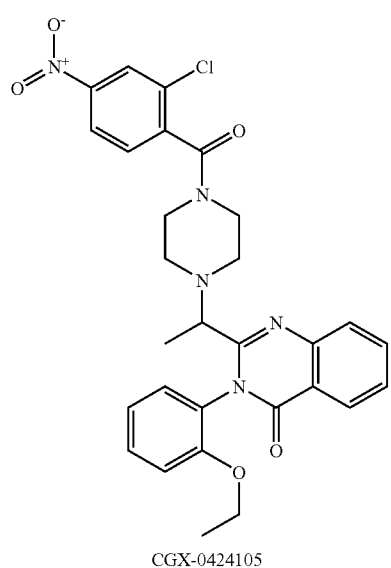 CGX-0424105 | −49% | −6% |

TABLE 2-continued
| Molecule | Average % inhibition/enhancement of BJELR cells | Average % inhibition/enhancement of BJEH cells |
| --- | --- | --- |
| 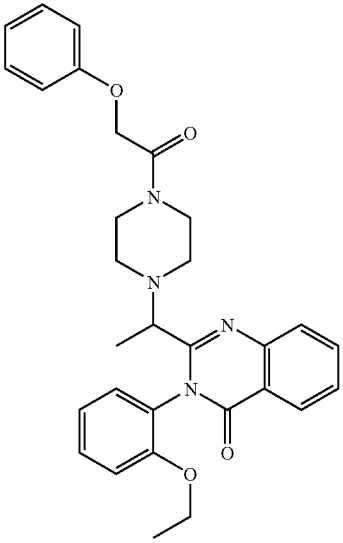<br>CGX-0424105 | −13% | −5% |
| 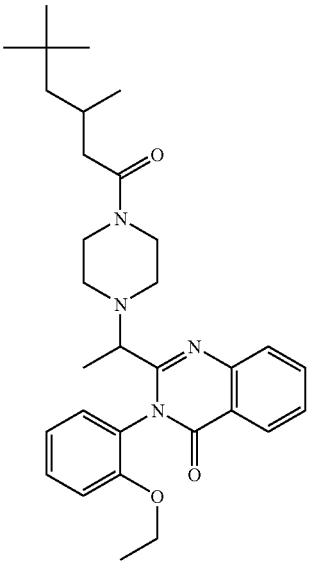<br>CGX-0424105 | −40% | −2% |

TABLE 2-continued
| Molecule | Average % inhibition/enhancement of BJELR cells | Average % inhibition/enhancement of BJEH cells |
|---|---|---|
| 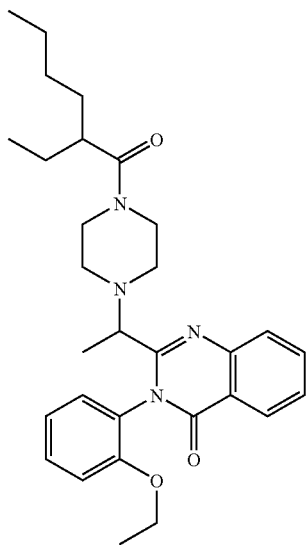 CGX-0424105 | −39% | 3% |
| 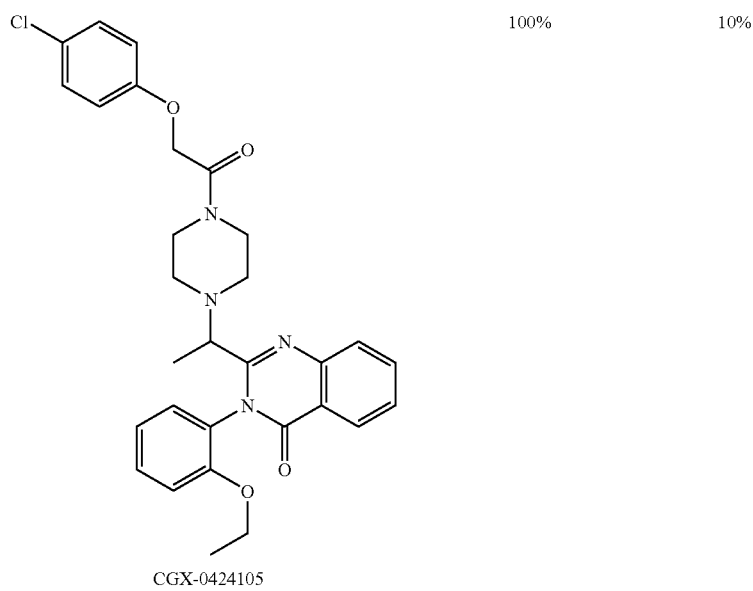 CGX-0424105 | 100% | 10% |

TABLE 2-continued
| Molecule | Average % inhibition/enhancement of BJELR cells | Average % inhibition/enhancement of BJEH cells |
| --- | --- | --- |
| 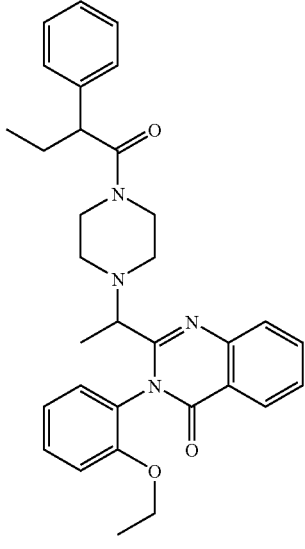<br>CGX-0424105 | −48% | −2% |
| 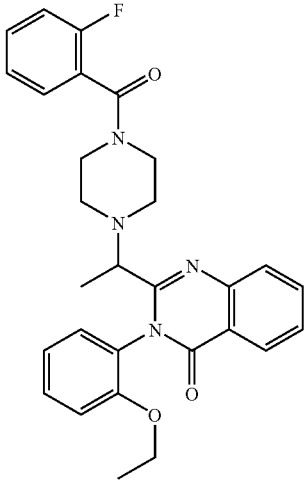<br>CGX-0424105 | −31% | 9% |

TABLE 2-continued
| Molecule | Average % inhibition/enhancement of BJELR cells | Average % inhibition/enhancement of BJEH cells |
|---|---|---|
| 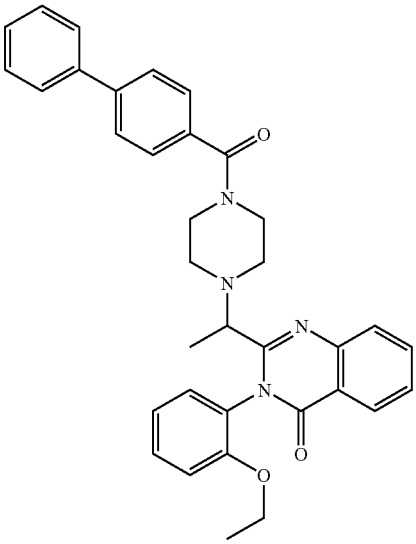
CGX-0424105 | −25% | 5% |
| 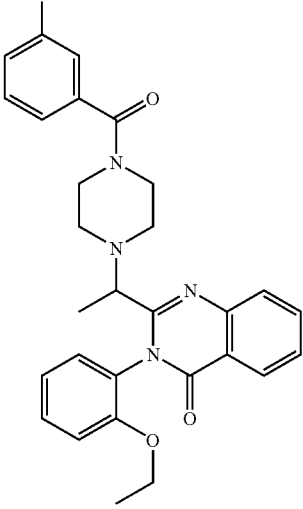
CGX-0424105 | −38% | −11% |

TABLE 2-continued
| Molecule | Average % inhibition/enhancement of BJELR cells | Average % inhibition/enhancement of BJEH cells |
| --- | --- | --- |
| 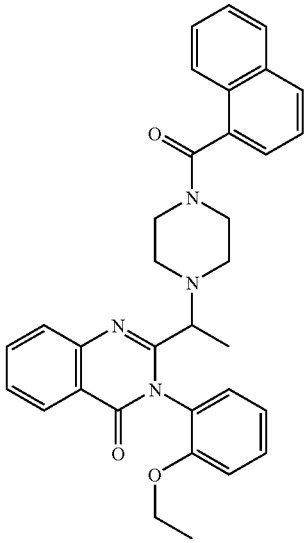<br>CGX-0424105 | −41% | 4% |
| 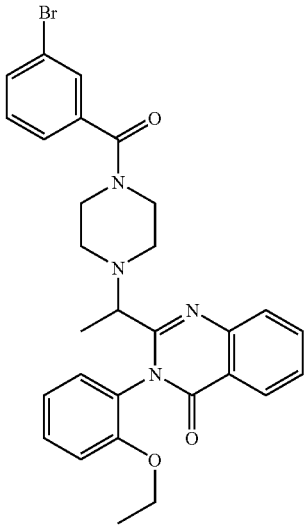<br>CGX-0424105 | −49% | 3% |

TABLE 2-continued
| Molecule | Average % inhibition/enhancement of BJELR cells | Average % inhibition/enhancement of BJEH cells |
| --- | --- | --- |
| 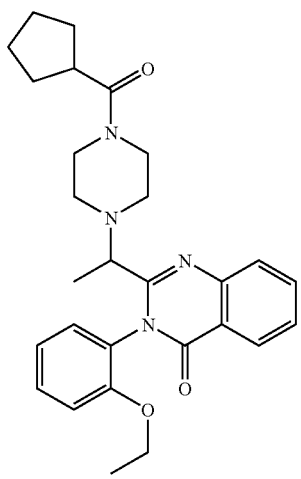<br>CGX-0424105 | −42% | 1% |
| 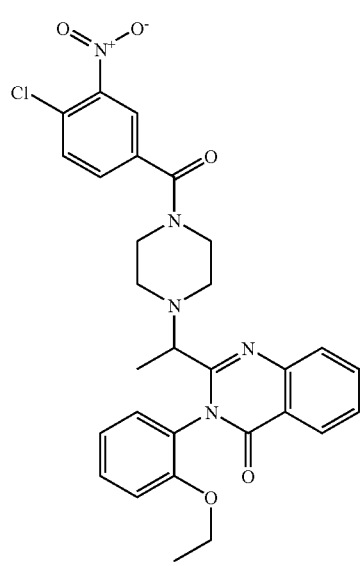<br>CGX-0424105 | −57% | −11% |

TABLE 2-continued
| Molecule | Average % inhibition/enhancement of BJELR cells | Average % inhibition/enhancement of BJEH cells |
| --- | --- | --- |
| 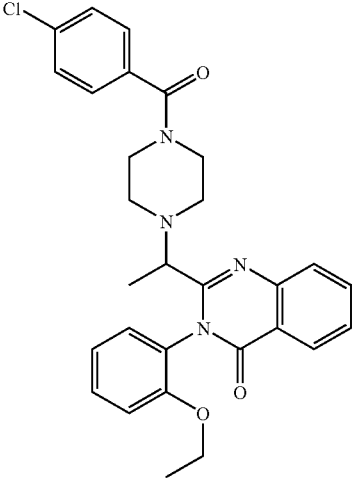<br>CGX-0424105 | −31% | 3% |
| 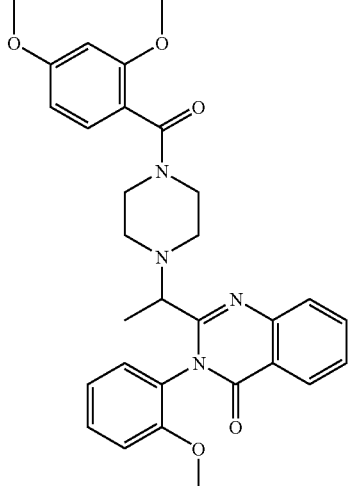<br>CGX-0424105 | −42% | −3% |

TABLE 2-continued
| Molecule | Average % inhibition/enhancement of BJELR cells | Average % inhibition/enhancement of BJEH cells |
| --- | --- | --- |
| 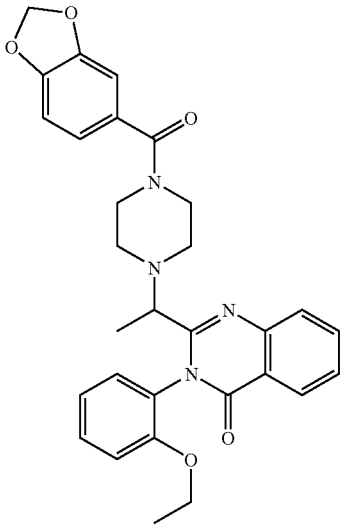<br>CGX-0424105 | −42% | −4% |
| 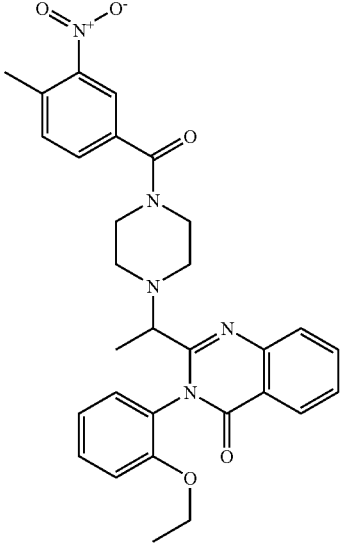<br>CGX-0424105 | −38% | −11% |

TABLE 2-continued
| Molecule | Average % inhibition/enhancement of BJELR cells | Average % inhibition/enhancement of BJEH cells |
| --- | --- | --- |
| 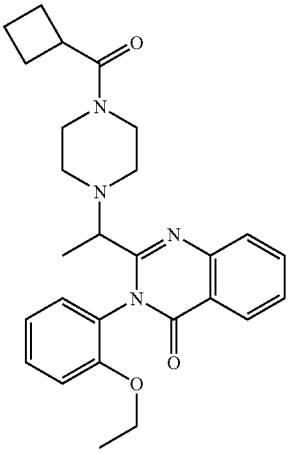<br>CGX-0424105 | −4% | 27% |
| 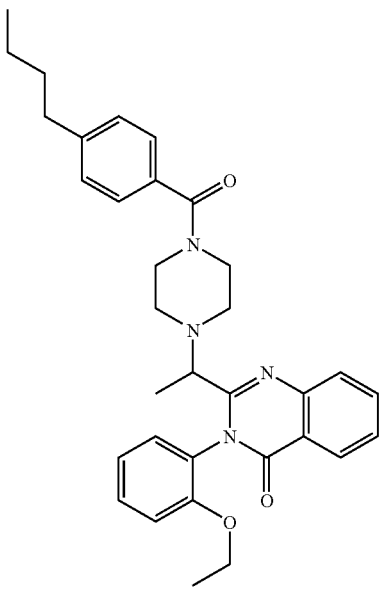<br>CGX-0424105 | −33% | 8% |

TABLE 2-continued
| Molecule | Average % inhibition/enhancement of BJELR cells | Average % inhibition/enhancement of BJEH cells |
| --- | --- | --- |
| 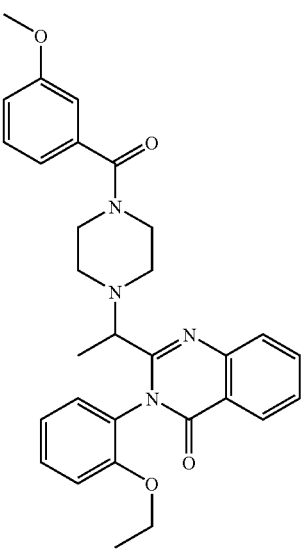<br>CGX-0424105 | −26% | −4% |
| 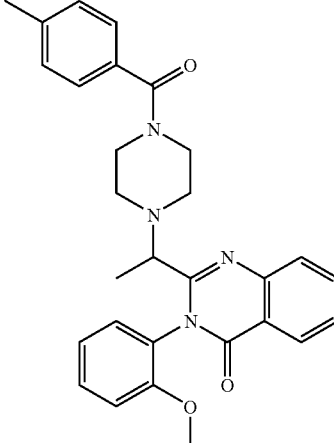<br>CGX-0424105 | −41% | −5% |

TABLE 2-continued
| Molecule | Average % inhibition/enhancement of BJELR cells | Average % inhibition/enhancement of BJEH cells |
| --- | --- | --- |
| 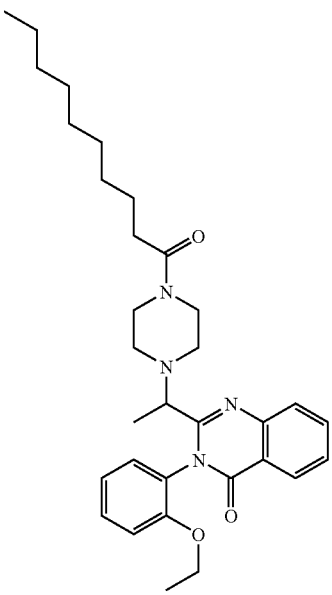 CGX-0424105 | −35% | −2% |
| 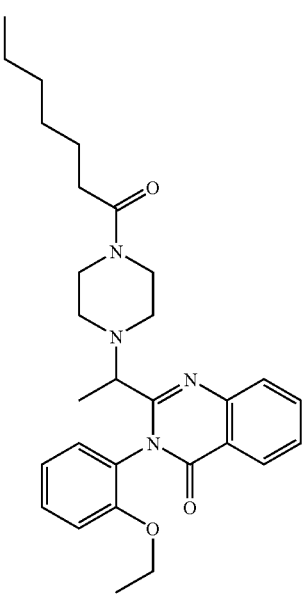 CGX-0424105 | −30% | 12% |

TABLE 2-continued
| Molecule | Average % inhibition/enhancement of BJELR cells | Average % inhibition/enhancement of BJEH cells |
| --- | --- | --- |
| 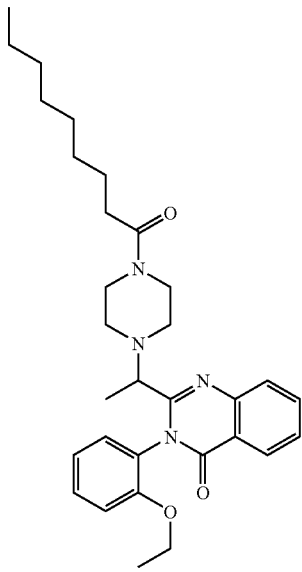<br>CGX-0424105 | −28% | 2% |
| 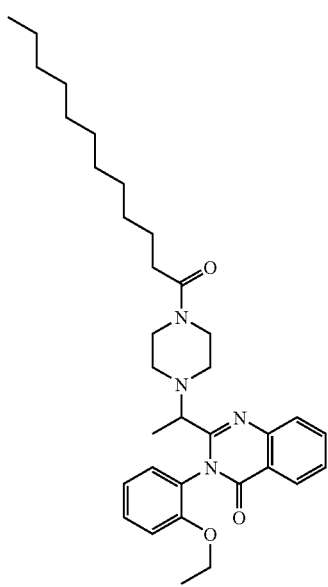<br>CGX-0424105 | −46% | −14% |

TABLE 2-continued
| Molecule | Average % inhibition/enhancement of BJELR cells | Average % inhibition/enhancement of BJEH cells |
|---|---|---|
| 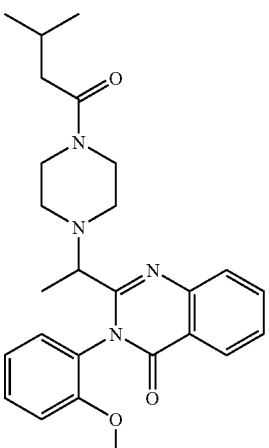<br>CGX-0424105 | −33% | 6% |
| 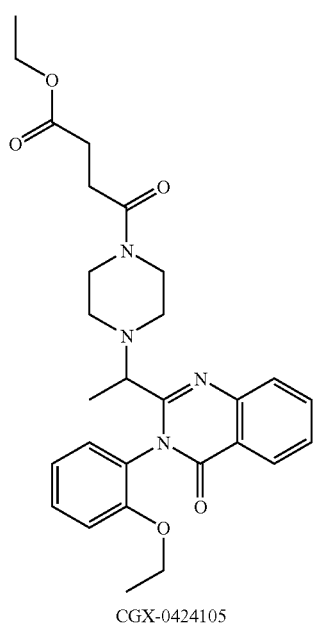<br>CGX-0424105 | −40% | −4% |

TABLE 2-continued
| Molecule | Average % inhibition/enhancement of BJELR cells | Average % inhibition/enhancement of BJEH cells |
| --- | --- | --- |
| 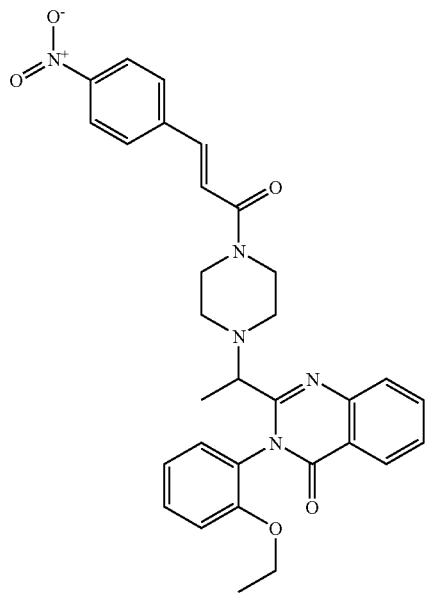<br>CGX-0424105 | −17% | 2% |
| 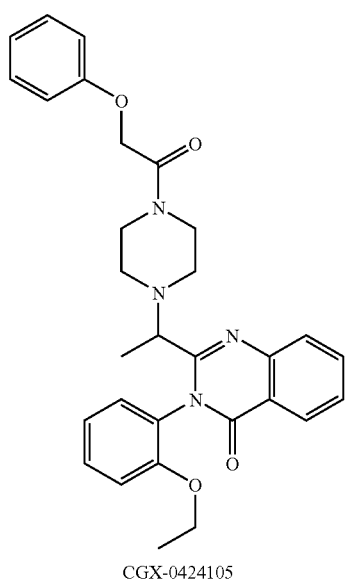<br>CGX-0424105 | −32% | −6% |

TABLE 2-continued
| Molecule | Average % inhibition/enhancement of BJELR cells | Average % inhibition/enhancement of BJEH cells |
|---|---|---|
| 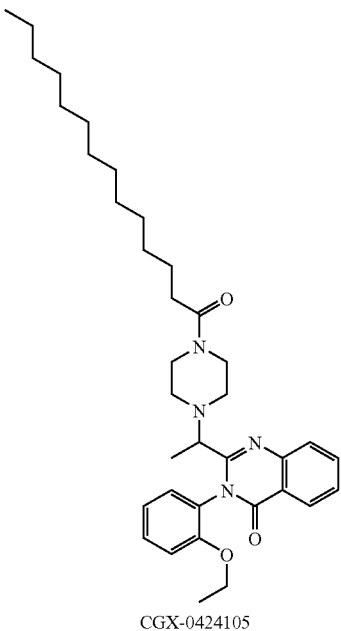 CGX-0424105 | −38% | −1% |
| 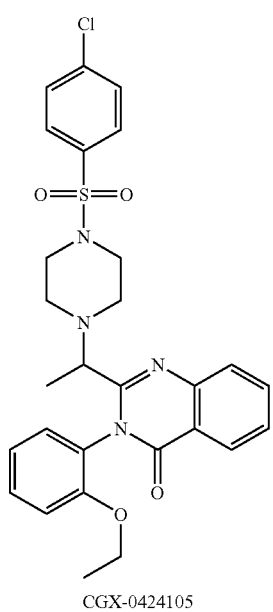 CGX-0424105 | −45% | 0% |

TABLE 2-continued
| Molecule | Average % inhibition/enhancement of BJELR cells | Average % inhibition/enhancement of BJEH cells |
| --- | --- | --- |
| 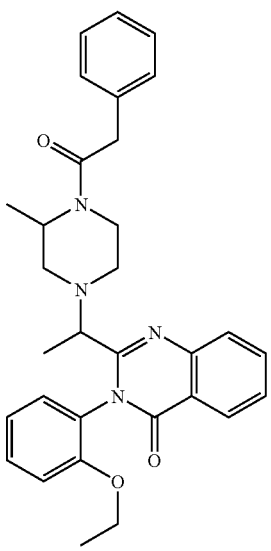<br>CGX-0424105 | −26% | 6% |
| 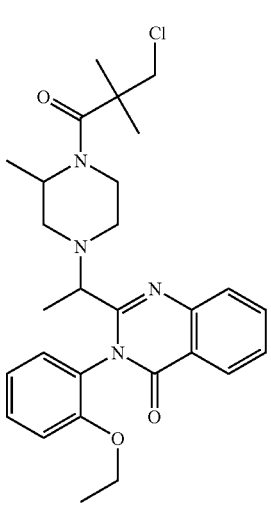<br>CGX-0424105 | −28% | 2% |

TABLE 2-continued

| Molecule | Average % inhibition/enhancement of BJELR cells | Average % inhibition/enhancement of BJEH cells |
|---|---|---|
| 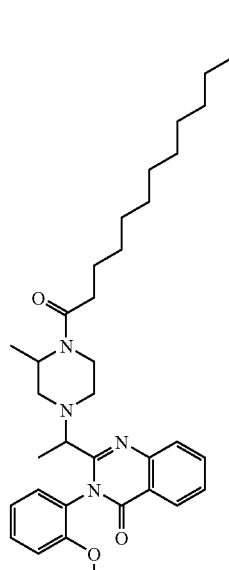 CGX-0424105 | −37% | −5% |

EXAMPLE 4

Identification and Characterization of Binding Partners of Erastin

Pull-down assays using immobilized erastin and cell lysates were used in an initial attempt to identify erastin binding partners inside a cell. Initial pull-down experiments were performed with HEK293, BJEH and BJELR whole cell lysates. In those experiments, a methyl-amino derivative of erastin (ERA-A6) was immobilized to Affigel 10 and incubated with lysate under standard pull-down conditions. The beads were washed and either eluted with 100 µM erastin or 0.8% N-lauroylsarcosine (sarkosyl). The eluates were subjected to mass spectrometric analysis.

Analysis of the erastin pull-down assay results turned up a high rate of mitochondrial or ER-membrane proteins, identified in this first set of pull-down experiments with HEK293 or BJEH and BJELR lysates. This suggested that membrane pores may be one target of erastin or its analogues. However, this result does not exclude the possibility that erastin might have additional and/or different targets that have not yet been identified in this set of pull-down experiments.

Several proteins were repeatedly observed in the pull-down experiments with erastin or erastin analogs. These proteins, including VDAC1, VDAC2, VDAC3, Prohibitin, Ribophorin, Sec61a and Sec22b, are presumably targets of erastin.

Since the whole cell lysate mixtures were still quite complex, those proteins were only detected in sarkosyl elutions of the pull-down experiments. This potentially complicates the mass spectrometric analysis. Thus, to simplify the mixture, various separation methods were used-to isolate or pre-concentrate some of the proteins identified from the whole cell lysate pull-down experiments.

Figure 14:
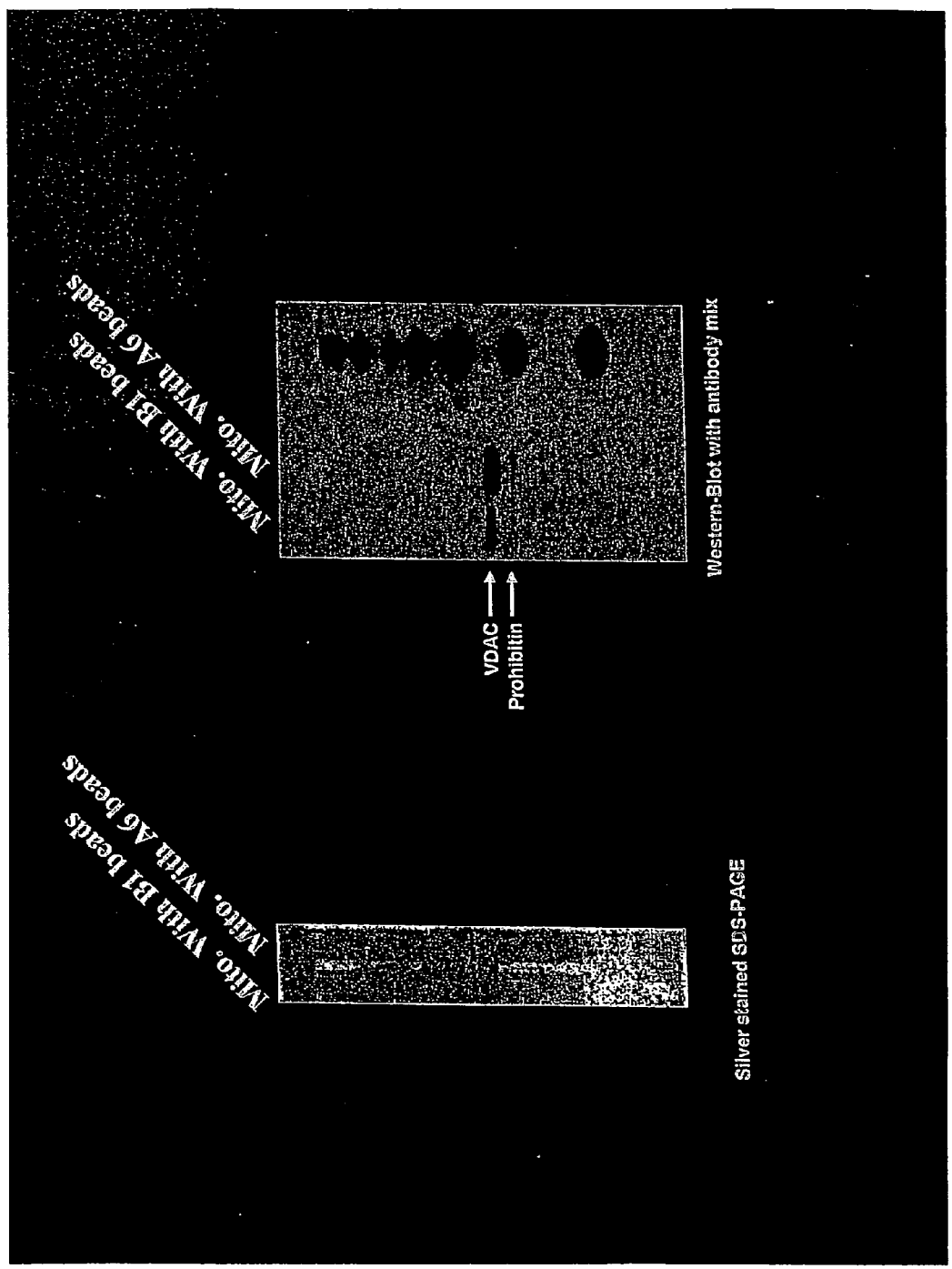
FIG. 14 shows proteins identified by Western blot and SDS-PAGE from pull-down experiments using mitochondrial extract with immobilized active (A6) and inactive (B1) Erastin derivatives.
Figure 15A:
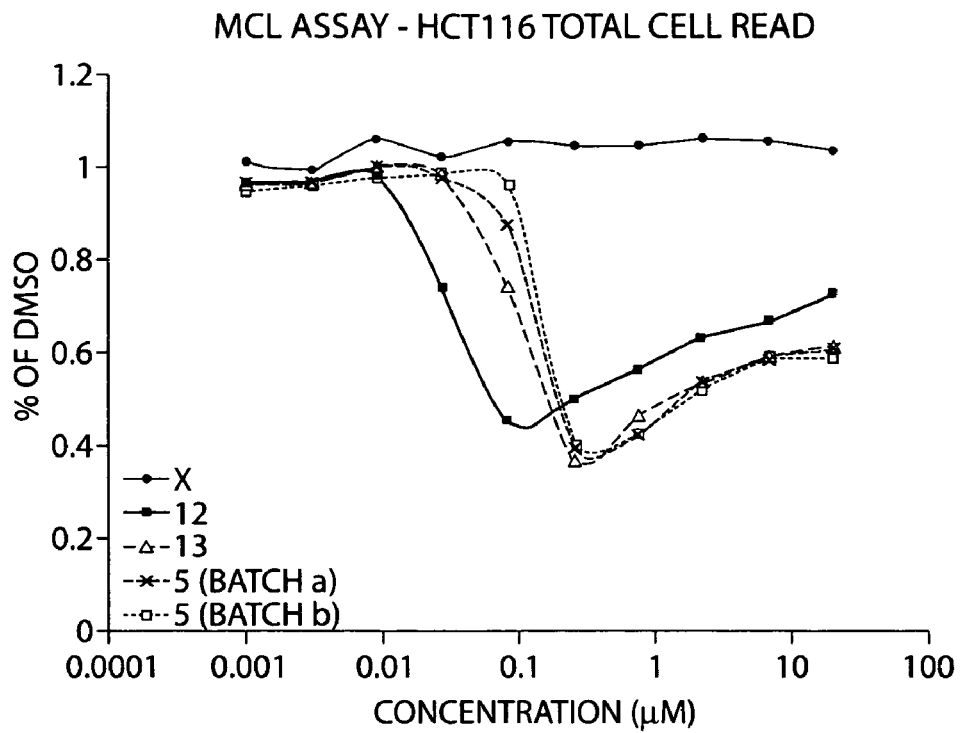
FIG. 15 shows compounds 12, 13 and 5 in MCL assays in (a) HCT116 cells, (b) DLD-1 cells, (c) OVCAR-3 cells, and (d) BT549 cells.
Figure 15B:
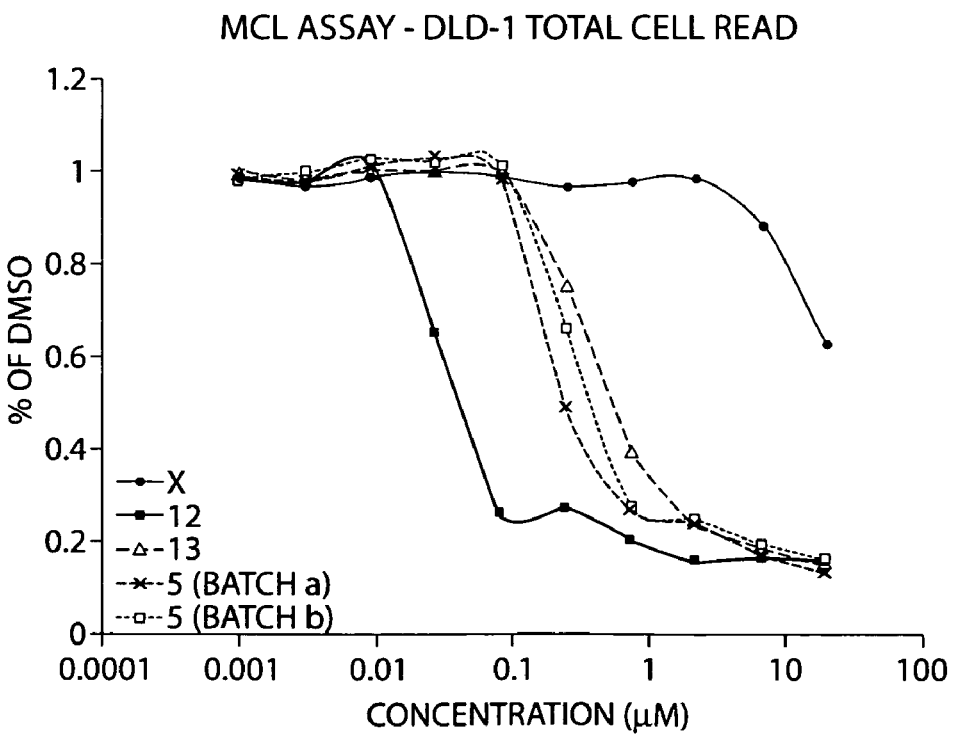
Figure 15C:
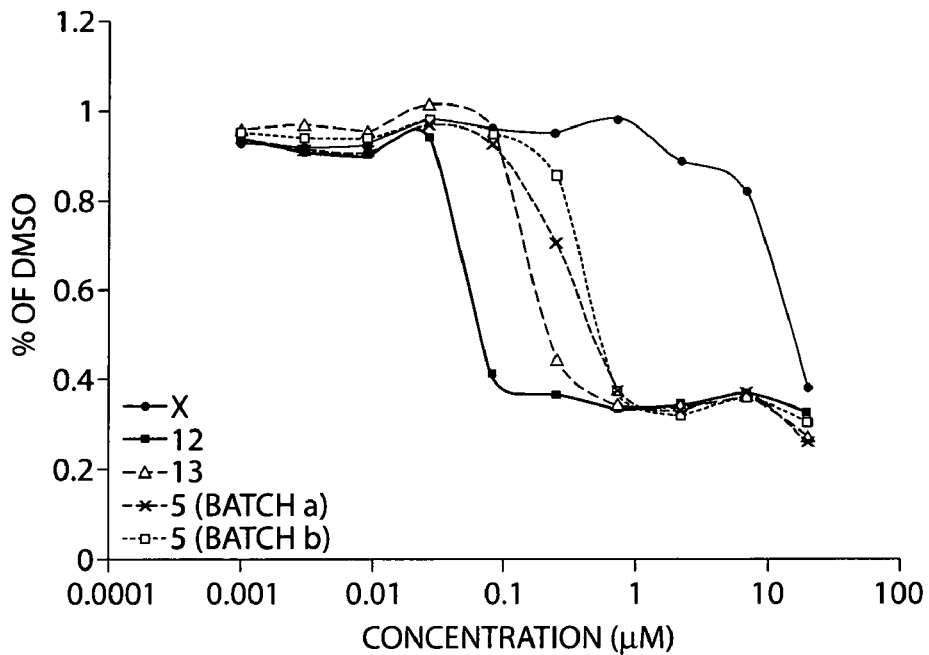
Figure 15D:
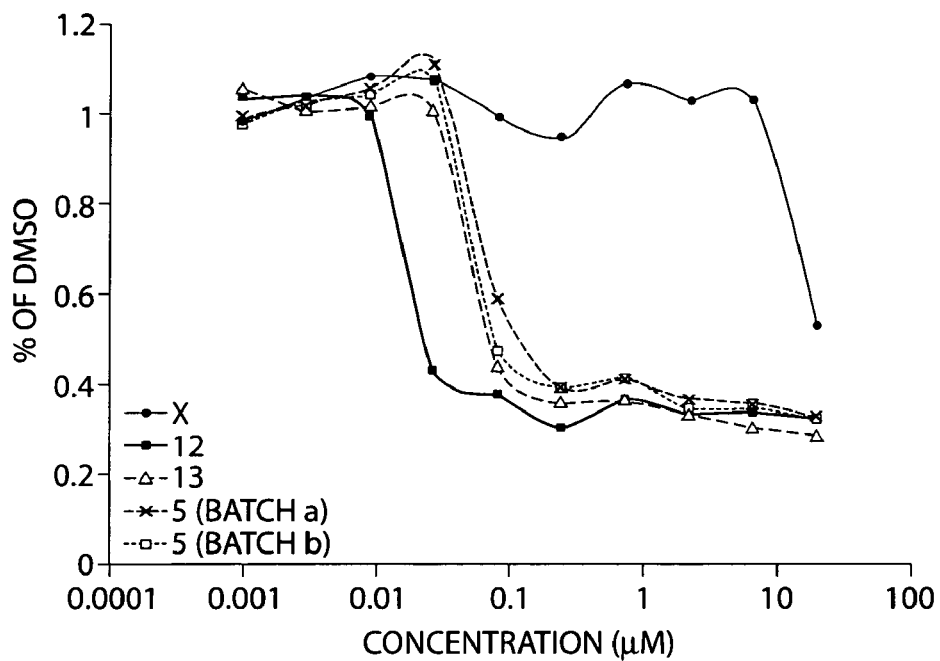
Figure 16A:
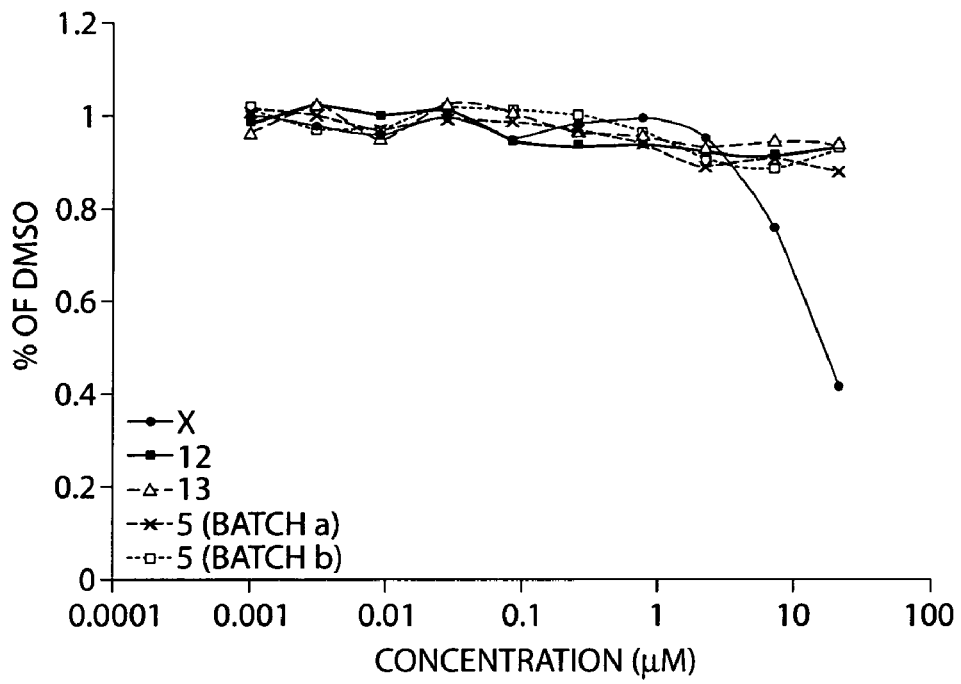
FIG. 16 shows compounds 12, 13 and 5 in MCL assays in (a) MiaPaca2 cells, (b) DU145 cells, (c) SK-Mel 28 cells, and (d) Malm3M cells.
Figure 16B:
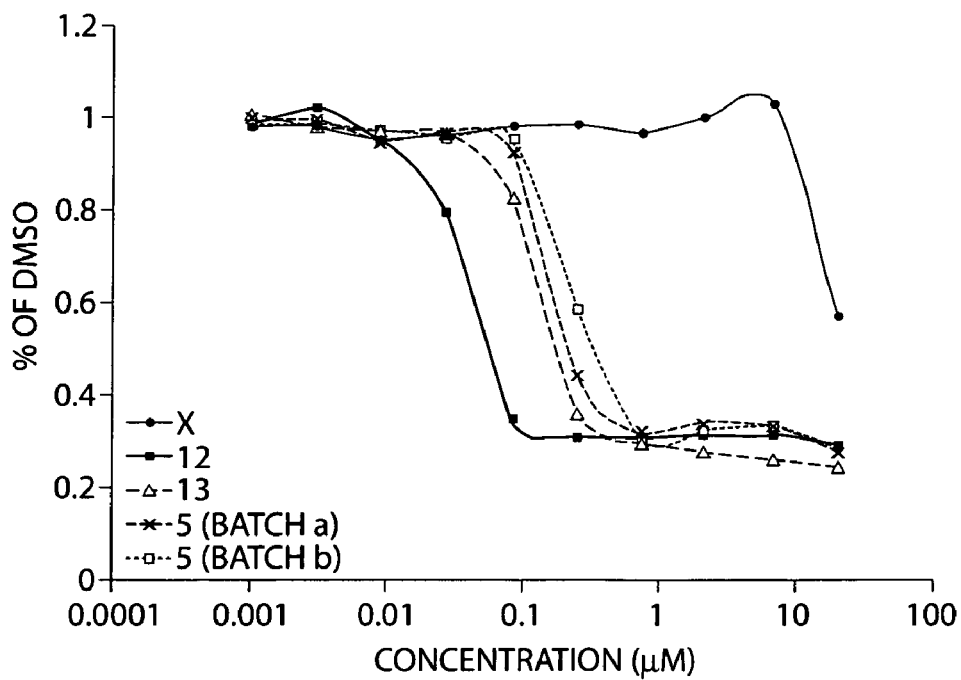
Figure 16C:
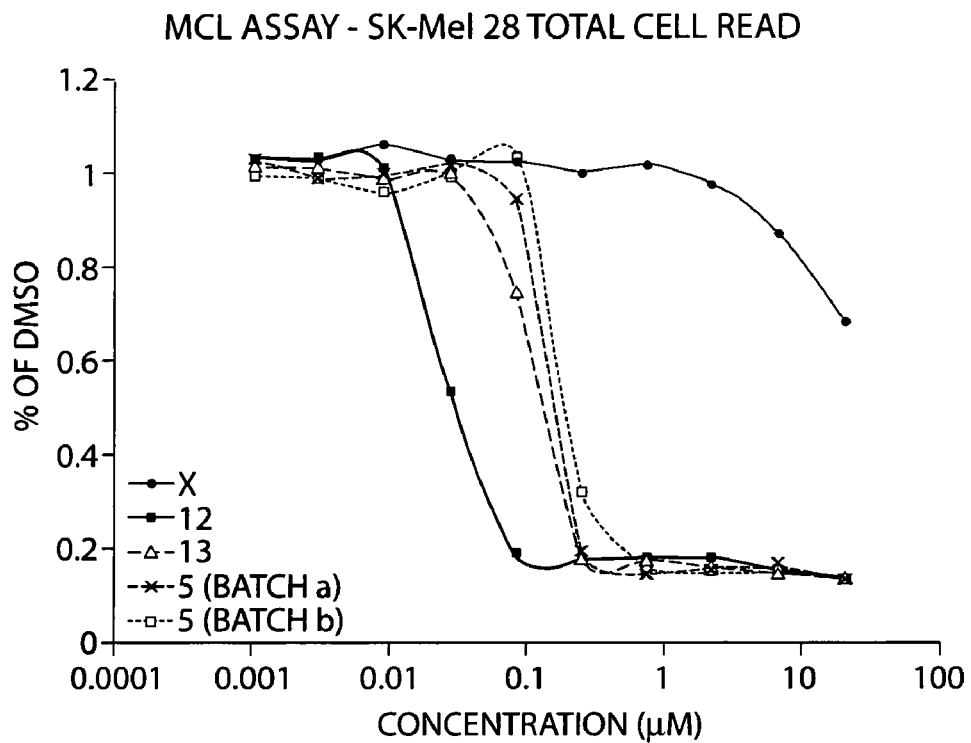
Figure 16D:
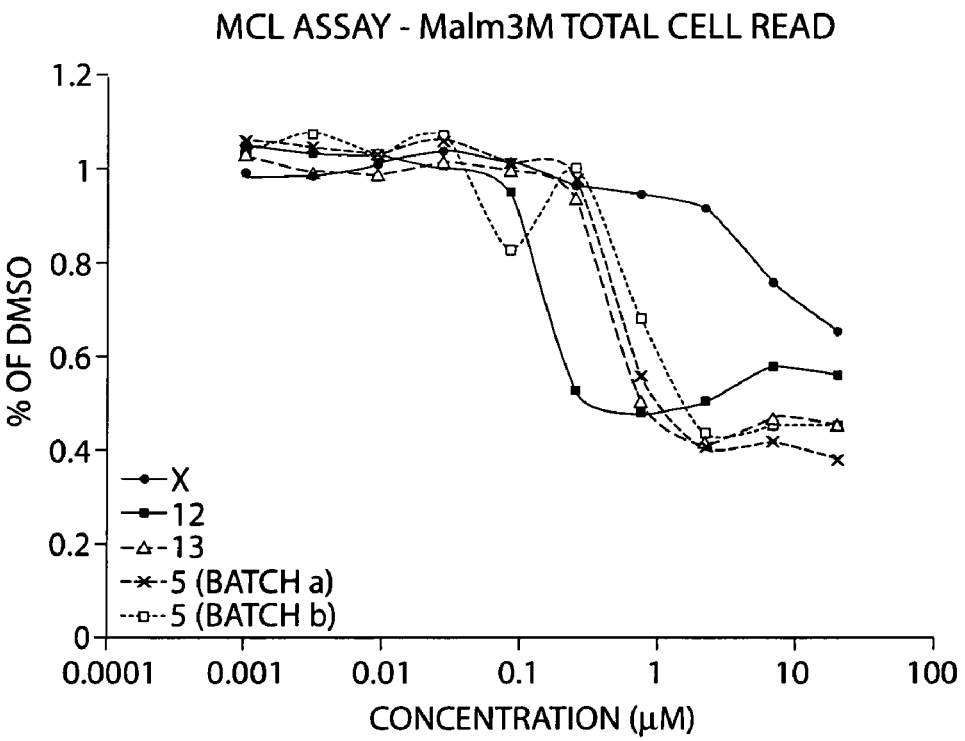
Figure 17A:
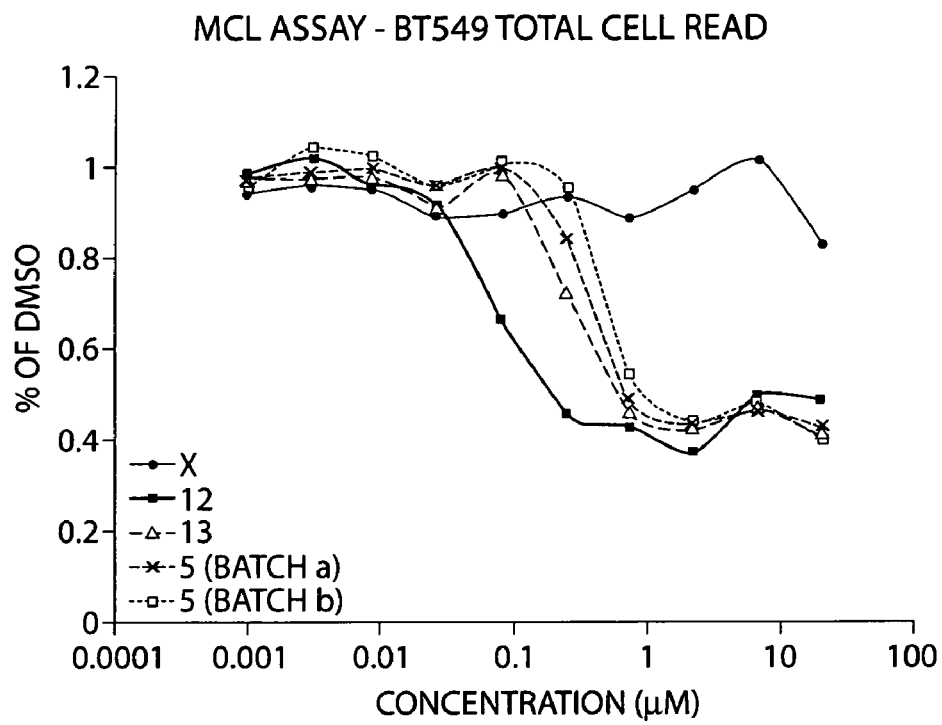
FIG. 17 shows compounds 12, 13 and 5 in MCL assays in (a) BT549 cells, (b) MCF-7 cells, (c) HOP-92 cells, and (d) HOP-62 cells.
Figure 17B:
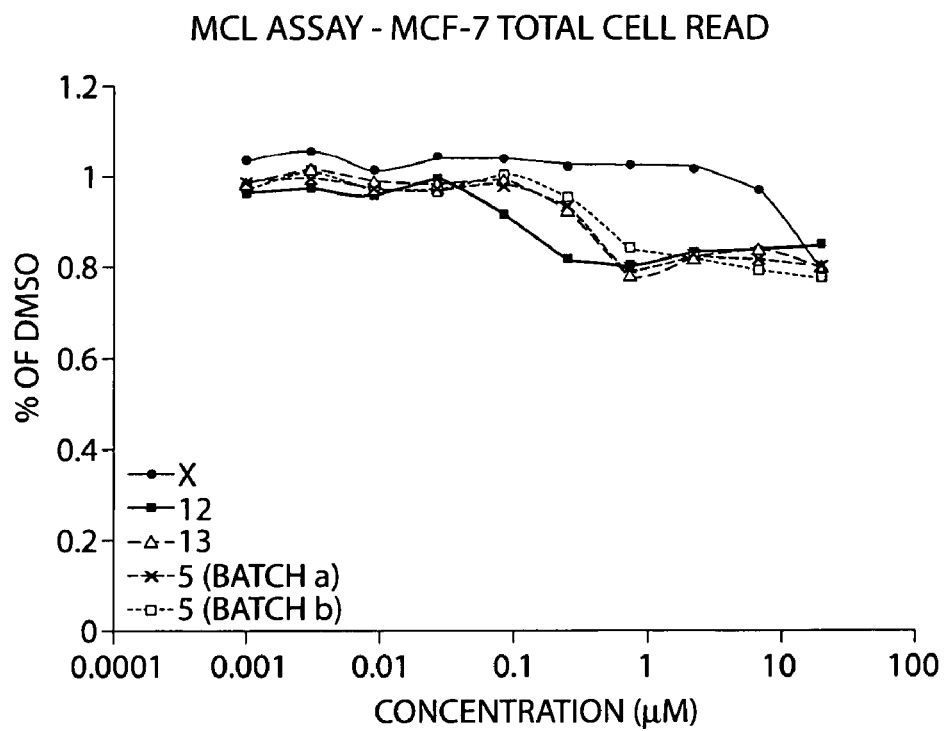
Figure 17C:
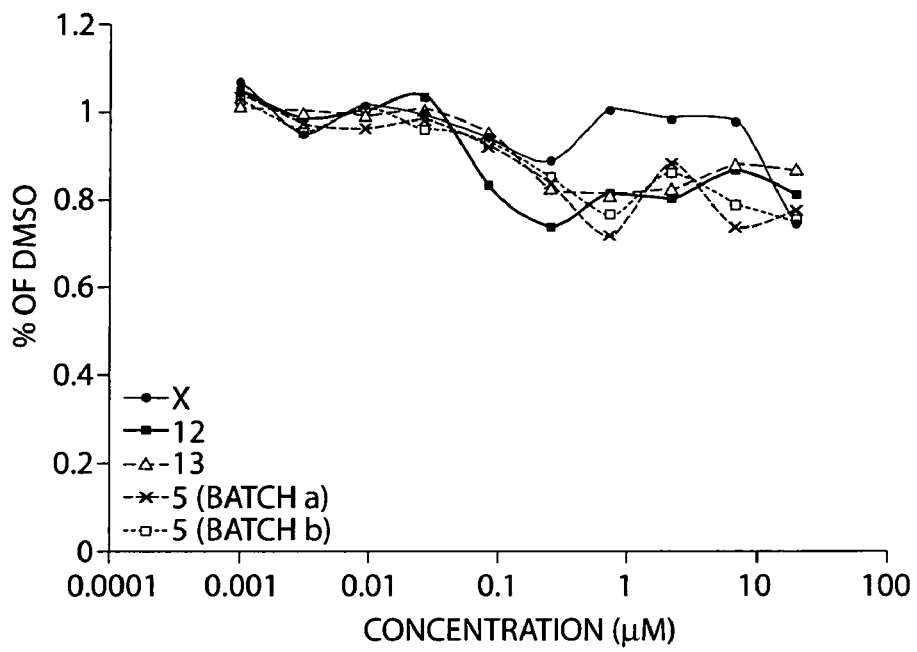
Figure 17D:
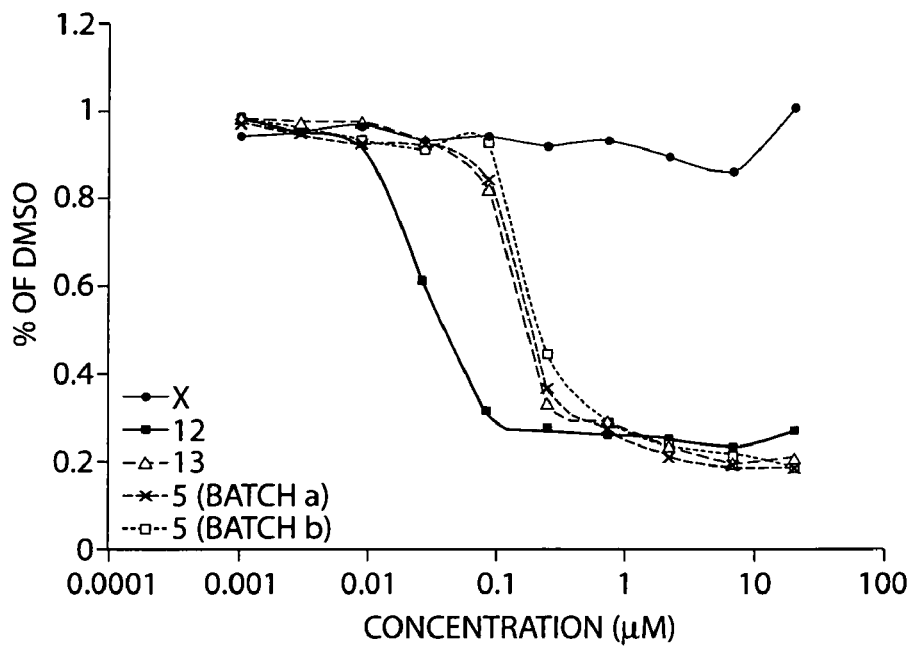

Since Prohibitin and the VDAC isoforms are all mitochondrial proteins, Applicants enriched potential erastin targets by isolating mitochondria from cell lysates. The isolated mitochondrial extracts were then used in erastin pull-down experiments. In those erastin pull-down experiments with the mitochondrial extracts, Prohibitin, VDAC and Ribophorin were also identified by Western blot. FIG. 14 shows Western blots of a pull-down where a mitochondrial extract was contacted with active (A6) and inactive (B1) Erastin derivatives immobilized on beads. The pull-downs were performed with 0.25 mg total protein of the mitochondrial extract. The beads were incubated with the extracts for 1.5 h at 4° C. and then washed several times. Proteins bound to the immobilized Erastin derivatives were eluted with 50 µL of 0.8% N-lauroylsarcosine solution. Proteins were identified by western blot with a mix of anti-Ribophorin, -Sec6, -Prohibitin and anti-VDAC antibodies. Proteins were also identified by MS-analysis.

Ribophorin and Prohibitin are rather acidic proteins with a calculated PI of 5.57 (Prohibitin) and 5.96 (Ribophorin I). Applicants separated those two proteins from the more basic proteins (VDAC isoforms, Sec22 and Sec61a) by ion exchange chromatography on a MonoQ column at a pH of 6.8. The fractions were then tested for their Prohibitin or Ribophorin contents using antibodies. The fractions were also tested for their binding to a BIACORE™ surface containing immobilized ERA-A6 and ERA-B1 compounds. Prohibitin and Ribophorin were found in the fractions that showed binding in the BIACORE™ experiments. Interestingly, an unknown 45 kDa protein that didn't react with any of the antibodies used was observed to bind to the ERA-A6 or ERA-B1 beads in a silver-stained SDS-PAGE gel.

To confirm those hits, pull-down experiments with ERA-A6 and ERA-B1 were performed from the fractions of the MonoQ elutions. Again, Prohibitin and Ribophorin were identified as binding to the Erastin beads from several fractions. Those experiments clearly support the notion that the VDAC isoforms, as well as Prohibitin and Ribophorin bind to erastin and the erastin analogues. Thus these proteins are all potential targets/binding partners of erastin in vivo.

EXAMPLE 5

Expression Levels of Various VDAC Isoforms

Successful pull-downs with the ERA-A6 analog of erastin consistently yielded higher MS-based identification scores for VDAC3 when the pull-downs were performed from the BJELR lysate, as compared to lysate derived from the BJEH cells. The higher scores for that VDAC isoform are consistent with a higher abundance of that isoform in the BJELR lysate relative to the BJEH lysate, given a comparable total protein amount. These different levels of target protein might have an impact on the selectivity of Erastin.

To address this point, Applicants tested the relative expression levels of the various VDAC isoforms using quantitative PCR (Q-PCR). Other possible methods include Western blot and mass spectrometry.

Quantitative PCR (Q-PCR) experiments were performed to determine the relative quantities of mRNA (as a surrogate marker for gene expression) for a variety of genes in the "normal" BJEH cell line, and the tumorigenic BJELR line. For each of the VDAC isoforms (VDAC1, 2 and 3), two regions of the mRNA were targeted for amplification. These regions were referred to as 1 and 1-2, 2-1 and 2-2, and 3-1 and 3-2, respectively. The Q-PCR signal for mRNA fragment amplification for each gene of interest was compared to a series of internal standards, and scaled relative to the signal derived from GAPDH mRNA in the target cells. The results depicted in FIG. 11 indicate that expression of VDAC3 is significantly elevated in the BJELR cells relative to that in the BJEH cells. This finding is in contrast to the results observed for several other genes, which were suppressed in the BJELR cells relative to that observed in the BJEH cells.

Figure 11:
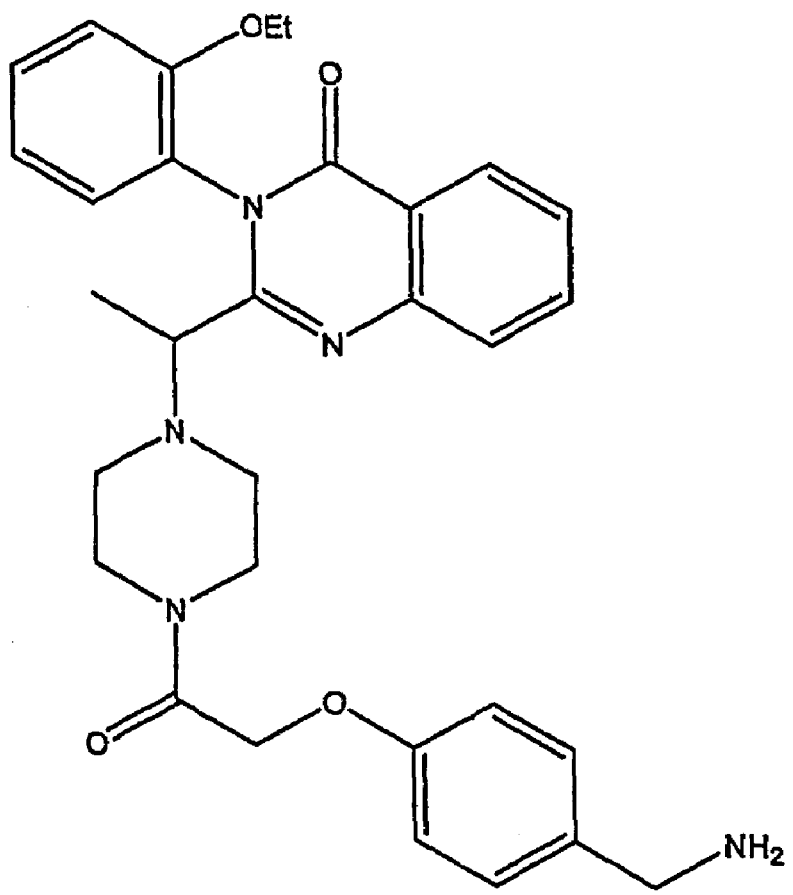
FIG. 11 shows the chemical structure of erastin A.
Figure 12:
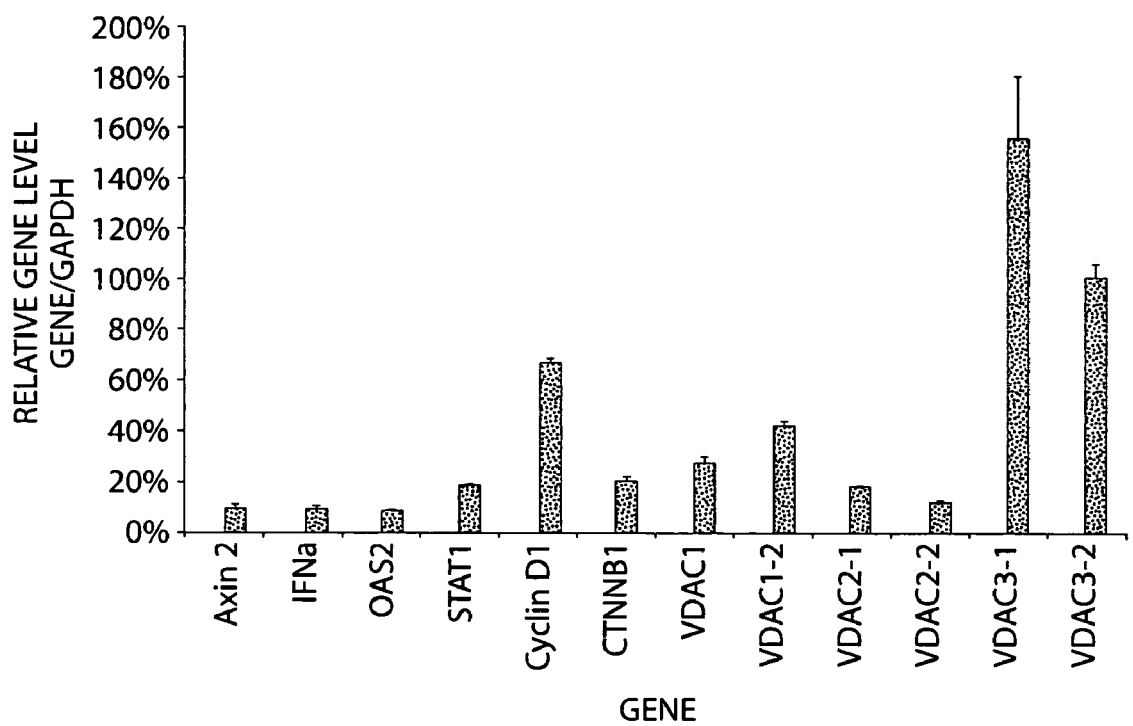
FIG. 12 indicates that expression of VDAC3 is significantly elevated in the tumorigenic BJELR cells relative to that in the non-tumorigenic BJEH cells.
Figure 13:
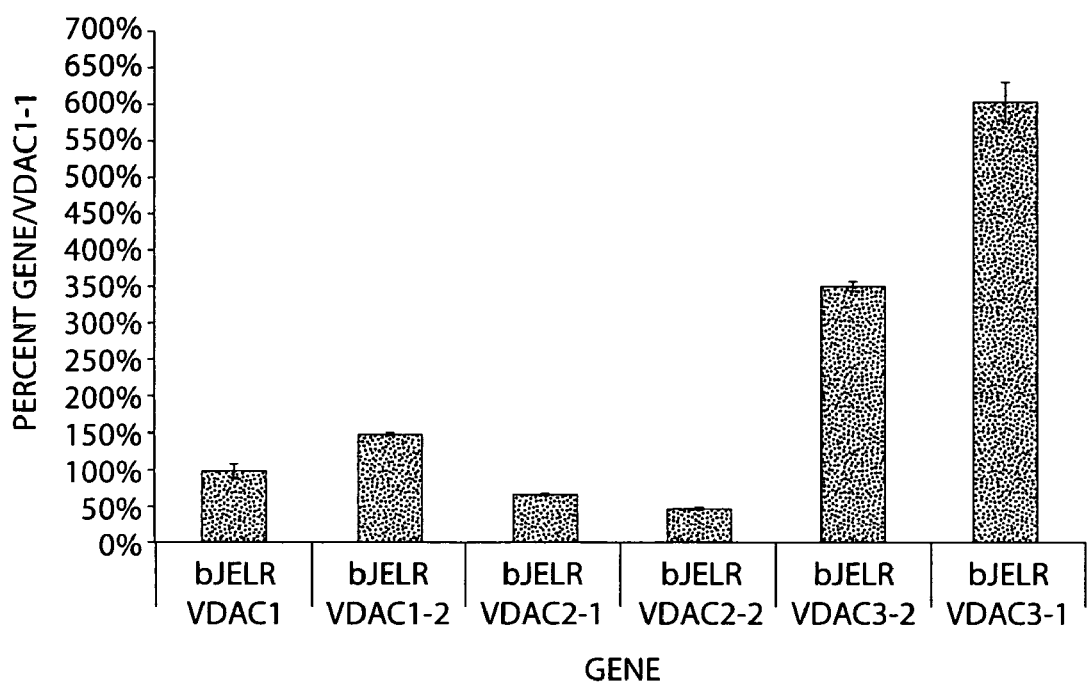
FIG. 13 shows the relative expression levels of the VDAC isoforms in target cells using the level of VDAC-1 set to 100%.

FIG. 12 was generated using the same Q-PCR data as in FIG. 11, but FIG. 12 focuses exclusively on the relative expression levels of the VDAC isoforms in the target cells. The Q-PCR signal for each amplified mRNA fragment was compared to a series of internal standards, and is expressed relative to the signal derived from VDAC1 mRNA in the target cells, which is defined as 100%. As in FIG. 11, the two amplified regions of the mRNA for each of the VDAC isoforms (VDAC1, 2 and 3), are referred to as 1, 1-2, 2-1, 2-2, 3-1, and 3-2, respectively. The results indicate that expression of VDAC3 is expressed at a level 2 to 2.5 fold greater in the BJELR cells than in the BJEH cells.

Taken together, these findings suggest a possible mechanism to explain the differential sensitivity of the BJELR cells to erastin treatment.

EXAMPLE 6

Functional Evaluation of Erastin on Various VDAC Isoforms

Functional assays help to validate the identified proteins as functional targets for erastin. In certain embodiments, isolated mitochondria might be used to see if erastin has any functional or phenotypic effects on mitochondria function. For example, phenotypic effects could be observed by microscope, while the detection of changes in the mitochondrial membrane potential, or the release of oxidative species upon erastin treatment could be observed by using certain dyes, known in the art for detecting reactive oxygen species (ROS).

In certain other embodiments, validation experiments might include photo-alfinity labeling of the target protein with azido-erastin derivatives, or erastin analogs or derivatives coupled to a bidentate affinity-tagged crosslinker (such as SBED), or a cleavable cross-linker.

In yet other embodiments, recombinant and over-expressed proteins might be used in certain in vitro assays to assess any possible effects erastin might have on their functions. Such in vitro assays could include, but are not limited to: direct binding (in vitro or BIACORE™), or efflux assays that could determine the channel properties of the VDAC isoforms.

In yet other embodiments, knockout mutants (cells or organisms) of those target proteins may be used. Compared to wild-types, these mutants could become either resistant or hypersensitive to erastin. Those knockout cell lines could also be used in high throughput screenings (HTS) to determine and/or evaluate the specificity of erastin or its analogs.

In yet other embodiments, RNAi experiments for VDACs, Prohibitin and Ribophorin may also be used to assess any phenotypes upon erastin treatment (e.g., erastin resistance or hypersensitivity). According to this embodiment of the invention, SMARTPOOL® siRNAs targeting VDAC1, VDAC2 and VDAC3, respectively, can be purchased from Dharmacon (Lafayette, Colo.). Transfection conditions are then optimized, for example, using FUGENET™ and olignfectamine in 384-well plates, and a fluorescently labeled siRNA duplex. Such procedure resulted in ~90% transfection efficiency. ELR tumor cells can then be transfected with siRNAs against VDAC1, VDAC2, or VDAC3, and the dose-response to erastin can be measured.

EXAMPLE 7

Inhibition of Cell Growth

The ability of a compound to inhibit the growth of BJELR and BJEH cells is measured. The compounds are assayed by the Sytox primary screen, a phenotypic assay which monitors alterations in cell survival-proliferation as a result of compound treatment. It is devised as high throughput method to identify compounds which specifically alter the growth potential of cells harboring the causative mutations found in cancer patients while not affecting the growth of normal cells. The assay relies upon an inexpensive, simple and reliable readout of a membrane impermeable fluorescent dye (Sytox, from Molecular Probes) which binds to nucleic acid. In healthy cells, no signal is detected because the cell's membrane is intact and the dye will not enter. However, if a cell's membrane is compromised as a result of apoptosis or necrosis, a fluorescent signal proportional to the number of similarly affected cells will be detected. By utilizing a two-step readout (final read in the presence of detergent to permit labeling of all cells), the assay can identify compounds which produce cytostasis, cytotoxicity and/or mitogenesis. The first read or "dead cell" read, provides an estimate of the toxicity of a given compound by indicating the number of dead or dying cells in the culture at the time of assay. The second read or "total cell" read, captures both the cumulative effects of cytotoxicity in reducing the size of the cell population as well as any cytostatic or anti-proliferative effects a test compound may exert on the cells in the test population in the absence of toxicity.

For the purpose of screening, the previously described BJ-TERT line is defined as the "normal" reference cell line and BJ-TERT/LT/ST/RAS$^{V12}$ cells are the tumorigenic cell line. Cells are seeded overnight in 96 well plates at densities that without treatment would permit 95% confluence in the wells 72 hours later. The following day, the cells are exposed to test compounds in a dilution series for a period of 48 hours. Following this incubation period, the Sytox reagent is added to the cultures at the manufacturer's recommended concentration and the dead cell fluorescence read is taken. After completion of this measurement, the detergent Saponin is added to each well of the cultures to permeabilize the membranes allowing the Sytox reagent to enter every cell, thereby facilitating measurement of the total number of cells remaining in the culture.

EXAMPLE 8

Synthesis of 3-(2-ethoxyphenyl)-2-(piperazin-1-ylinethyl)quinazolin-4(3H)-one (Compound 5)

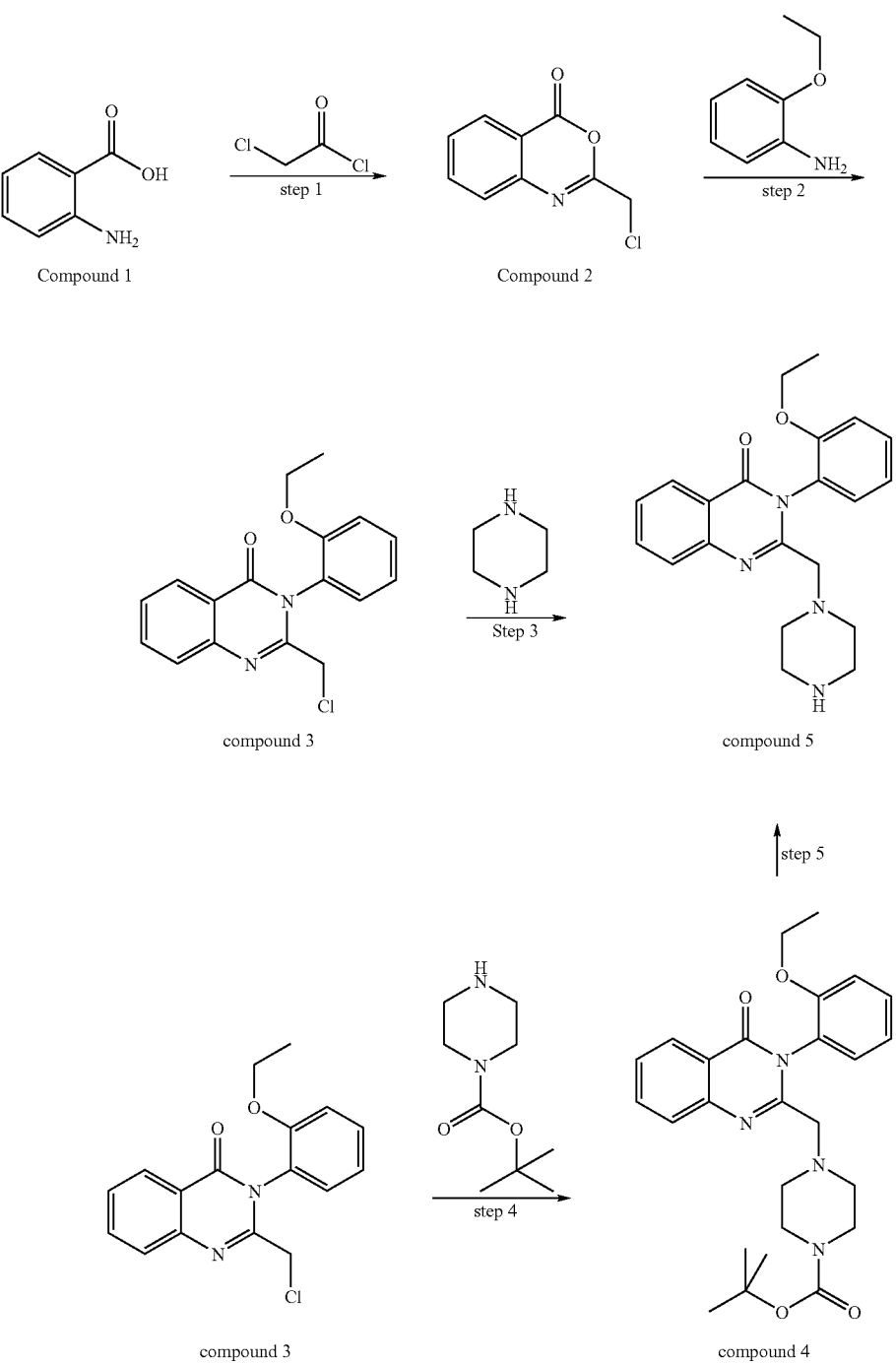

Step 1: Preparation of 2-(chloromethyl)4H-benzo[d][1,3]oxazin4-one (Compound 2)

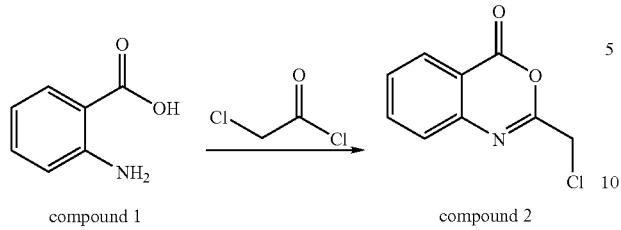

Method 1:

Under an atmosphere of nitrogen, anthranilic acid (compound 1, 15.3 g) was dissolved in 300 mL of dichloromethane ($CH_2Cl_2$). Triethylamine (TEA, 1.1 equiv) was then added and the mixture was cooled in an ice water bath. A solution of chloroacetyl chloride (1.1 equiv) in dichloromethane (150 mL) was added dropwise and the mixture allowed to stir for two hours with warming to ambient temperature. (The ice bath may be removed at the end of the addition or the mix may be allowed to warm to ambient temperature over two hours.) The solids were isolated by filtration and washed with cold water (2×) followed by 5% diethyl ether ($Et_2O$) in hexane and were air dried to afford compound 2 as a white powdery solid (22.5 g, quantitative yield). The final product was characterized by LC/MS m/z MH+, 196.13; >95% pure; $^1$HNMR.

Method 2—Use of Dimethylformamide (DMF) as Reaction Solvent:

10 grams of anthranilic acid were dissolved in 300 mL of DMF. TEA (1.5 equiv) was added and the mix cooled in an ice/water bath. A solution of chloroacetyl chloride (1.3 equiv) in DMF (100 mL) was added dropwise to the cooled reaction mixture. The ice/water bath was removed, and the reaction mixture was allowed to stir for 2 hours. The reaction mixture was poured into ice-cold water (200-300 mL) and extracted with ethyl acetate (EtOAc, 3× extraction). The organic layers were combined, washed with water and brine and dried over sodium sulfate ($Na_2SO_4$). Concentration afforded a solid which was triturated with 100 mL of 10% $Et_2O$/hexane to obtain compound 2 as a white powder (12 g; 85% yield). The final product was characterized by LC/MS.

Step 2: Preparation of 2-(chloromethyl)-3-(2-ethoxyphenyl) quinazolin-4(3H)-one (Compound 3)

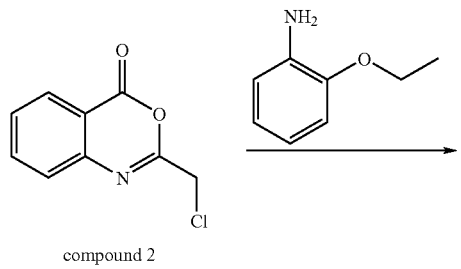

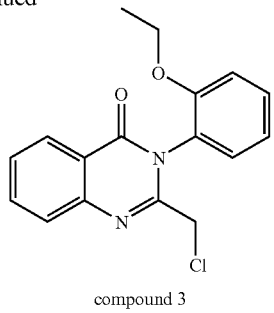

Method 1—Using Trichlorophosphine ($PCl_3$):

Under an atmosphere of nitrogen, compound 2 (8.8 g) was dissolved in 440 mL of acetonitrile ($CH_3CN$) and to it 2-ethoxybenzeneamine (1.5 equiv) was added and stirred. To this well-stirred reaction mixture, $PCl_3$ (2 equiv) was added dropwise. The resulting slurry was heated at 50° C. for 6-12 hours. The reaction mixture was poured into saturated $Na_2CO_3$/ice mix, stirred for 30 min, and extracted with EtOAc (3×300 mL). The combined organic layers were washed with (a minimum amount of) water and brine and dried over $Na_2SO_4$. The solution was concentrated, and the crude solid/oil mixture was triturated with 3% $Et_2O$/Hexane (2×100 mL) to remove most of the unreacted phenetidine. The resulting solids were isolted by filtration and further purified by passing through a column of silica gel (20% EtOAc/hexane). Compound 3 was isolated as a white powder (11 g, 75-80%). The final product was characterized by LC/MS m/z MH+, 315/317; >98% pure.

Method 2—Using Phosphoryl Trichloride ($POCl_3$):

Under an atmosphere of nitrogen, compound 2 (1.2 g; 6.0 mmol; 1.0 equiv.) and 2-ethoxybenzeneamine (1.2 mL; 9.0 mmol, 1.5 equiv.) were dissolved in 30 mL of $CH_3CN$. To this solution $POCl_3$ (1.1 mL, 12 mmol, 2.0 equiv.) was added dropwise and the mixture was heated at reflux over a 3 hour period. The reaction was cooled to ambient temperature, poured into a slurry of ice/saturated $NaHCO_3$, and extracted with EtOAc (3×200 mL). The combined organic layers were washed with water and brine and dried over $Na_2SO_4$. Analysis of the crude reaction mixture by LC/MS confirmed the presence of the desired product compound 3 (97%) along with a small amount of a by-product compound 3c (2-3%). The MH+ m/z (333/334/335) in the LC/MS is consistent with the diamide structure of compound 3c. The desired product was typically isolated after chromatography on silica gel (as described earlier in Method 1 of Step 2) to afford compound 3 as a white powder (1.3 g, 80-85% yield).

Step 3: Preparation of 3-(2-ethoxyphenyl)-2-(pierazin-1-yl-methyl)quinazolin-4(3H)-one (Compound 5)

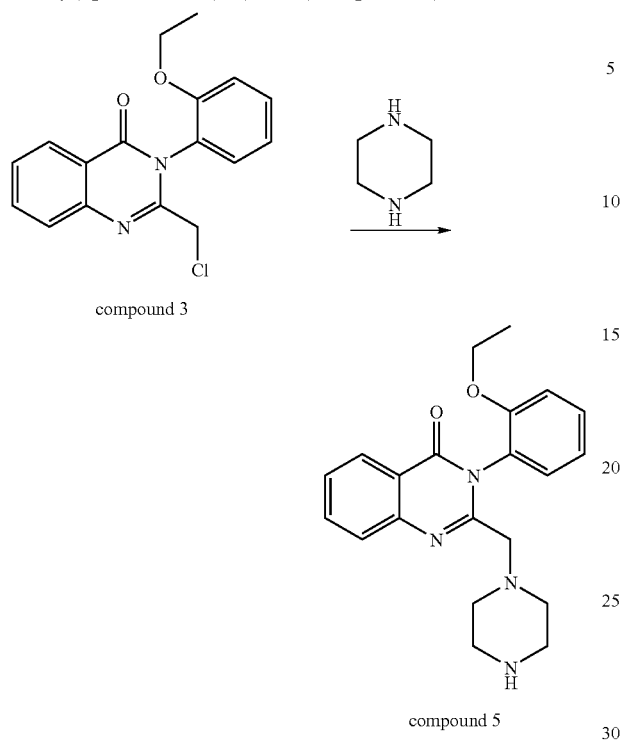

compound 3 compound 5

Method 1:

Under an atmosphere of nitrogen, Compound 3 (5 g) was dissolved in CH₃CN (0.08-0.2 M compound concentration) and to it potassium carbonate (K₂CO₃, 1.2 equiv., commercial powder), piperazine (2 equiv.) and tetrabutylammonium iodide (0.2 equiv) were added in that order. The mixture was heated at 60° C. (bath temp) for 8-10 hours. The reaction was worked up in either of the following two ways: (a) 80% of the solvent was evaporated, water (20 mL) was added and the mixture extracted with EtOAc (4×60 mL); or (b) the reaction mixture was diluted with 400 mL of EtOAc and washed with water (3×20mL). The combined organic layers were washed with brine and concentrated to afford a slightly yellow oil. Compound 5 was obtained as a white powder (80-85% yield) after purification by medium pressure chromatography (CombiFlash®) on silica (10-25% MeOH/dichloromethane). The product was characterized by ¹HNMR and LC/MS MH+, 365.

Step 4: Preparation of tert-butyl4-((3-(2-ethoxyphenyl)4-oxo-3,4-dihydroquinazolin-2-yl)methyl) pipierazine-1-carboxylate (Compound 4)

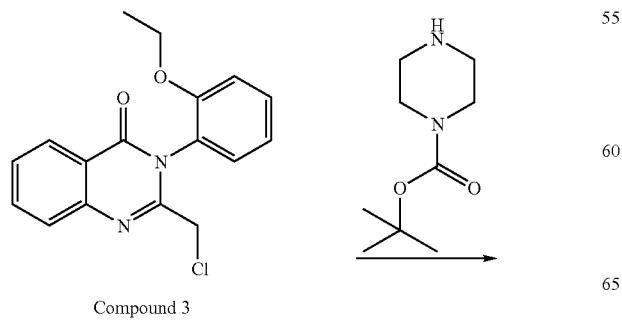

Compound 3

-continued

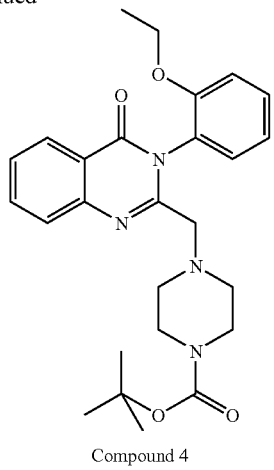

Compound 4

Method 1:

Under-an atmosphere of nitrogen, Compound 3 (4.0 g, 12.7 mmol, 1.0 equiv.) was dissolved in 60 mL of CH₃CN, and to this solution solid samples of K₂CO₃ (2.1 g, 15 mmol, 1.2 equiv.), Boc-piperazine (4.73 g, 25 mmol, 2.0 equiv.) and sodium iodide (NaI, 570 mg, 3 mmol, 0.3 equiv.) were added in that order. The mixture (a suspension) was heated at 80° C. for 3-6 h. A white suspension resulted. Examination of the reaction using TLC and LC/MS showed complete conversion of Compound 3 to Compound 4. Approximately 30 mL of CH₃CN were removed by distillation under reduced pressure, and to the resulting slurry 60 mL of water was added and the mixture was-extracted with EtOAc (4×60 mL). The combined organic layers were washed with water, a saturated solution of ammonium chloride (to remove unreacted Boc-piperazine), a saturated solution of NaHCO₃ and brine and dried over Na₂SO₄. Filtration concentration afforded solids which were triturated with hexane to afford compound 4 as a white solid (5.6 g, quantitative yield). This material was used in the subsequent deprotection step without further purification. The final compound was characterized by ¹HNMR, LCMS Step 5: Preparation of 3-(2-ethoxyphenyl)-2-(piperazin-1-yl-methyl)quinazolin-4(3H)-one (Compound 5)

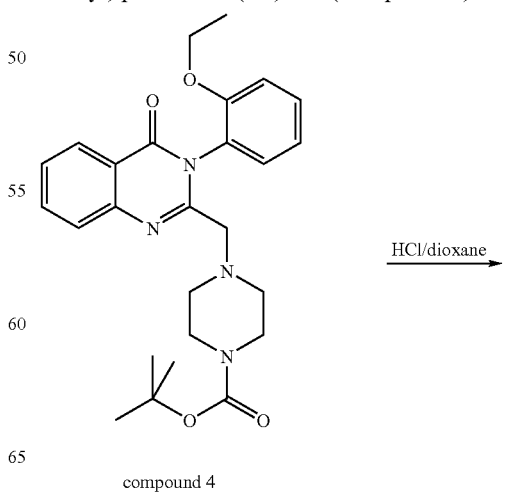

compound 4

HCl/dioxane

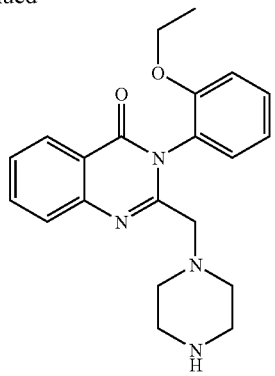

compound 5

Method 1:

Compound 4 (2.7 g, 5.8 mmol, 1.0 equiv.) was suspended in 15 mL of anhydrous dioxane at ambient temperature. A solution of 4N HCl/dioxane (17 mL, 12 equiv.) was added dropwise at ambient temperature; after 30 min of reaction an additional 17 mL of 4N HCl/dioxane was added and reaction progress was monitored by LC/MS. (This was an exothermic reaction and gas evolution was observed. The reaction system must be opened for pressure release while maintaining anhydrous conditions.) If any amount of unreacted compound 4 remains, a further 8-10 mL of 4N HCl/dioxane may be added to drive the reaction to completion. At the end of the reaction 40 mL each of water and $CH_2Cl_2$ were added to the reaction and the mixture was made basic by adding a sufficient amount of saturated aqueous $Na_2CO_3$ solution to achieve a pH of 8-9. Layers were separated and the aqueous layer was extracted with $CH_2Cl_2$ (3×60 mL). The organic layers were combined, washed with water (4×10 mL, until pH of aqueous extract is around neutrality) and brine and dried over $Na_2SO_4$. Concentration afforded a slightly yellow oil which was purified by medium pressure chromatography. (CombiFlash®) on silica (10-25% MeOH/dichloromethane) to afford compound 5 as a white powder (85-95% yield) after trituration with hexane containing 5-10% diethylether. Compound 5 was characterized by $^1$HNMR and LC/MS.

General: Analytical Method

The following LC conditions were used to analyze Compound 5:

Column: XTerra® for MS; C18, 3.5 μm

Dimrension: 2.1×150 mm

Gradient: 75% $CH_3CN$ (containing 0.08% formic acid)/25% water (containing 0.1% formic acid)–90% $CH_3CN$ (containing 0.08% formic acid)/10% water (containing 0.1% formic acid)

All compounds were analyzed by LC/MS under the following column and mobile phase conditions:

| Column: Xterra ® for MS; C18, 3.5 μm Dimension: 2.1 × 150 mm | | | |
|---|---|---|---|
| Gradient: | Time | water/0.1% FA | CH3CN/0.08% FA |
| | 0:00 | 95 | 5 |
| | 7:00 | 5 | 95 |
| | 8:00 | 5 | 95 |

| Column: Xterra ® for MS; C18, 3.5 μm Dimension: 2.1 × 150 mm | | | |
|---|---|---|---|
| Gradient: | Time | water/0.1% FA | CH3CN/0.08% FA |
| | 9:00 | 95 | 5 |
| | 13:00 | 95 | 5 |

EXAMPLE 9

Sytox Primary Screen

The Sytox primary screen is a phenotypic assay which monitors alterations in cell survival-proliferation as a result of compound treatment. It was devised as high throughput method to identify compounds which specifically alter the growth potential of cells harboring the causative mutations found in cancer patients while not affecting the growth of normal cells.

The assay relies upon an inexpensive, simple and reliable readout of a membrane impermeable fluorescent dye (Sytox, from Molecular Probes) which binds to nucleic acid. In healthy cells, no signal is detected because the cell's membrane is intact and the dye will not enter. However, if a cell's membrane is compromised as a result of apoptosis or necrosis, a fluorescent signal proportional to the number of similarly affected cells will be detected. By utilizing a two-step readout (final read in the presence of detergent to permit labeling of all cells), the assay can identify compounds which produce cytostasis, cytotoxicity and/or mitogenesis. The first read or "dead cell" read provides an estimate of the toxicity of a given compound by indicating the number of dead or dying cells in the culture at the time of assay. The second read or "total cell" read captures both the cumulative effects of cytotoxicity in reducing the size of the cell population as well as any cytostatic or anti-proliferative effects a test compound may exert on the cells in the test population in the absence of toxicity.

For the purpose of screening, the previously described BJ-TERT line was defined as the "normal" reference cell line and and BJ-TERT/LT/ST/RAS$^{V12}$ cells were the tumorigenic cell line. Cells were seeded overnight in 96 well plates at densities which without treatment would permit 95% confluence in the wells 72 H later. The following day, the cells were exposed to test compounds in a dilution series for a period of 48 hours. Following this incubation period, the Sytox reagent was added to the cultures at the manufacturer's recommended concentration and the dead cell fluorescence read was taken. After completion of this measurement, the detergent Saponin was added to each well of the cultures to permeabilize the membranes allowing the Sytox reagent to enter every cell thereby, facilitating measurement of the total number of cells remaining in the culture.

For data evaluation, we did not distinguish between compounds which exhibited cytotoxic or cytostatic effects. In order to be considered for further testing, compounds had to meet two stringent criteria:

i. produce a change in signal of at least 2 standard deviation magnitude on the tumor cell lines in either the dead cell or total cell reads (or both)

ii. produce a change in signal of less than one standard deviation magnitude on the "normal" control cells.

See Tables 3 and 4 and FIGS. 15-17 for in vitro data corresponding to compounds of the invention.

TABLE 3

| Compound Code | IC$_{50}$ in BJELR (μM) |
|---|---|
| 5 | <0.100 |
| 6 | ≧1.000 |
| 7 | ≧0.100 |
| 8 | ≧1.000 |
| 9 | ≧1.000 |
| 14 | ≧0.100 |
| 15 | ≧1.000 |
| 10 | ≧1.000 |
| 11 | ≧0.100 |
| 16 | ≧0.100 |
| 17 | ≧0.100 |
| 12 | <0.100 |
| 13 | <0.100 |

TABLE 4

| Cell Line Name | Cell Type | VDAC2 &3 | Ras status | Compound 5: IC 50 (nM) |
|---|---|---|---|---|
| MCF7 | Breast | + | activated pathway | ≧1000 |
| BT-549 | Breast | + | activated pathway | ≧100 |
| COLO 205 | Colon | + | B-raf V600E mut, ras wt | |
| SW-620 | Colon | + | K-ras G12V mutation, wt B-raf | |
| DLD-1 | Colon | | K-ras G13D mutation, wt B-raf, positive for p53 antigen expression (the p53 antigen produced has a C -> T mutation resulting in Ser -> Phe at position 241 | ≧100 |
| LS174T | Colon | | K-ras2 G12D mutation | |
| HCT116 | Colon | | K-ras G12D | ≧100 |
| HT1080 | fibrosarcoma | | n-ras mutation | <100 |
| MALME-3M | Melanoma | + | B-raf V600E mut, ras wt | ≧100 |
| SK-MEL-28 | Melanoma | + | B-raf V600E mut, ras wt | ≧100 |
| SK-MEL-5 | Melanoma | + | B-raf V600E mut heterozygote | ≧100 |
| A375 | Melanoma | | Wt ras, constit. Active MEK1 | |
| HOP-62 | Non-Small Cell Lung | + | K-ras G12V | ≧100 |
| HOP-92 | Non-Small Cell Lung | + | Wt ras | ≧1000 |
| NCI-H322M | Non-Small Cell Lung | + | | |
| OVCAR-3 | Ovarian | + | K-ras amplification | ≧100 |
| SK-OV-3 | Ovarian | + | | ≧100 |
| OVCAR-5 | Ovarian | + | K-ras G12V | <100 |
| DU-145 | Prostate | + | Wt ras | ≧100 |
| PC-3 | Prostate | + | | ≧1000 |
| BJEH | fibroblast, primary | + | normal | |
| BJELR | fibroblast, primary | + | ras V12 mutation and normal | <100 |
| PANC-1 | Pancreatic | | K-ras V12 mutant | <100 |
| MIA-PaCa-2 | Pancreatic | | K-ras mutant (G12C) | ≧1000 |

EXAMPLE 10

HT-1080 Tumor Treatment Study: Evaluation of Antitumor Activity of PRLX Compound 6 and PRLX Compound 5

Mouse Strain:

Nude Balb/c (Nu/Nu strain, Charles River Laboratories), female, 5-6 week old (~20 g average body weight).

Formulation of Test Articles:

Both compounds were formulated in an identical manner. For the 100 mg/kg dose level, each compound was delivered at a concentration of 10.0 mg/ml, in an injection volume of 0.2 ml. For the 50 mg/kg dose level, each compound was delivered at a concentration of 5.0 mg/ml, in an injection volume of 0.2 ml. For both dose levels, the vehicle contained 0.025% Tween-80, 0.01% benzyl alcohol, 35 mM acetic acid (HOAc), 100 mM potassium phosphate-buffer, and 32 mM sucrose, pH=6.5.

Study Groups:

A: PRLX compound 6 @ 100 mg/Kg, QD×5 days, IP, n=8
B: PRLX compound 6 @ 50 mg/Kg, QD×5 days, IP, n=8
C: PRLX compound 5 @ 100 mg/Kg, QD×5 days, IP, n=8
D: PRLX compound 5 @ 50 mg/Kg, QD×5 days, IP, n=8
E: Vehicle Control, QD×5 days, IP, n=8
F: Untreated Control, n=8

Treatment Schedule:

Beginning when the mean tumor volume reached ~200 mm$^3$, and continuing through day 5, every day, each animal was administered a single IP injection of one of the above treatments, for a total of 5 doses.

Tumor Implants and Staging:

Each of 70 mice was implanted with 1×10$^7$ HT-1080 cells by SC injection of 0.1 cc of inoculum into the right hind flank. A 25 G×5/8" needle size was used. The tumor cell inoculum was prepared using HT-1080 cells (ATCC isolate, 6$^{th}$ passage freezer stock) which had been cultured in DMEM [Gibco, No. 10569-010]+10% FCS [Gibco, No. F-2442]. At the time of cell harvest, cells had grown to 95-100% confluence. HT-1080 inoculum was prepared in sterile DMEM medium+ 10% FCS at a density of 1.0×10$^8$ cells/ml. On day+9 post tumor implant, the animals were group-matched into treatment and control groups, with each group consisting of 8 mice. A total of 22 outliers were excluded from the study due to tumors that were either too small or too large. This was considered study Day 1, and treatment was initiated on this day.

Preparation of Injection Solutions:

The following injection solutions were prepared fresh on each of the 5 days of compound administration:

100 mg/kg dose (groups A and C)

First, a 100 mg/ml stock solution was prepared for each compound by dissolving 35 mg of PRLX compound 6 or PRLX compound 5 in 0.35 ml of solvent (0.25% Tween-80, 0.1% benzyl alcohol, and 350 mM acetic acid). The final injection solutions were then prepared by diluting the resulting stock solutions 1:10, by mixing each with 3.15 ml of diluent (100 mM potassium phosphate buffer and 32 mM sucrose, pH 6.8). The solutions were then filter-sterilized (0.45 µm membrane). The resulting solutions contained PRLX compound 6 or PRLX compound 5 at a final concentration of 10.0 mg/ml, pH=6.5.

50 mg/Kg Dose (groups B and D).

For each of the two compounds, 1.0 ml of the 10 mg/ml injection solutions (described above) were diluted 1:2 by the addition of 1.0 ml of diluent (100 mM potassium phosphate buffer and 32 mM sucrose, pH 6.8). The resulting solutions will contain a final concentration of PRLX compound 6 or PRLX compound 5 of 5.0 mg/ml at pH=6.5.

Vehicle Control (group E).

The Vehicle Control was prepared by diluting the solvent (0.25% Tween-80, 0.1% benzyl alcohol, and 350 mM acetic acid) 1:10 using the diluent (100 mM potassium phosphate buffer and 32 mM sucrose, pH 6.8). The final composition of the Vehicle Control contained 0.025% Tween-80, 0.01% benzyl alcohol, and 35 mM HOAc, in 100 mM potassium phosphate and 32 mM sucrose with a final pH=6.8.

Dosing Summary:

| Study Group | Treatment | Conc'n of Inj. Sol'n | Amt. Compound Given (mg) | Volume of Inj. Sol'n Given |
|---|---|---|---|---|
| A | PRLX compound 6 @ 100 | 10.0 mg/ml | 2.0 | 0.2 ml |
| B | PRLX compound 6 @ 50 | 5.0 mg/ml | 1.0 | 0.2 ml |
| C | PRLX compound 5 @ 100 | 10.0 mg/ml | 2.0 | 0.2 ml |
| D | PRLX compound 5 @ 50 | 5.0 mg/ml | 1.0 | 0.2 ml |
| E | Vehicle Control | 0 mg/ml | Vehicle Only | 0.2 ml |
| F | Untreated Control | 0 | 0 | 0 |

Tumor Measurement:

Starting on Day 1, all animals were weighed, and tumor dimensions (length (L) and width (W)) were measured, every other day. The tumor measurements were then converted to tumor volume (mm$^3$) using the following formula:

$$\text{Tumor Volume} = L \times W \times W/2.$$

The resulting tumor volume values were averaged for each study group for each time point, and were then plotted against time. Variance was expressed as standard error of the mean (±SEM).

Figure 18:
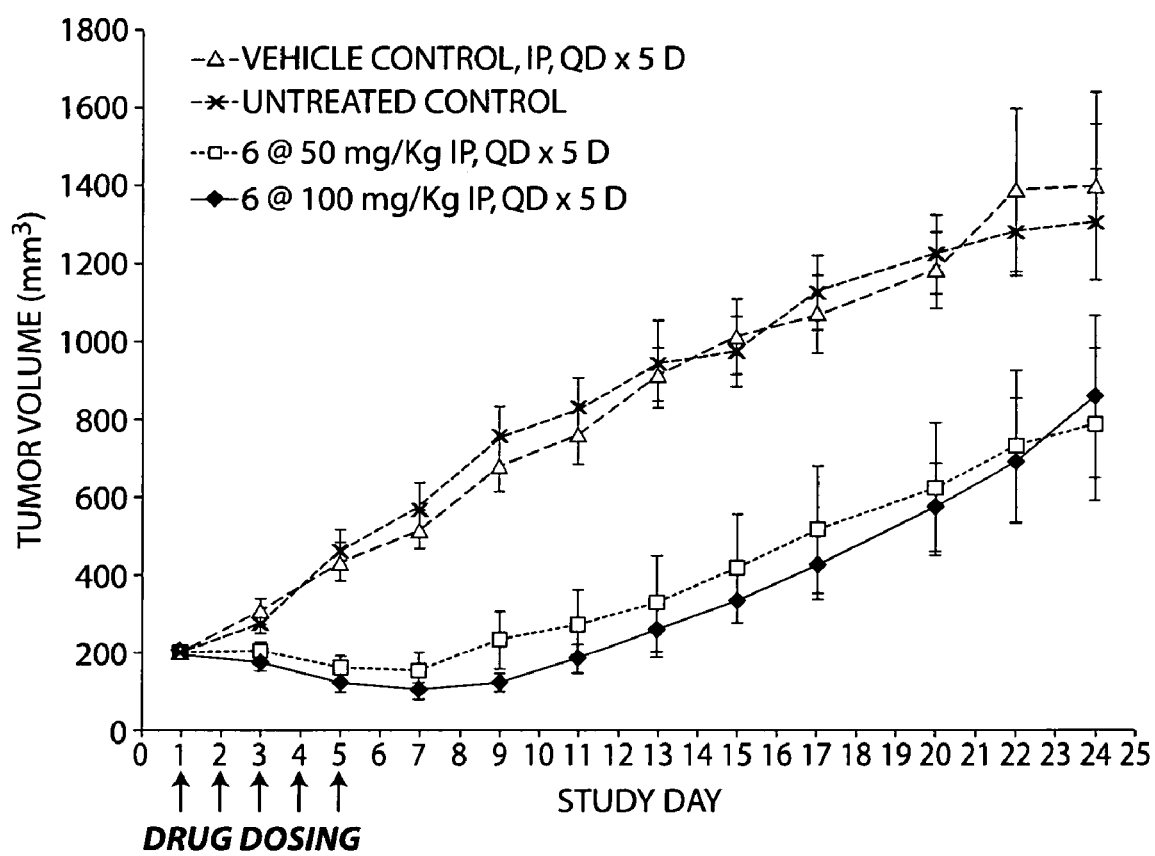
FIG. 18 shows the induction of tumor growth inhibition in HT-1080 xenografts by compound 6.
Figure 19:
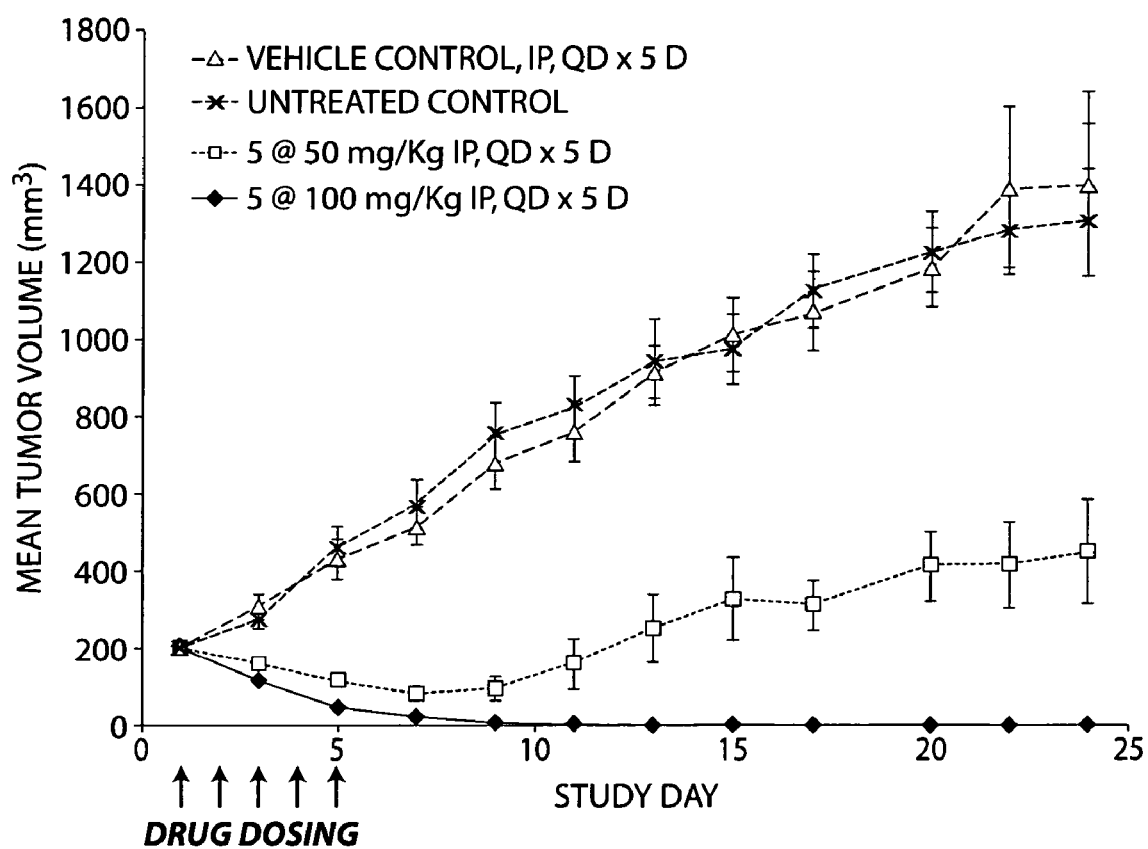
FIG. 19 shows the induction of robust tumor regression in HT-1080 xenografts by compound 5.
Figure 20:
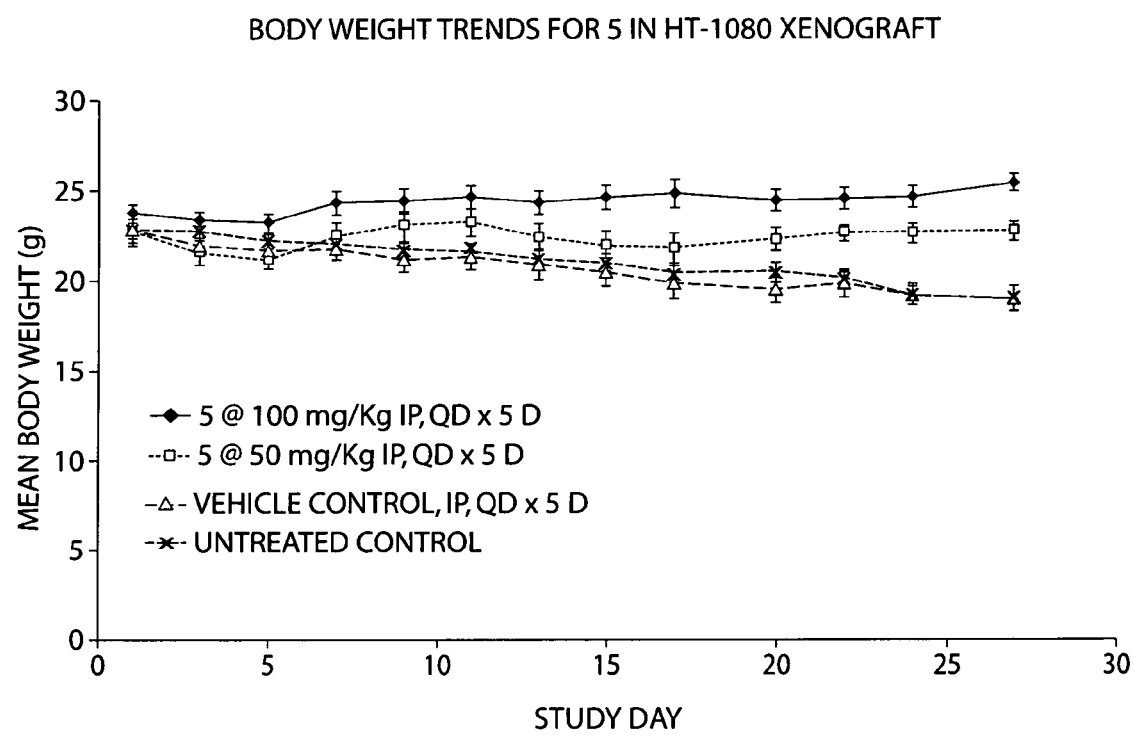
FIG. 20 shows body weight trends in HT-1080 xenografts by compound 5.

Results from these experiments are shown in FIGS. 18-20.

EXAMPLE 11

PANC-1 Tumor Treatment Study: Evaluation of Antitumor Activity of PRLX Compound 6 and PRLX Compound 5

PANC-1 Xenograft Preparation and Implantation

The experimental plan for the PANC-1 study was essentially identical to that of the HT-1080 study outlined above in Example 10 with the following exceptions: approximately 30-40 mg fragment of passaged PANC-1 tumor tissue was implanted subcutaneously in the right flank of an immunodeficient nude mouse. Tumor growth was monitored daily and when the tumors reached approximately 100 mm$^3$, animals harboring similarly sized tumors were group matched and compound dosing was initiated. Administration of compound 5 occurred once a day for five consecutive days at the doses listed below. In the PANC-1 xenografts, gemcitabine, administered at the maximum tolerated dose for the model, was used as a control. The gemcitabine regimen was 180 mg/kg three times daily on every third day over a period of 9 days.

Figure 21:
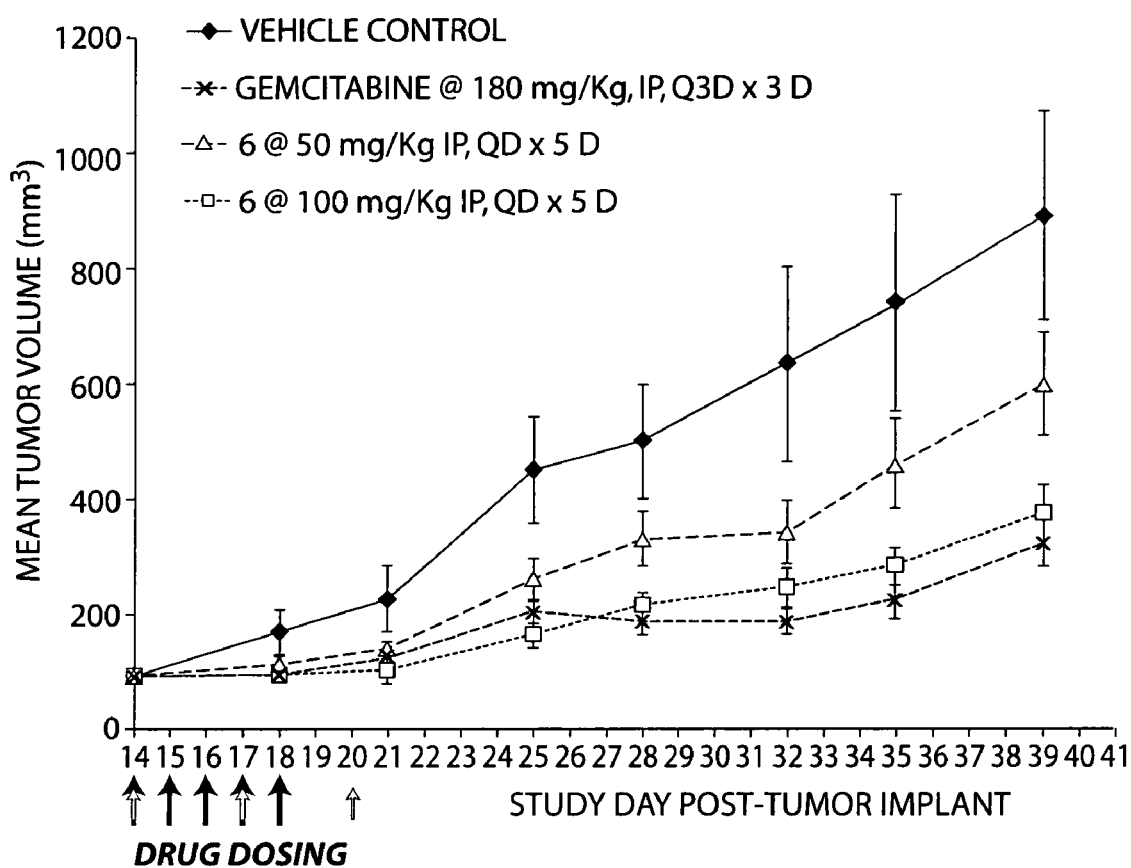
FIG. 21 shows the induction of tumor growth inhibition in PANC-1 xenografts by compound 6.
Figure 22:
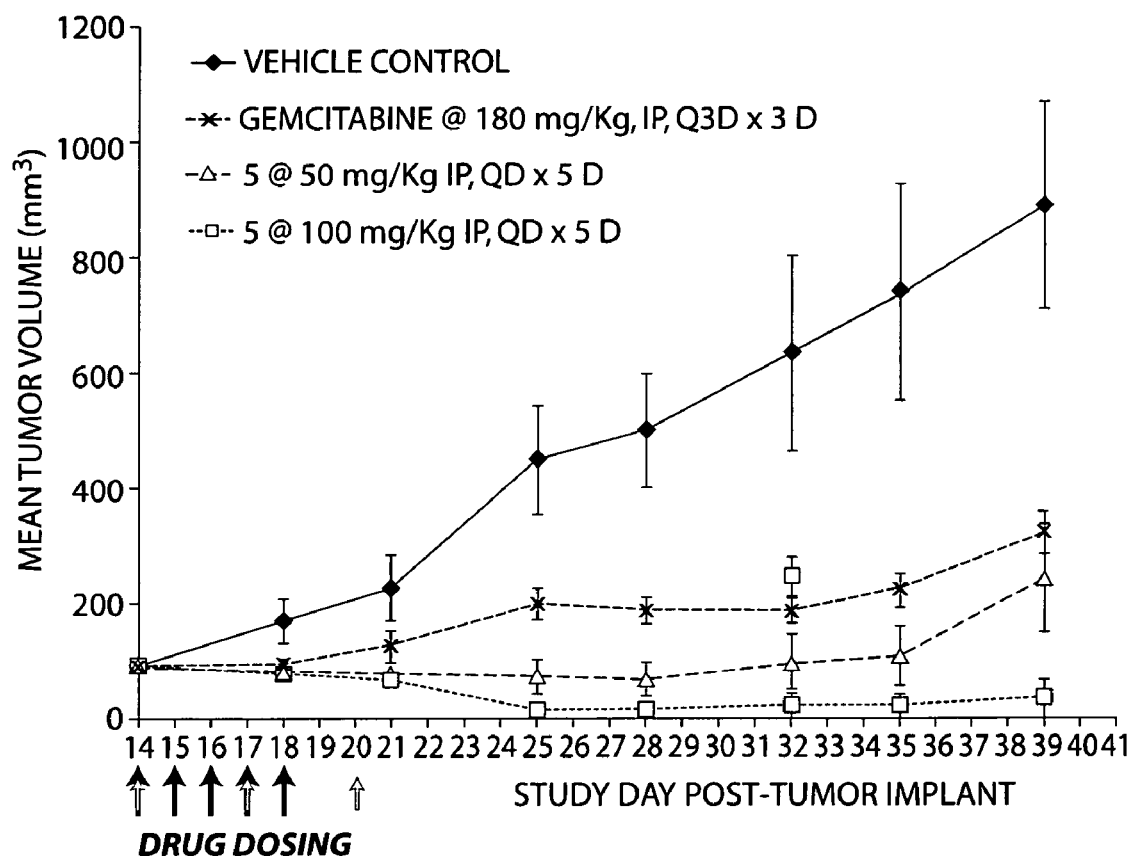
FIG. 22 shows the induction of tumor regression in PANC-1 xenografts by compound 5.

Results from these experiments are shown in FIGS. 21-22.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound having a structure of Formula V or a pharmaceutically acceptable salt thereof,

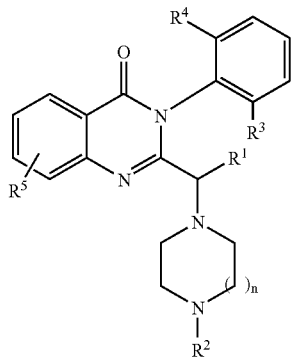

(V)

wherein
R¹ is selected from H and $C_{1-8}$ alkyl;
R² is selected from H and $C_{1-8}$ alkyl wherein $C_{1-8}$-alkyl is optionally substituted by one or more of hydroxyl, halo, cyano, alkoxy, nitro, carbonyl, thiocarbonyl, phosphoryl, phosphate, phosphonate, phosphinate, amino, amido, amidine, imine, azido, sulfhydryl, alkylthio, sulfate, sulfonate, sulfamoyl, sulfamido, sulfonyl and heterocyclyl;
R³ is selected from alkoxy and unsubstituted $C_{1-8}$alkyl;
R⁴ is selected from H, alkoxy and unsubstituted $C_{1-8}$alkyl;
R₅ is selected from H, halogen; and
n is 1 or 2.

2. The compound of claim 1, having the structure 6,

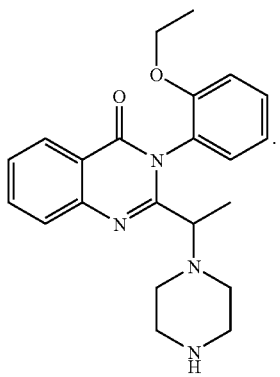

6

3. The compound of claim 1, having the structure 5,

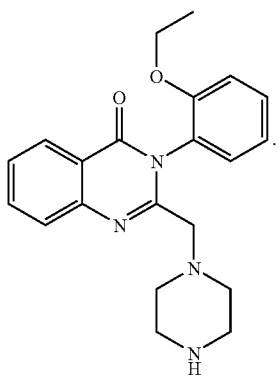

5

4. The compound of claim 1, having the structure 13,

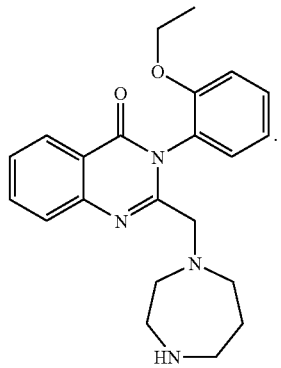

13

5. The compound of claim 1, having the structure 12,

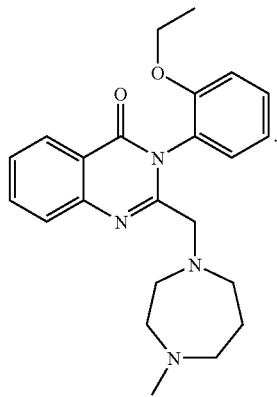

12

6. A method of killing a cell, promoting cell death or inhibiting cellular proliferation of a breast cancer, colon cancer, ovarian cancer, lung cancer, prostate cancer or melanoma cell, comprising administering to said cancer cell an effective amount of a compound having a structure of Formula V or a pharmaceutically acceptable salt thereof,

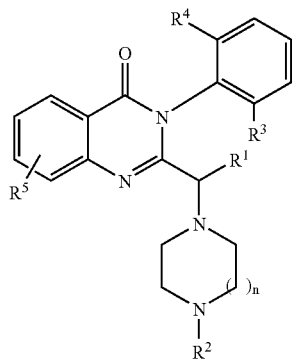

(V)

wherein
R¹ is selected from H and $C_{1-8}$alkyl;
R² is selected from H and $C_{1-8}$alkyl;
R³ is selected from halogen, alkoxy and $C_{1-8}$alkyl;
R⁴ is selected from H, halogen, alkoxy and $C_{1-8}$alkyl;
R⁵ is selected from H, halogen and nitro; and
n is 1 or 2.

7. A method of increasing sensitivity of a breast cancer, colon cancer, ovarian cancer, lung cancer, prostate cancer or melanoma tumor cell or a normal cell to a chemotherapeutic agent comprising contacting said cells with a compound having a structure of Formula V or a pharmaceutically acceptable salt thereof,

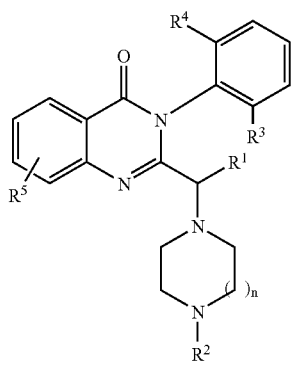

(V)

wherein
$R^1$ is selected from H and $C_{1-8}$alkyl;
$R^2$ is selected from H and $C_{1-8}$alkyl;
$R^3$ is selected from halogen, alkoxy and $C_{1-8}$alkyl;
$R^4$ is selected from H, halogen, alkoxy and $C_{1-8}$alkyl;
$R^5$ is selected from H, halogen and nitro; and
n is 1 or 2.

8. A method of treating breast, colon, ovarian, lung or prostate cancer or melanoma in a mammal, comprising administering to the mammal a therapeutically effective amount of a compound having a structure of Formula V or a pharmaceutically acceptable salt thereof,

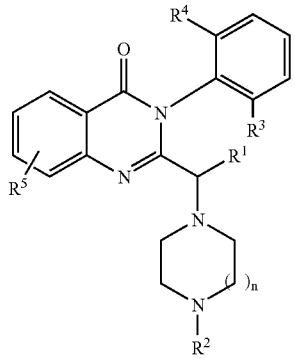

(V)

wherein
$R^1$ is selected from H and $C_{1-8}$alkyl;
$R^2$ is selected from H and $C_{1-8}$alkyl;
$R^3$ is selected from halogen, alkoxy and $C_{1-8}$alkyl;
$R^4$ is selected from H, halogen, alkoxy and $C_{1-8}$alkyl;
$R^5$ is selected from H, halogen and nitro; and
n is 1 or 2.

9. The method of claim 6, wherein the compound has structure 6,

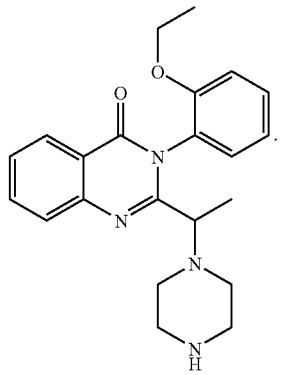

6

10. The method of claim 6, wherein the compound has structure 5,

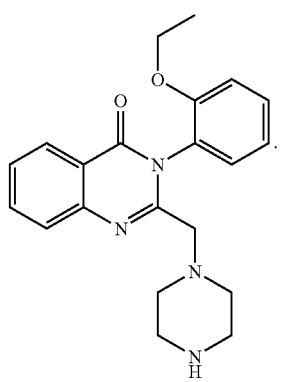

5

11. The method of claim 6, wherein the compound has structure 13,

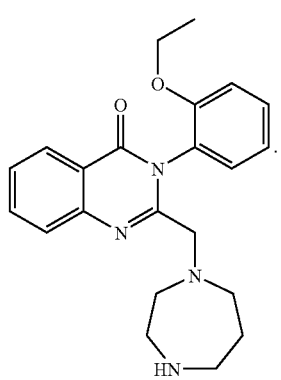

13

12. The method of claim 6, wherein the compound has structure 12,
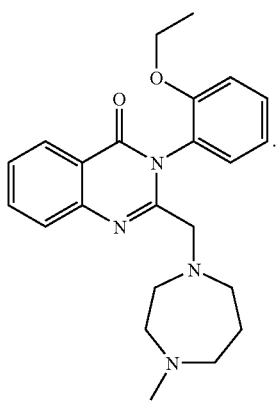
13. The method of claim 6, wherein the compound has structure 16,
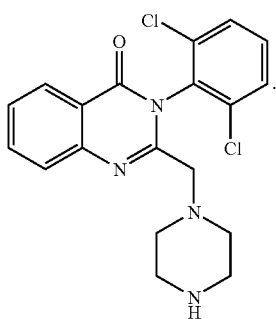
14. The method of claim 7, wherein the compound has structure 6,
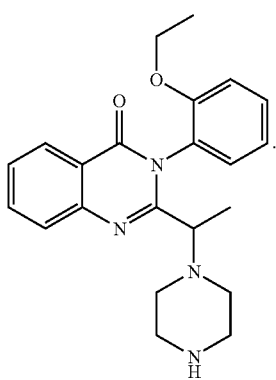
15. The method of claim 7, wherein the compound has structure 5,
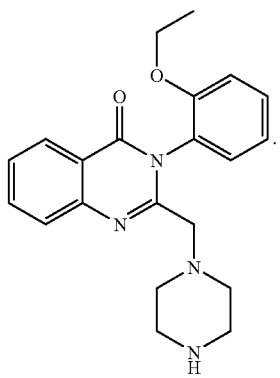
16. The method of claim 7, wherein the compound has structure 13,
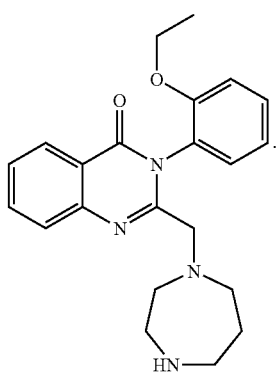
17. The method of claim 7, wherein the compound has structure 12,
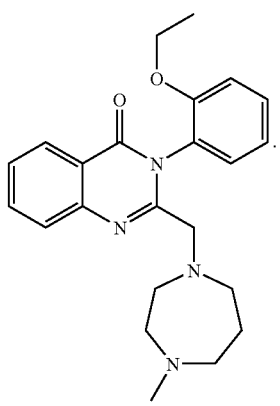

18. The method of claim 7, wherein the compound has structure 16,
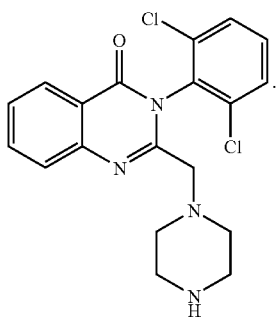
16
19. The method of claim 8, wherein the compound has structure 6,
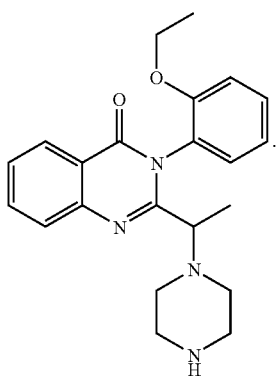
6
20. The method of claim 8, wherein the compound has structure 5,
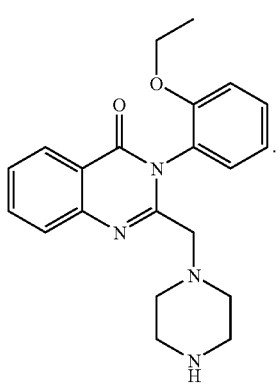
5
21. The method of claim 8, wherein the compound has structure 13,
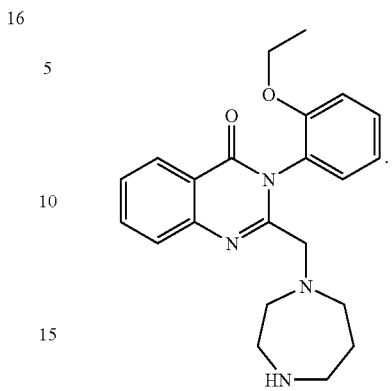
13
22. The method of claim 8, wherein the compound has structure 12,
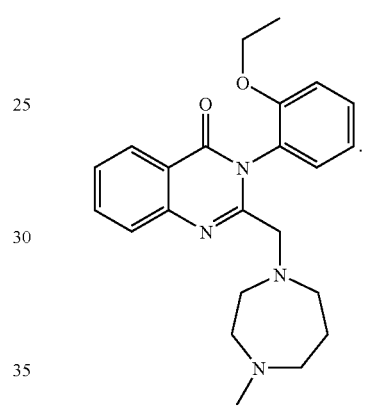
12
23. The method of claim 8, wherein the compound has structure 16,
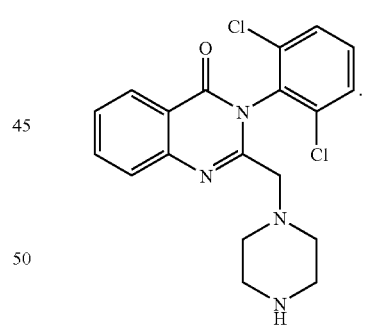
16
* * * * *

UNITED STATES PATENT AND TRADEMARK OFFICE
CERTIFICATE OF CORRECTION

PATENT NO. : 7,615,554 B2  Page 1 of 1
APPLICATION NO. : 11/340430
DATED : November 10, 2009
INVENTOR(S) : Selliah et al.

It is certified that error appears in the above-identified patent and that said Letters Patent is hereby corrected as shown below:

In Claim 7, Column 201, Line 3, after the word "cell" please delete "or a normal cell".

Signed and Sealed this

Fifth Day of January, 2010

David J. Kappos
*Director of the United States Patent and Trademark Office*